(12) United States Patent
Ryu et al.

(10) Patent No.: US 9,368,733 B2
(45) Date of Patent: Jun. 14, 2016

(54) COMPOUND FOR ORGANIC OPTOELECTRONIC DEVICE, ORGANIC LIGHT-EMITTING DEVICE CONTAINING THE SAME, AND DISPLAY DEVICE INCLUDING SAID ORGANIC LIGHT-EMITTING DEVICE

(71) Applicant: SAMSUNG SDI CO., LTD., Yongin-si, Gyeonggi-do (KR)

(72) Inventors: Dong-Wan Ryu, Suwon-si (KR); Nam-Heon Lee, Suwon-si (KR); Han-Ill Lee, Suwon-si (KR); Sung-Hyun Jung, Suwon-si (KR); Young-Kyoung Jo, Suwon-si (KR); Mi-Young Chae, Suwon-si (KR); Dal-Ho Huh, Suwon-si (KR); Jin-Seok Hong, Suwon-si (KR)

(73) Assignee: SAMSUNG SDI CO., LTD., Yongin-si, Gyeonggi-do (KR)

( * ) Notice: Subject to any disclaimer, the term of this patent is extended or adjusted under 35 U.S.C. 154(b) by 0 days.

(21) Appl. No.: 14/610,005

(22) Filed: Jan. 30, 2015

(65) Prior Publication Data
US 2015/0137111 A1 May 21, 2015

Related U.S. Application Data

(63) Continuation of application No. PCT/KR2013/003897, filed on May 6, 2013.

(30) Foreign Application Priority Data

Sep. 28, 2012 (KR) .......... 10-2012-0109449

(51) Int. Cl.
*H01L 27/146* (2006.01)
*H01L 51/00* (2006.01)
(Continued)

(52) U.S. Cl.
CPC .......... *H01L 51/0074* (2013.01); *C07D 311/78* (2013.01); *C07D 319/24* (2013.01);
(Continued)

(58) Field of Classification Search
CPC ............ C07F 7/08116; H01L 51/0069; C07D 327/08; C07D 319/24; C07D 310/24; C07D 311/78
USPC ....................... 257/258; 544/38, 104; 549/382
See application file for complete search history.

(56) References Cited

U.S. PATENT DOCUMENTS 8,927,117 B2 * 1/2015 Buesing .................. C07C 13/62
257/40
2004/0131881 A1 * 7/2004 Zheng ..................... C07C 13/62
428/690

(Continued)

FOREIGN PATENT DOCUMENTS

JP    2009-267257 A    11/2009
JP    2010-202599 A    9/2010

(Continued)

*Primary Examiner* — Caridad Everhart
(74) *Attorney, Agent, or Firm* — Lee & Morse, P.C.

(57) ABSTRACT

A compound for an organic optoelectronic device, an organic light-emitting device including the same and a display device including the organic light-emitting device are provided, and the compound for an organic optoelectronic device represented by a combination of the following Chemical Formula 1 and 2 is provided and thus an organic light-emitting device has improved life-span characteristics due to excellent electrochemical and thermal stability, and high luminous efficiency at a low driving voltage.

17 Claims, 3 Drawing Sheets

(51) Int. Cl.
| | | |
|---|---|---|
| *C09K 11/06* | (2006.01) | |
| *C07D 311/78* | (2006.01) | |
| *C07D 319/24* | (2006.01) | |
| *C07D 327/08* | (2006.01) | |
| *C07D 335/12* | (2006.01) | |
| *C07D 339/08* | (2006.01) | |
| *C07D 405/04* | (2006.01) | |
| *C07D 413/04* | (2006.01) | |
| *C07D 417/04* | (2006.01) | |
| *C07F 7/08* | (2006.01) | |
| *H01L 51/50* | (2006.01) | |
| *H01L 51/52* | (2006.01) | |

(52) U.S. Cl.
CPC ............ *C07D327/08* (2013.01); *C07D 335/12* (2013.01); *C07D 339/08* (2013.01); *C07D 405/04* (2013.01); *C07D 413/04* (2013.01); *C07D 417/04* (2013.01); *C07F 7/0816* (2013.01); *C09K 11/06* (2013.01); *H01L 51/006* (2013.01); *H01L 51/0061* (2013.01); *H01L 51/0069* (2013.01); *H01L 51/0071* (2013.01); *H01L 51/0072* (2013.01); *H01L 51/0073* (2013.01); *H01L 51/0094* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/1096* (2013.01); *H01L 51/0055* (2013.01); *H01L 51/0081* (2013.01); *H01L 51/5012* (2013.01); *H01L 51/5056* (2013.01); *H01L 51/5072* (2013.01); *H01L 51/5088* (2013.01); *H01L 51/5221* (2013.01); *H01L 2251/308* (2013.01); *Y02E 10/549* (2013.01)

(56) References Cited

U.S. PATENT DOCUMENTS

| | | | | |
|---|---|---|---|---|
| 2008/0026135 | A1* | 1/2008 | Bentsen | C07D 271/107 427/66 |
| 2013/0027636 | A1* | 1/2013 | Marrocco, III | C08G 61/10 349/69 |
| 2013/0207048 | A1* | 8/2013 | Schwaiger | C07D 487/04 252/500 |

FOREIGN PATENT DOCUMENTS

| | | | |
|---|---|---|---|
| JP | 2011-178742 | A | 9/2011 |
| KR | 10-2008-0037699 | A | 4/2008 |
| KR | 10-2010-0075830 | A | 7/2010 |
| KR | 10-2010-0130197 | A | 12/2010 |
| KR | 10-2010-0133467 | A | 12/2010 |
| KR | 10-2011-0018688 | A | 2/2011 |
| KR | 10-2011-0058247 | A | 6/2011 |
| KR | 10-2011-0079402 | A | 7/2011 |
| KR | 10-2012-0078301 | A | 7/2012 |
| WO | WO 2010/050779 | A1 | 5/2010 |
| WO | WO 2011/016648 | A1 | 2/2011 |

* cited by examiner

COMPOUND FOR ORGANIC OPTOELECTRONIC DEVICE, ORGANIC LIGHT-EMITTING DEVICE CONTAINING THE SAME, AND DISPLAY DEVICE INCLUDING SAID ORGANIC LIGHT-EMITTING DEVICE

CROSS-REFERENCE TO RELATED APPLICATIONS

This application is a continuation of pending International Application No. PCT/KR2013/003897, entitled "Compound for Organic Optoelectronic Device, Organic Light-Emitting Device Containing the Same, and Display Device Including Said Organic Light-Emitting Device," which was filed on May 6, 2013, the entire contents of which are hereby incorporated by reference.

Korean Patent Application No. 10-2012-0109449, filed on Sep. 28, 2012, in the Korean Intellectual Property Office, and entitled: "Compound for Organic Optoelectronic Device, Organic Light-Emitting Device Containing the Same, and Display Device Including Said Organic Light-Emitting Device," is incorporated by reference herein in its entirety.

BACKGROUND

1. Field

A compound for an organic optoelectronic device having excellent life-span, efficiency, electrochemical stability, and thermal stability, an organic light-emitting device including the compound, and a display device including the organic light-emitting device are disclosed.

2. Description of the Related Art

An organic optoelectronic device is a device requiring a charge exchange between an electrode and an organic material by using holes or electrons.

An organic optoelectronic device may be classified as follows in accordance with its driving principles. A first organic optoelectronic device is an electronic device driven as follows: excitons are generated in an organic material layer by photons from an external light source; the excitons are separated into electrons and holes; and the electrons and holes are transferred to different electrodes as a current source (voltage source).

A second organic optoelectronic device is an electronic device driven as follows: a voltage or a current is applied to at least two electrodes to inject holes and/or electrons into an organic material semiconductor positioned at an interface of the electrodes, and the device is driven by the injected electrons and holes.

Examples of an organic optoelectronic device include an organic photoelectric device, an organic light-emitting device, an organic solar cell, an organic photo conductor drum, an organic transistor, and the like, which require a hole injecting or transport material, an electron injecting or transport material, or a light emitting material.

Particularly, an organic light-emitting device (OLED) has recently drawn attention due to an increase in demand for flat panel displays. In general, organic light emission refers to conversion of electrical energy into photo-energy.

Such an organic light-emitting device converts electrical energy into light by applying current to an organic light emitting material. It has a structure in which a functional organic material layer is interposed between an anode and a cathode. The organic material layer includes a multi-layer including different materials, for example a hole injection layer (HIL), a hole transport layer (HTL), an emission layer, an electron transport layer (ETL), and an electron injection layer (EIL), in order to improve efficiency and stability of an organic light-emitting device.

In such an organic light-emitting device, when a voltage is applied between a anode and a cathode, holes from the anode and electrons from the cathode are injected to an organic material layer and recombined to generate excitons having high energy. The generated excitons generate light having certain wavelengths while shifting to a ground state.

Recently, it has become known that a phosphorescent light emitting material may be used for a light emitting material of an organic light-emitting device in addition to the fluorescent light emitting material. Such a phosphorescent material emits lights by transporting the electrons from a ground state to an exited state, non-radiance transiting of a singlet exciton to a triplet exciton through intersystem crossing, and transiting a triplet exciton to a ground state to emit light.

As described above, in an organic light-emitting device, an organic material layer includes a light emitting material and a charge transport material, for example a hole injection material, a hole transport material, an electron transport material, an electron injection material, and the like.

The light emitting material is classified as blue, green, and red light emitting materials according to emitted colors, and yellow and orange light emitting materials to emit colors approaching natural colors.

When one material is used as a light emitting material, a maximum light emitting wavelength is shifted to a long wavelength or color purity decreases because of interactions between molecules, or device efficiency decreases because of a light emitting quenching effect. Therefore, a host/dopant system is included as a light emitting material in order to improve color purity and increase luminous efficiency and stability through energy transfer.

In order to implement excellent performance of an organic light-emitting device, a material constituting an organic material layer, for example a hole injection material, a hole transport material, a light emitting material, an electron transport material, an electron injection material, and a light emitting material such as a host and/or a dopant, should be stable and have good efficiency. However, development of an organic material layer forming material for an organic light-emitting device has thus far not been satisfactory and thus there is a need for a novel material. This material development is also required for other organic optoelectronic devices.

The low molecular organic light-emitting device is manufactured as a thin film in a vacuum deposition method and can have good efficiency and life-span performance. A polymer organic light-emitting device is manufactured in an inkjet or spin coating method has an advantage of low initial cost and being large-sized.

Both low molecular organic light emitting and polymer organic light-emitting devices have an advantage of self-light emitting, high speed response, wide viewing angle, ultra-thin, high image quality, durability, large driving temperature range, and the like. In particular, they have good visibility due to self-light emitting characteristics compared with a conventional LCD (liquid crystal display) and have an advantage of decreasing thickness and weight of LCD up to a third, because they do not need a backlight.

In addition, since they have a response speed 1000 time faster microsecond unit than LCD, they can realize a perfect motion picture without after-image. Based on these advantages, they have been remarkably developed to have 80 times efficiency and more than 100 times life-span since they come out for the first time in the late 1980s. Recently, they keep being rapidly larger such as a 40-inch organic light-emitting device panel.

They are simultaneously required to have improved luminous efficiency and life-span in order to be larger. Herein, their luminous efficiency need smooth combination between holes and electrons in an emission layer. However, since an organic material in general has slower electron mobility than hole mobility, it has a drawback of inefficient combination between holes and electrons. Accordingly, while increasing electron injection and mobility from a cathode and simultaneously preventing movement of holes is required.

In order to improve life-span, a material crystallisation caused by Joule heats generated during device operating is required to be prevented. Accordingly, there has been a strong need for an organic compound having excellent electron injection and mobility, and high electrochemical stability.

SUMMARY

A compound for an organic optoelectronic device that may act as hole injection and transport or electron injection and transport material, and also act as a light emitting host along with an appropriate dopant is provided.

An organic light emitting device having excellent life-span, efficiency, driving voltage, electrochemical stability and thermal stability and a display device including the same are provided.

In one embodiment of the present invention, a compound for an organic optoelectronic device represented by a combination of the following Chemical Formulae 1 and 2 is provided.

[Chemical Formula 1]

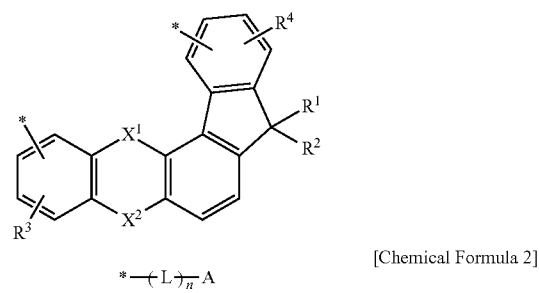

[Chemical Formula 2]

*—(L)$_n$—A

In the Chemical Formulae 1 and 2, $X^1$ and $X^2$ are independently —O—, —S—, —S(O)$_2$—, —CR$^a$R$^b$—, —SiR$^a$R$^b$— or —GeR$^a$R$^b$—, wherein the R$^a$ and R$^b$ are independently hydrogen, deuterium, a substituted or unsubstituted C1 to C10 alkyl group, a substituted or unsubstituted C6 to C30 aryl group or a substituted or unsubstituted C2 to C30 heteroaryl group, R1 to R4 are independently hydrogen, deuterium, a substituted or unsubstituted C1 to C10 alkyl group, a substituted or unsubstituted C6 to C30 aryl group or a substituted or unsubstituted C2 to C30 heteroaryl group, A is a substituted or unsubstituted C6 to C30 aryl group, a substituted or unsubstituted C2 to C30 heteroaryl group or —N(L$^1_m$R')(L$^2_o$R"), wherein the R' and R" are independently hydrogen, deuterium, a substituted or unsubstituted C1 to C10 alkyl group, a substituted or unsubstituted C6 to C30 aryl group or a substituted or unsubstituted C2 to C30 heteroaryl group, L is —SiR'R"—, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, wherein the R' and R" are independently hydrogen, deuterium, a substituted or unsubstituted C1 to C10 alkyl group, a substituted or unsubstituted C6 to C30 aryl group or a substituted or unsubstituted C2 to C30 heteroaryl group, $L^1$ and $L^2$ are independently a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group n, m and o are independently integers of 0 to 3, and * of Chemical Formula 2 indicates a binding position with one of two *'s of Chemical Formula 1.

The $X^1$ and $X^2$ may be independently —O—, —S—, —CR$^a$R$^b$—, or —SiR$^a$R$^b$, wherein the R$^a$ and R$^b$ may be independently a substituted or unsubstituted C1 to C10 alkyl group, or a substituted or unsubstituted C6 to C30 aryl group.

The $R^1$ to $R^4$ may be independently hydrogen, deuterium, a substituted or unsubstituted C1 to C10 alkyl group, or a substituted or unsubstituted C6 to C30 aryl group.

The A may be a substituted or unsubstituted C6 to C30 aryl group or a substituted or unsubstituted C2 to C30 heteroaryl group.

The A may be —N(L$^1_m$R')(L$^2_o$R"), wherein one of the R' or R" is a substituent represented by the following Chemical Formula 3.

[Chemical Formula 3]

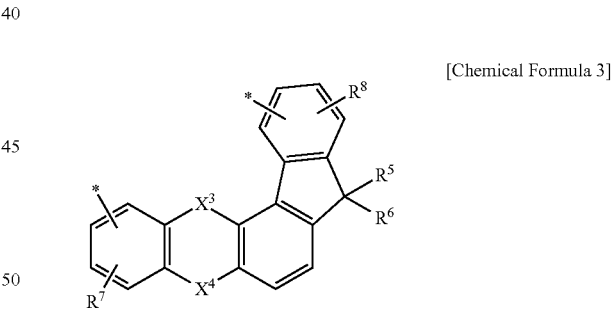

In the Chemical Formula 3, $X^3$ and $X^4$ are independently —O—, —S—, —S(O)$_2$—, —CR$^a$R$^b$—, —SiR$^a$R$^b$— or —GeR$^a$R$^b$—, wherein the R$^a$ and R$^b$ are independently hydrogen, deuterium, a substituted or unsubstituted C1 to C10 alkyl group, a substituted or unsubstituted C6 to C30 aryl group or a substituted or unsubstituted C2 to C30 heteroaryl group, $R^5$ to $R^8$ are independently hydrogen, deuterium, a substituted or unsubstituted C1 to C10 alkyl group, a substituted or unsubstituted C6 to C30 aryl group or a substituted or unsubstituted C2 to C30 heteroaryl group, and one of two *'s of the Chemical Formula 3 indicates a bond with the $L^1$ or $L^2$ of —N(L$^1_m$R')(L$^2_o$R").

The R' may be a substituent represented by the Chemical Formula 3, and the R" may be a substituent represented by the Chemical Formula 4.

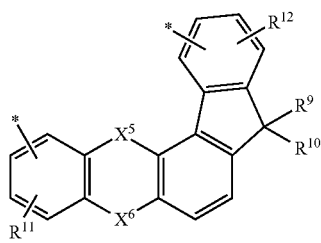

[Chemical Formula 4]

In the Chemical Formula 4, $X^5$ and $X^6$ are independently —O—, —S—, —S(O)—, —CR$^a$R$^b$—, —SiR$^a$R$^b$— or —GeR$^a$R$^b$—, wherein the R$^a$ and R$^b$ are independently hydrogen, deuterium, a substituted or unsubstituted C1 to C10 alkyl group, a substituted or unsubstituted C6 to C30 aryl group or a substituted or unsubstituted C2 to C30 heteroaryl group, $R^9$ to $R^{12}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, and one of two *'s of the Chemical Formula 4 indicates a bond with the $L^1$ or $L^2$ of —N(L$^1_m$R')(L$^2_o$R").

The A may be a substituent represented by the following Chemical Formula 3.

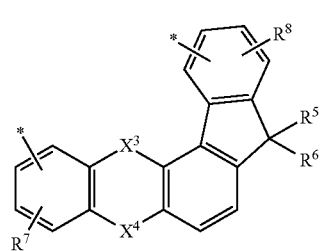

[Chemical Formula 3]

In the Chemical Formula 3, $X^3$ and $X^4$ are independently —O—, —S—, —S(O)$_2$—, —CR$^a$R$^b$—, —SiR$^a$R$^b$— or —GeR$^a$R$^b$—, wherein the R$^a$ and R$^b$ are independently hydrogen, deuterium, a substituted or unsubstituted C1 to C10 alkyl group, a substituted or unsubstituted C6 to C30 aryl group or a substituted or unsubstituted C2 to C30 heteroaryl group, R5 to R8 are independently hydrogen, deuterium, a substituted or unsubstituted C1 to C10 alkyl group, a substituted or unsubstituted C6 to C30 aryl group or a substituted or unsubstituted C2 to C30 heteroaryl group, and one of two *'s of the Chemical Formula 3 indicates a bond with the L of the Chemical Formula 2.

The compound for an organic optoelectronic device may have triplet exciton energy (T1) of 2.0 eV or greater.

The organic optoelectronic device may be selected from the group consisting of an organic photoelectric device, an organic light emitting device, an organic solar cell, an organic transistor, an organic photo conductor drum and an organic memory device.

In another embodiment of the present invention, an organic light-emitting device includes an anode, a cathode, and at least one or more organic thin layer between the anode and the cathode, wherein at least one of the organic thin layers includes the compound for an organic optoelectronic device.

The organic thin layer may be selected from the group consisting of an emission layer, a hole transport layer (HTL), a hole injection layer (HIL), an electron transport layer (ETL), an electron injection layer (EIL), a hole blocking layer and a combination thereof.

The compound for an organic optoelectronic device may be included in a hole transport layer (HTL) or a hole injection layer (HIL).

The compound for an organic optoelectronic device may be included in an emission layer.

The compound for an organic optoelectronic device may be used as a phosphorescent or fluorescent host material in an emission layer.

In yet another embodiment of the present invention, a display device including the organic light-emitting device is provided.

A compound having high hole or electron transport properties, film stability thermal stability and high triplet exciton energy is provided.

Such a compound may be used as a hole injection/transport material, host material, or an electron injection/transport material of an emission layer. The organic optoelectronic device using the same has improved life-span characteristics due to excellent electrochemical and thermal stability, and high luminous efficiency at a low driving voltage.

BRIEF DESCRIPTION OF THE DRAWINGS

Features will be apparent to those of skill in the art by describing in detail exemplary embodiments with reference to the attached drawings in which.

DESCRIPTION OF SYMBOLS

Figure 1:
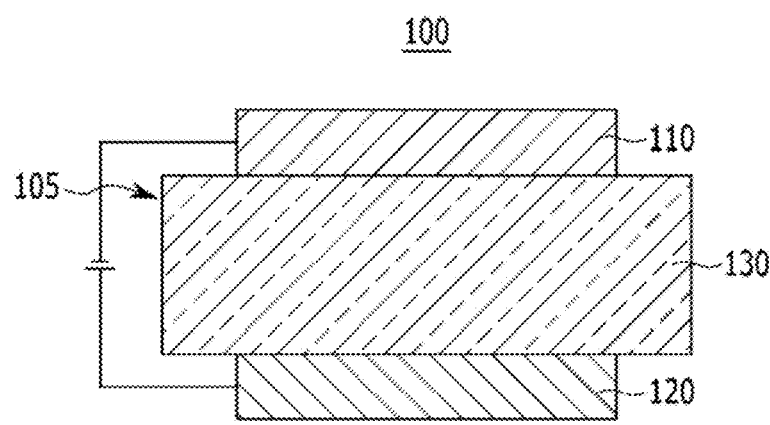
FIGS. 1 to 5 illustrate cross-sectional views showing organic light-emitting devices according to various embodiments of the present invention using a compound for an organic optoelectronic device according to one embodiment.

100: organic light-emitting device 110: cathode
120: anode 105: organic thin layer
130: emission layer 140: hole transport layer (HTL)
150: electron transport layer (ETL) 160: electron injection layer (EIL)
170: hole injection layer (HIL) 230: emission layer+ electron transport layer (ETL)

DETAILED DESCRIPTION

Hereinafter, embodiments of the present invention are described in detail. However, these embodiments are exemplary, and do not limit the present invention, and the present invention is defined by the scope of the claims which will be described later.

In the present specification, when specific definition is not otherwise provided, "substituted" refers to one substituted with deuterium, a halogen, a hydroxy group, an amino group, a substituted or unsubstituted C1 to C30 amine group, a nitro group, a substituted or unsubstituted C1 to C40 silyl group, C1 to C30 alkyl group, C1 to C10 alkylsilyl group, C3 to C30 cycloalkyl group, C6 to C30 aryl group, C1 to C20 alkoxy group, a fluoro group, a C1 to C10 trifluoroalkyl group such as trifluoromethyl group and the like, or a cyano group, instead of at least one hydrogen of a substitutent or a compound.

Two substituents of the substituted halogen, hydroxy group, amino group, substituted or unsubstituted C1 to C20 amine group, nitro group, substituted or unsubstituted C1 to C40 silyl group, C1 to C30 alkyl group, C1 to C10 alkylsilyl group, C3 to C30 cycloalkyl group, C6 to C30 aryl group, C1 to C20 alkoxy group, fluoro group, C1 to C10 trifluoroalkyl group such as trifluoromethyl group and the like or cyano group may be fused with each other to form a ring. Specifically, the substituted C6 to C30 aryl group may be fused with another adjacent substituted C6 to C30 aryl group to form a substituted or on substituted fluorene ring.

In the present specification, when specific definition is not otherwise provided, "hetero" refers to one including 1 to 3 hetero atoms selected from the group consisting of N, O, S, and P, and remaining carbons in one compound or substituent.

In the present specification, when a definition is not otherwise provided, the term "combination thereof" refers to at least two substituents bound to each other by a linker, or at least two substituents condensed to each other.

In the present specification, when a definition is not otherwise provided, "alkyl group" refers to a aliphatic hydrocarbon group. The alkyl group may be "a saturated alkyl group" without a double bond or a triple bond.

The alkyl group may be a C1 to C20 alkyl group. More specifically, the alkyl group may be a C1 to C10 alkyl group or a C1 to C6 alkyl group. For example, a C1 to C4 alkyl group may have 1 to 4 carbon atoms and may be selected from the group consisting of methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

The alkyl group may be an "unsaturated alkyl group" including at least one double bond or triple bond.

The "alkenylene group" refers to a functional group consisting of at least one carbon-carbon double bond of at least two carbons, and the "alkynylene group" refers to a functional group consisting of at least one carbon-carbon triple bond of at least two carbons. Regardless of being saturated or unsaturated, the alkyl group may be branched, linear or cyclic.

"Aromatic group" refers to a cyclic functional group where all elements have p-orbitals, and these p-orbitals forms conjugation. Specific examples we aryl group and a heteroaryl group.

"Aryl group" refers to a substituent including all element of the cycle having p-orbitals which form conjugation, and may be monocyclic, polycyclic or fused ring polycyclic (i.e., rings sharing adjacent pairs of carbon atoms) functional group.

"Heteroaryl group" refers to an aryl group including 1 to 3 hetero atoms selected from the group consisting of N, O, S, P, and Si and remaining carbons. The heteroaryl group may be a fused ring where each ring may include the 1 to 3 heteroatoms.

In the present specification, the carbazole-based derivative may refer to a substituted structure where a nitrogen atom of a substituted or unsubstituted carbazolyl group is substituted with a hetero atom except nitrogen, or carbon. Specific examples may be dibenzofuran (dibenzofuranyl group), dibenzothiophene (dibenzothiophenyl group), fluorene (fluorenyl group), and the like.

In the present specification, hole characteristics refer to characteristics that holes formed in the anode is easily injected into the emission layer and transported in the emission layer due to conductive characteristics according to HOMO level. More specifically, it is similar to electron-repelling characteristics.

Electron characteristics refer to characteristics that electron formed in the cathode is easily injected into the emission layer and transported in the emission layer due to conductive characteristics according to LUMO level. More specifically, it is similar to electron-withdrawing characteristics.

A compound for an organic optoelectronic device according to one embodiment of the present invention may have a core structure represented by a combination of the following Chemical Formulae 1 and 2.

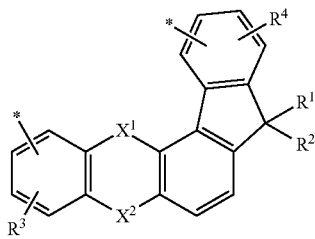

[Chemical Formula 1]

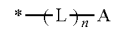

[Chemical Formula 2]

In the Chemical Formulae 1 and 2, $X^1$ and $X^2$ are independently —O—, —S—, —S(O)$_2$—, —CR$^a$R$^b$—, —SiR$^a$R$^b$ or —GeR$^a$R$^b$—, wherein the R$^a$ and R$^b$ are independently hydrogen, deuterium, a substituted or unsubstituted C1 to C10 alkyl group, a substituted or unsubstituted C6 to C30 aryl group or a substituted or unsubstituted C2 to C30 heteroaryl group, $R^1$ to $R^4$ are independently hydrogen, deuterium, a substituted or unsubstituted C1 to C10 alkyl group, a substituted or unsubstituted C6 to C30 aryl group or a substituted or unsubstituted C2 to C30 heteroaryl group, A is a substituted or unsubstituted C6 to C30 aryl group, a substituted or unsubstituted C2 to C30 heteroaryl group or —N(L$^1_m$R')(L$^2_o$R"), wherein the R' and R" are independently hydrogen, deuterium, a substituted or unsubstituted C1 to C10 alkyl group, a substituted or unsubstituted C6 to C30 aryl group or a substituted or unsubstituted C2 to C30 heteroaryl group, L is —SiR'R"—, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, wherein the R' and R" are independently hydrogen, deuterium, a substituted or unsubstituted C1 to C10 alkyl group, a substituted or unsubstituted C6 to C30 aryl group or a substituted or unsubstituted C2 to C30 heteroaryl group, $L^1$ and $L^2$ are independently a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, n, m and o are independently integers of 0 to 3, and * of Chemical Formula 2 indicates a binding position with one of two *'s of Chemical Formula 1.

The core structure may be used as a light emitting material, a hole injection material or a hole transport material of an organic optoelectronic device. Particularly, it may be suitable as a hole injection material or a hole transport material.

The compound for an organic optoelectronic device includes a core part and various substituents for a substitutent for substituting the core part and thus may have various energy bandgaps.

The compound may have an appropriate energy level depending on the substituents and thus, may fortify hole transport capability or electron transport capability of an organic optoelectronic device and bring about excellent effects on efficiency and driving voltage and also, have excellent electrochemical and thermal stability and thus, improve life-span characteristics during the operation of the organic optoelectronic device.

When the A is combined with the Chemical Formula 1 while a linking group L being interposed therebetween, charge mobility may be increased, and thus, a driving voltage of a device may be deteriorated.

In addition, when the compound is used as a light-emitting material, a light-emitting wavelength may be controlled since a conjugation length all over the compound is determined by selectively adjusting the L, $L^1$ and $L^2$, and thus, a bandgap of the compound is changed. Furthermore, when the compound for an organic optoelectronic device is used to form a charge transport layer, charge injection and transport characteristics may be changed by adjusting HOMO and LUMO levels.

Specific examples of the L, $L^1$ and $L^2$ may be a substituted or unsubstituted phenylene group, a substituted or unsubstituted biphenylene group, a substituted or unsubstituted terphenylene group, a substituted or unsubstituted naphthylene group, a substituted or unsubstituted anthracenylene group, a substituted or unsubstituted phenanthrylene group, a substituted or unsubstituted pyrenylene group, a substituted or unsubstituted fluorenylene group, a substituted or unsubstituted naphthacenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group and a substituted or unsubstituted phenoxazinyl group.

More specifically, the substituted or unsubstituted phenylene group may be, for example the following Chemical Formulae S-1, S-2 and S-3.

[Chemical Formula S-1]

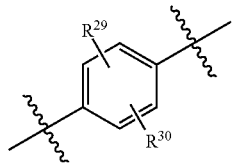

[Chemical Formula S-2]

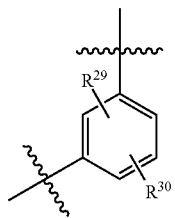

[Chemical Formula S-3]

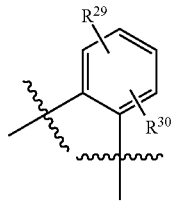

More specifically, the substituted or unsubstituted biphenylene group may be, for example the following Chemical Formulae S-4, S-5 and S-6.

[Chemical Formula S-4]

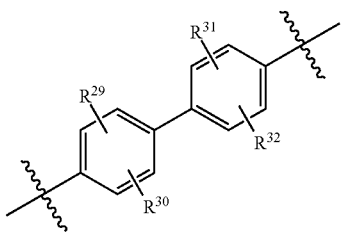

[Chemical Formula S-5]

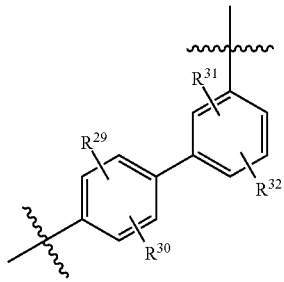

[Chemical Formula S-6]

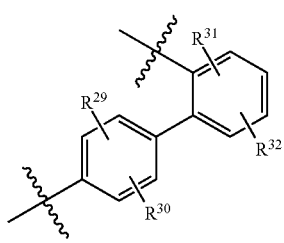

More specifically, the substituted or unsubstituted p-terphenylene group may be, for example the following Chemical Formulae S-7, S-8 and S-9.

[Chemical Formula S-7]

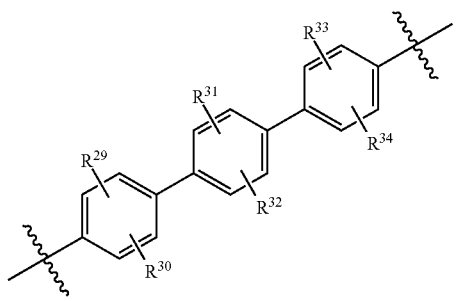

[Chemical Formula S-8]

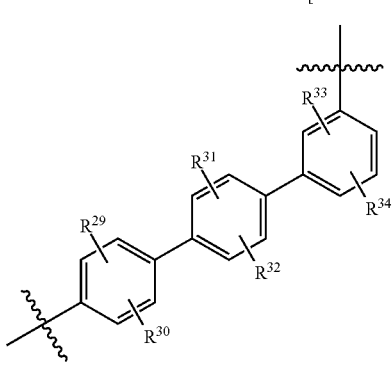

[Chemical Formula S-9]

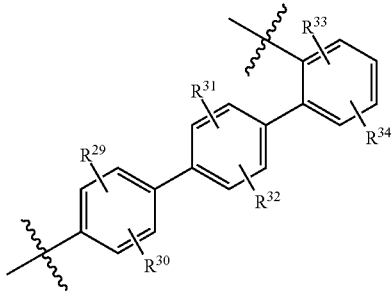

More specifically, the substituted or unsubstituted m-terphenylene group may be, for example the following Chemical Formulae S-10, S-14 and S-12.

[Chemical Formula S-10]

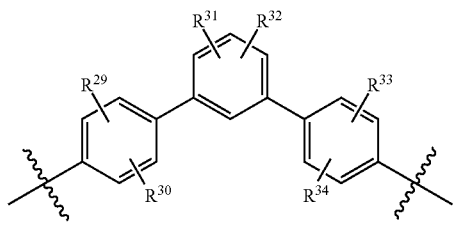

[Chemical Formula S-11]

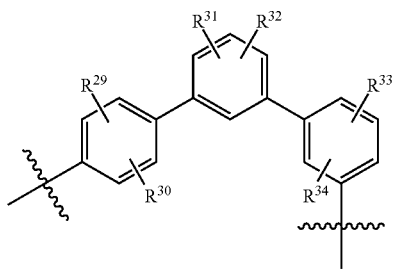

[Chemical Formula S-12]

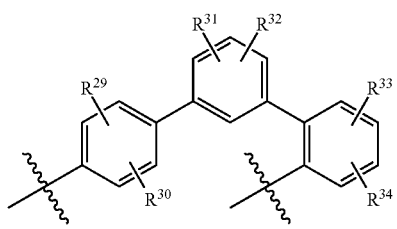

More specifically, the substituted or unsubstituted o-terphenylene group may be, for example the following Chemical Formulae S-13, S-14 and S-15.

[Chemical Formula S-13]

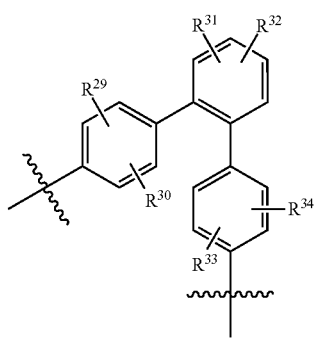

[Chemical Formula S-14]

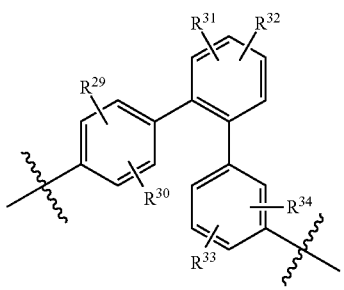

[Chemical Formula S-15]

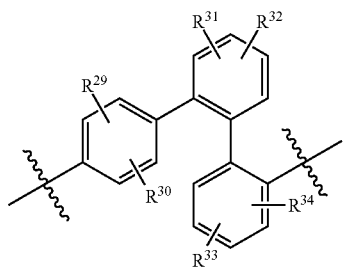

More specifically, the substituted or unsubstituted naphthylene group may be, for example the following Chemical Formulae S-16, S-17, S-18, S-19, S-20, S-21 and S-22.

[Chemical Formula S-16]

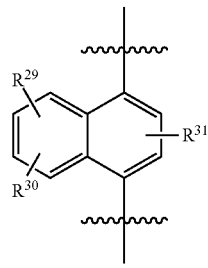

[Chemical Formula S-17]

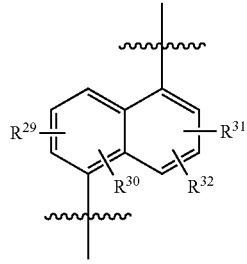

[Chemical Formula S-18]

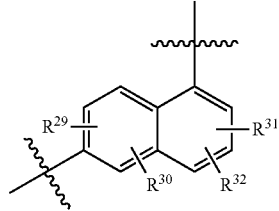

[Chemical Formula S-19]

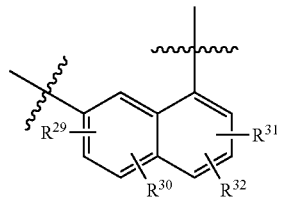

[Chemical Formula S-20]

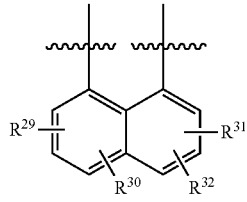

[Chemical Formula S-21]

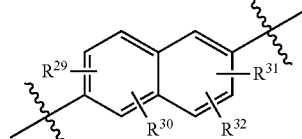

[Chemical Formula S-22]

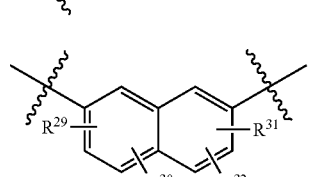

More specifically, the substituted or unsubstituted anthracenylene group may be, for example the following Chemical Formulae S-23, S-24, S-25, S-26, S-27, S-28 and S-29.

[Chemical Formula S-23]

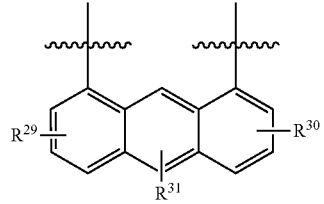

[Chemical Formula S-24]

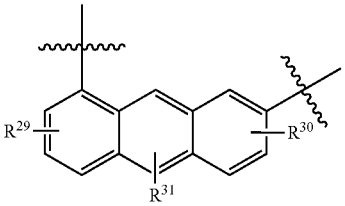

[Chemical Formula S-25]

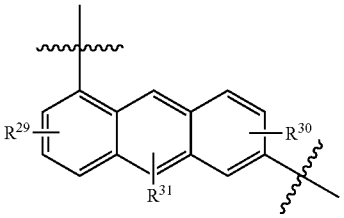

[Chemical Formula S-26]

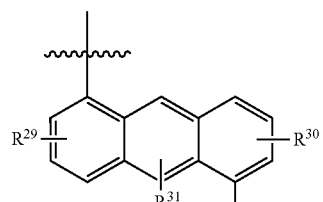

[Chemical Formula S-27]

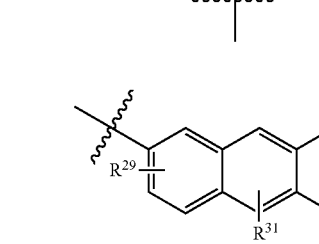

[Chemical Formula S-28]
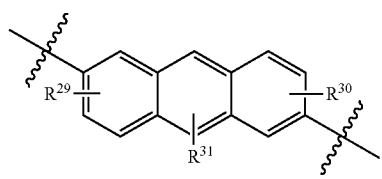
[Chemical Formula S-29]
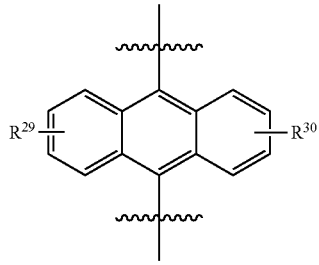
More specifically, the substituted or unsubstituted phenanthrylene group may be, for example the following Chemical Formulae S-30, S-31, S-32, S-33, S-34, S-35, S-36, S-37, S-38, S-39 and S-40.
[Chemical Formula S-30]
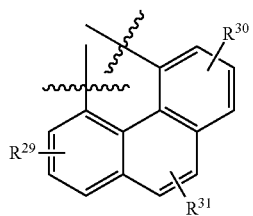
[Chemical Formula S-31]
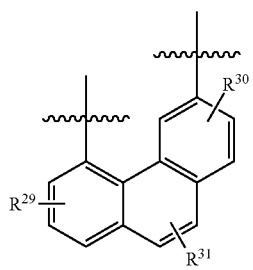
[Chemical Formula S-32]
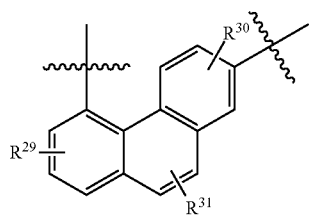
[Chemical Formula S-33]
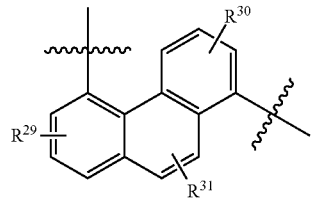
[Chemical Formula S-34]
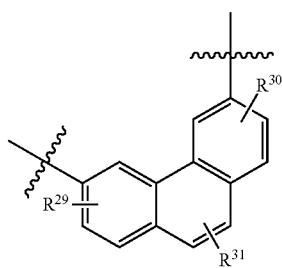
[Chemical Formula S-35]
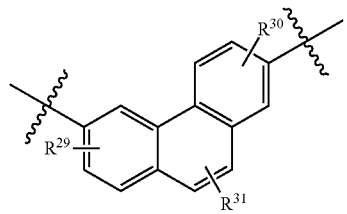
[Chemical Formula S-36]
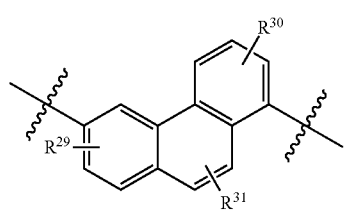
[Chemical Formula S-37]
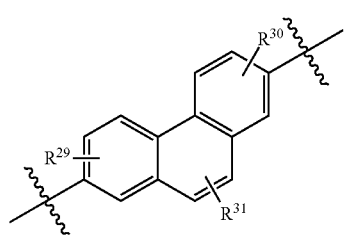
[Chemical Formula S-38]
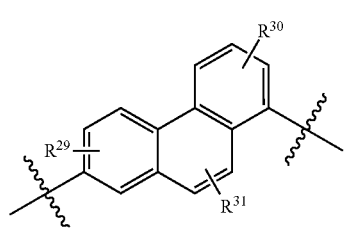

[Chemical Formula S-39]

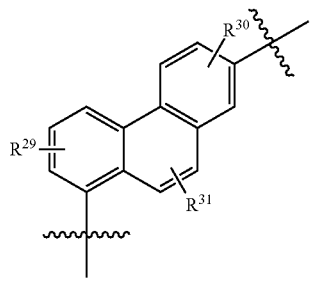

[Chemical Formula S-40]

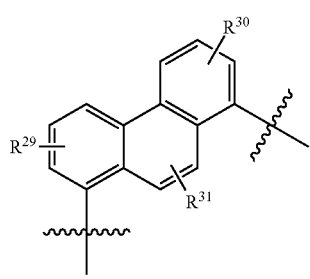

More specifically, the substituted or unsubstituted pyrenylene group may be, for example the following Chemical Formulae S-41, S-42, S-43, S-44, S-45 and S-46.

[Chemical Formula S-41]

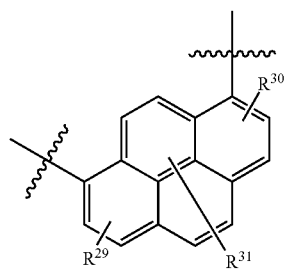

[Chemical Formula S-42]

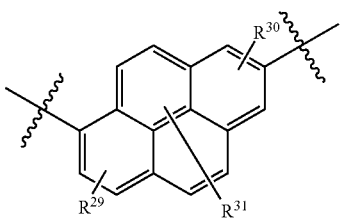

[Chemical Formula S-43]

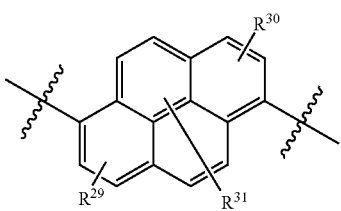

[Chemical Formula S-44]

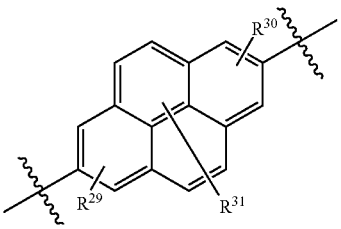

[Chemical Formula S-45]

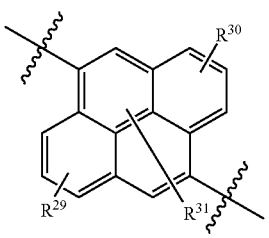

[Chemical Formula S-46]

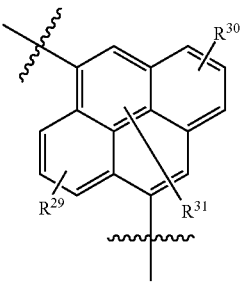

More specifically, the substituted or unsubstituted fluorenylene group may be, for example the following Chemical Formulae S-47, S-48, S-49, S-50, S-51, S-52, S-53, S-54, S-55 and S-56.

[Chemical Formula S-47]

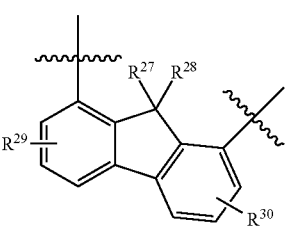

[Chemical Formula S-48]

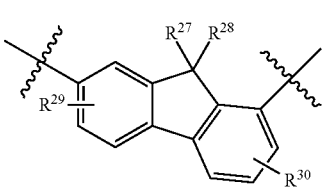

[Chemical Formula S-49]

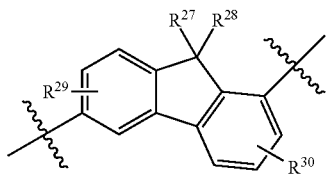

[Chemical Formula S-50]

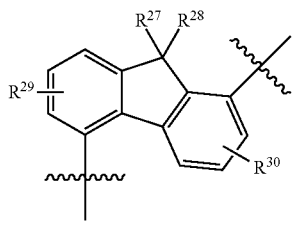

[Chemical Formula S-51]

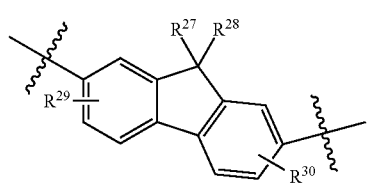

[Chemical Formula S-52]

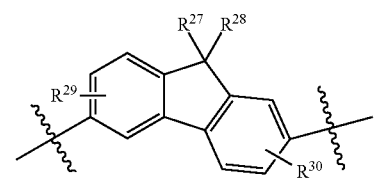

[Chemical Formula S-53]

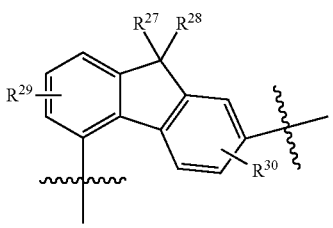

[Chemical Formula S-54]

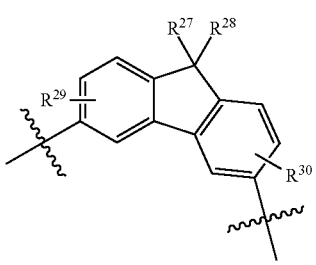

[Chemical Formula S-55]

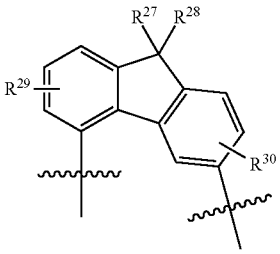

[Chemical Formula S-56]

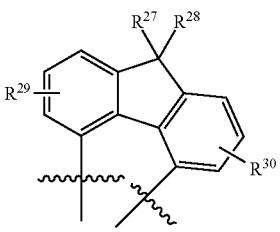

In specific examples of the L, $L^1$ and $L^2$, $R^{27}$ to $R^{34}$ may be independently hydrogen, deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group and the like or a cyano group.

The compound has steric hindrance and thus, may be suppressed from crystallization due to small interaction among molecules. Accordingly, a yield of manufacturing a device may be improved. In addition, life-span characteristics of the device may be improved.

Furthermore, the compound has a relatively large molecular weight and thus, may be suppressed from decomposition during deposition.

More specifically, the $X^1$ and $X^2$ may be independently —O—, —S—, —$CR^aR^b$—, or —$SiR^aR^b$, wherein the $R^a$ and $R^b$ are independently a substituted or unsubstituted C1 to C10 alkyl group, or a substituted or unsubstituted C6 to C30 aryl group, the $R^1$ to $R^4$ may be independently hydrogen, deuterium, a substituted or unsubstituted C1 to C10 alkyl group, or a substituted or unsubstituted C6 to C30 aryl group, and the A maybe a substituted or unsubstituted C6 to C30 aryl group or a substituted or unsubstituted C2 to C30 heteroaryl group. In this case, when a conjugation length is appropriately adjusted, the compound may be used as a host for an emission layer through fluorescence or phosphorescence light-emitting mechanism.

More specifically, the A is —$N(L^1{}_mR')(L^2{}_oR'')$, wherein one of the R' or R'' may be a substituent represented by the following Chemical Formula 3.

[Chemical Formula 3]

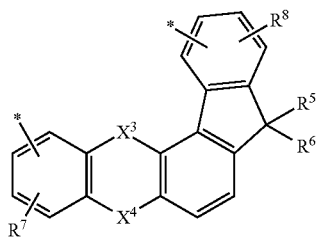

In the Chemical Formula 3, $X^3$ and $X^4$ are independently —O—, —S—, —S(O)$_2$—, —CR$^a$R$^b$—, —SiR$^a$R$^b$— or —GeR$^a$R$^b$—, wherein the R$^a$ and R$^b$ are independently hydrogen, deuterium, a substituted or unsubstituted C1 to C10 alkyl group, a substituted or unsubstituted C6 to C30 aryl group or a substituted or unsubstituted C2 to C30 heteroaryl group, $R^5$ to $R^8$ are independently hydrogen, deuterium, a substituted or unsubstituted C1 to C10 alkyl group, a substituted or unsubstituted C6 to C30 aryl group or a substituted or unsubstituted C2 to C30 heteroaryl group, and one of two *'s of the Chemical Formula 3 indicates a bond with the $L^1$ or $L^2$ of —N($L^1_m$R')($L^2_o$R").

When the A is —N($L^1_m$R')($L^2_o$R"), and either one of the R' or R" is a substituent represented by the following Chemical Formula 3, two substituents out of three substituent of amine are represented by the above Chemical Formula 1 or 3.

The compound may be used to form a hole transport layer (HTL) or a hole injection layer (HIL).

More specifically, the R' may be a substituent represented by the Chemical Formula 3, and the R" may be a substituent represented by the Chemical Formula 4.

[Chemical Formula 4]

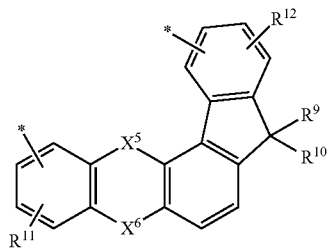

In the Chemical Formula 4, $X^5$ and $X^6$ are independently —O—, —S—, —S(O)$_2$—, —CR$^a$R$^b$—, —SiR$^a$R$^b$— or —GeR$^a$R$^b$—, wherein the R$^a$ and R$^b$ are independently hydrogen, deuterium, a substituted or unsubstituted C1 to C10 alkyl group, a substituted or unsubstituted C6 to C30 aryl group or a substituted or unsubstituted C2 to C30 heteroaryl group, $R^9$ to $R^{12}$ are independently hydrogen, deuterium, a substituted or unsubstituted C1 to C10 alkyl group, a substituted or unsubstituted C6 to C30 aryl group or a substituted or unsubstituted C2 to C30 heteroaryl group, and one of two *'s of the Chemical Formula 4 indicates a bond with the $L^1$ or $L^2$ of —N($L^1_m$R')($L^2_o$R").

When the A is —N($L^1_m$R')($L^2_o$R"), the R' is a substituent represented by the Chemical Formula 3, and the R" is a substituent represented by the Chemical Formula 4, three substituents of amine are represented by the above Chemical Formulae 1, 3 and 4.

The compound may be used to form a hole transport layer (HTL) or a hole injection layer (HIL).

More specifically, the A may be a substituent represented by the following Chemical Formula 3.

[Chemical Formula 3]

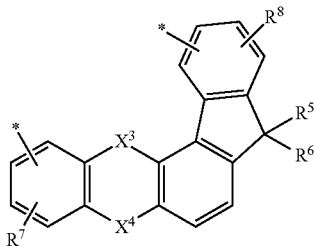

In the Chemical Formula 3, $X^3$ and $X^4$ are independently —O—, —S—, —S(O)$_2$—, —CR$^a$R$^b$—, —SiR$^a$R$^b$— or —GeR$^a$R$^b$—, wherein the R$^a$ and R$^b$ are independently hydrogen, deuterium, a substituted or unsubstituted C1 to C10 alkyl group, a substituted or unsubstituted C6 to C30 aryl group or a substituted or unsubstituted C2 to C30 heteroaryl group, R5 to R8 are independently hydrogen, deuterium, a substituted or unsubstituted C1 to C10 alkyl group, a substituted or unsubstituted C6 to C30 aryl group or a substituted or unsubstituted C2 to C30 heteroaryl group, and one of two *'s of the Chemical Formula 3 indicates a bond with the L of the Chemical Formula 2.

In this case, the compound has a structure that the above Chemical Formula 1 is selectively combined with the above Chemical Formula 3 with a linking group L between them. This compound may be prevented from crystallization due to overlapped molecules by three dimensionally changing its molecular structure. In addition, when an appropriate heteroaromatic substituent is introduced into the compound, efficiency may be increased by changing polarity distribution inside a molecule when used as a host for a phosphorescence emission layer.

The $R^1$ to $R^{12}$ may be independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof, but are not limited thereto.

More specifically, the substituted or unsubstituted phenyl group may be the following Chemical Formula S-57.

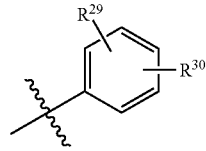

[Chemical Formula S-57]

More specifically, the substituted or unsubstituted biphenyl group may be the following Chemical Formulae S-58, S-59 and S-60.

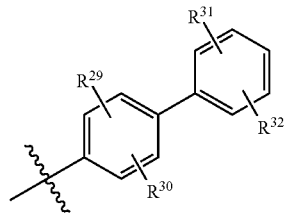

[Chemical Formula S-58]

[Chemical Formula S-59]

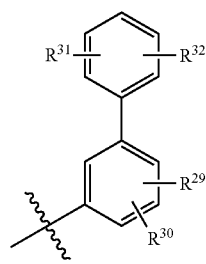

[Chemical Formula S-60]

More specifically, the substituted or unsubstituted naphthyl group may be the following Chemical Formulae S-61 and S-62.

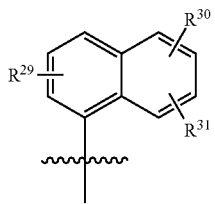

[Chemical Formula S-61]

[Chemical Formula S-62]

More specifically, the substituted or unsubstituted anthracenyl group may be the following Chemical Formulae S-63 and S-64.

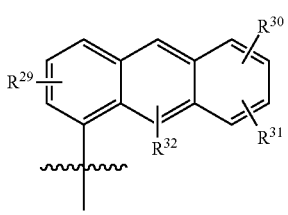

[Chemical Formula S-63]

[Chemical Formula S-64]

More specifically, the substituted or unsubstituted phenanthrenyl group may be the following Chemical Formulae S-65, S-66, S-67, S-68 and S-69.

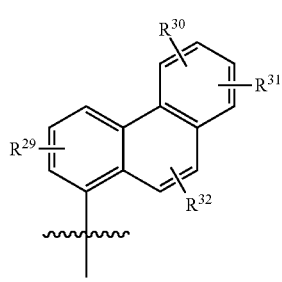

[Chemical Formula S-65]

[Chemical Formula S-66]

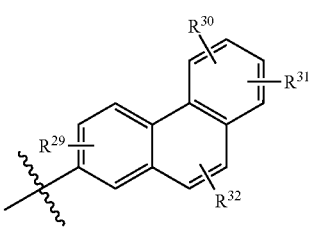

[Chemical Formula S-67]

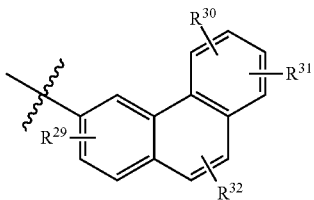

[Chemical Formula S-68]

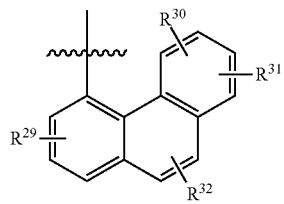

[Chemical Formula S-69]

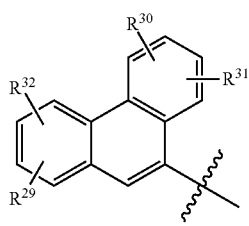

More specifically, the substituted or unsubstituted triphenyl group may be the following Chemical Formulae S-70 and S-71.

[Chemical Formula S-70]

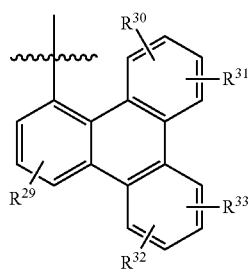

[Chemical Formula S-71]

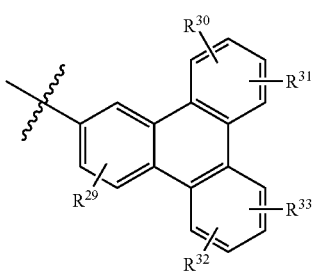

More specifically, the substituted or unsubstituted fluorenyl group may be the following Chemical Formulae S-72, S-73, S-74 and S-75.

[Chemical Formula S-72]

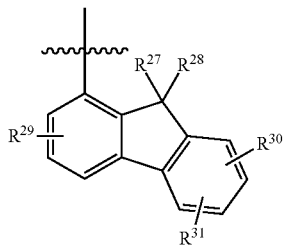

[Chemical Formula S-73]

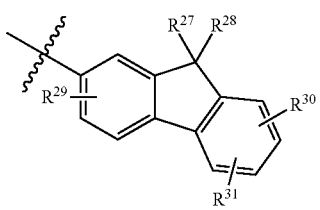

[Chemical Formula S-74]

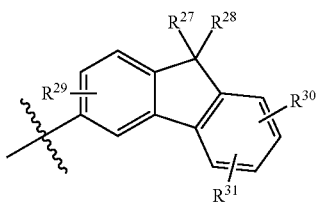

[Chemical Formula S-75]

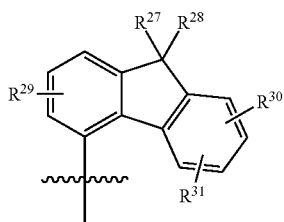

This may be applied to all the above Chemical Formulae 1 to 4.

The compound for an organic optoelectronic device may have light emission, hole or electron characteristics; film stability; thermal stability and high triplet exciton energy (T1) due to the substituents.

More specifically, the compound for an organic optoelectronic device may be represented by one of the following Chemical Formulae A-1 to A-183, but is not limited thereto.

[A-1]
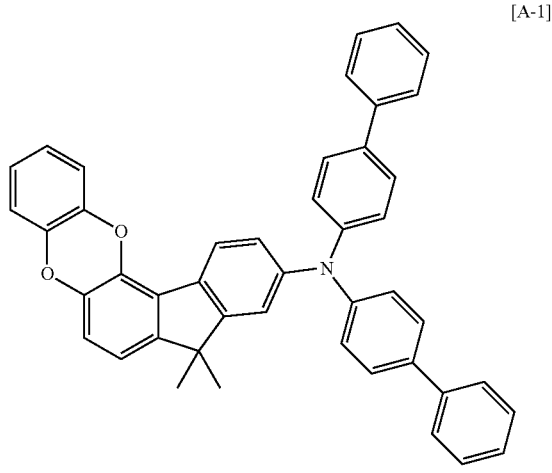
[A-4]
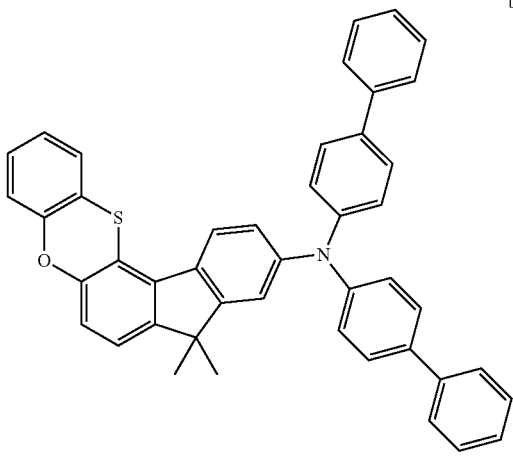
[A-2]
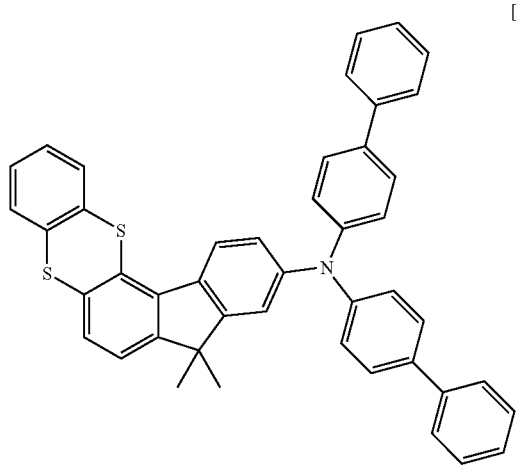
[A-5]
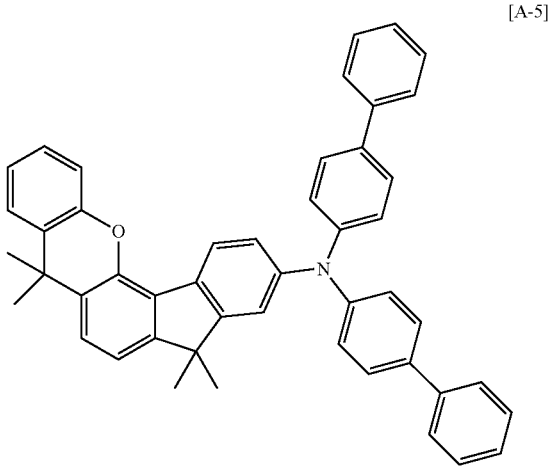
[A-3]
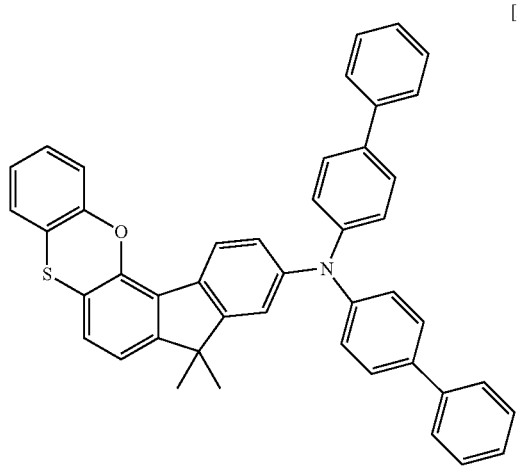
[A-6]
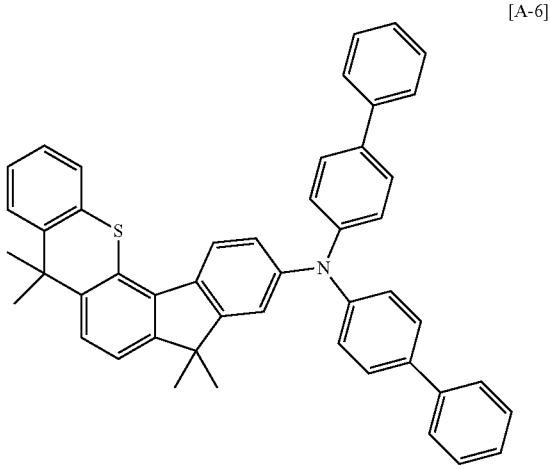

[A-7]
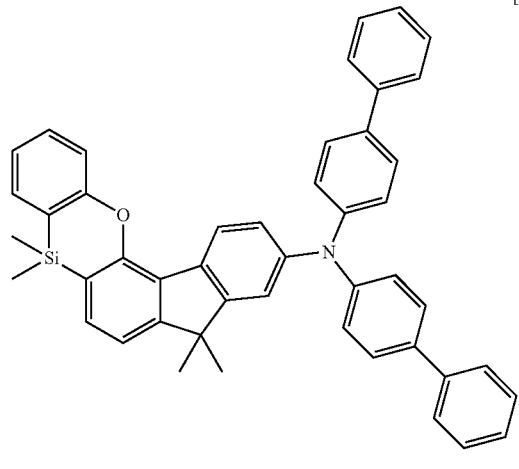
[A-10]
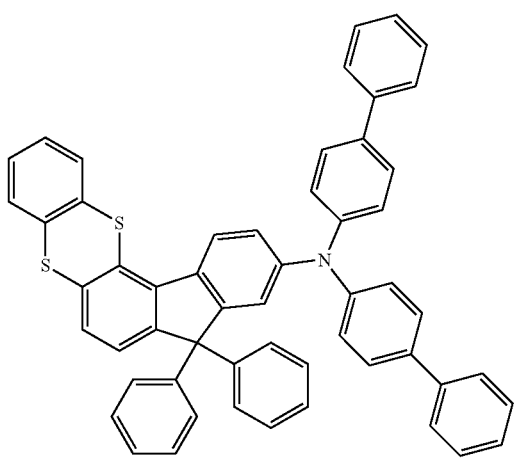
[A-8]
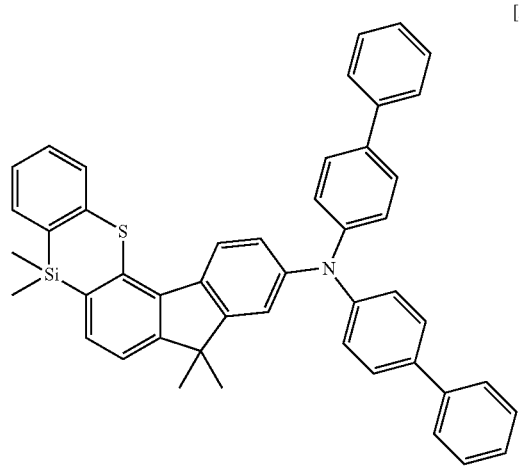
[A-11]
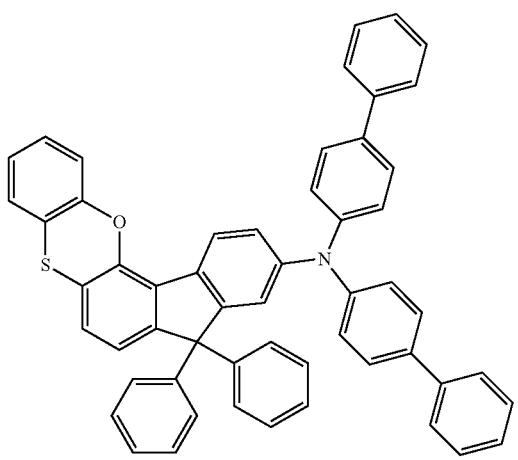
[A-9]
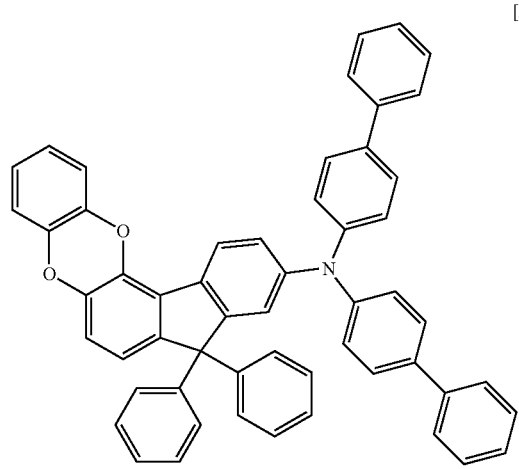
[A-12]
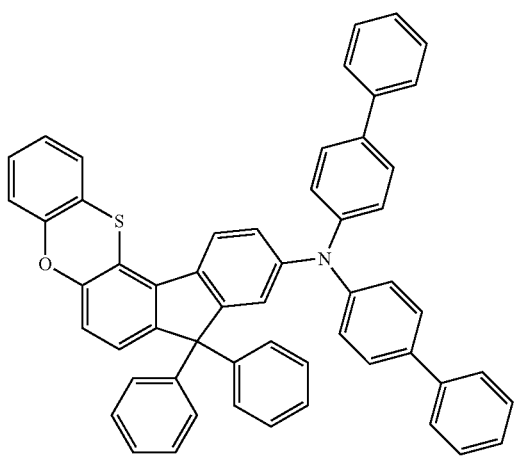

[A-13]
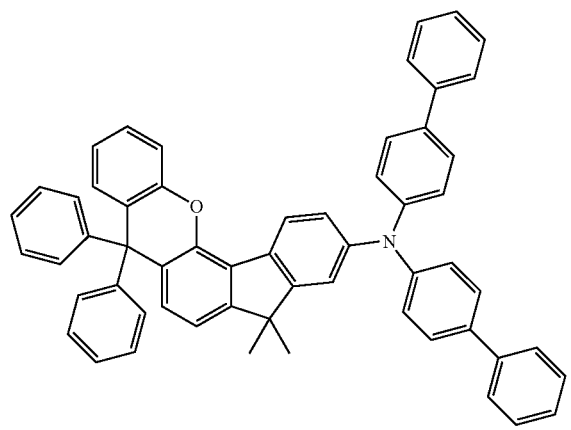
[A-14]
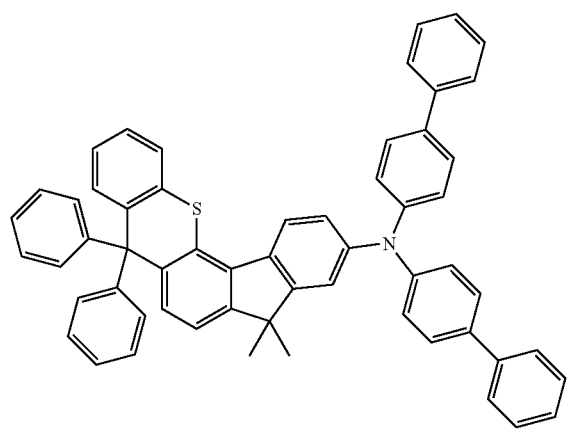
[A-15]
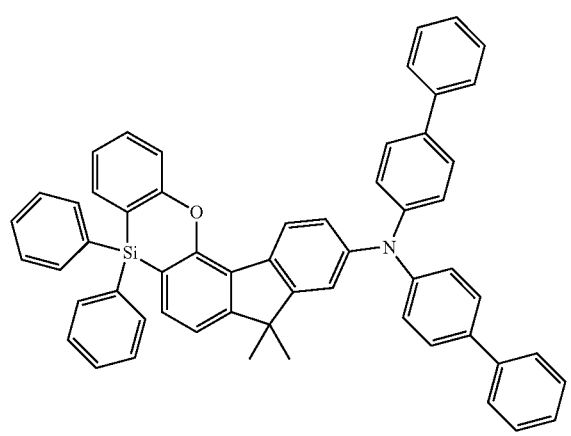
[A-16]
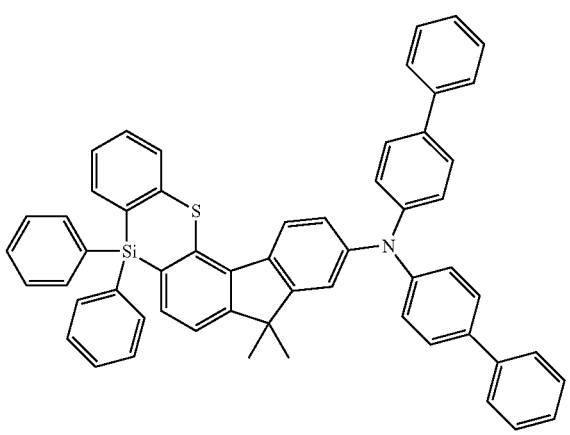
[A-17]
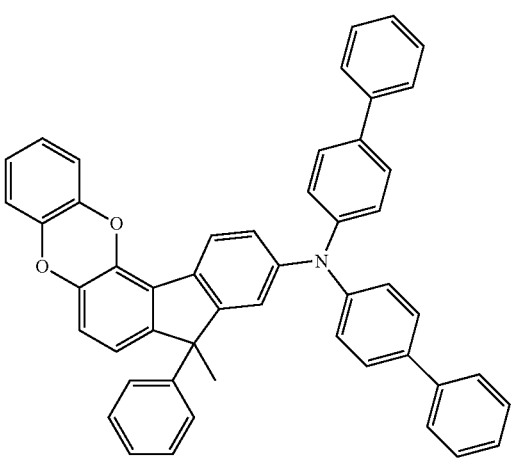
[A-18]
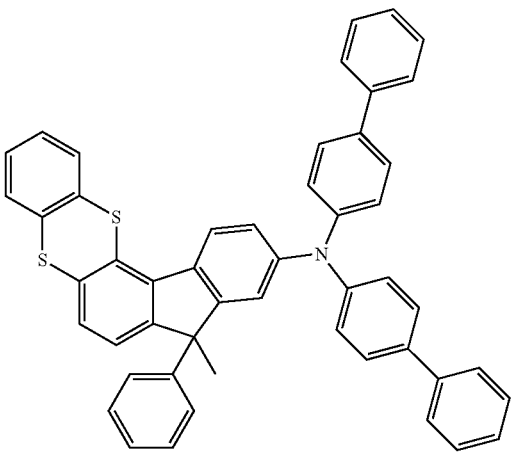

[A-19]
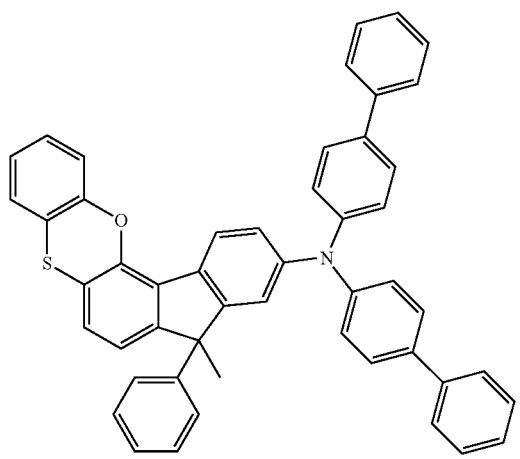
[A-22]
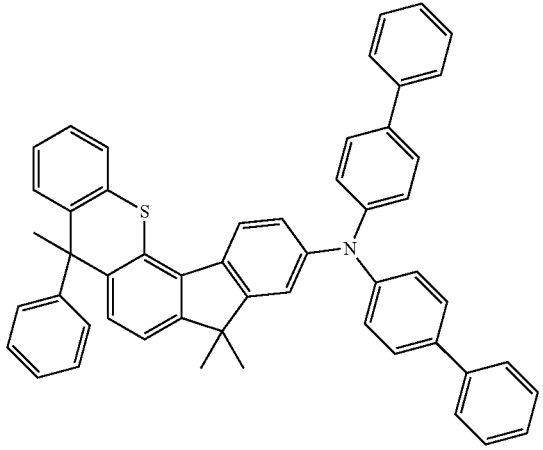
[A-20]
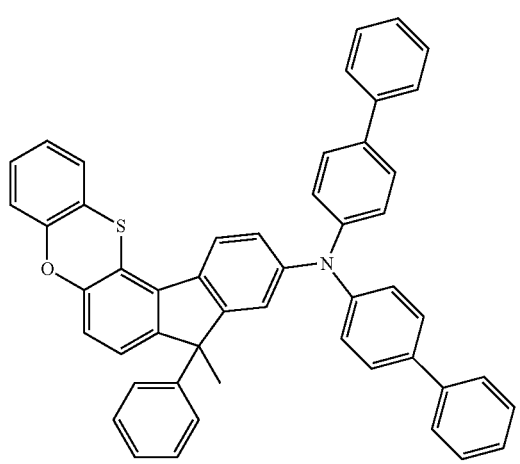
[A-23]
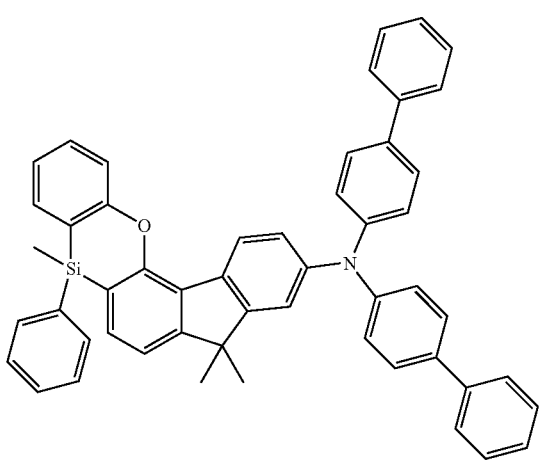
[A-21]
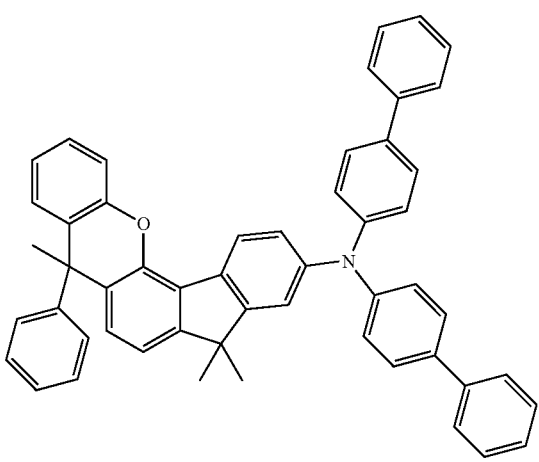
[A-24]
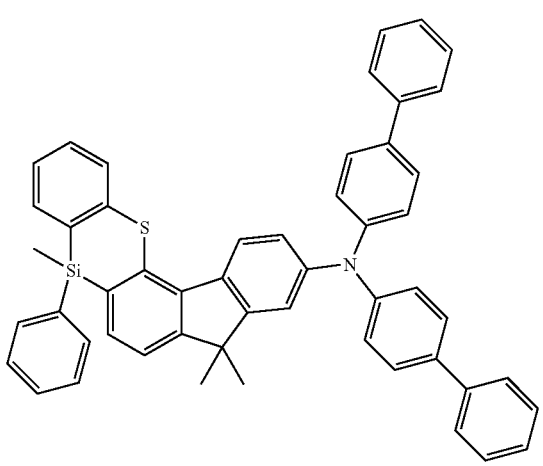

[A-25]
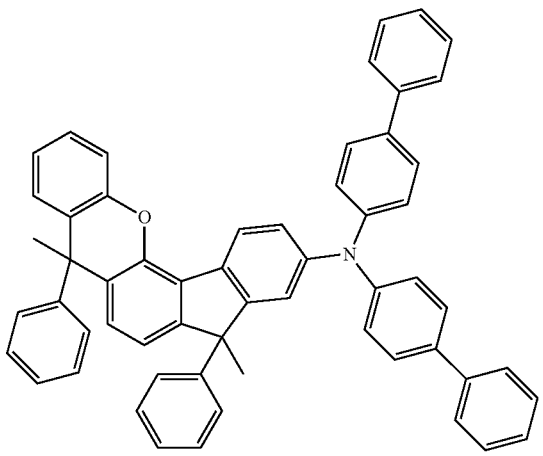
[A-28]
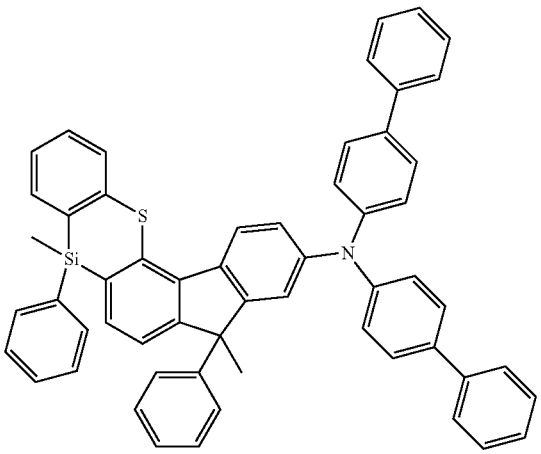
[A-26]
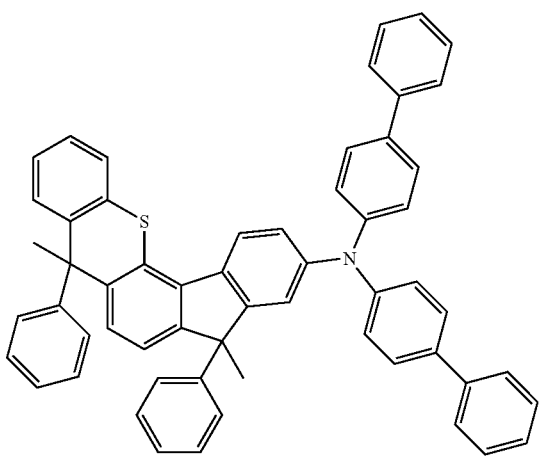
[A-29]
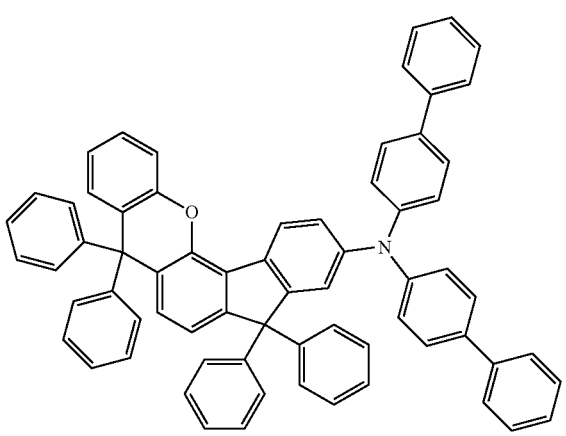
[A-27]
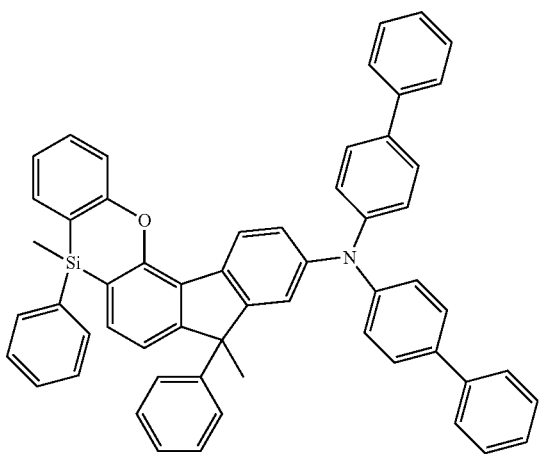
[A-30]
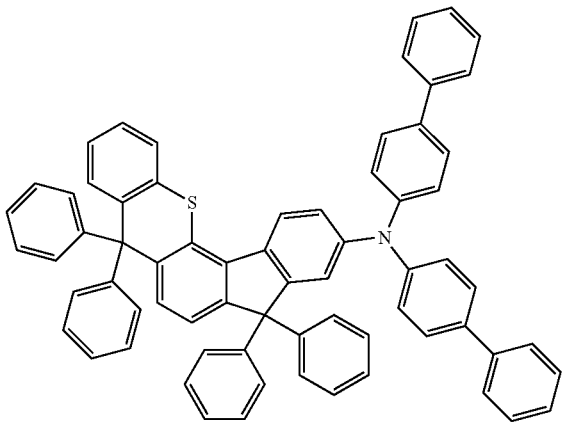

[A-31]
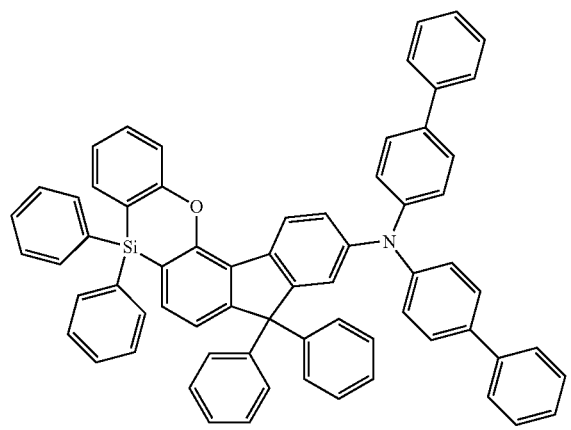
[A-32]
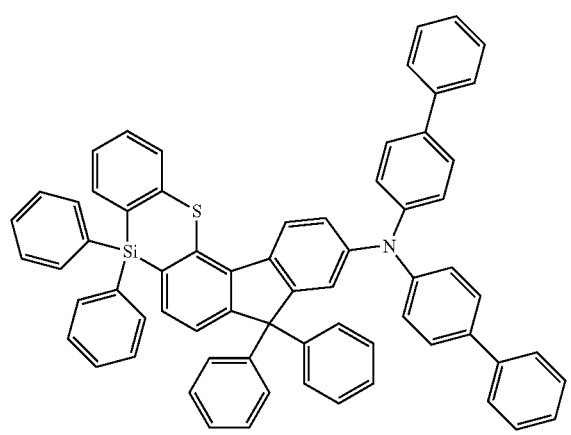
[A-33]
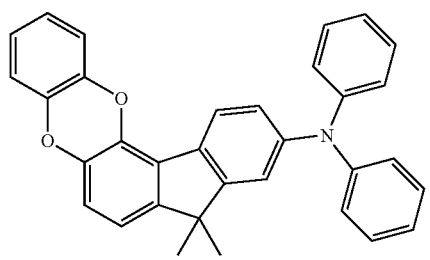
[A-34]
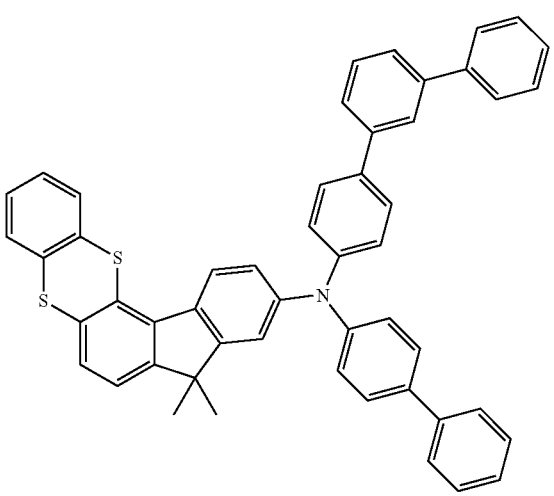
[A-35]
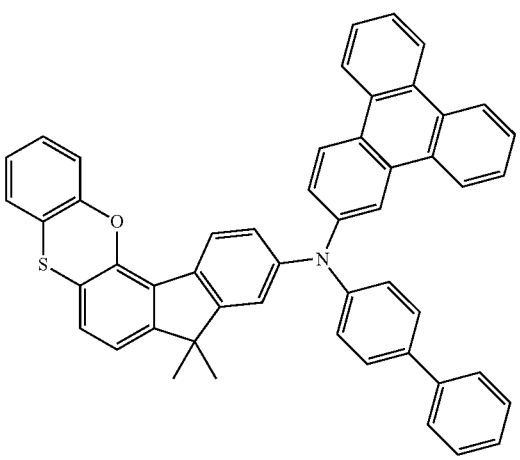
[A-36]
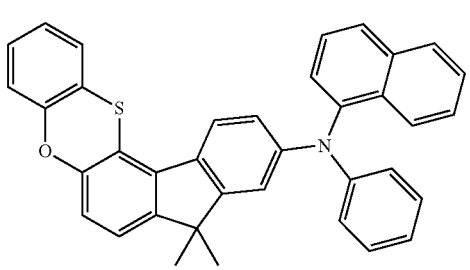
[A-37]
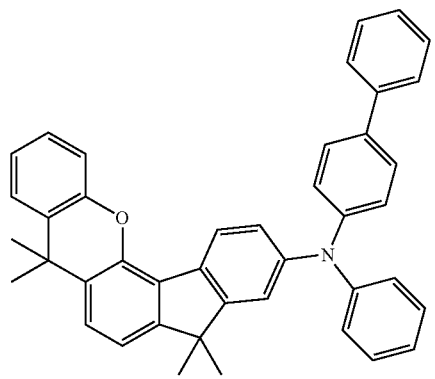

[A-38]
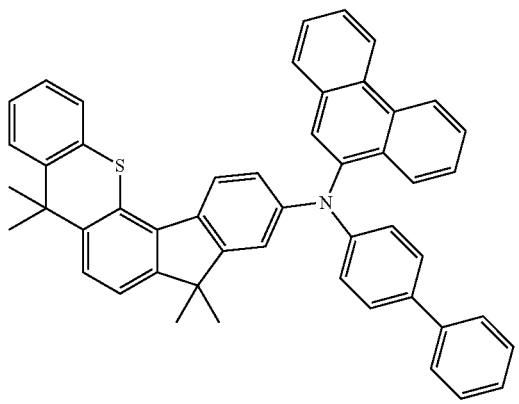
[A-39]
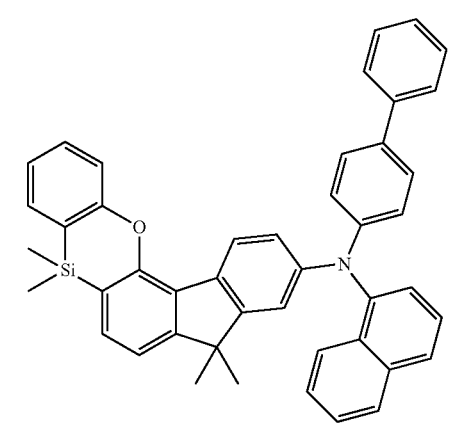
[A-40]
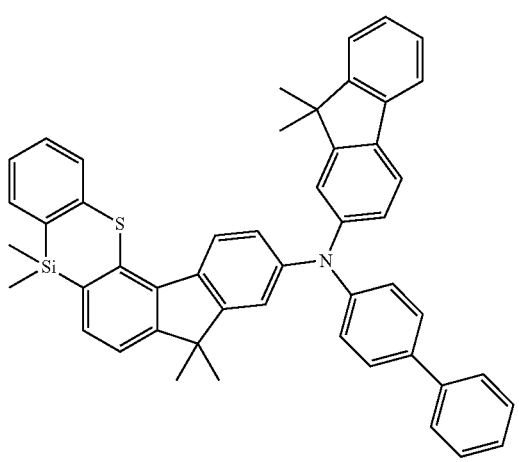
[A-41]
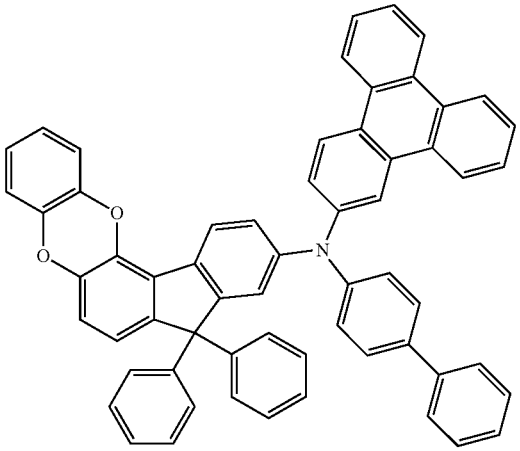
[A-42]
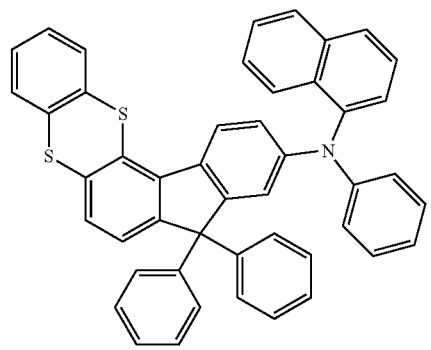
[A-43]
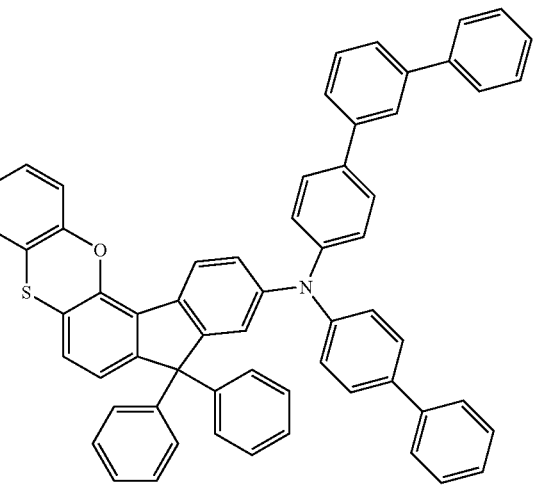
[A-44]
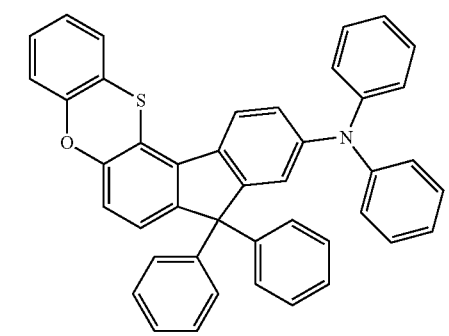

-continued
[A-45]
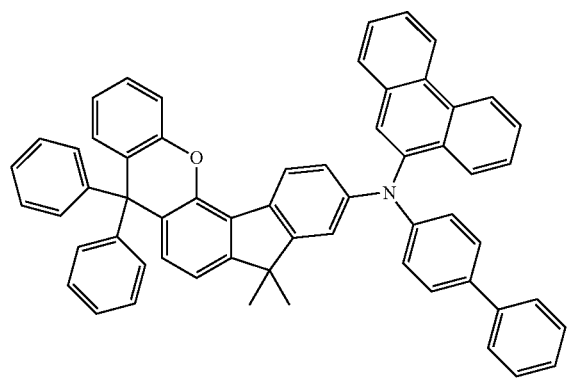
[A-46]
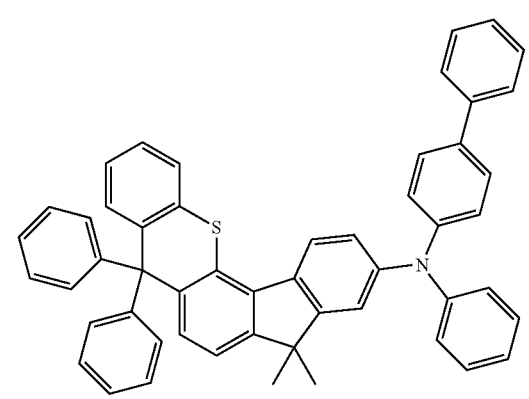
[A-47]
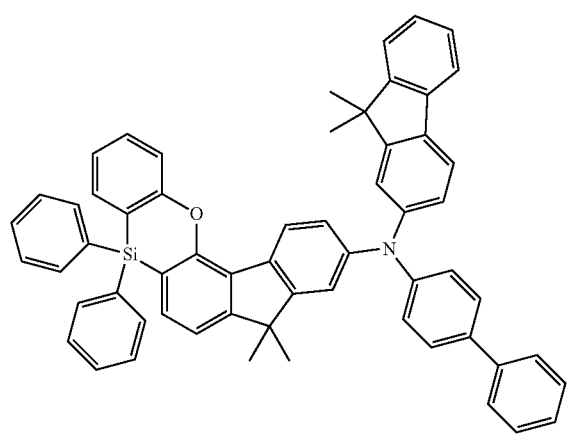
[A-48]
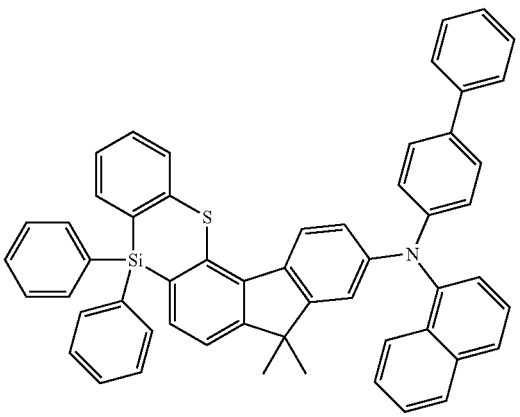
[A-49]
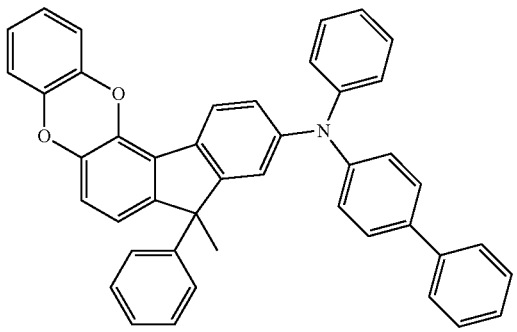
[A-50]
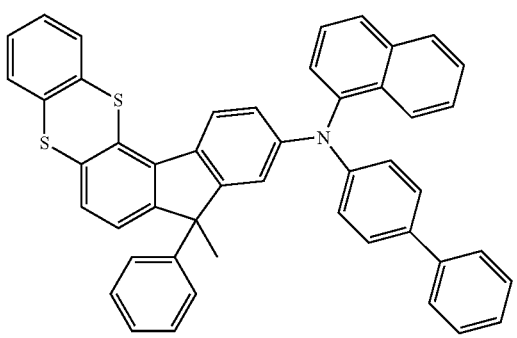
[A-51]
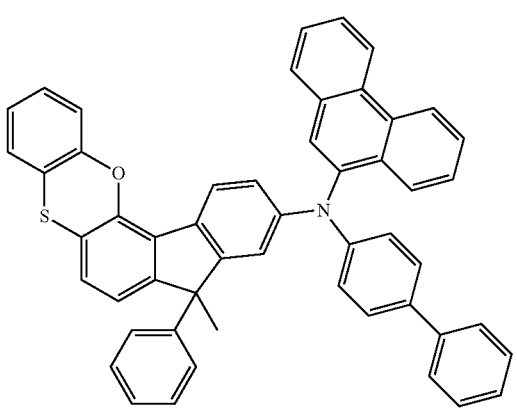

[A-52]
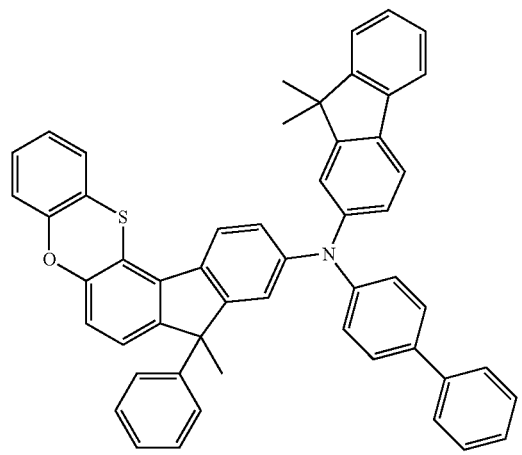
[A-53]
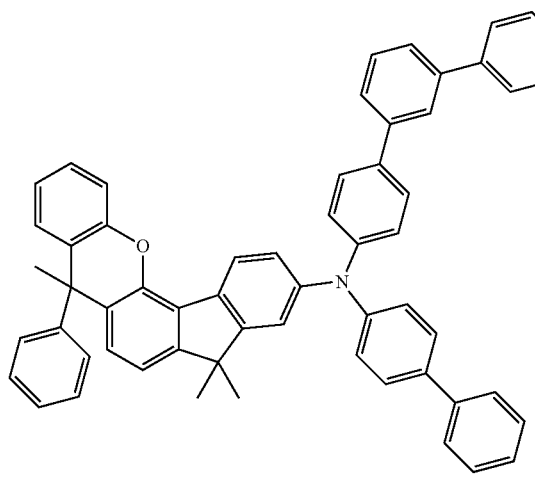
[A-54]
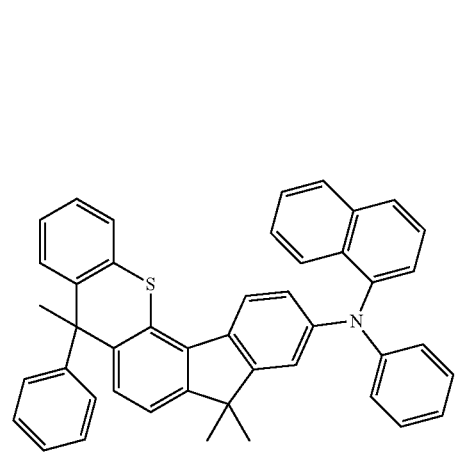
[A-55]
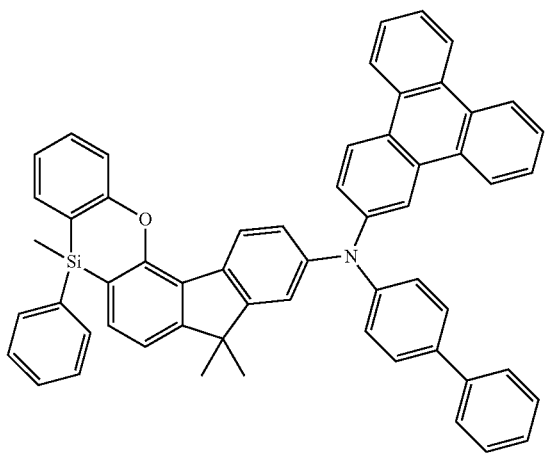
[A-56]
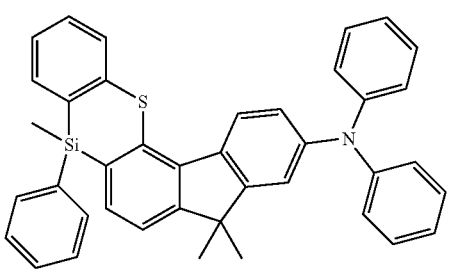
[A-57]
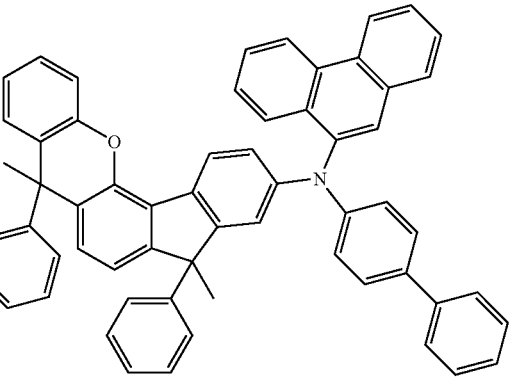
[A-58]
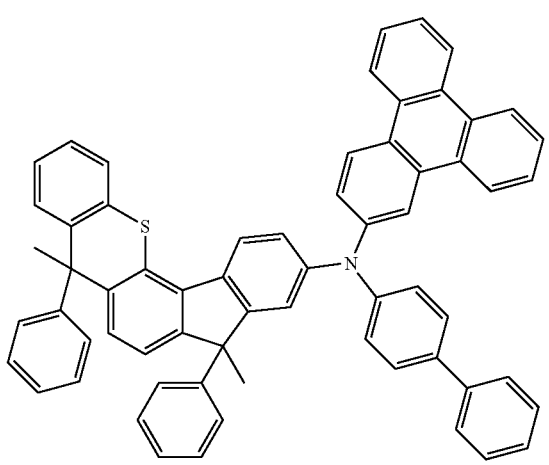

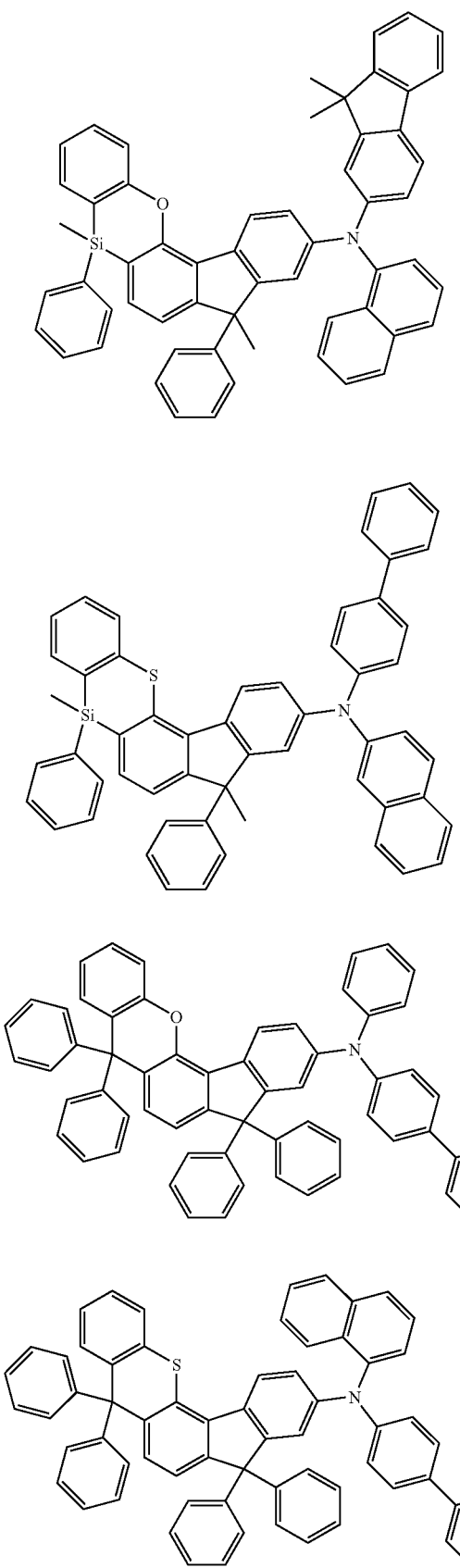
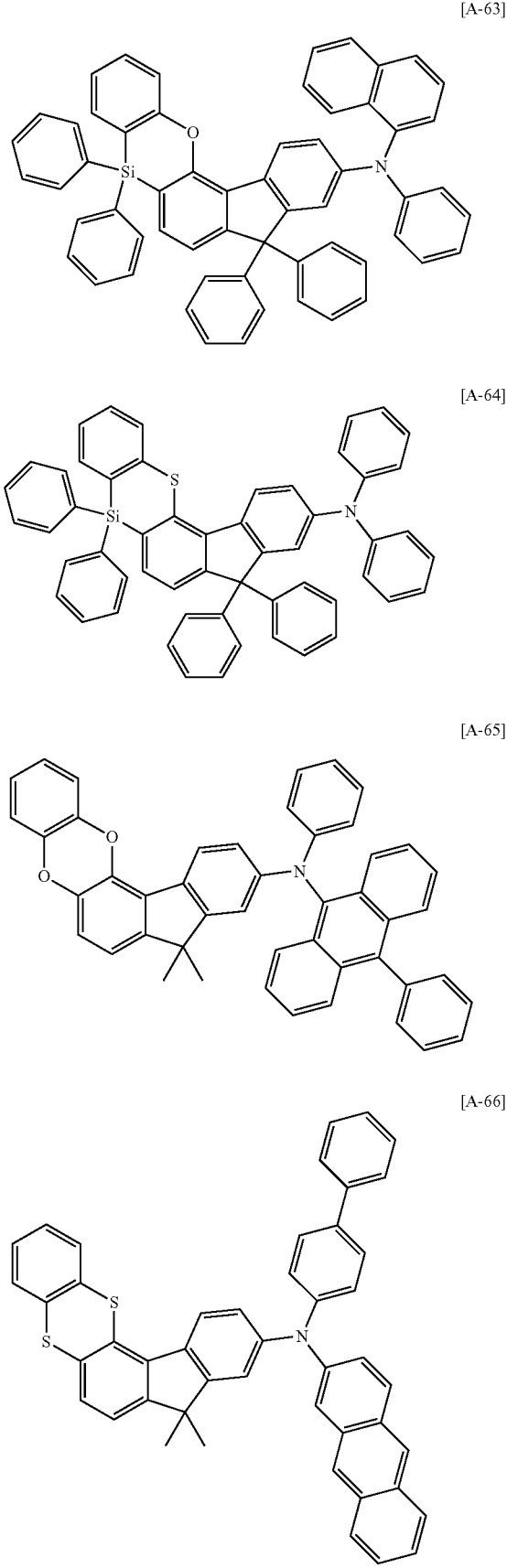

[A-67]
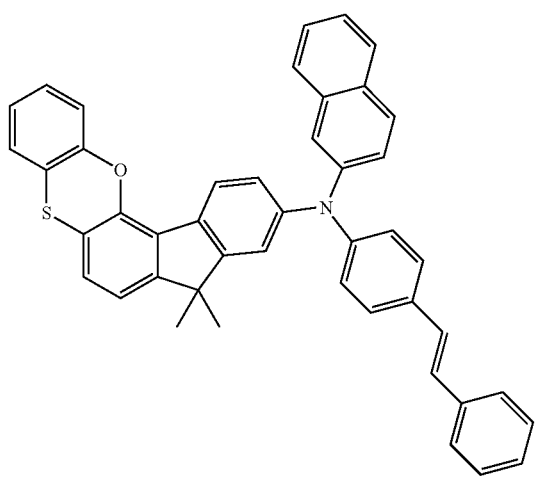
[A-68]
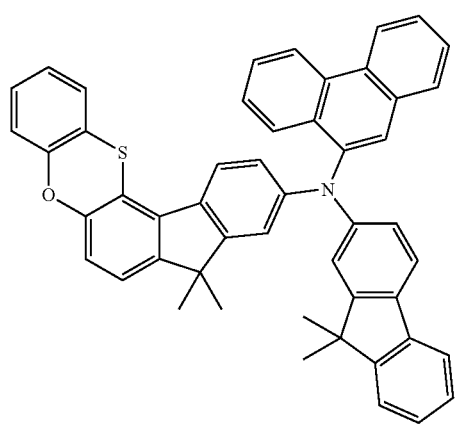
[A-69]
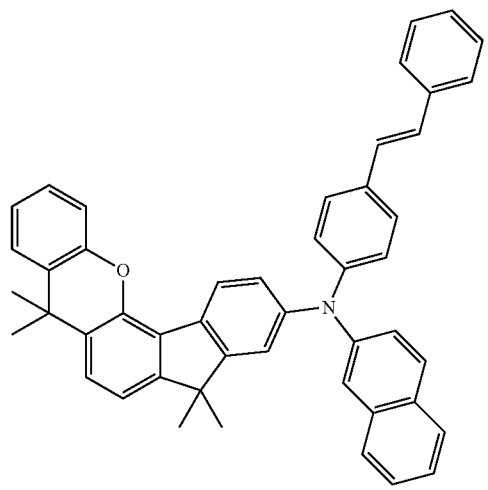
[A-70]
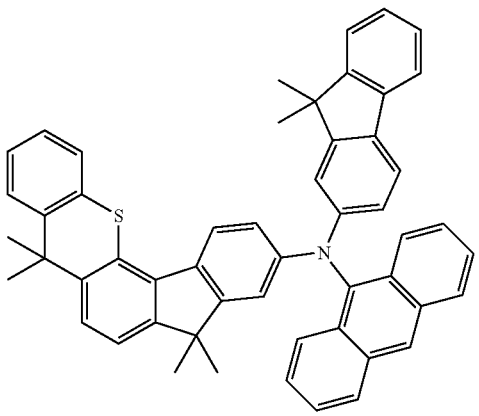
[A-71]
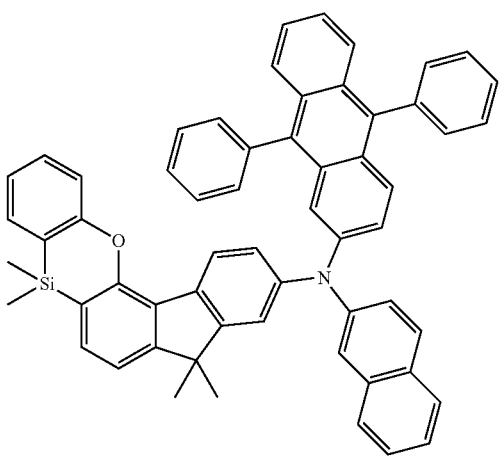
[A-72]
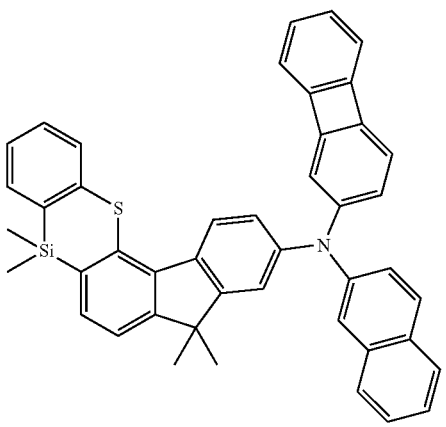

[A-73]
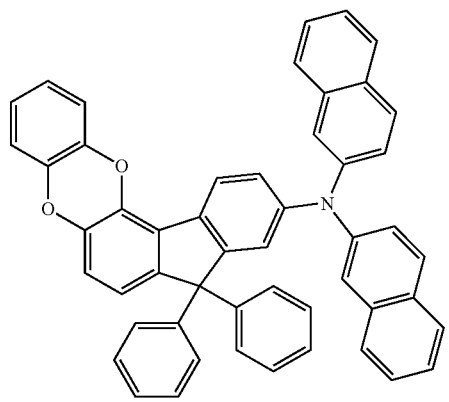
[A-79]
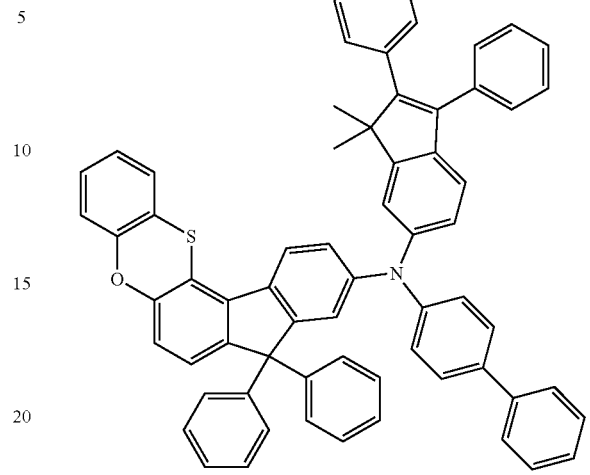
[A-74]
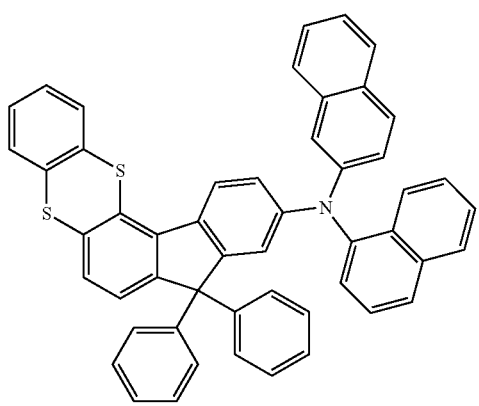
[A-80]
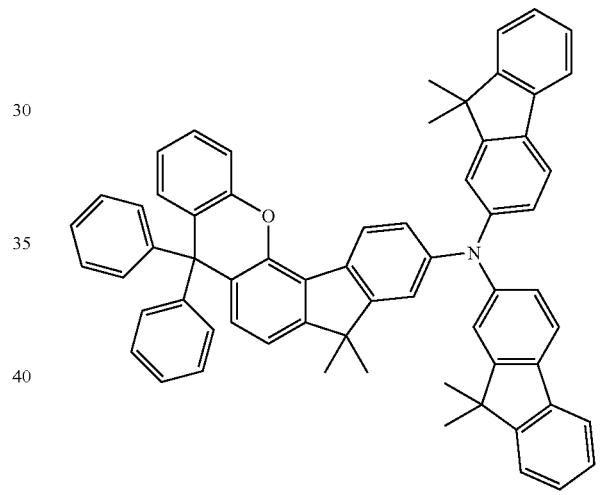
[A-78]
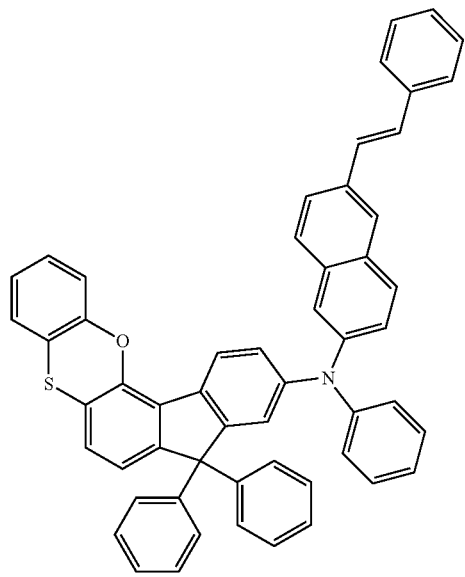
[A-81]
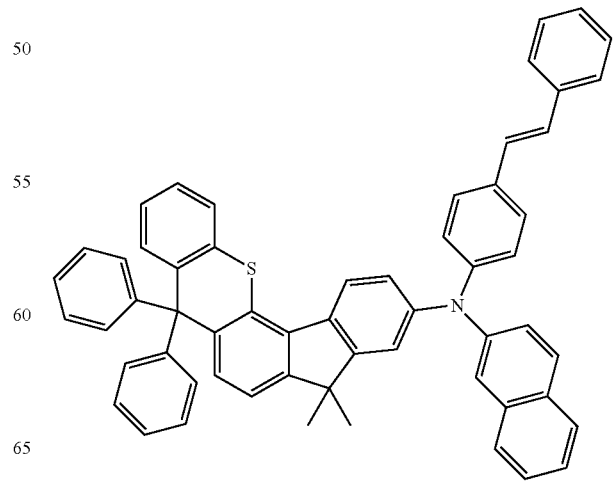

[A-82]
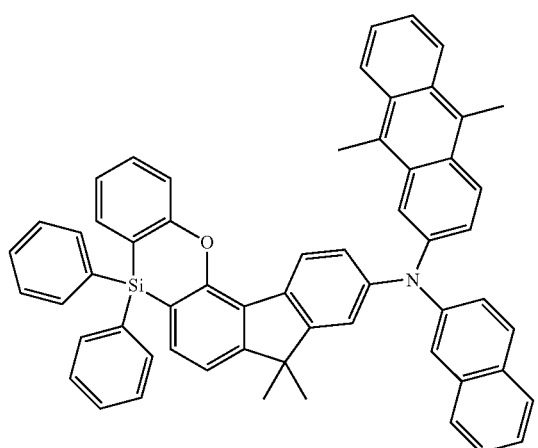
[A-83]
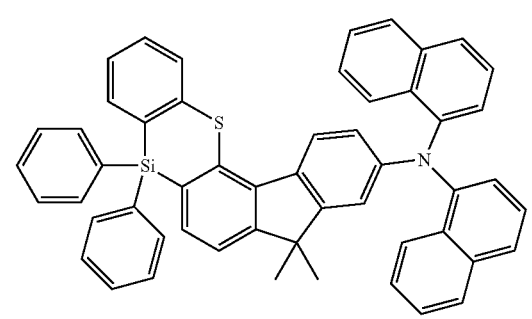
[A-84]
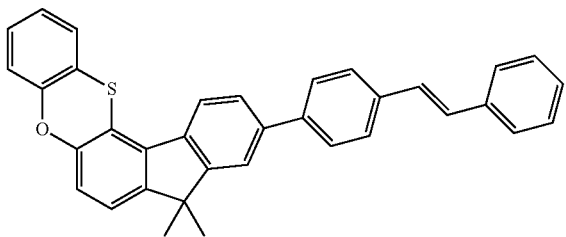
[A-85]
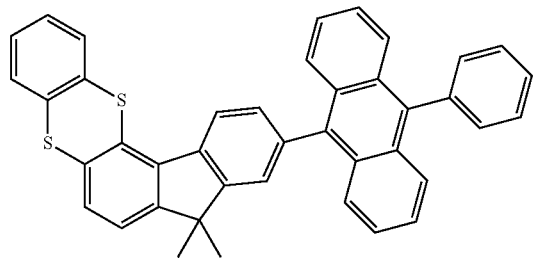
[A-86]
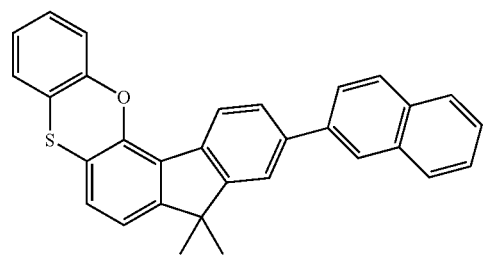
[A-87]
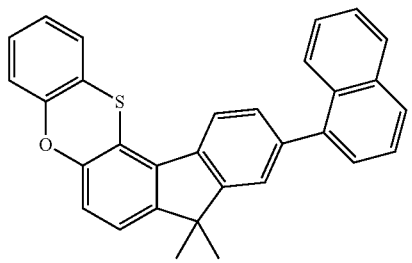
[A-88]
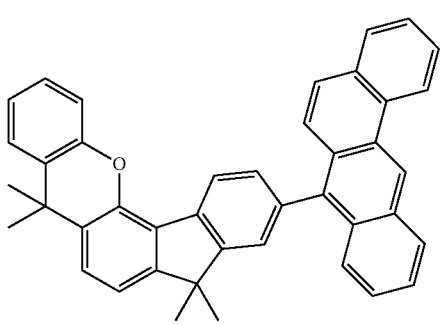
[A-89]
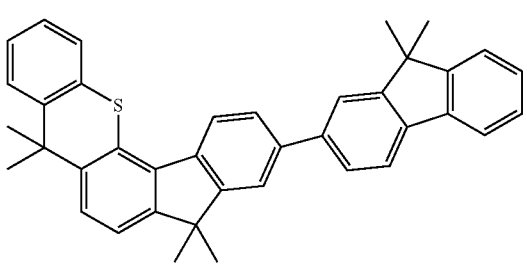
[A-90]
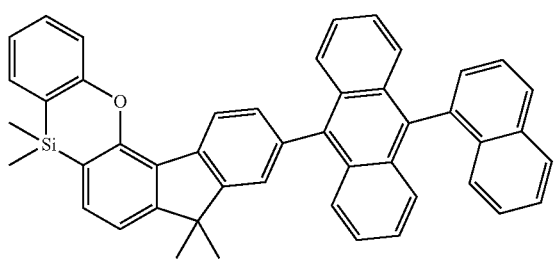
[A-91]
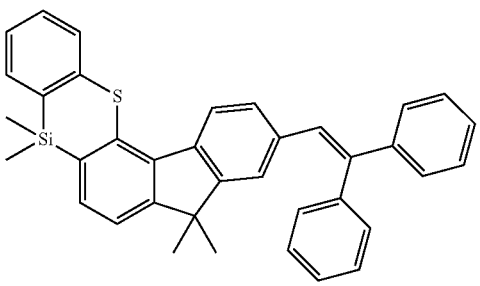

-continued
[A-92]
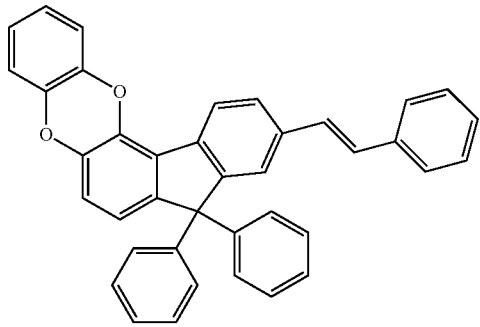
[A-93]
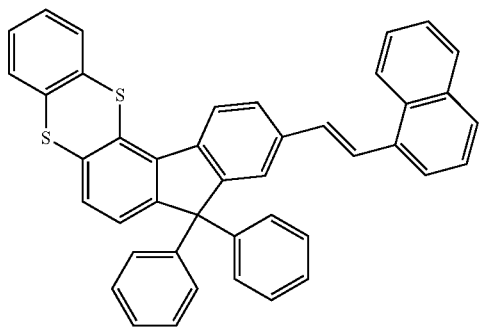
[A-94]
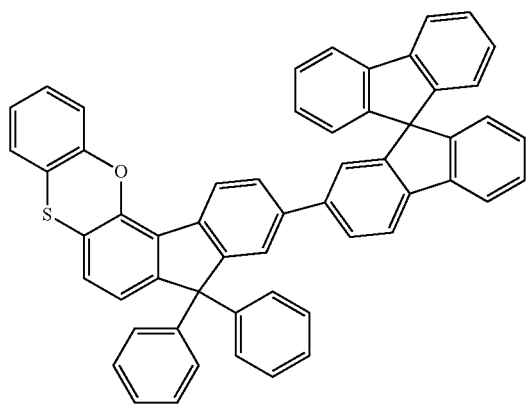
[A-95]
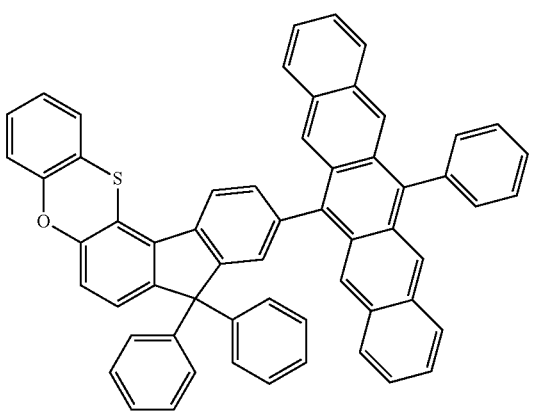
-continued
[A-96]
[A-97]
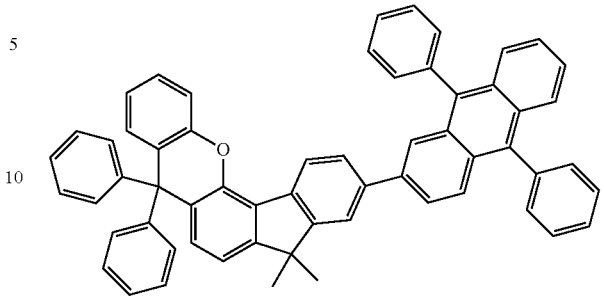
[A-98]
[A-99]
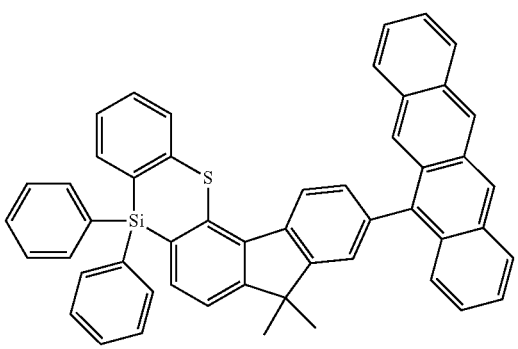

[A-100]
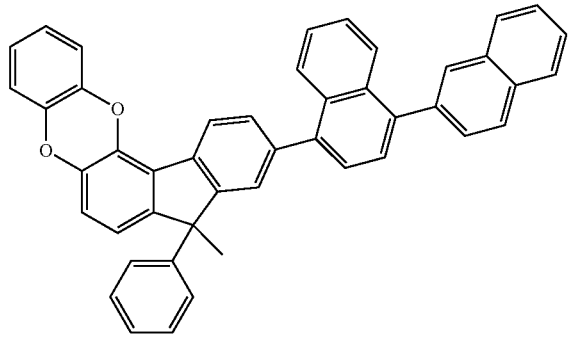
[A-101]
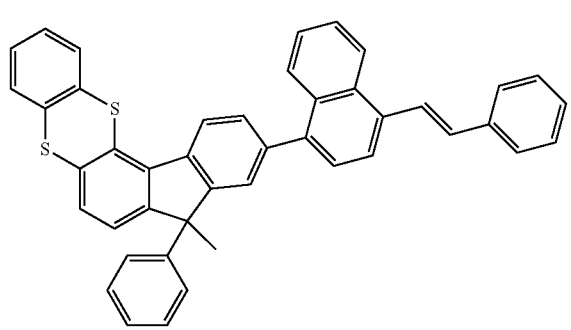
[A-102]
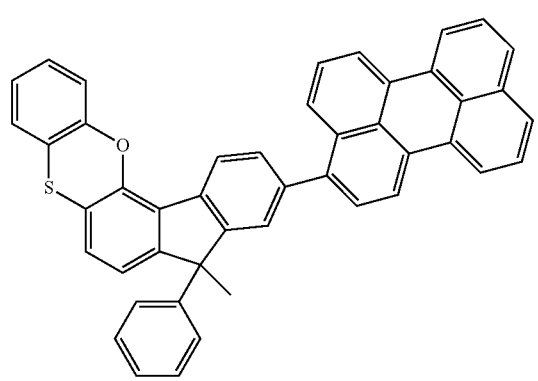
[A-103]
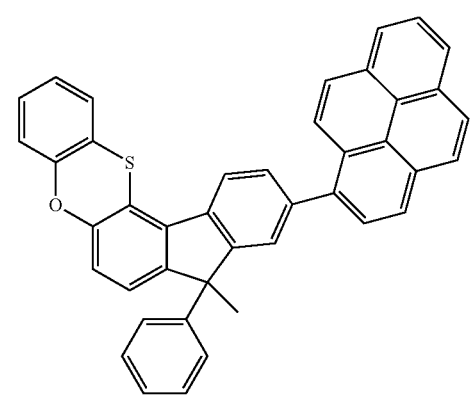
[A-104]
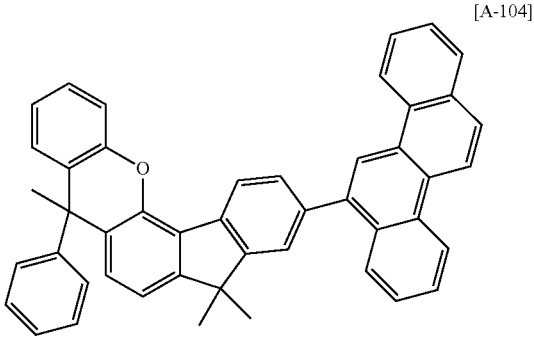
[A-105]
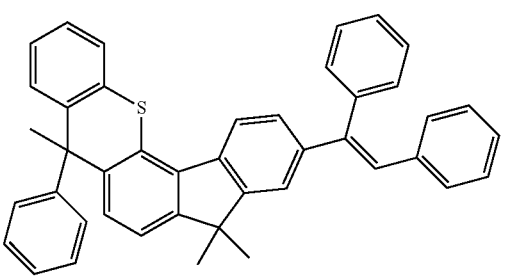
[A-106]
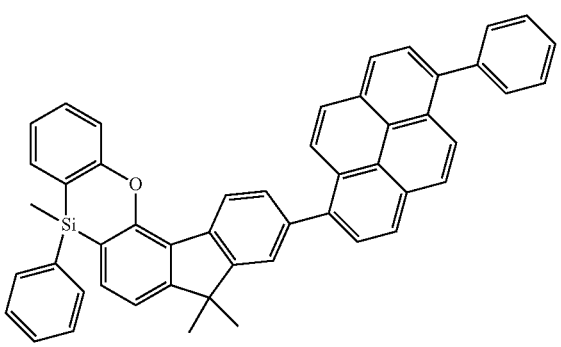
[A-107]
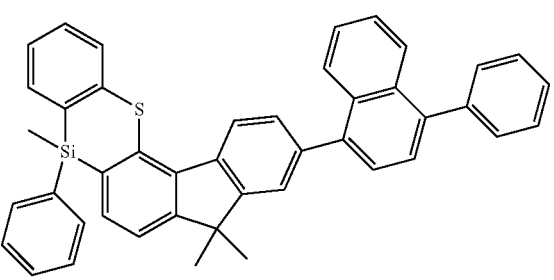
[A-108]
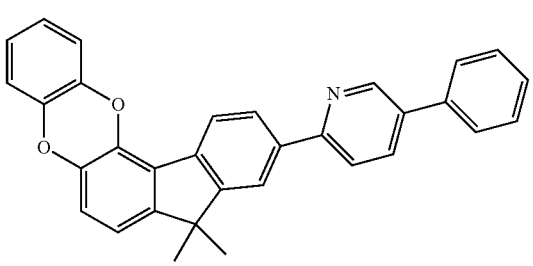

[A-109]
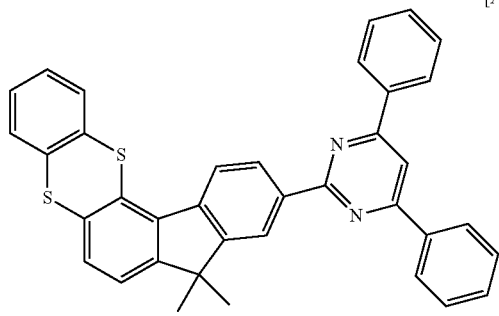
[A-114]
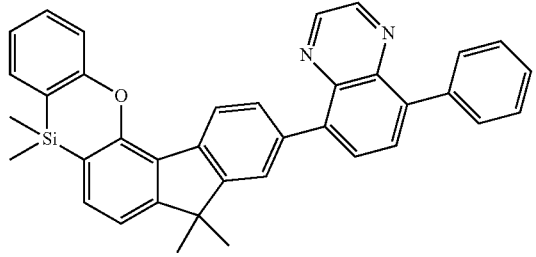
[A-110]
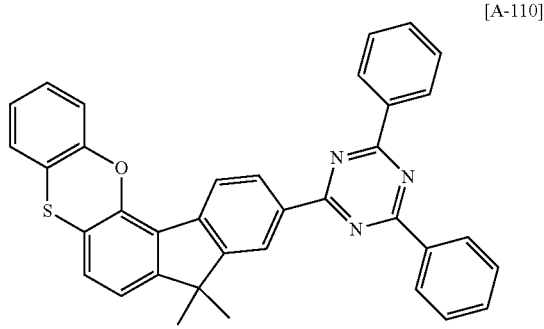
[A-115]
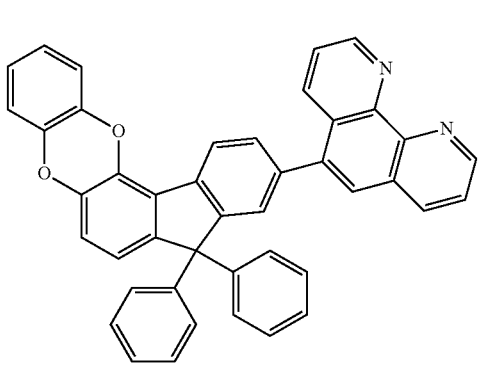
[A-111]
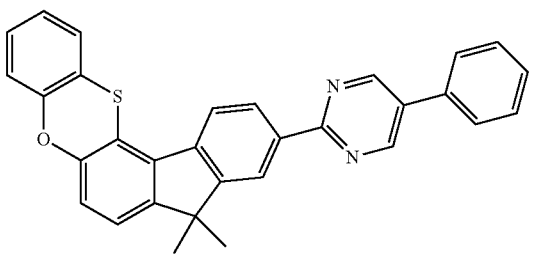
[A-116]
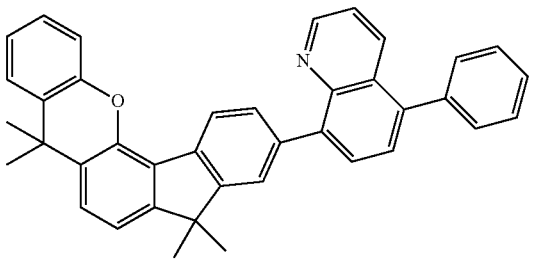
[A-112]
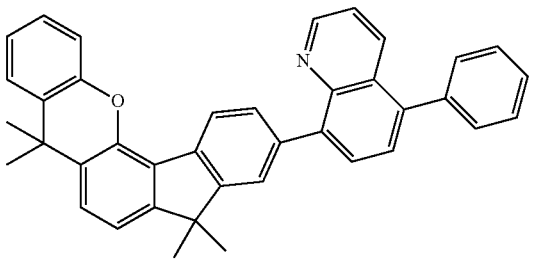
[A-117]
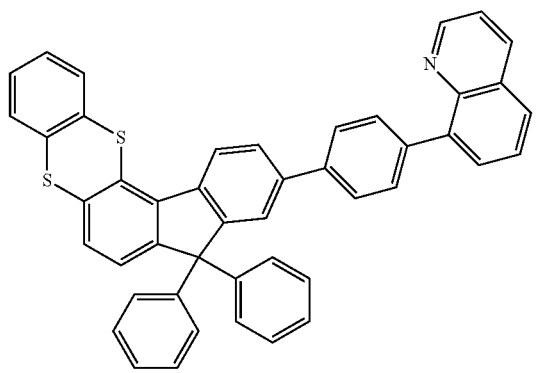
[A-113]
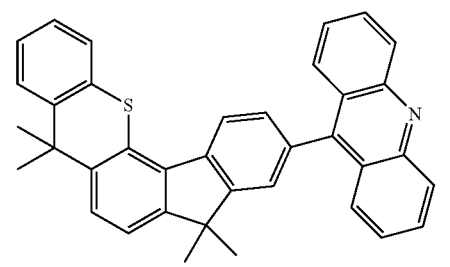

-continued
[A-118]
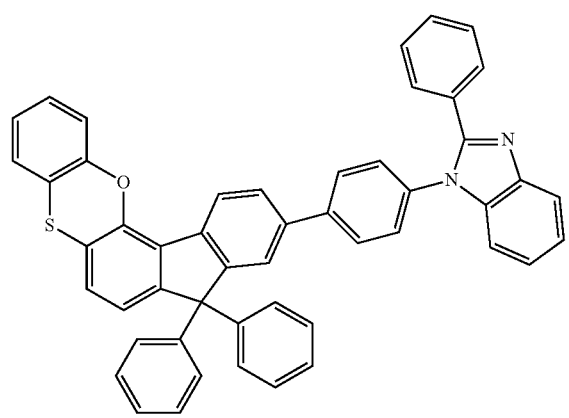
[A-119]
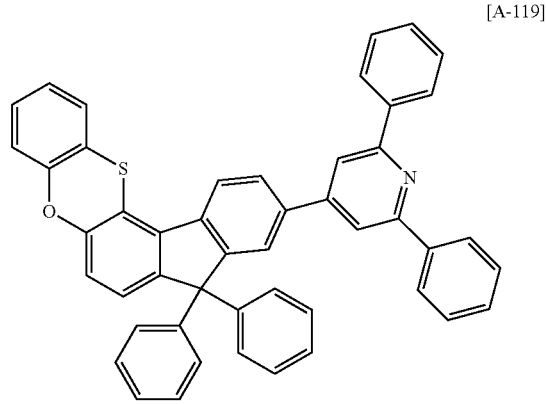
[A-120]
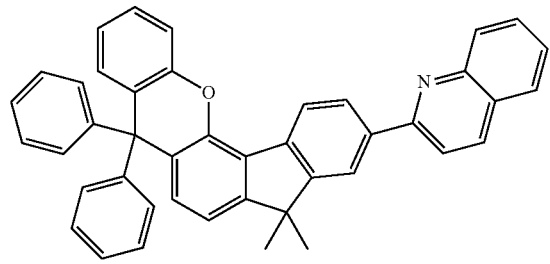
[A-121]
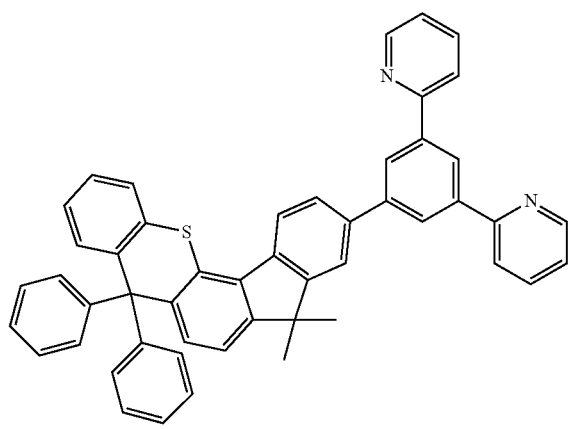
[A-122]
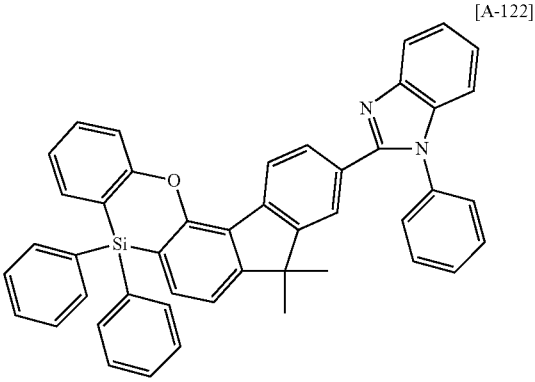
[A-123]
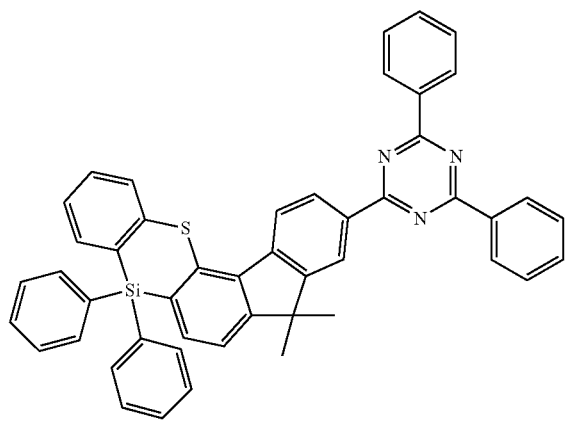
[A-124]
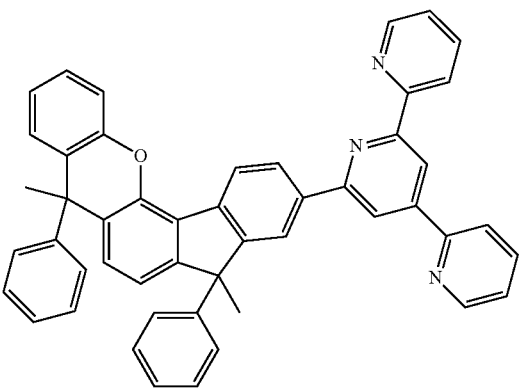
[A-125]
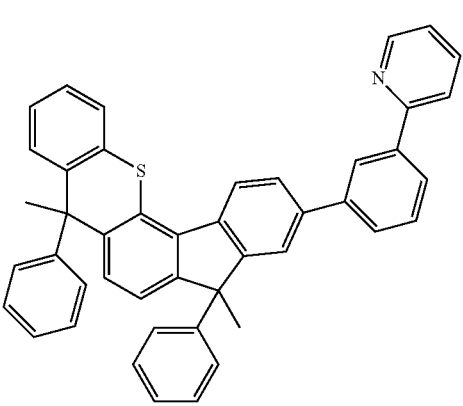

[A-126]
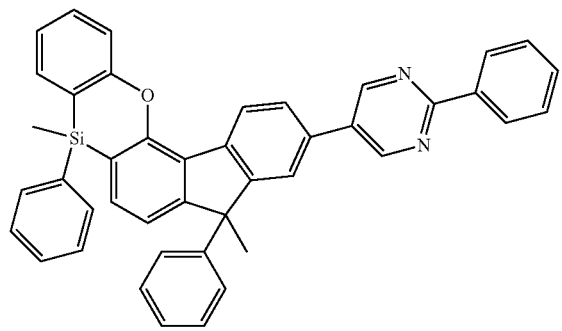
[A-130]
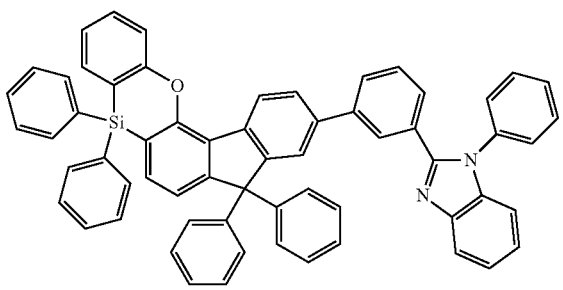
[A-127]
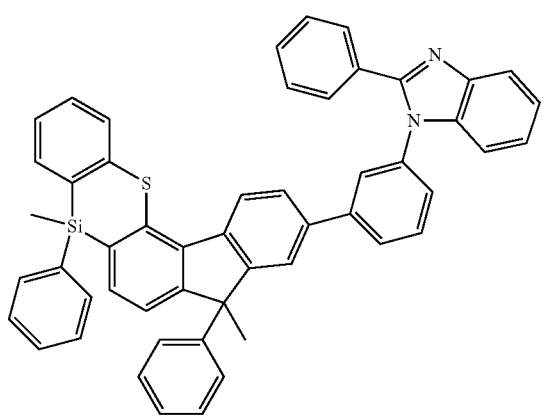
[A-131]
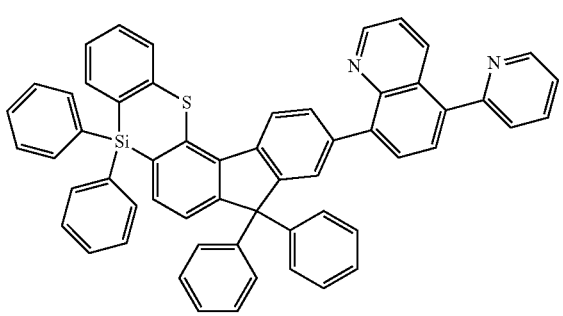
[A-132]
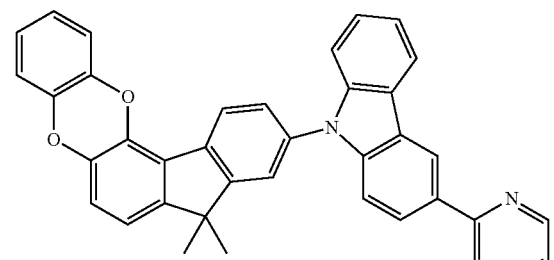
[A-128]
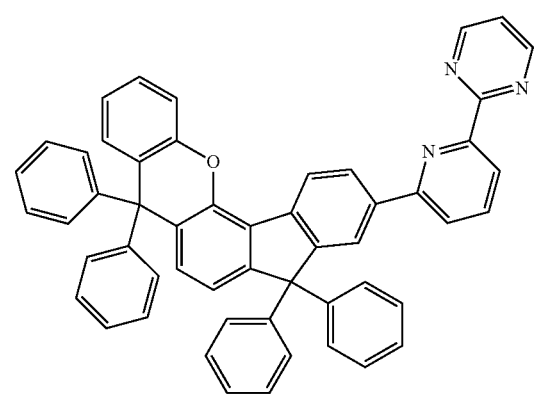
[A-133]
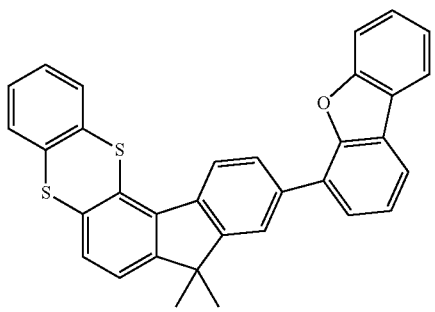
[A-129]
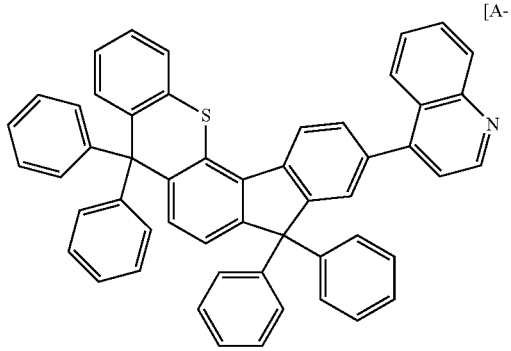
[A-134]
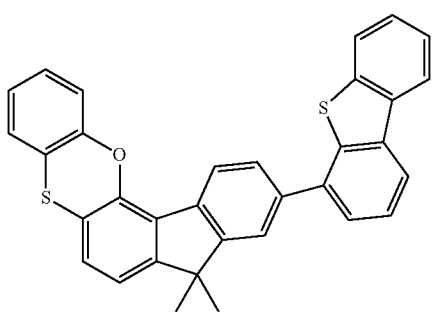

[A-135]
[A-136]
[A-137]
[A-138]
[A-139]
[A-140]
[A-141]
[A-142]

[A-143]
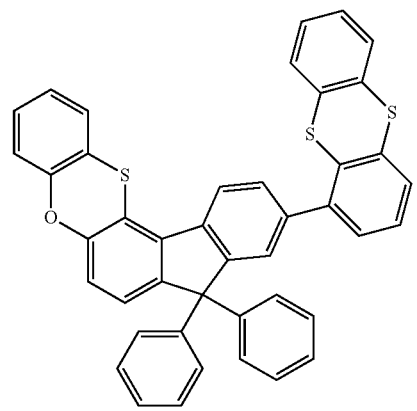
[A-147]
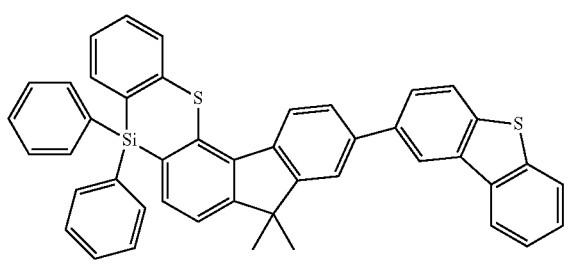
[A-144]
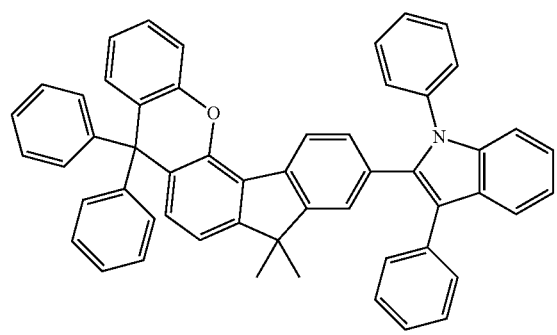
[A-148]
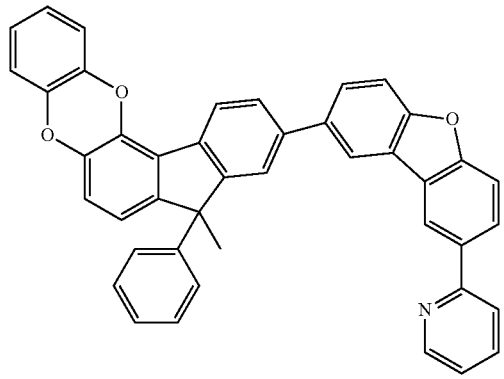
[A-145]
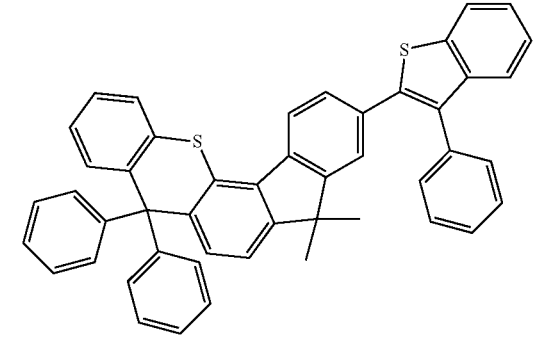
[A-149]
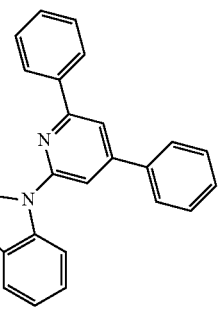
[A-146]
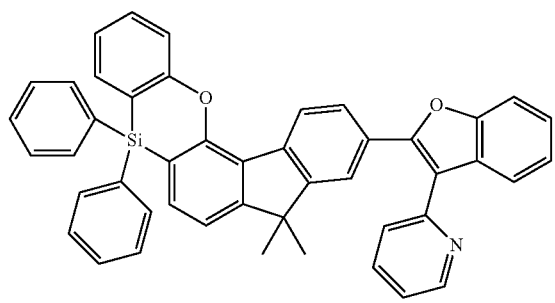
[A-150]
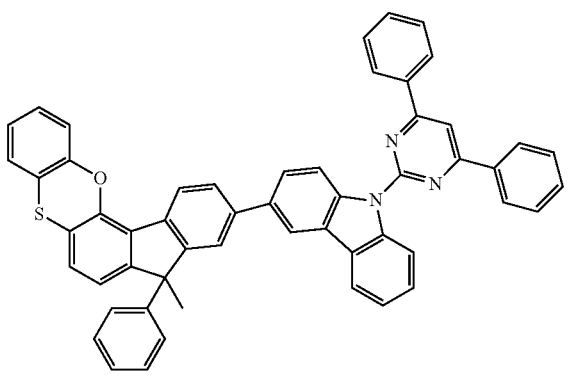

[A-151]
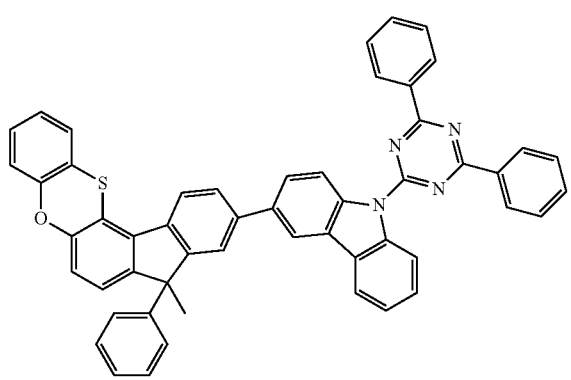
[A-156]
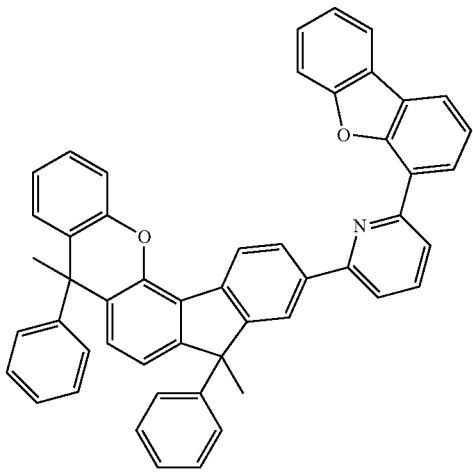
[A-152]
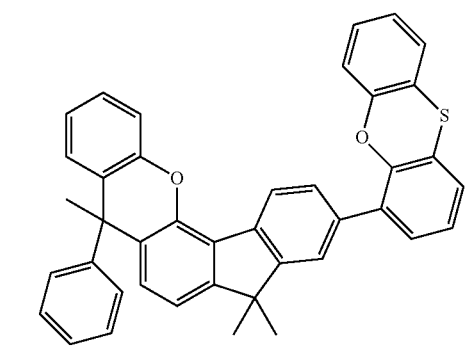
[A-157]
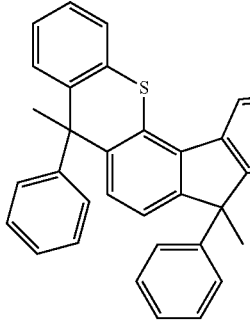
[A-153]
[A-158]
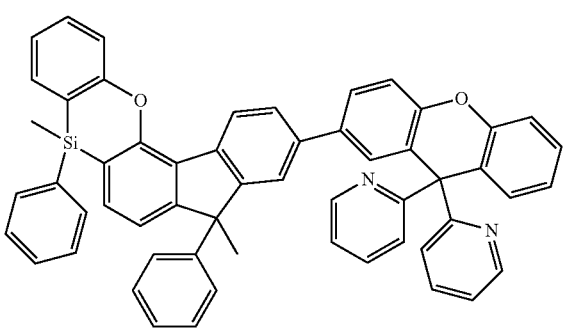
[A-154]
[A-155]
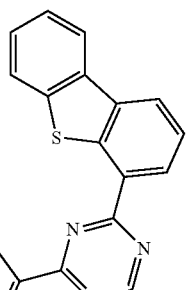
[A-159]
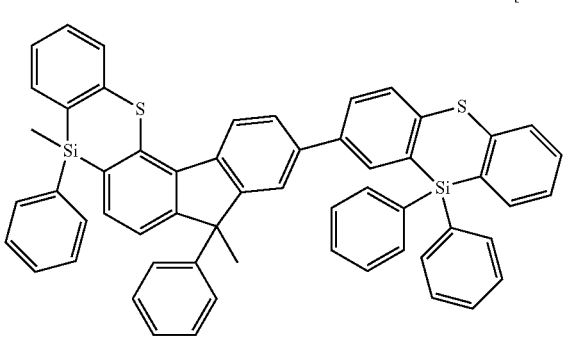

[A-160]
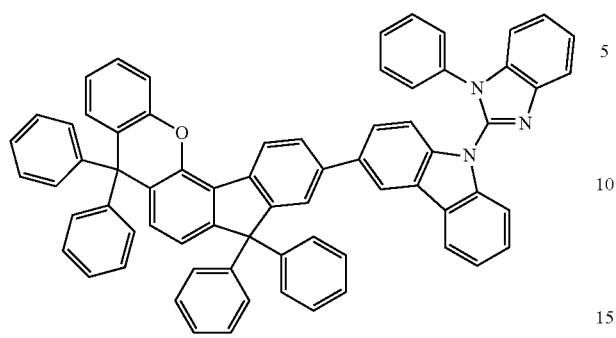
[A-164]
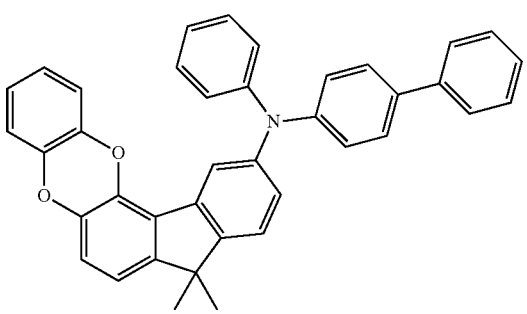
[A-161]
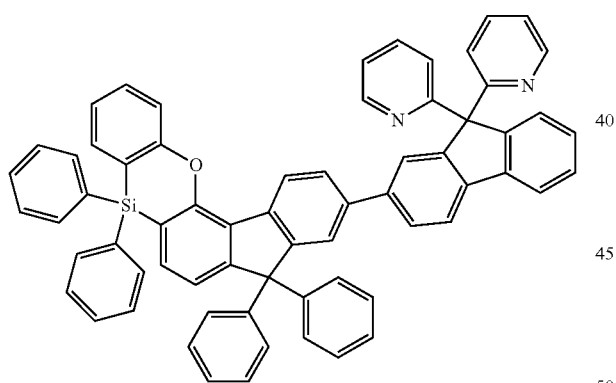
[A-165]
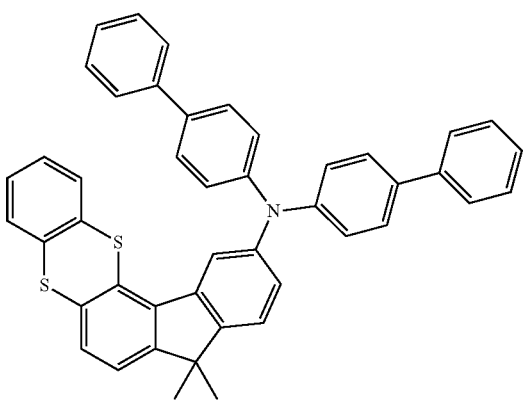
[A-162]
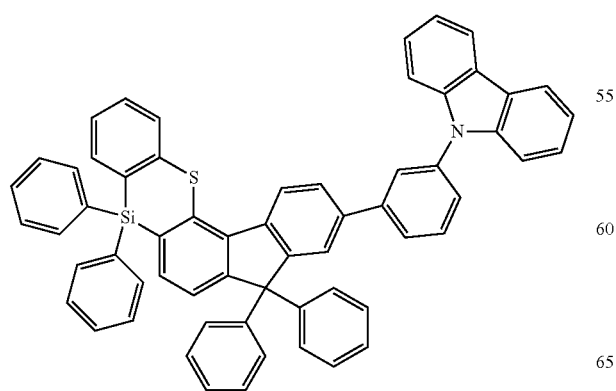
[A-166]
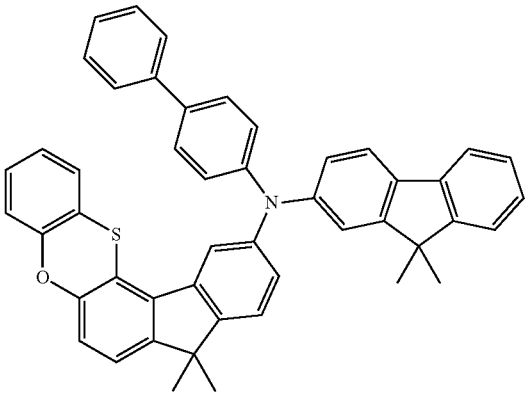
[A-163]
[A-167]

-continued
[A-168]
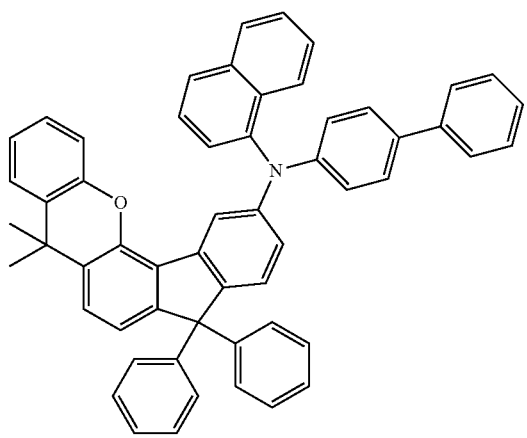
[A-169]
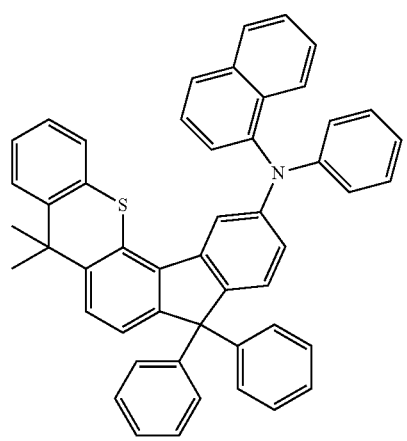
[A-170]
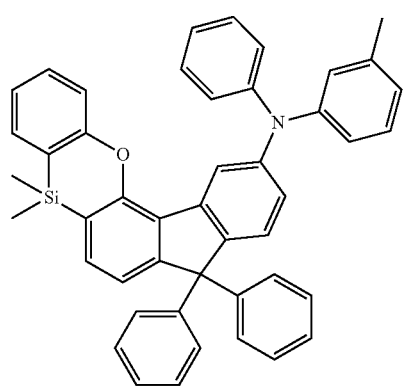
-continued
[A-171]
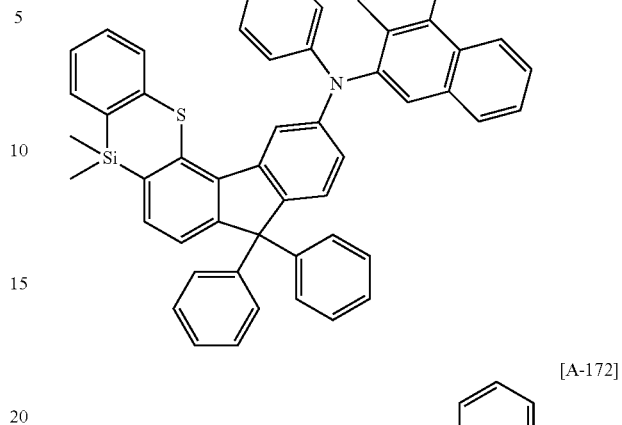
[A-172]
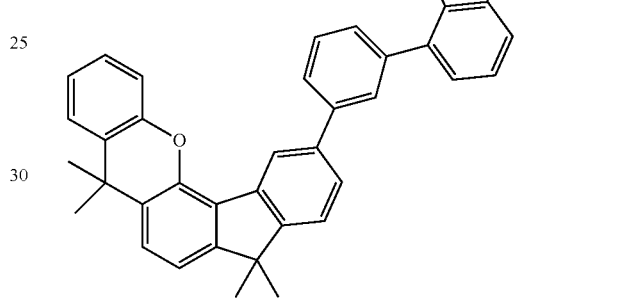
[A-173]
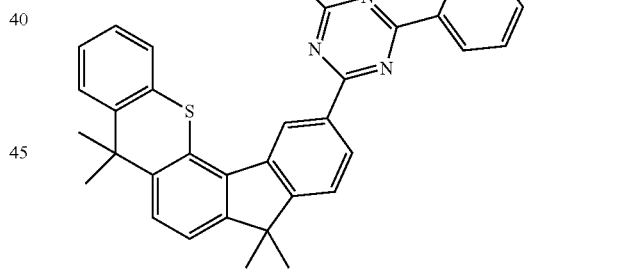
[A-174]
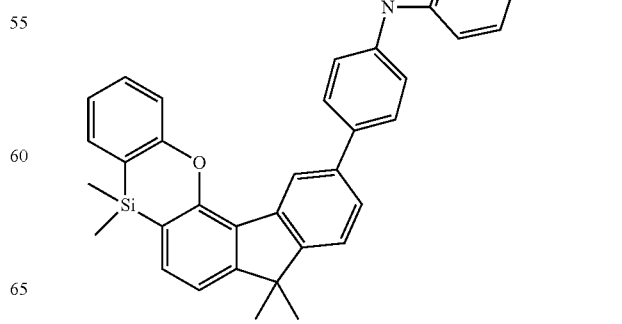

[A-175]
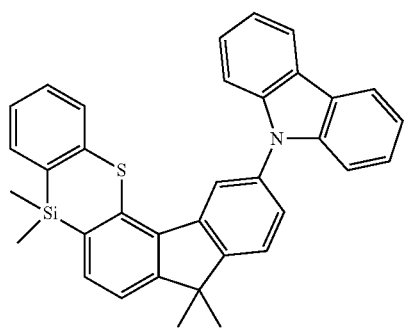
[A-176]
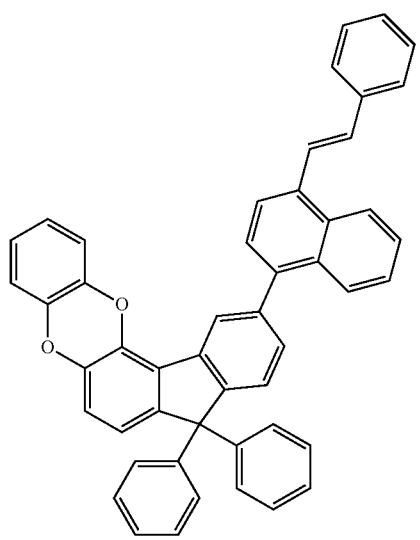
[A-177]
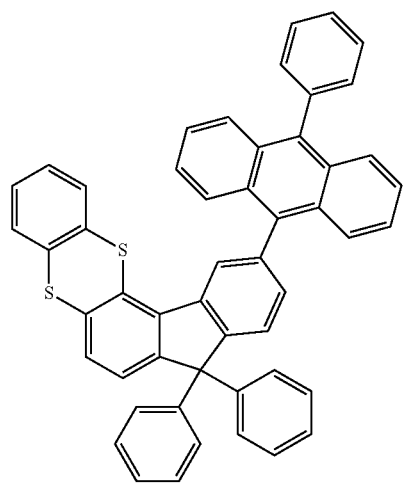
[A-178]
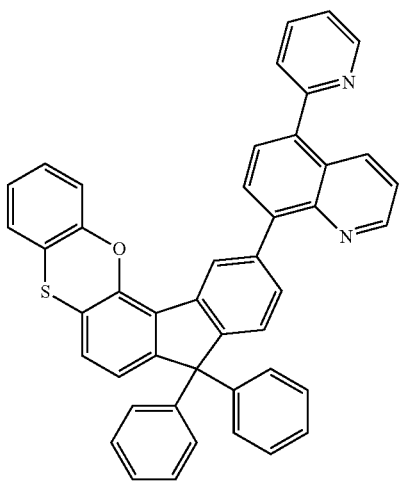
[A-179]
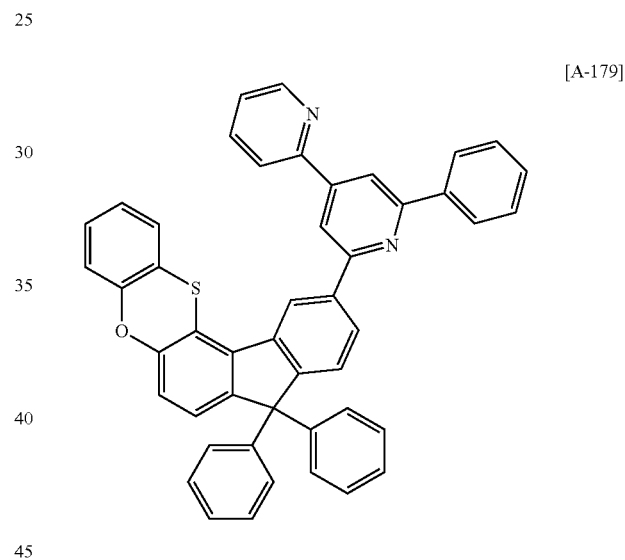
[A-180]
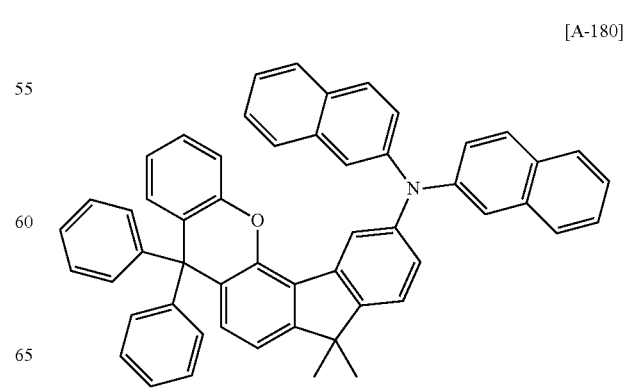

[A-181]
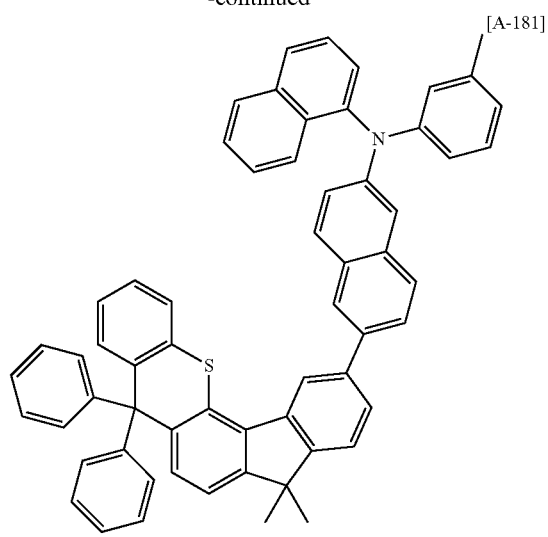
[A-182]
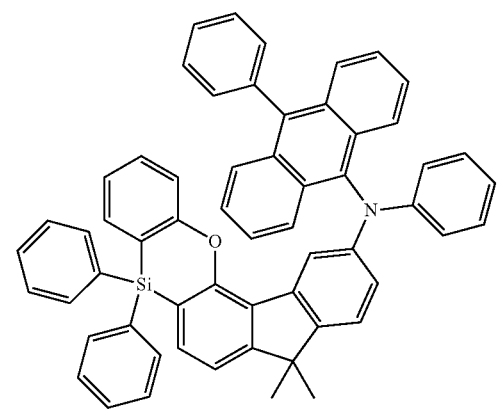
[A-183]
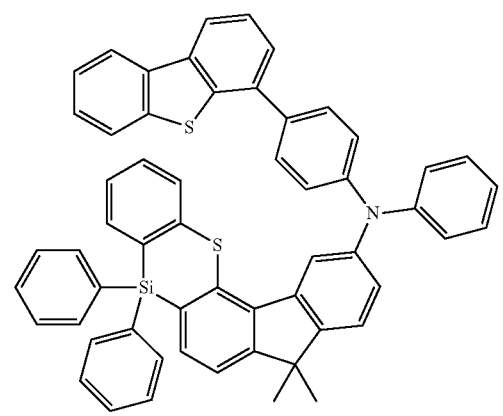
[B-1]
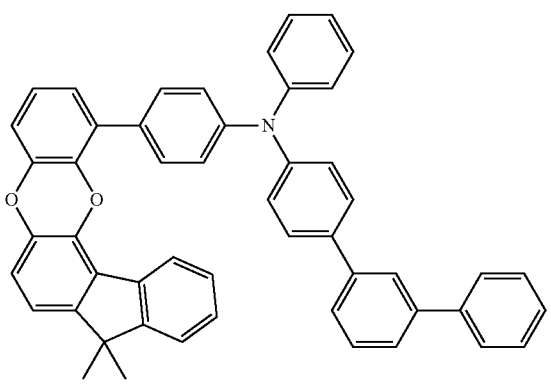
[B-2]
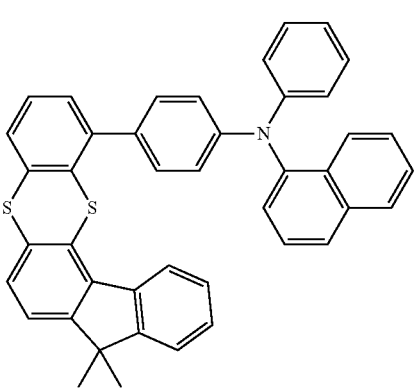
[B-3]
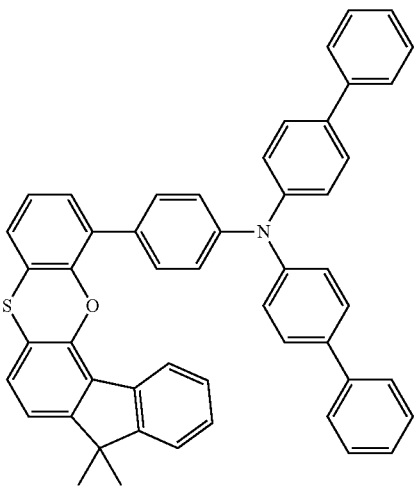
[B-4]
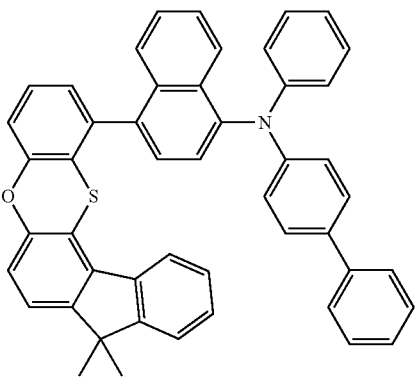
More specifically, the compound for an organic optoelectronic device may be represented by one of the following Chemical Formulae B-1 to B-88, but is not limited thereto.

[B-5]
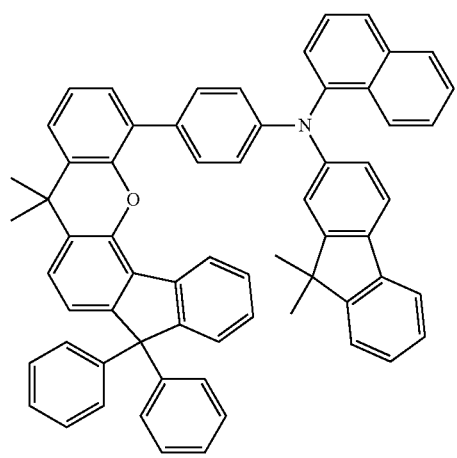
[B-6]
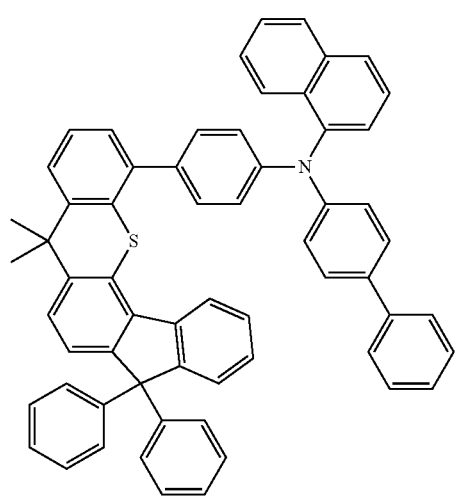
[B-7]
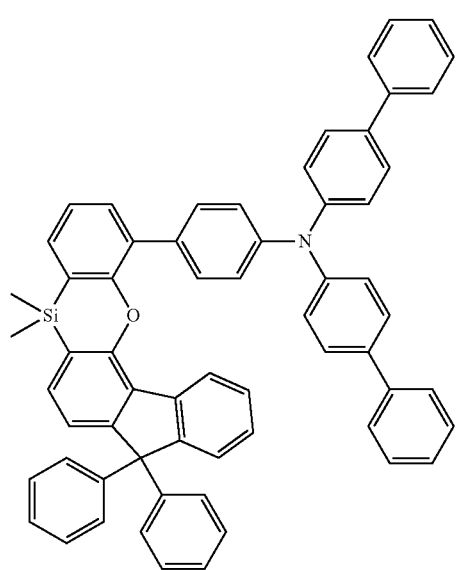
[B-8]
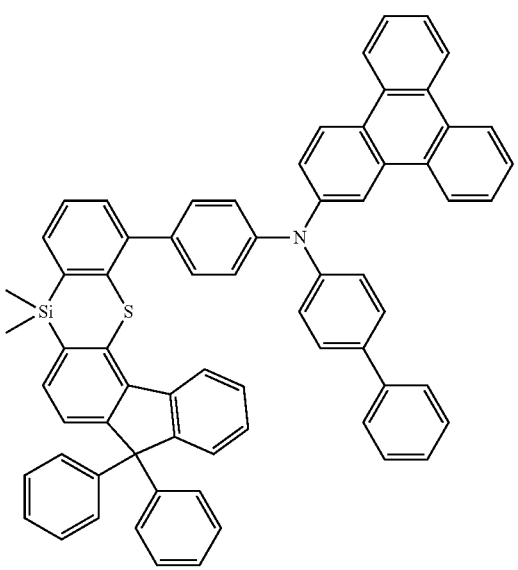
[B-9]
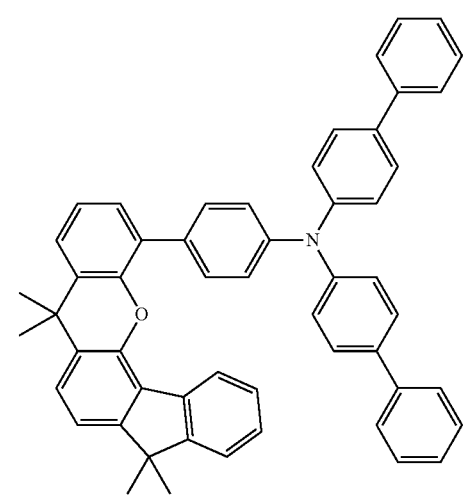
[B-10]
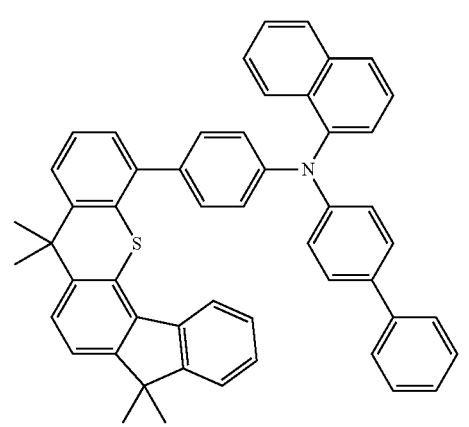

[B-11]
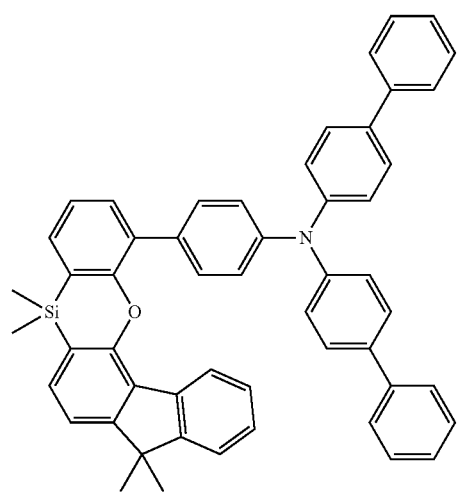
[B-14]
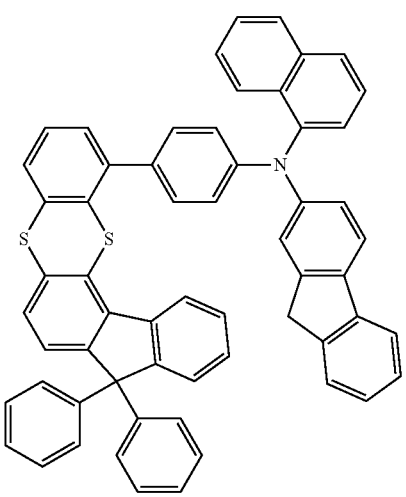
[B-12]
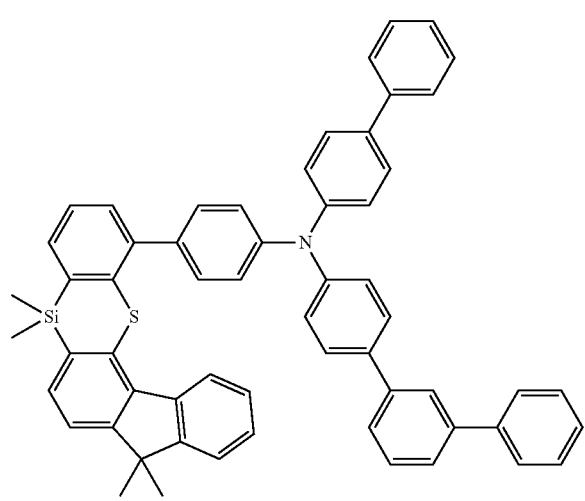
[B-15]
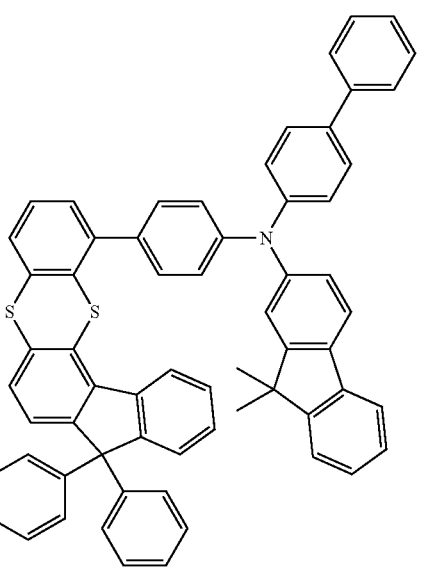
[B-13]
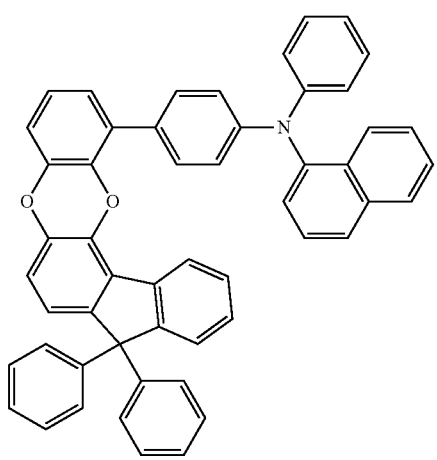
[B-16]
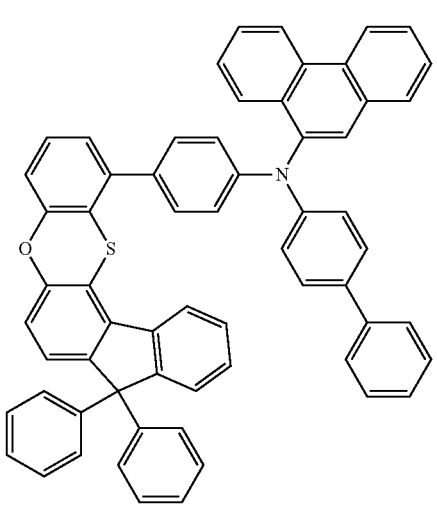

[B-17]
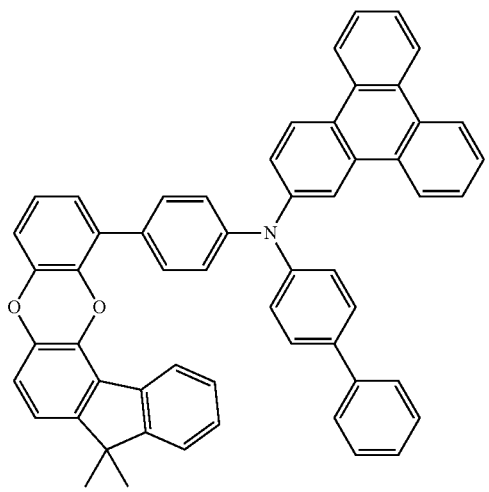
[B-20]
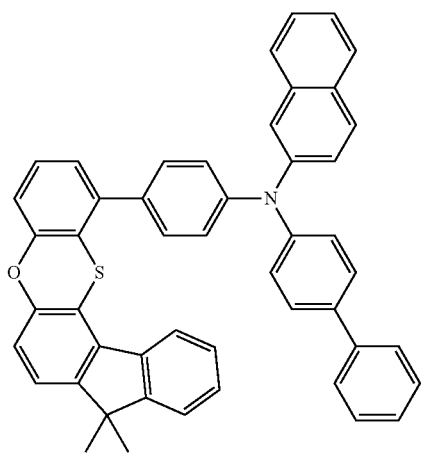
[B-18]
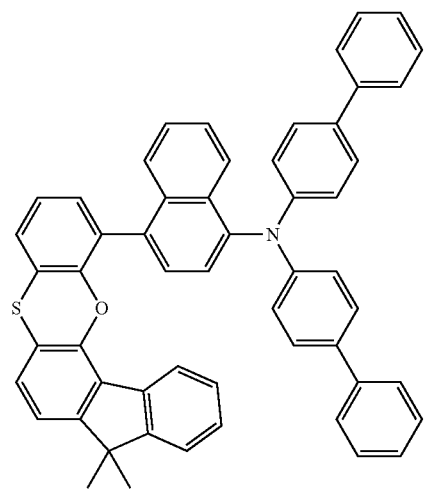
[B-21]
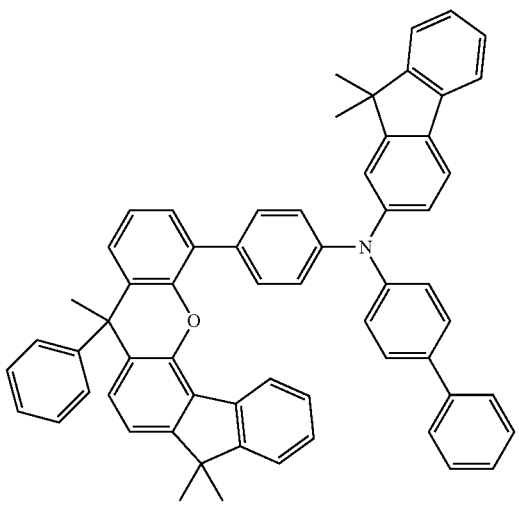
[B-19]
[B-22]
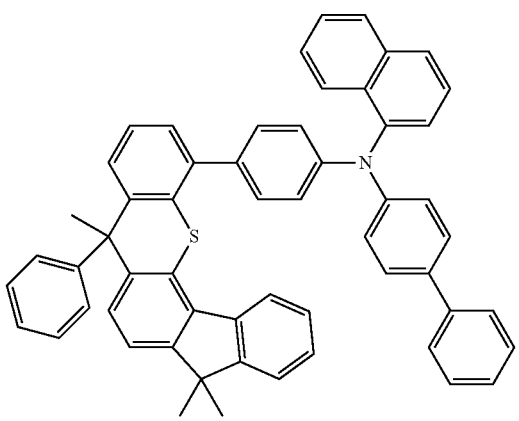

[B-23]
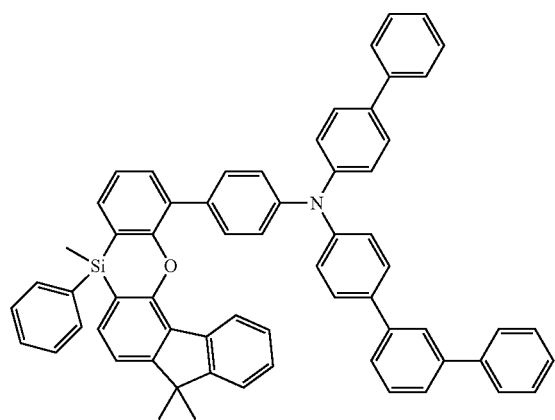
[B-24]
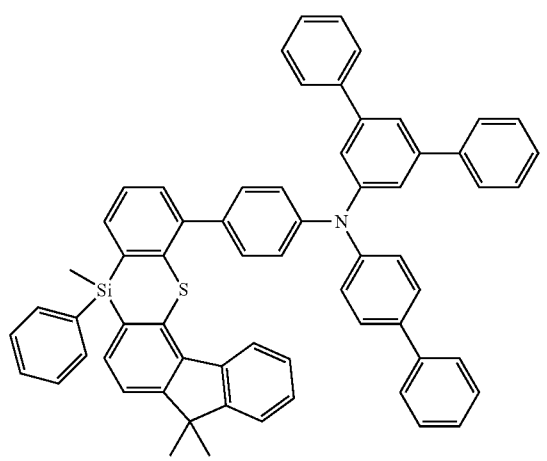
[B-25]
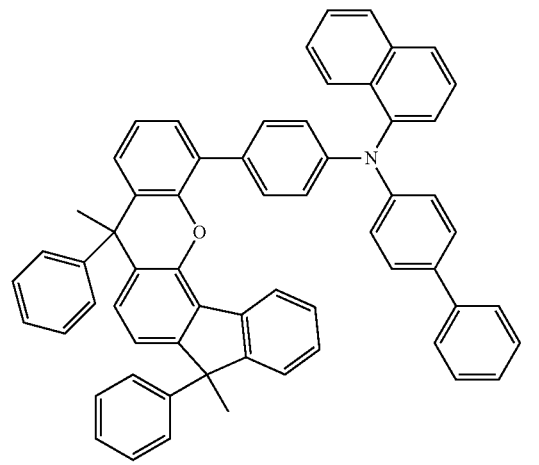
[B-26]
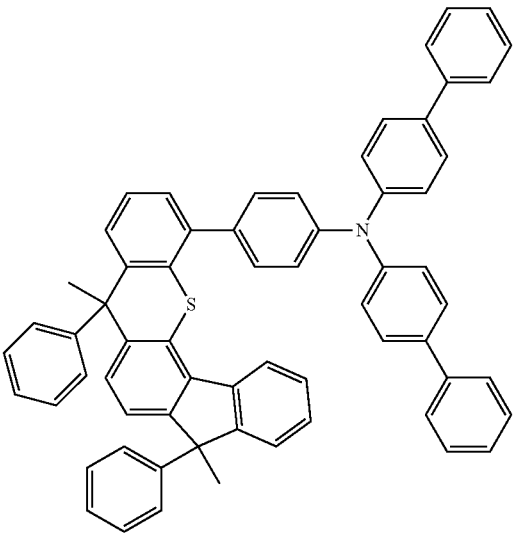
[B-27]
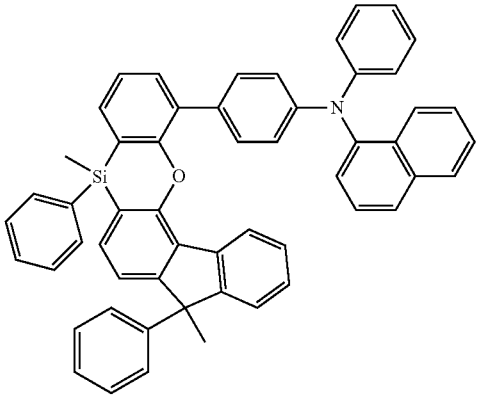
[B-28]
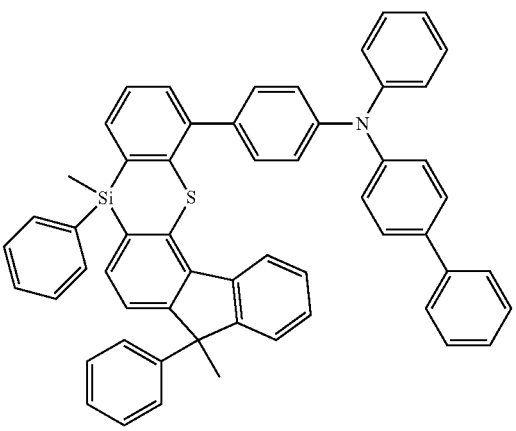

[B-29]
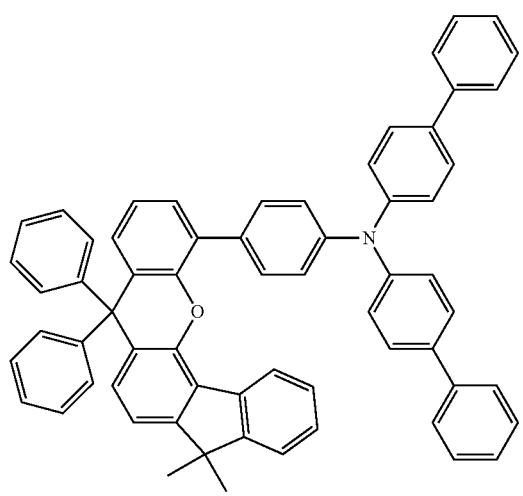
[B-30]
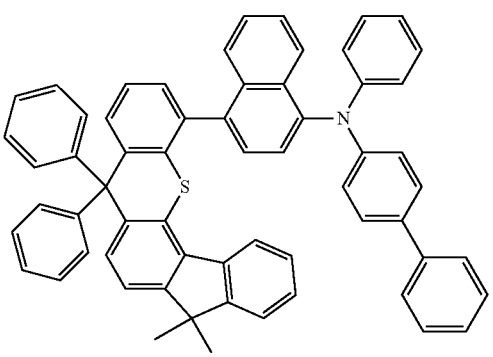
[B-31]
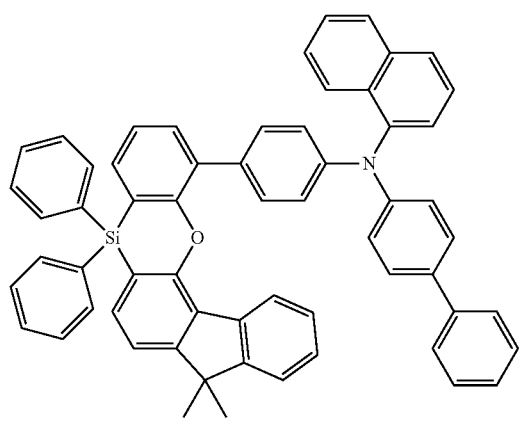
[B-32]
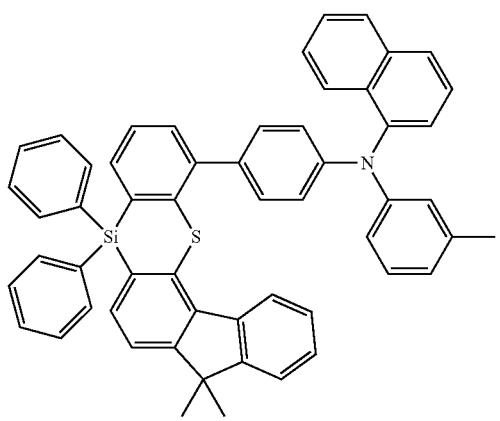
[B-33]
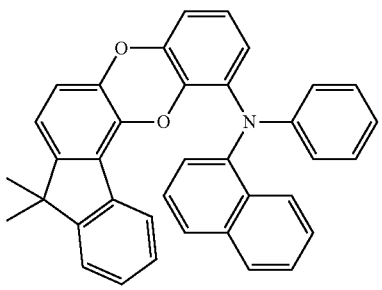
[B-34]
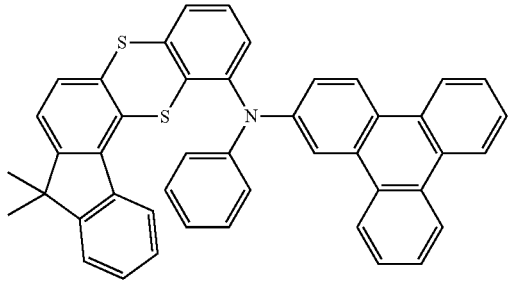
[B-35]
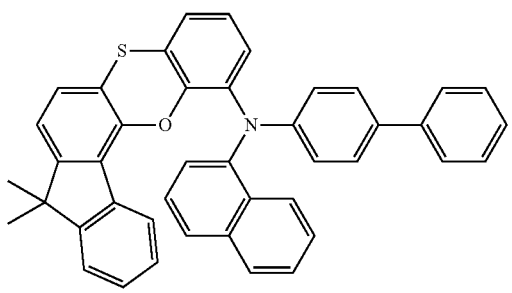
[B-36]
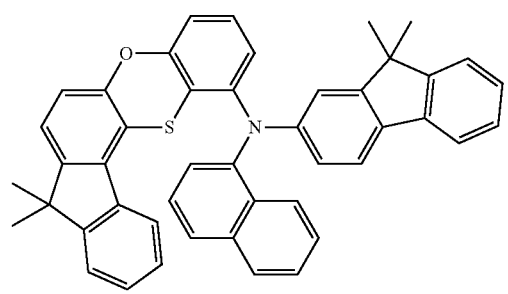

[B-37]
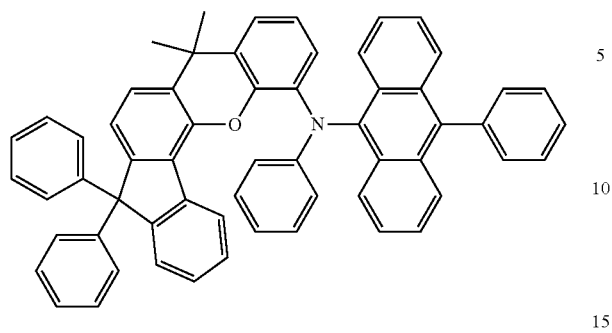
[B-41]
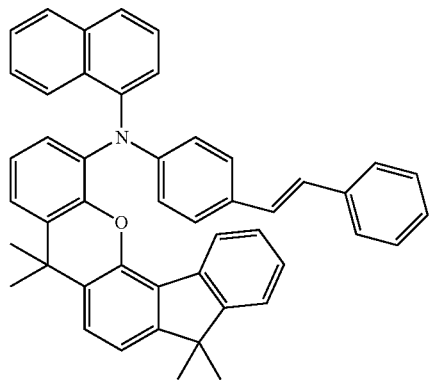
[B-38]
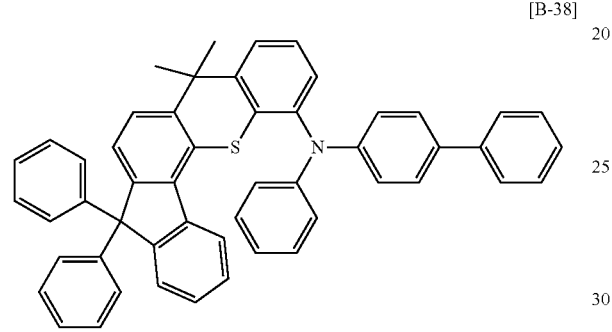
[B-42]
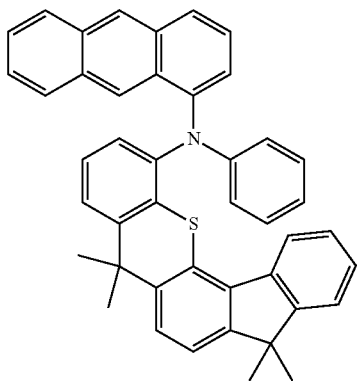
[B-39]
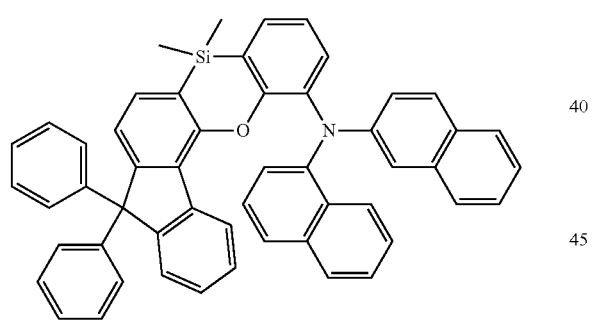
[B-43]
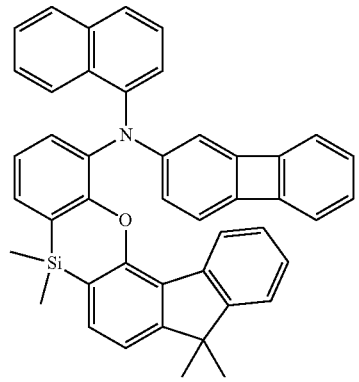
[B-40]
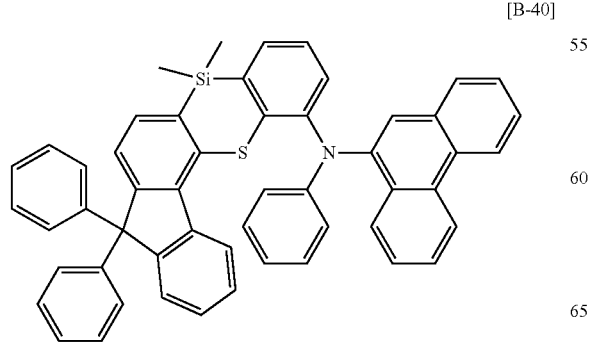
[B-44]
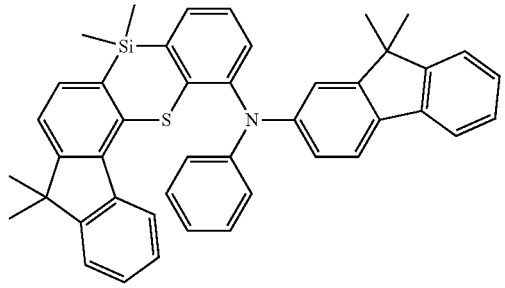

[B-45]
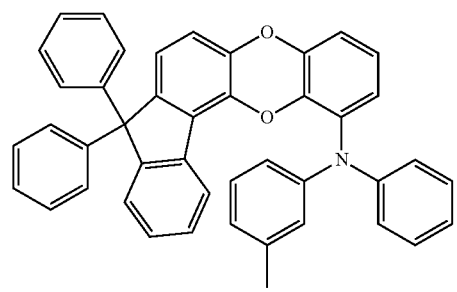
[B-46]
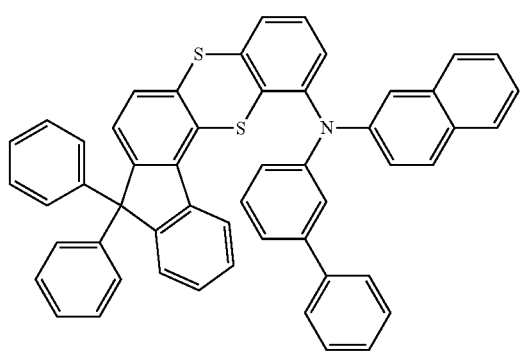
[B-47]
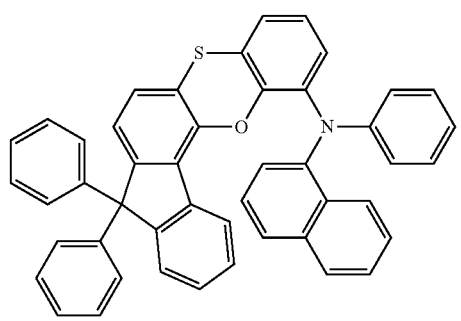
[B-48]
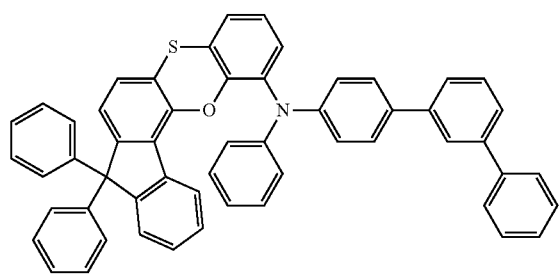
[B-49]
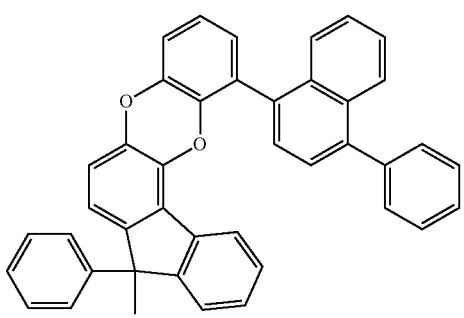
[B-50]
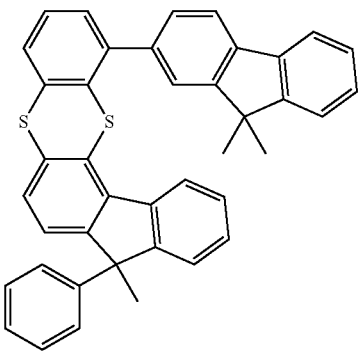
[B-51]
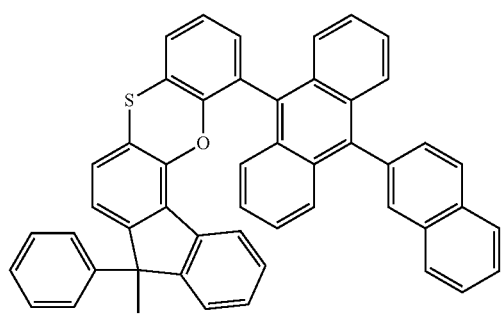
[B-52]
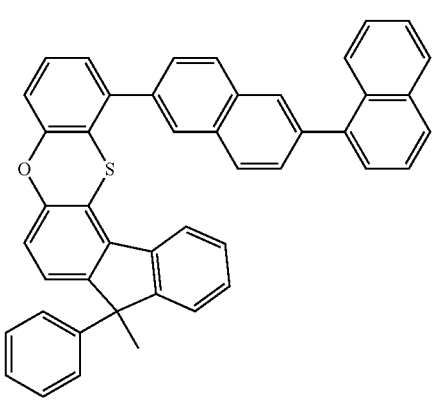
[B-53]
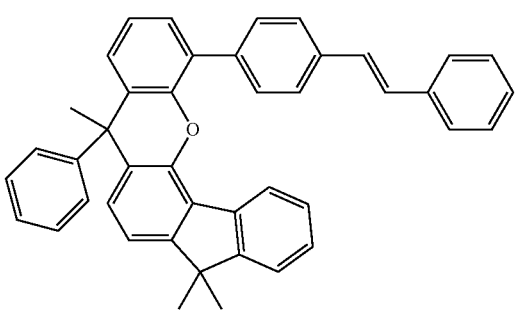

[B-54]
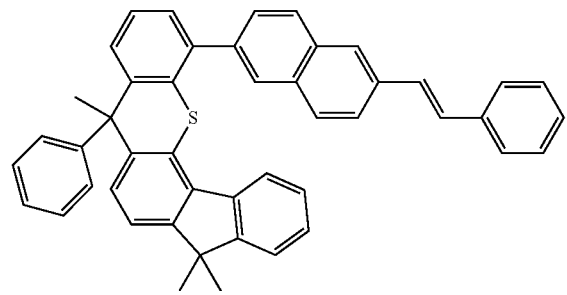
[B-58]
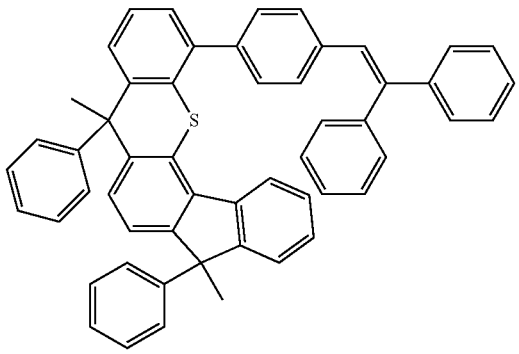
[B-55]
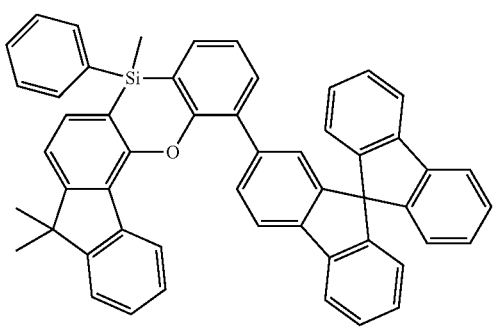
[B-59]
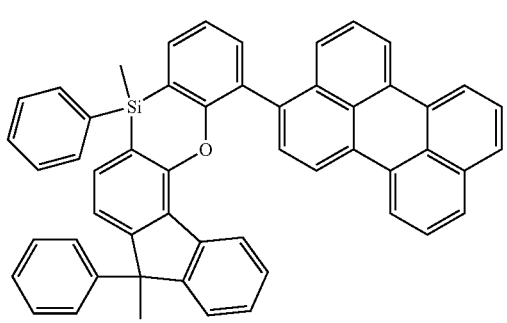
[B-56]
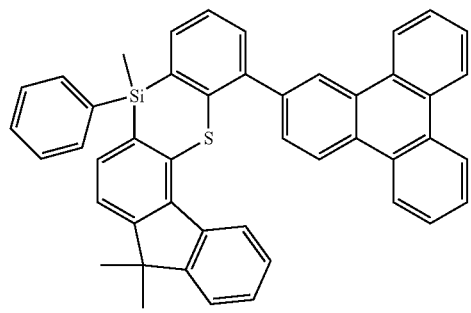
[B-60]
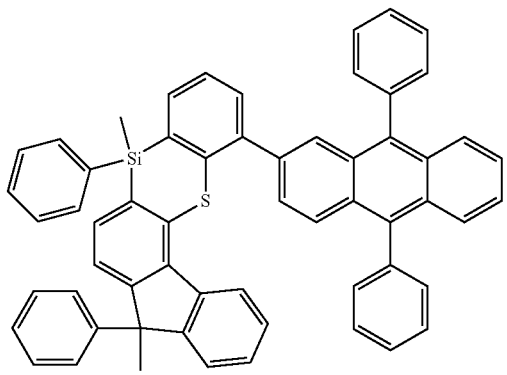
[B-57]
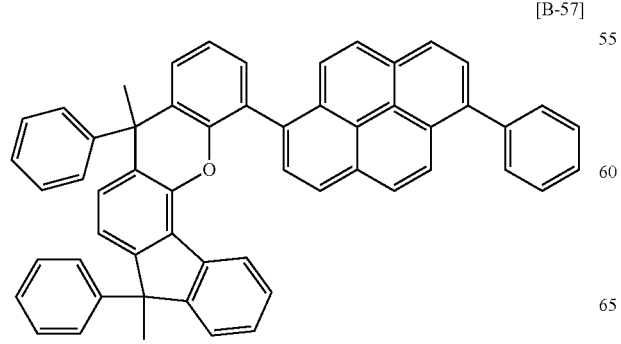
[B-61]
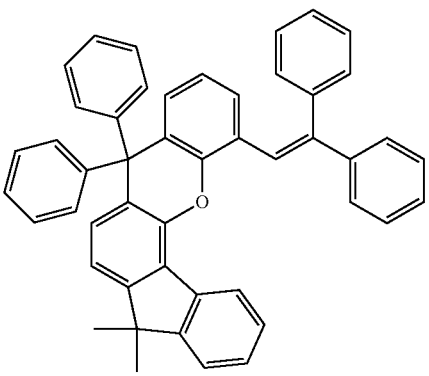

-continued
[B-62]
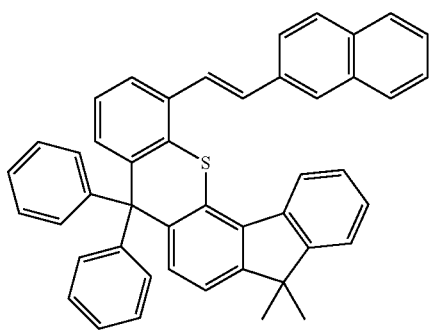
[B-63]
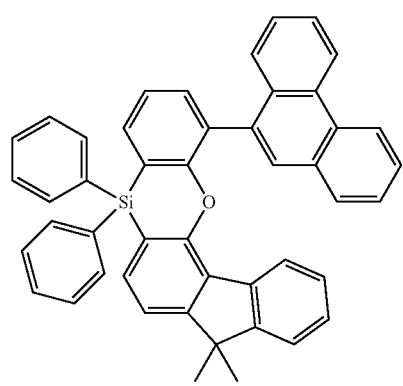
[B-64]
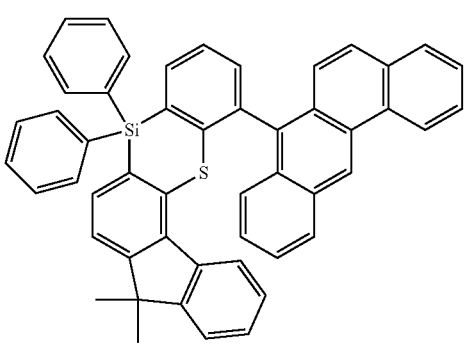
[B-65]
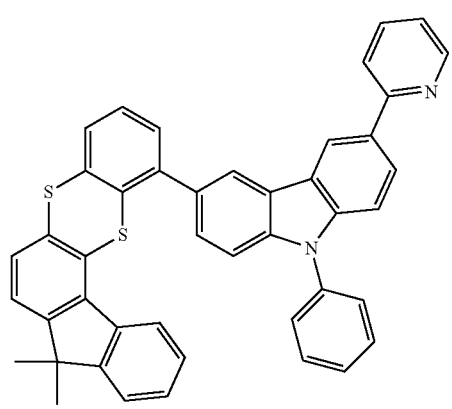
-continued
[B-66]
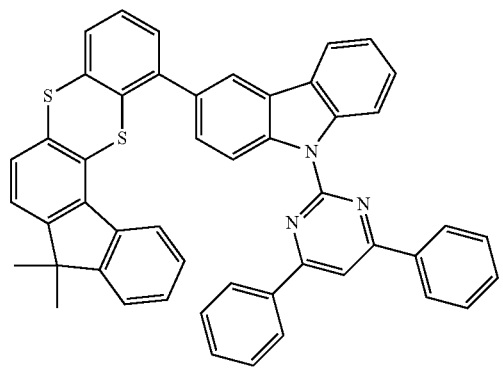
[B-67]
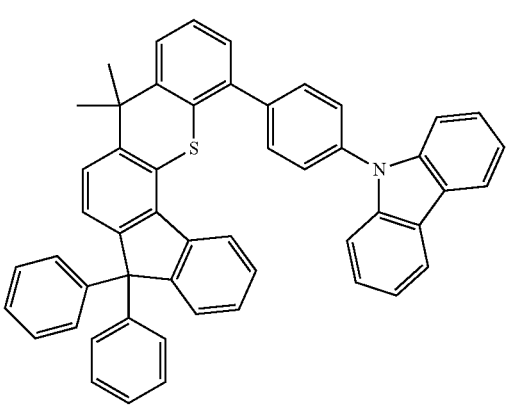
[B-68]
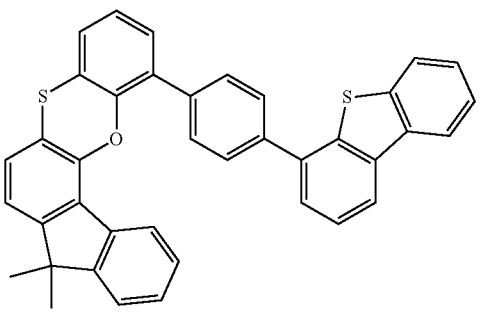
[B-69]
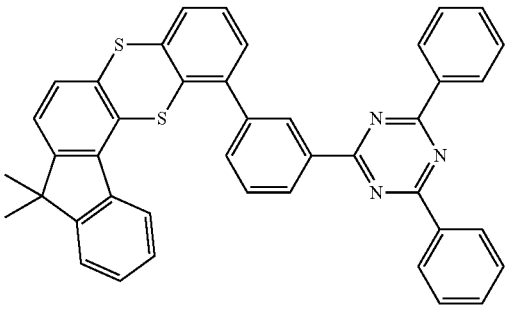

[B-70]
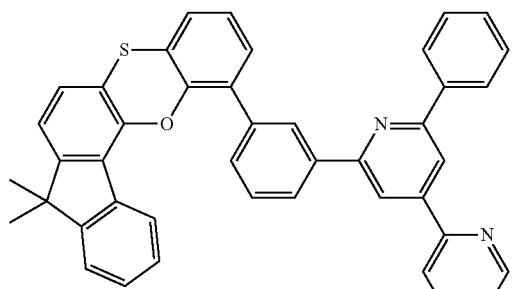
[B-71]
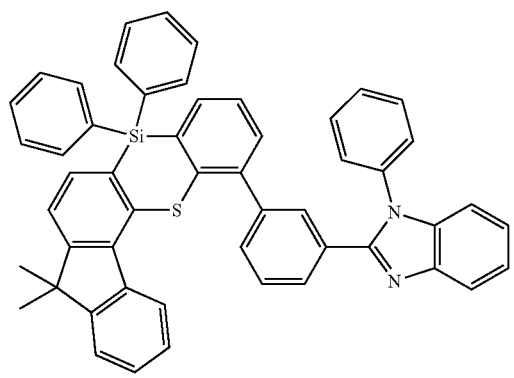
[B-72]
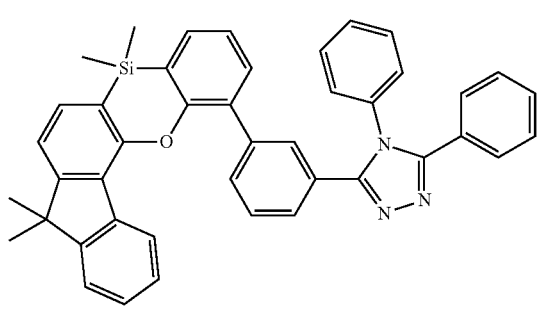
[B-73]
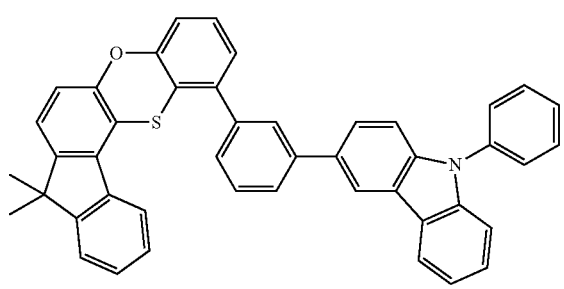
[B-74]
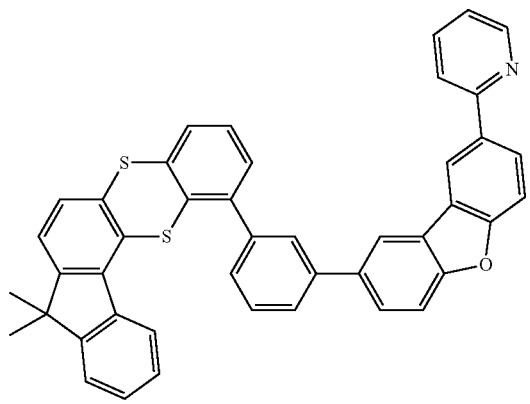
[B-75]
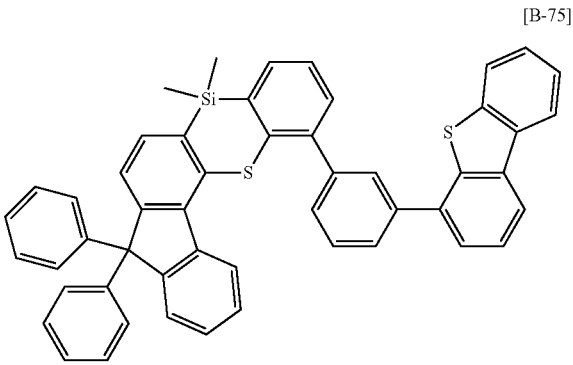
[B-76]
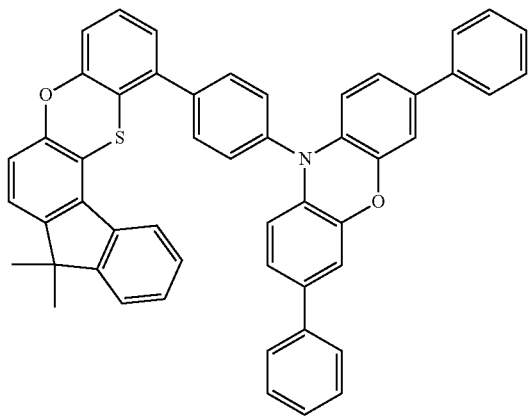
[B-77]
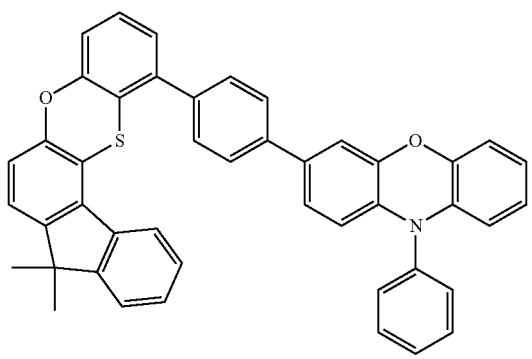

[B-78] 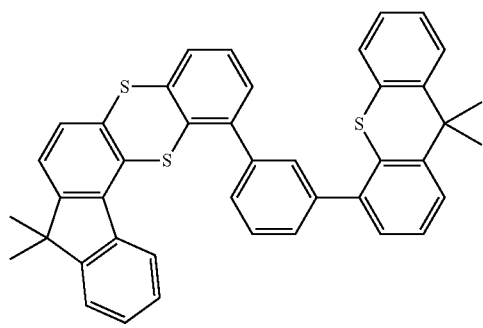
[B-79] 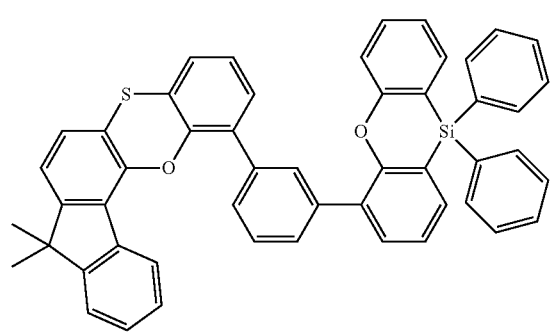
[B-80] 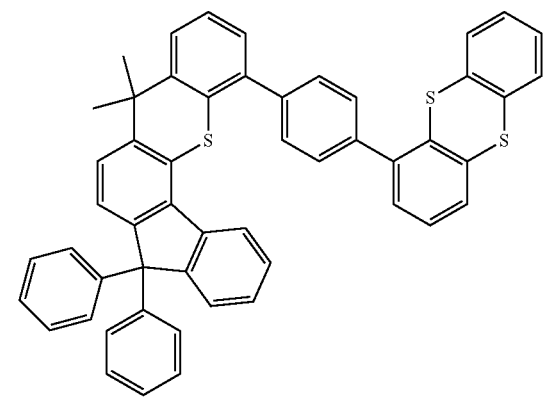
[B-81] 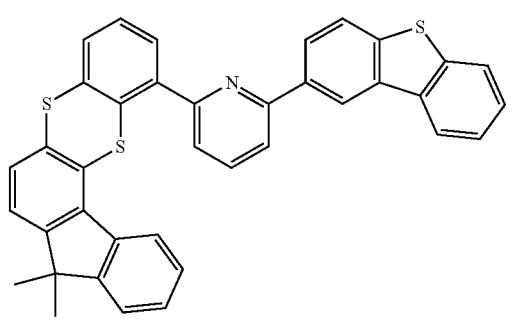
[B-82] 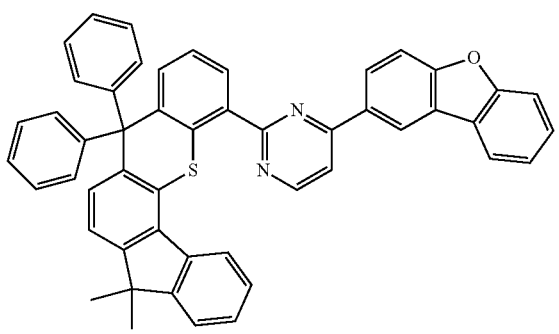
[B-83] 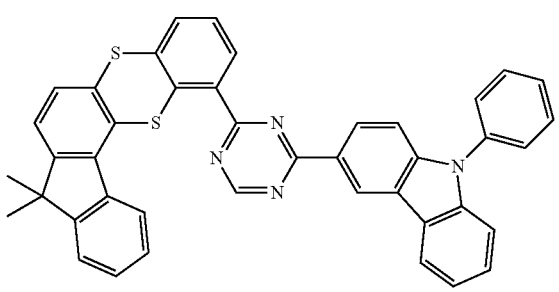
[B-84] 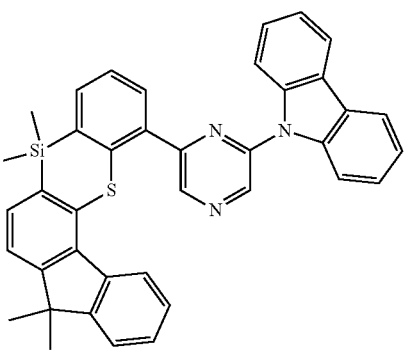
[B-85] 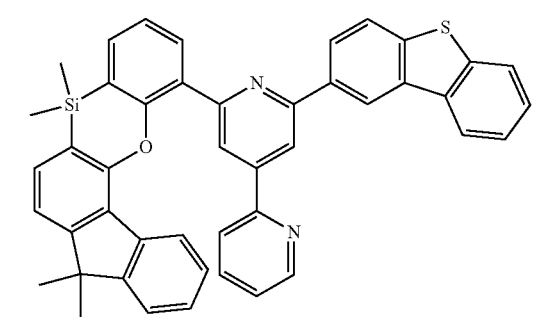
[B-86] 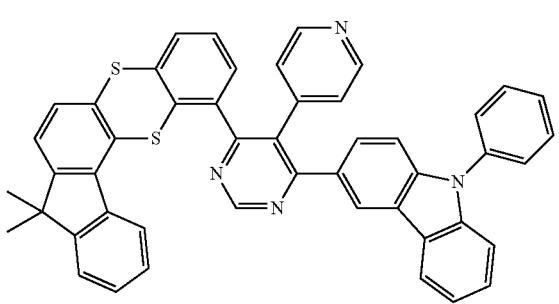

[B-87]
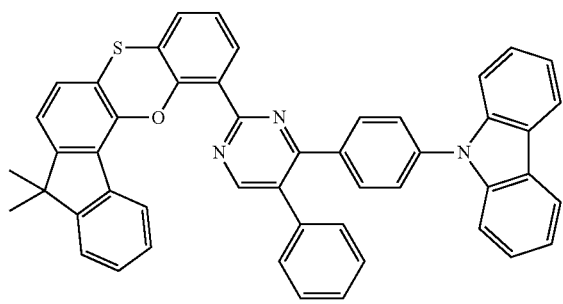
[C-2]
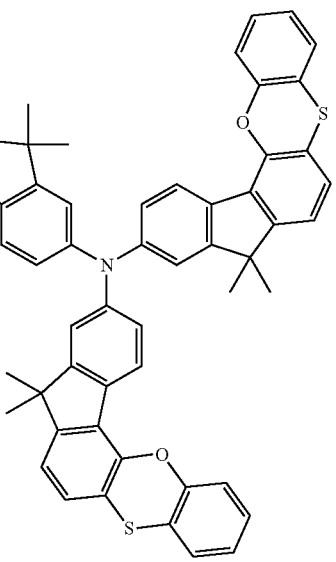
[B-88]
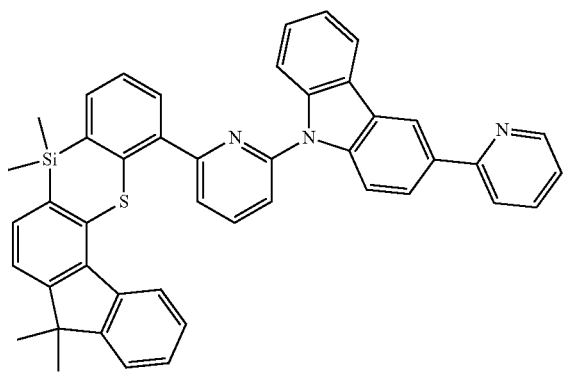
More specifically, the compound for an organic optoelectronic device may be represented by one of the following Chemical Formulae C-1 to C-32, but is not limited thereto.
[C-1]
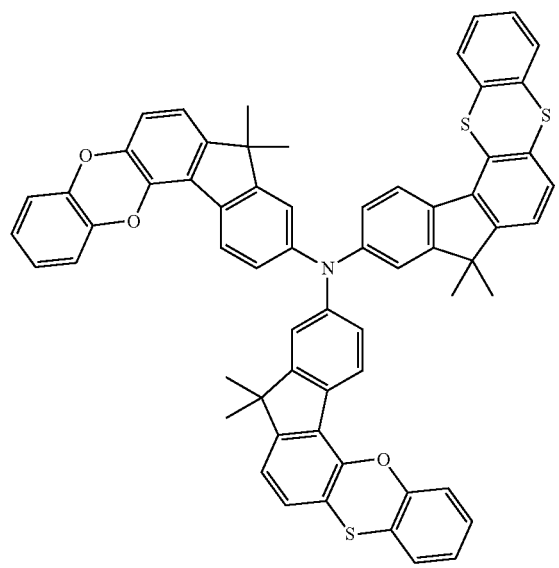
[C-3]
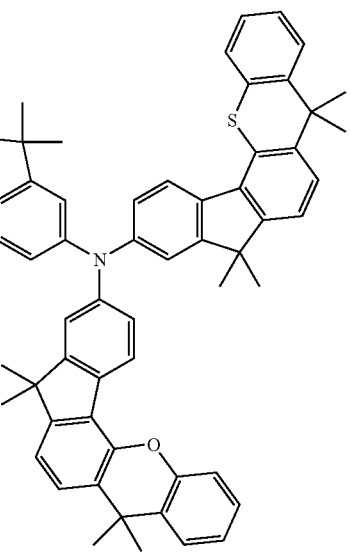

-continued
[C-4]
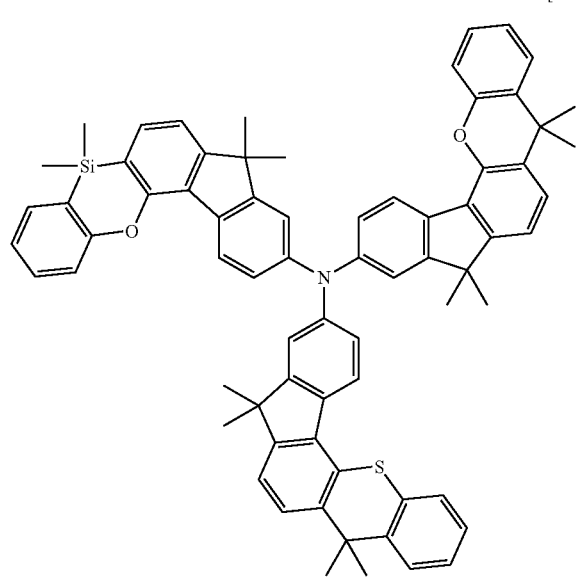
[C-6]
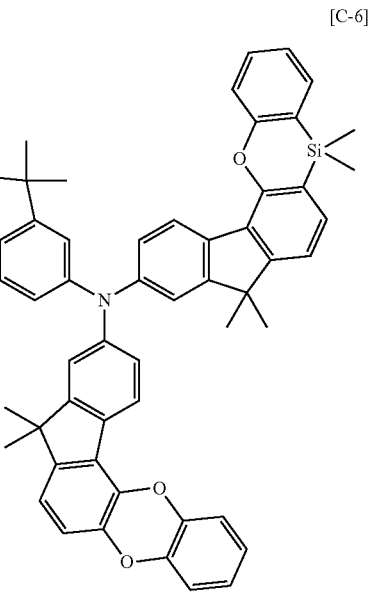
[C-5]
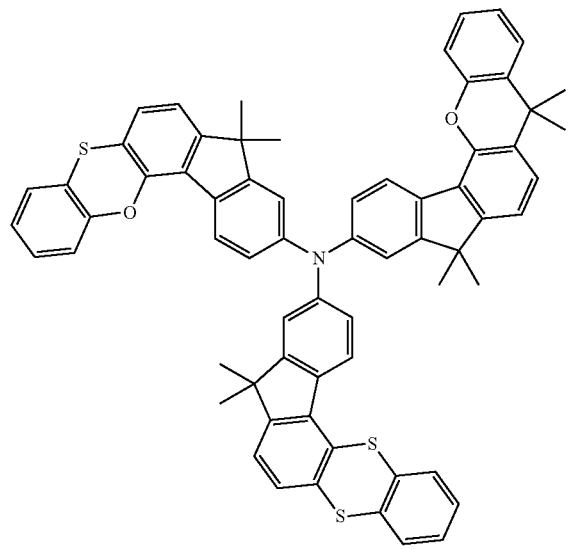
[C-7]
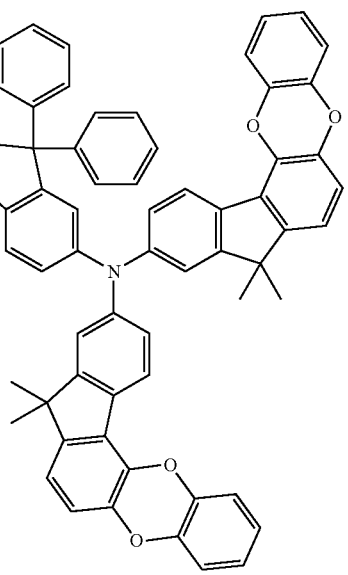

[C-8]
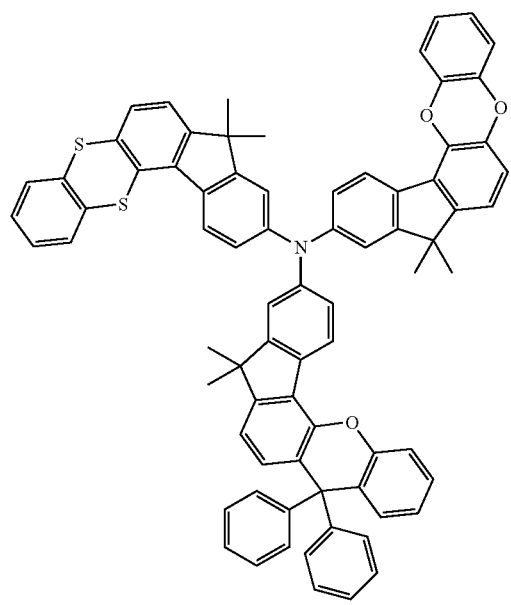
[C-9]
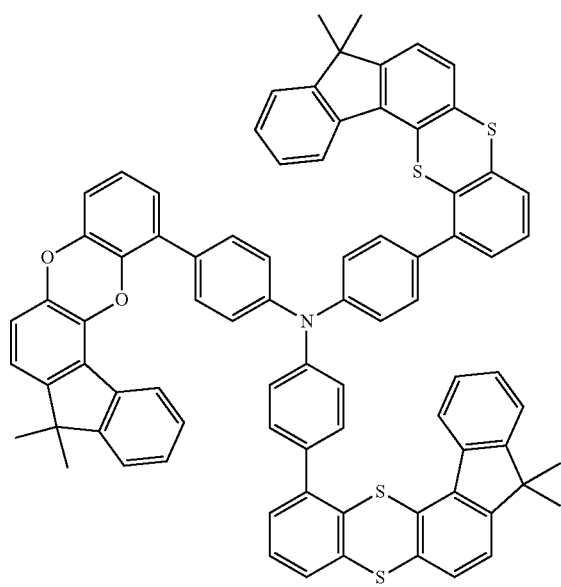
[C-10]
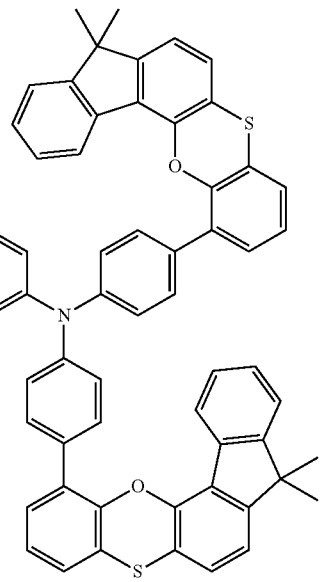
[C-11]
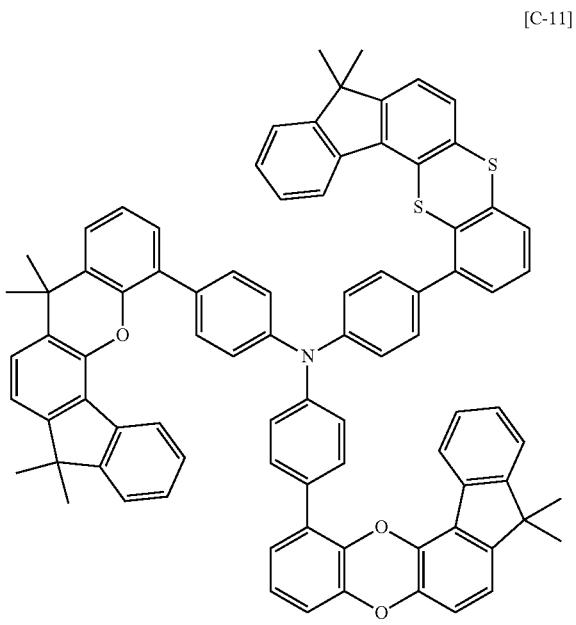

[C-12]
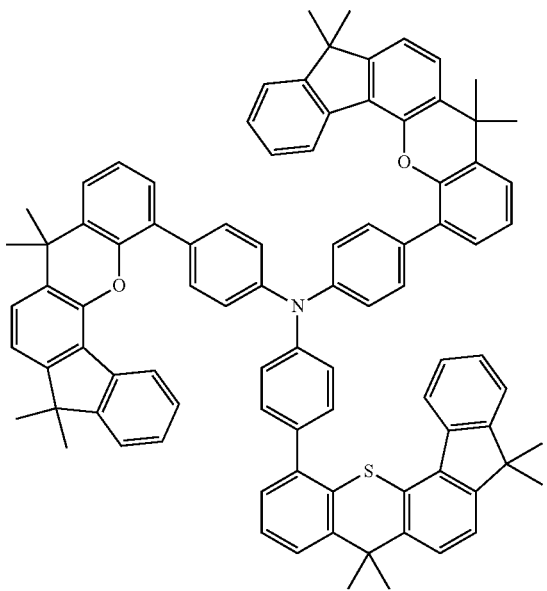
[C-14]
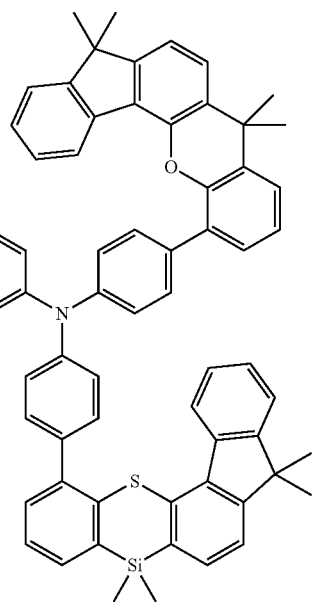
[C-13]
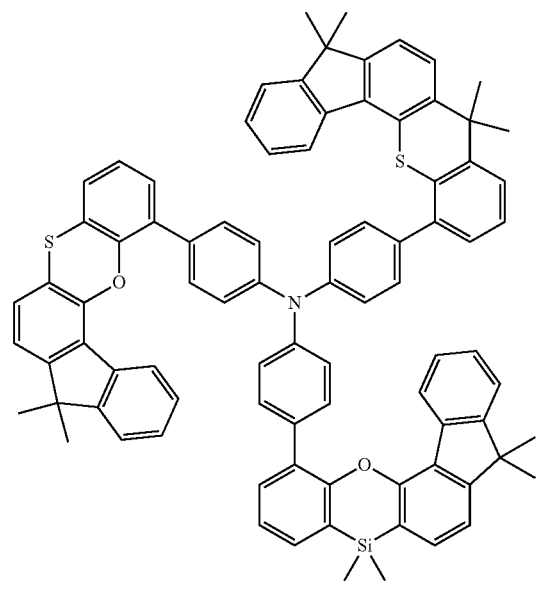
[C-15]
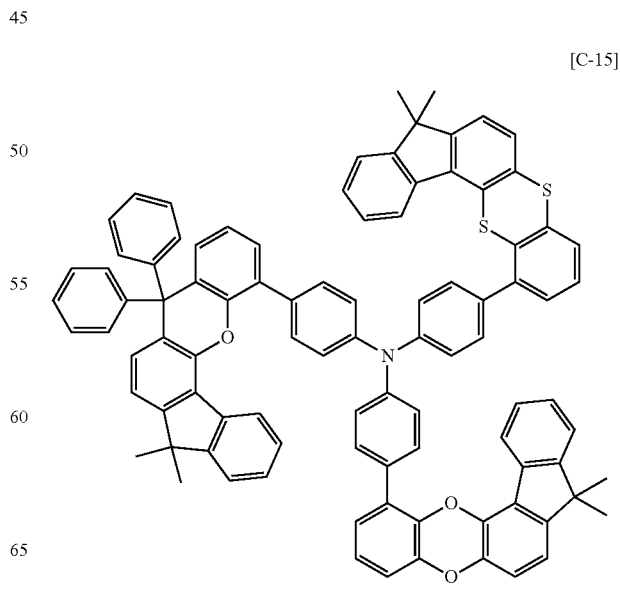

[C-16]
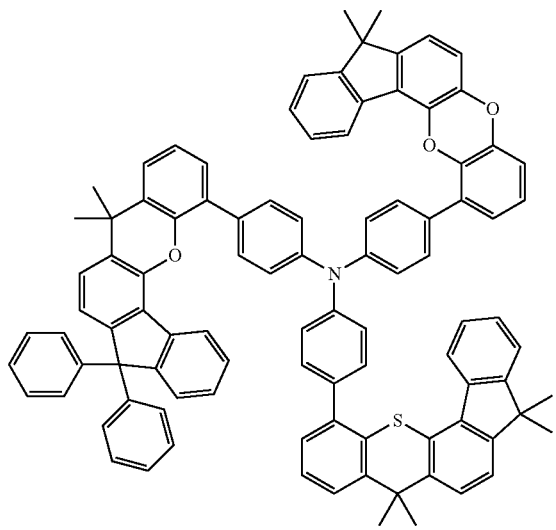
[C-17]
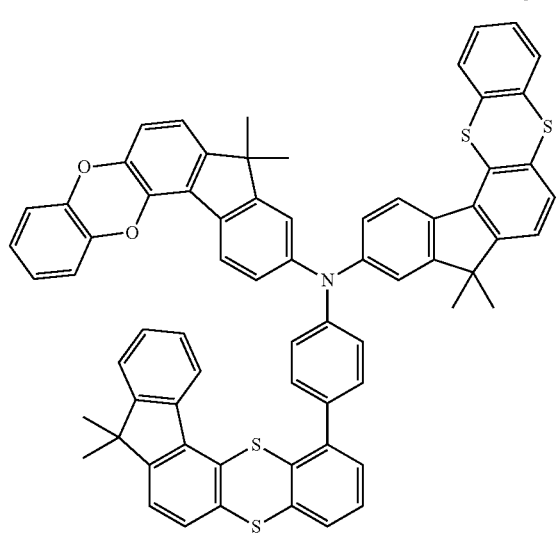
[C-18]
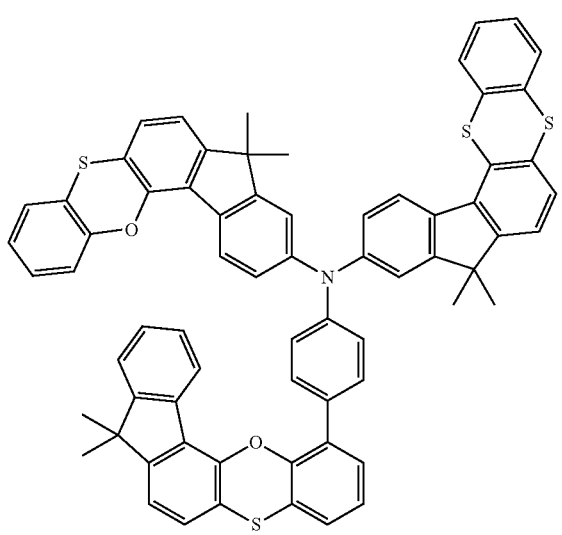
[C-19]
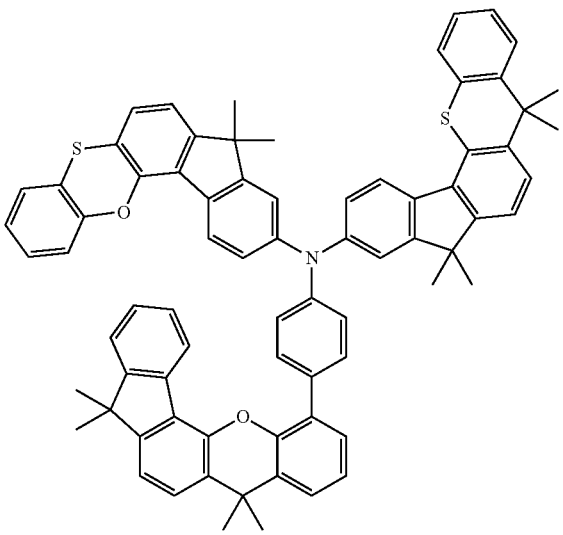
[C-20]
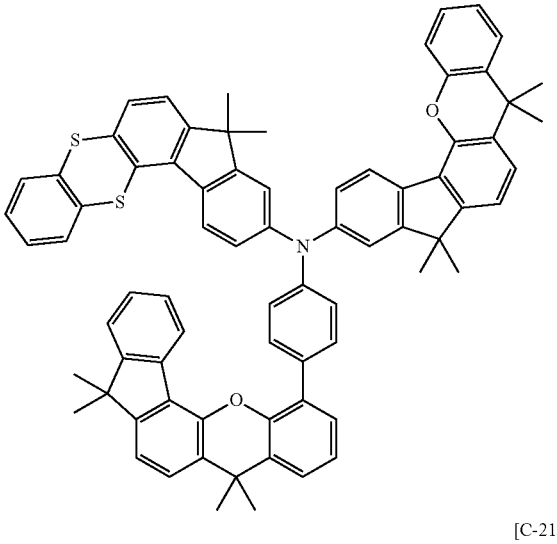
[C-21]
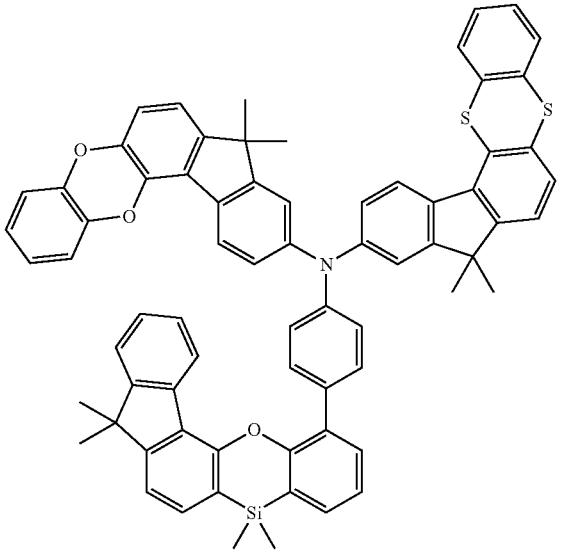

[C-22]
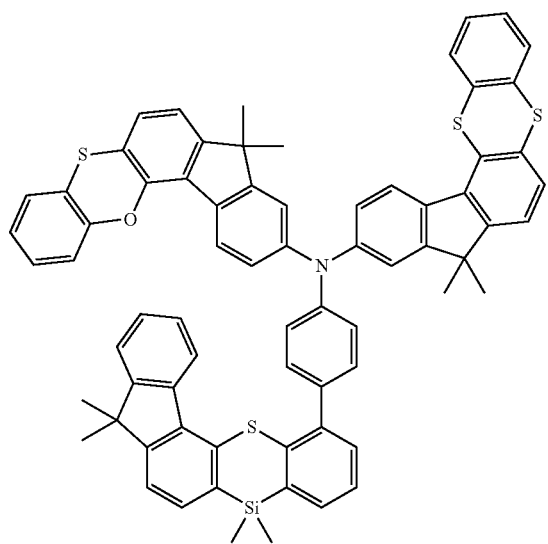
[C-24]
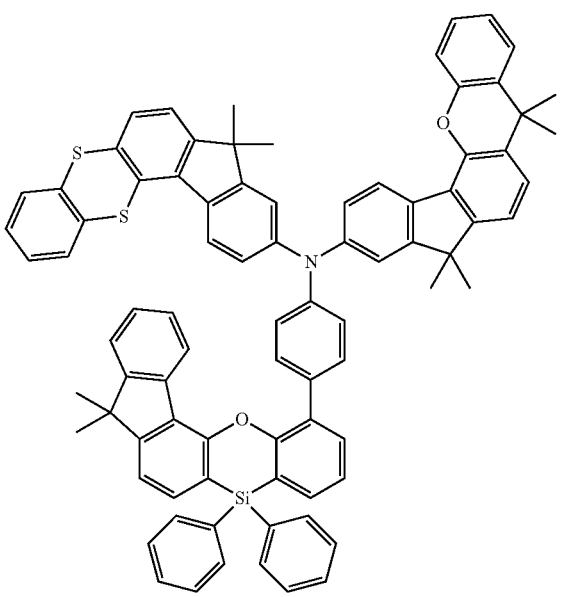
[C-23]
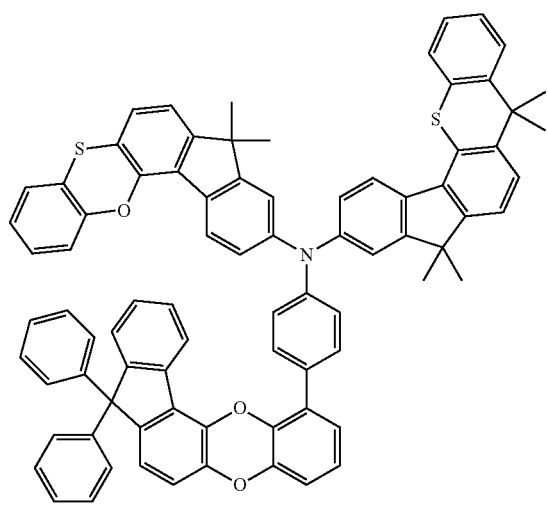
[C-25]
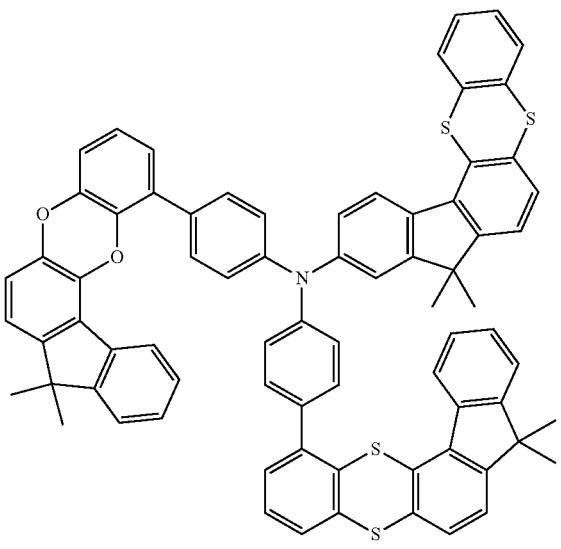

-continued
[C-26]
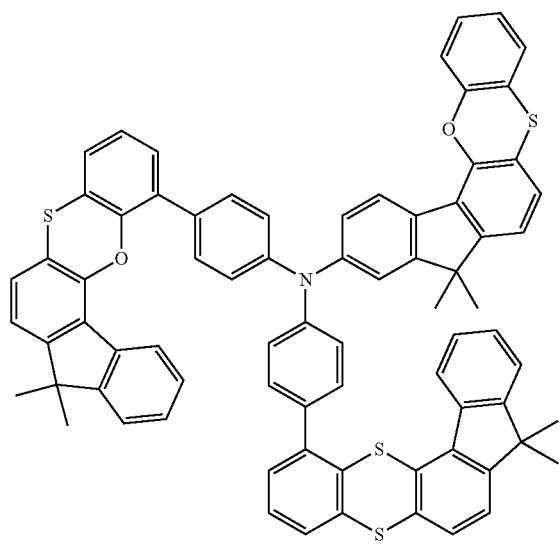
[C-28]
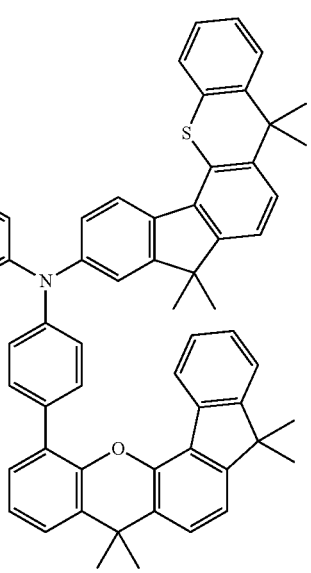
[C-27]
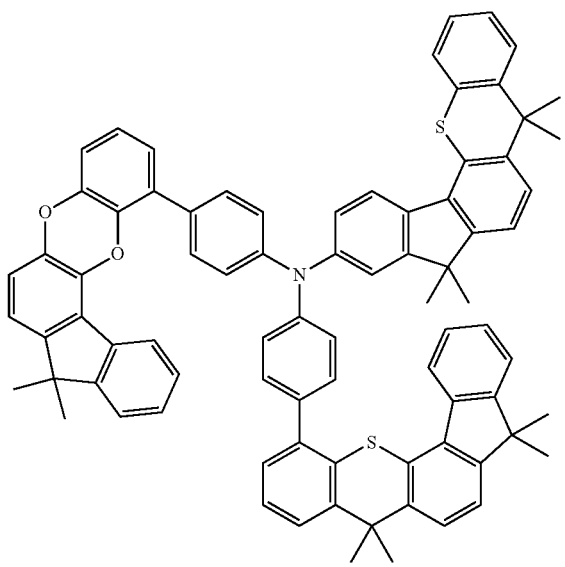
[C-29]
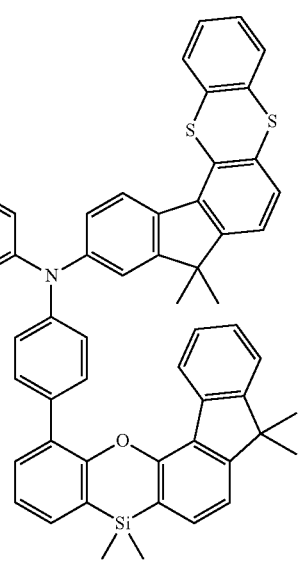

[C-30]
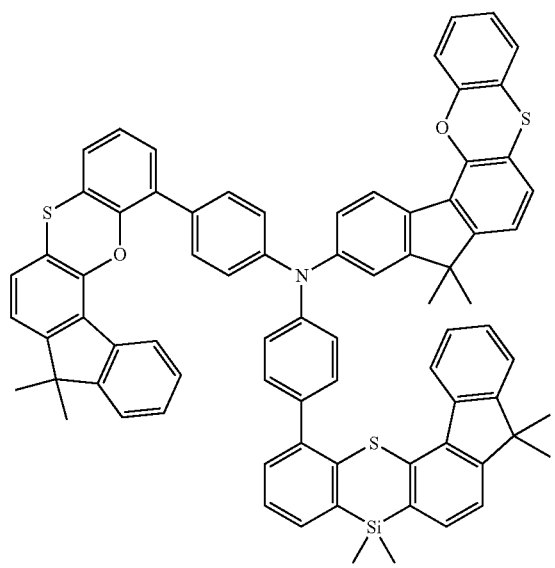
[C-31]
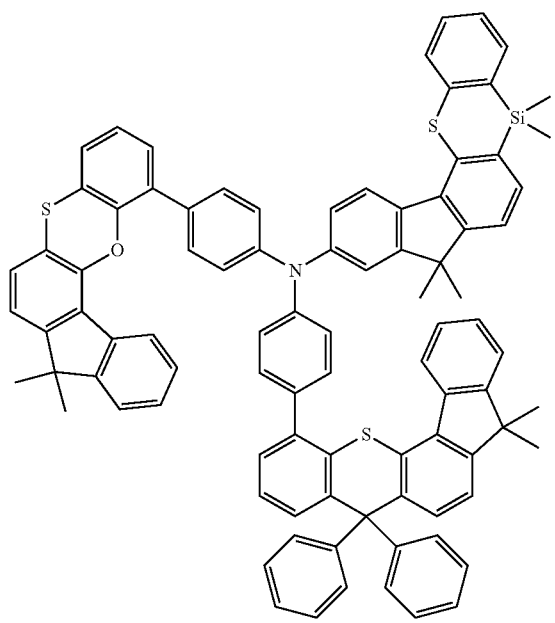
[C-32]
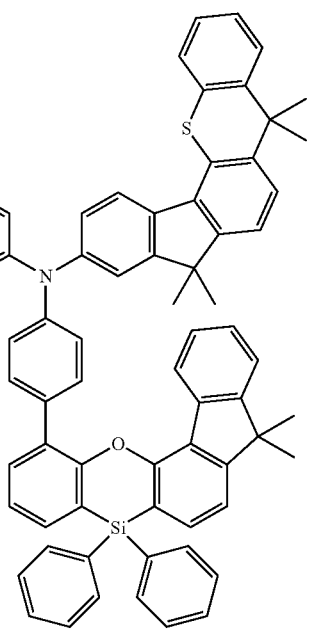
More specifically, the compound for an organic optoelectronic device may be represented by one of the following Chemical Formulae D-1 to D-64, but is not limited thereto.
[D-1]
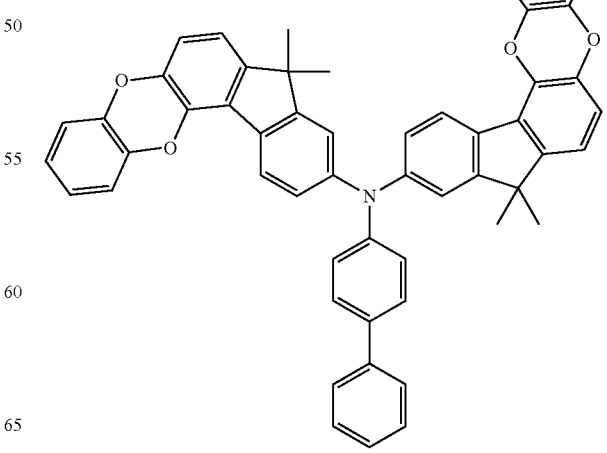

[D-2]
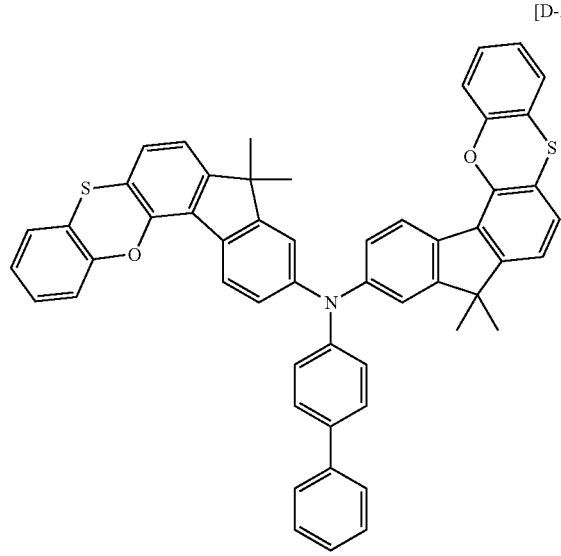
[D-5]
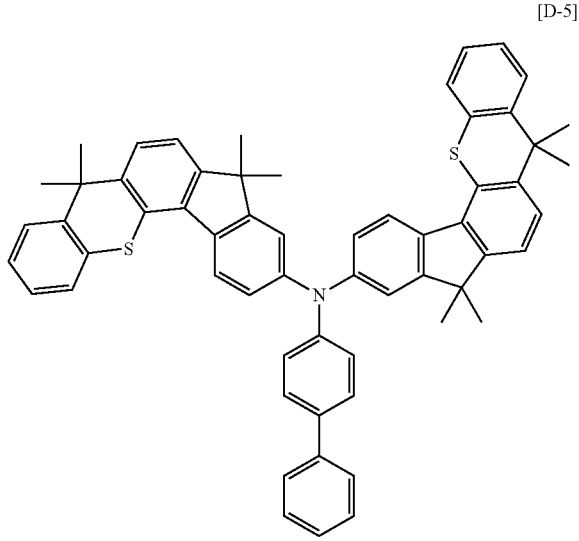
[D-3]
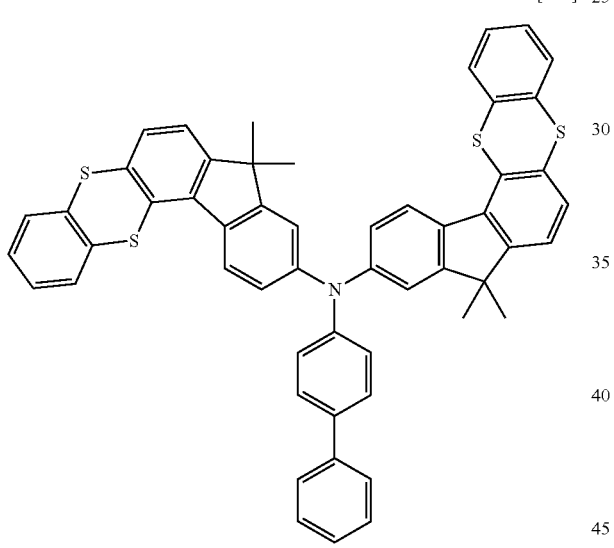
[D-6]
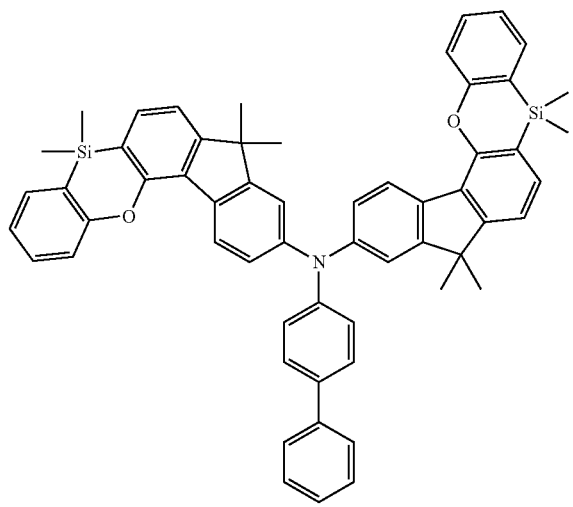
[D-4]
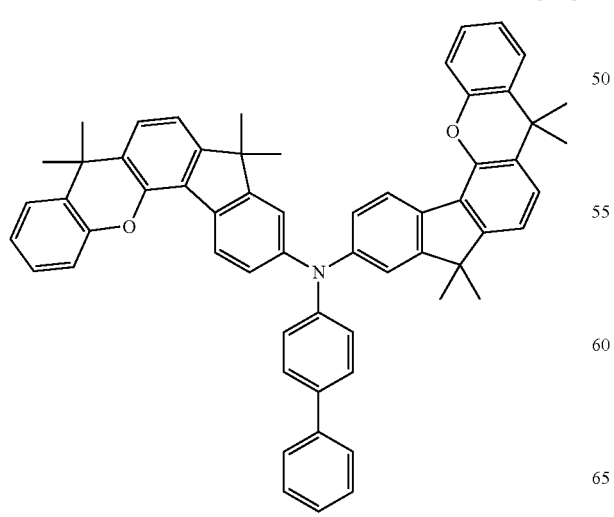
[D-7]
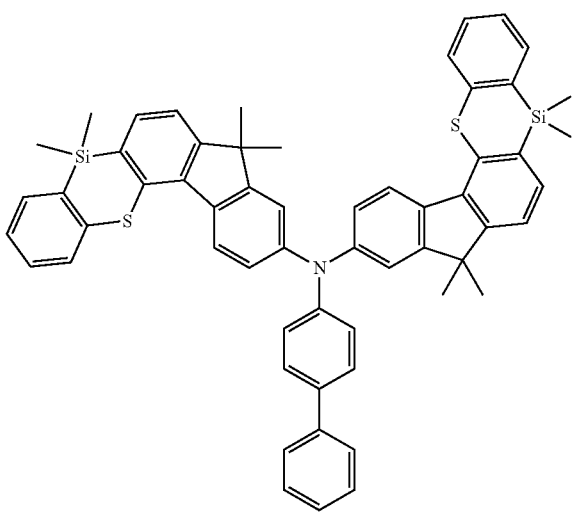

[D-8]
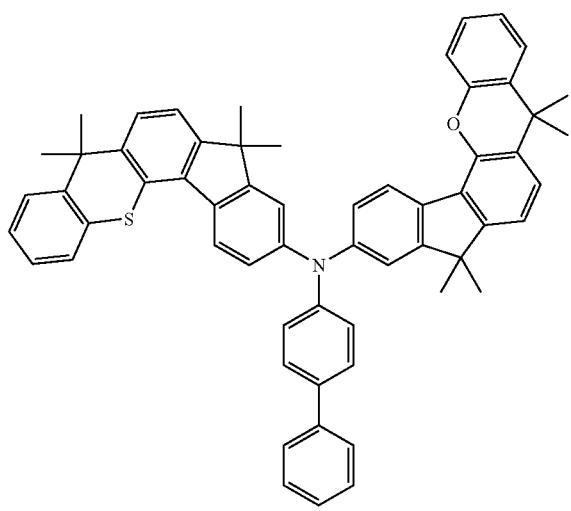
[D-11]
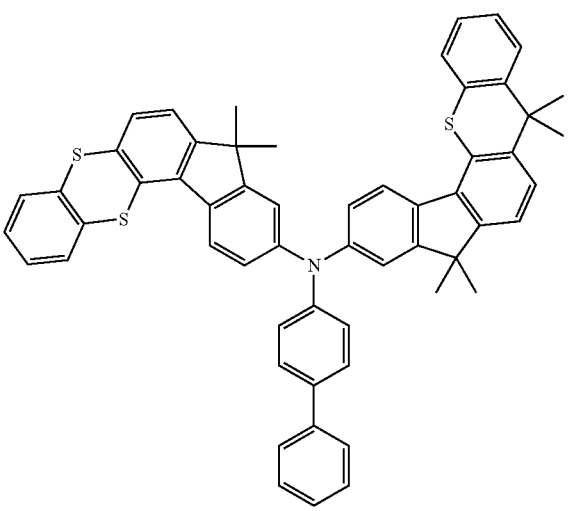
[D-9]
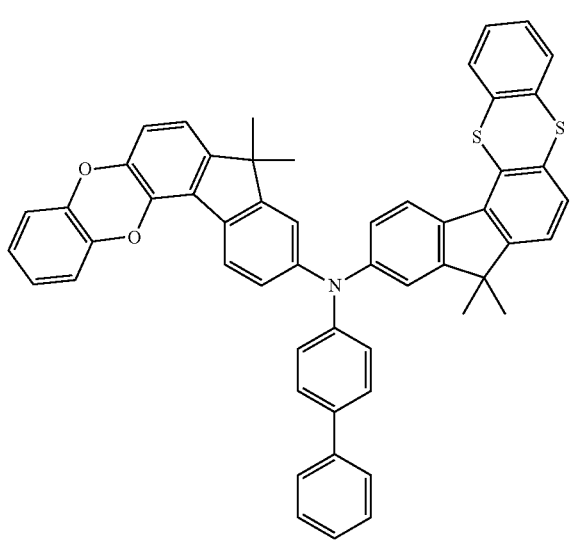
[D-12]
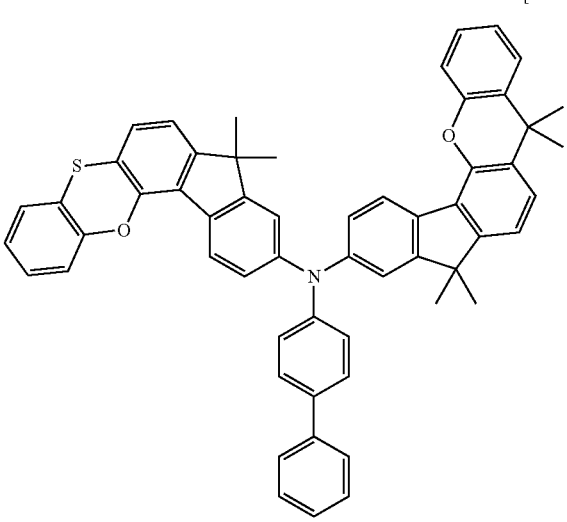
[D-10]
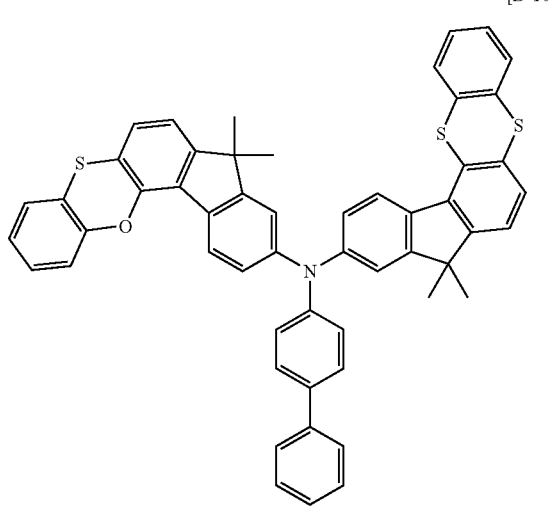
[D-13]
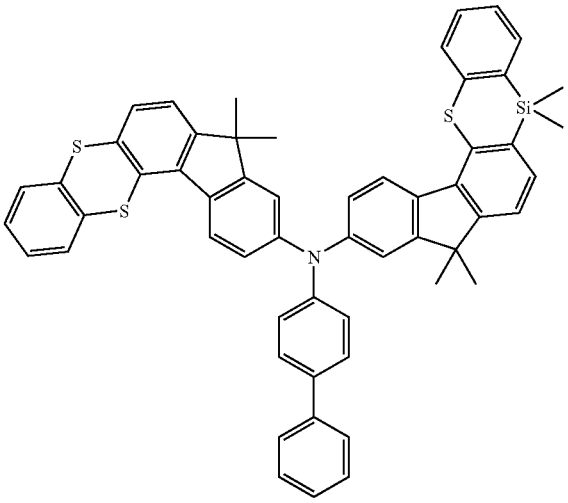

[D-13]
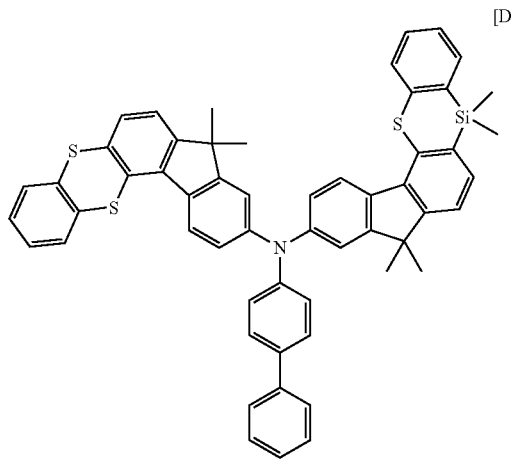
[D-17]
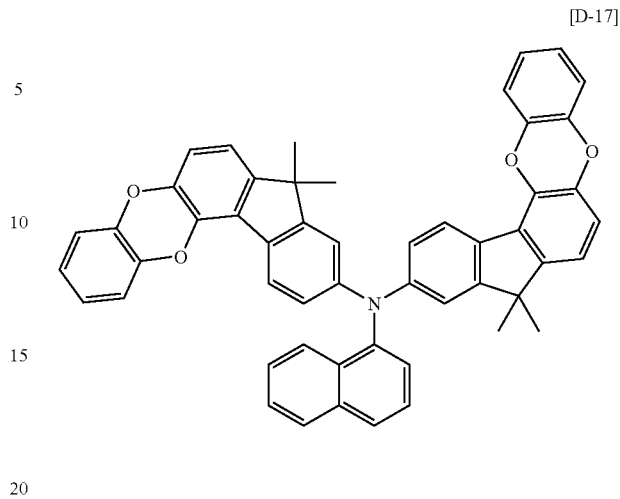
[D-15]
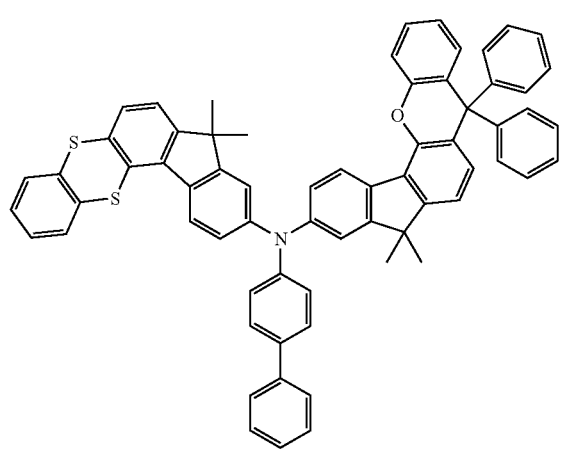
[D-18]
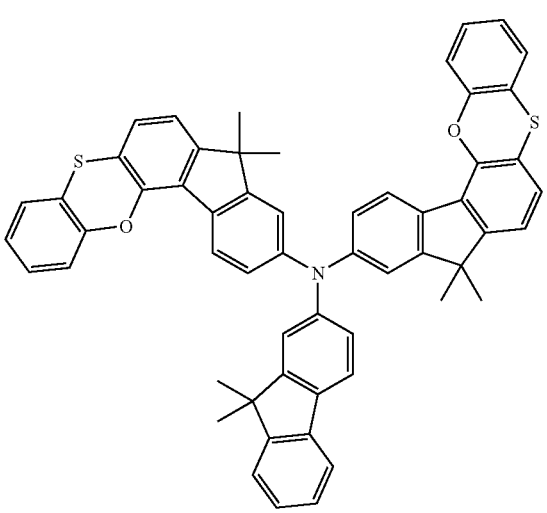
[D-16]
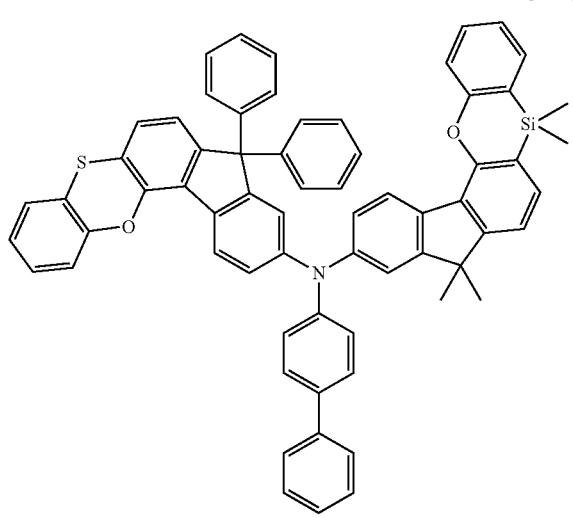
[D-19]

[D-20]
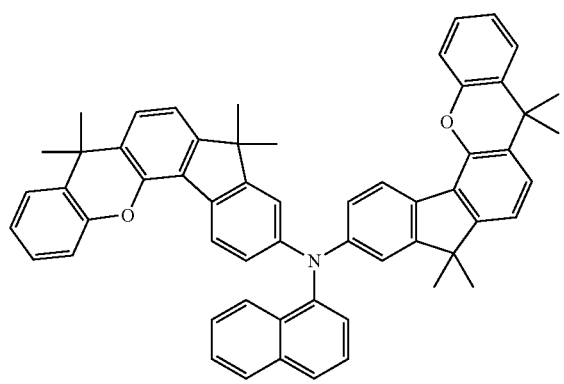
[D-23]
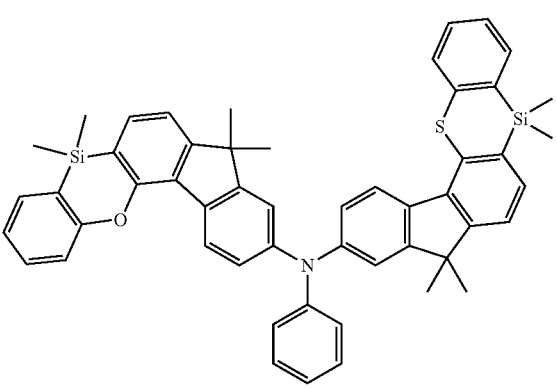
[D-21]
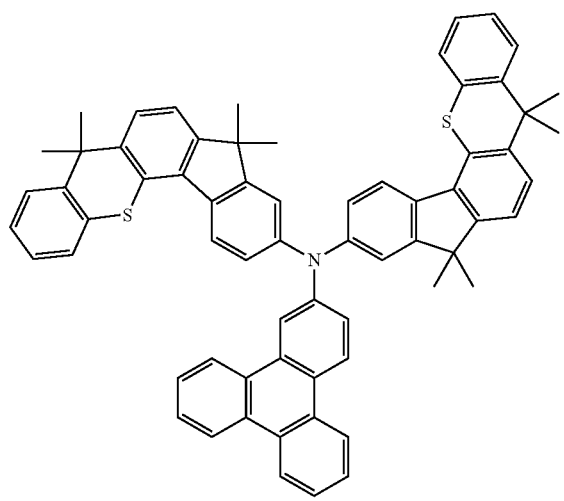
[D-24]
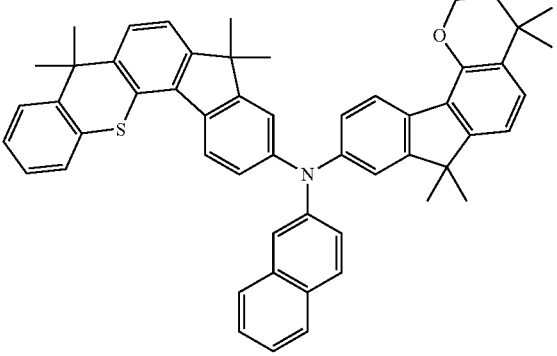
[D-22]
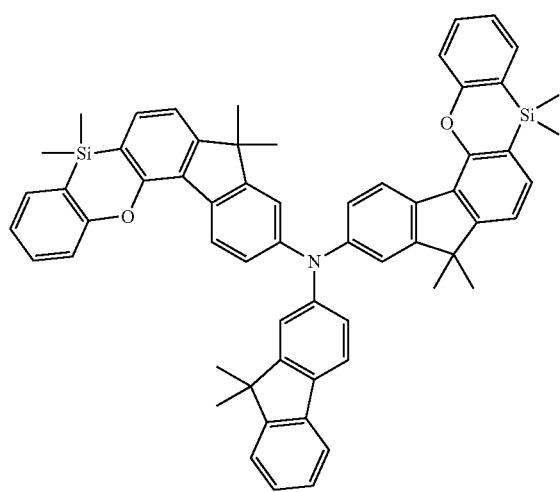
[D-25]
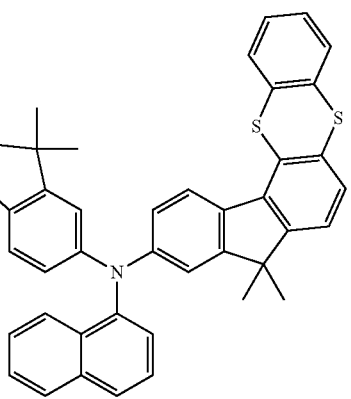

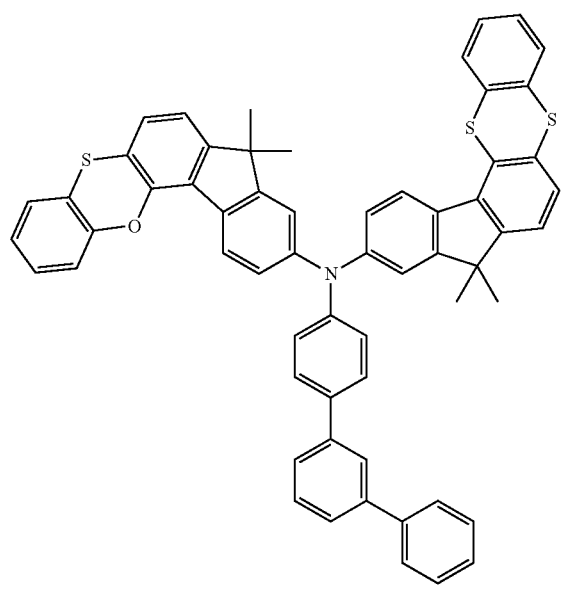
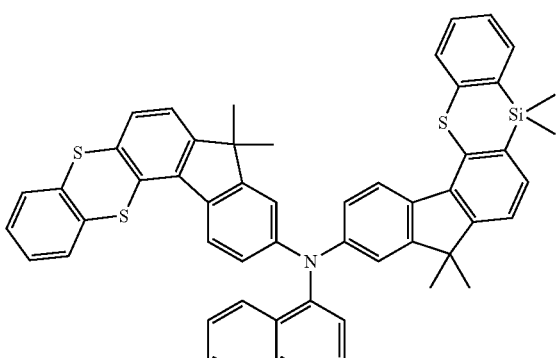

[D-33]
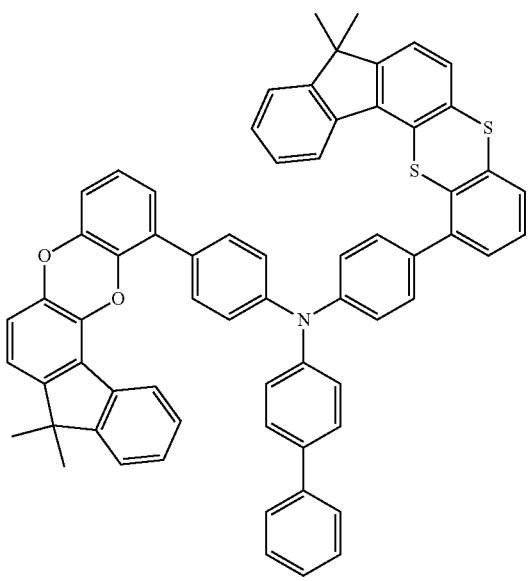
[D-35]
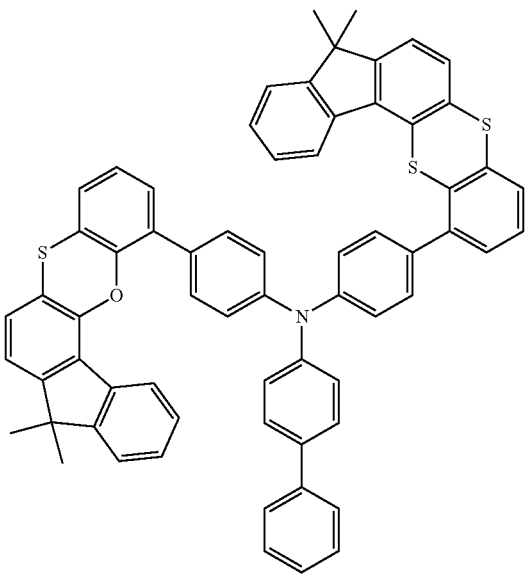
[D-34]
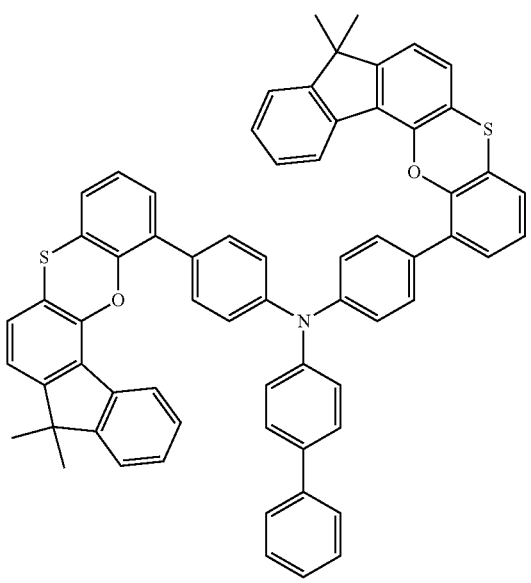
[D-36]
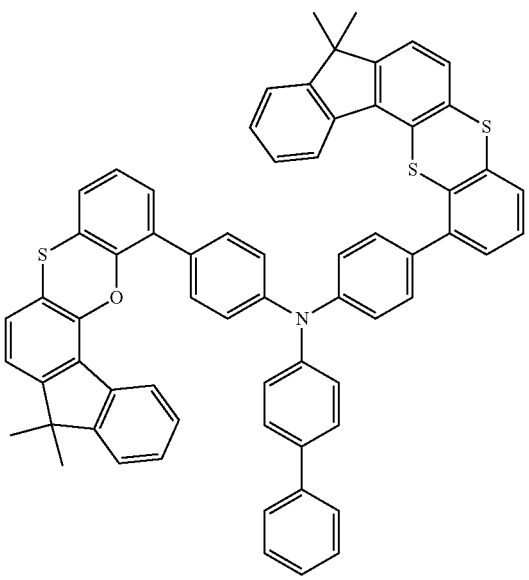

[D-37]
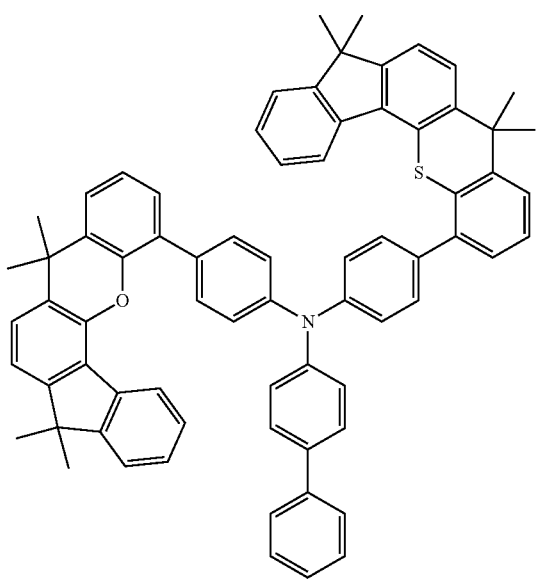
[D-38]
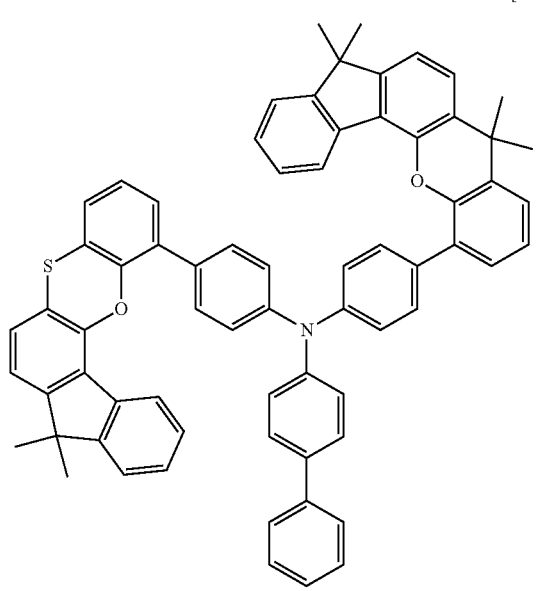
[D-39]
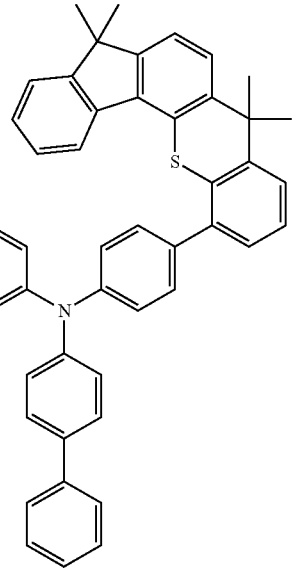
[D-40]
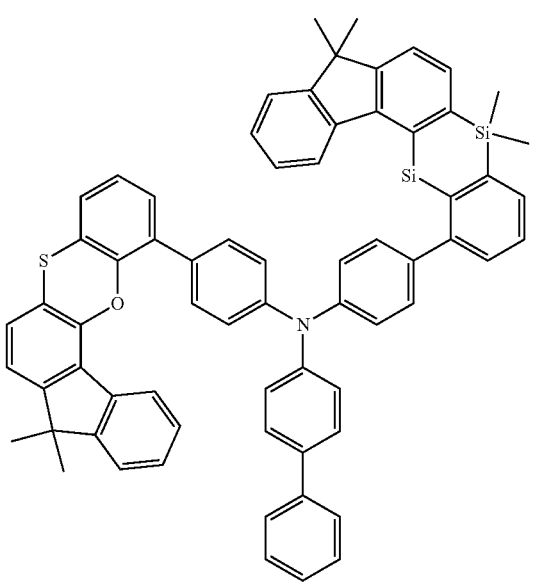
[D-41]
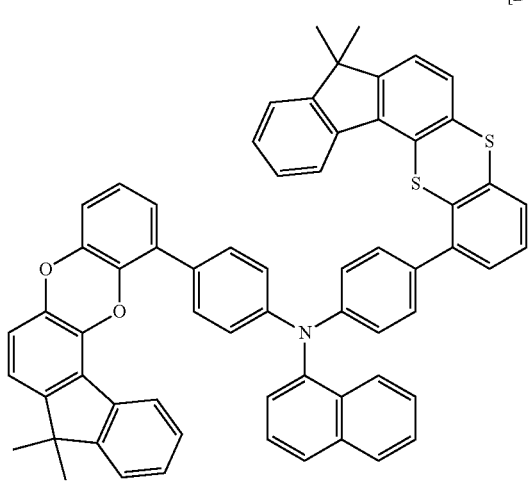

[D-42]
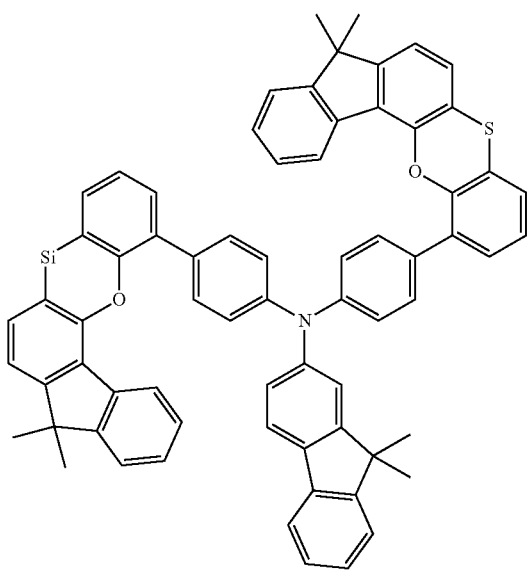
[D-43]
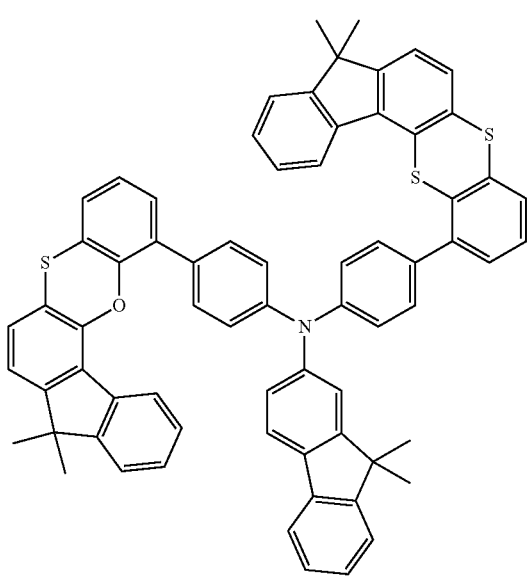
[D-44]
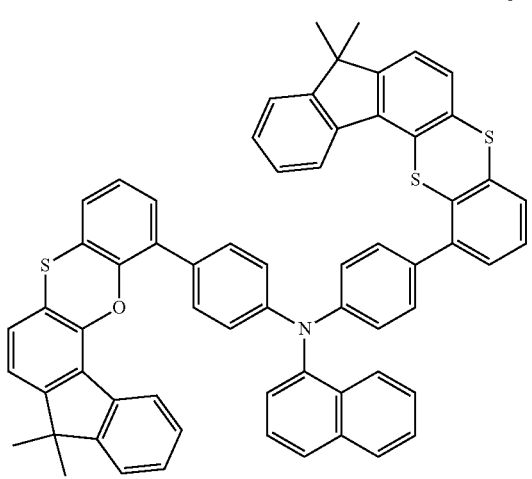
[D-45]
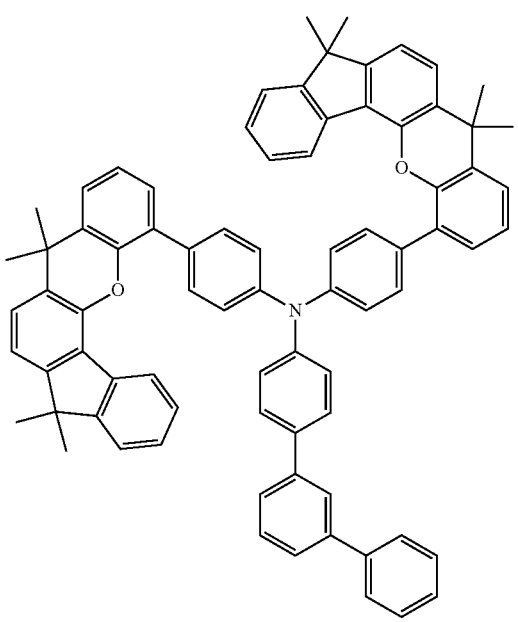
[D-46]
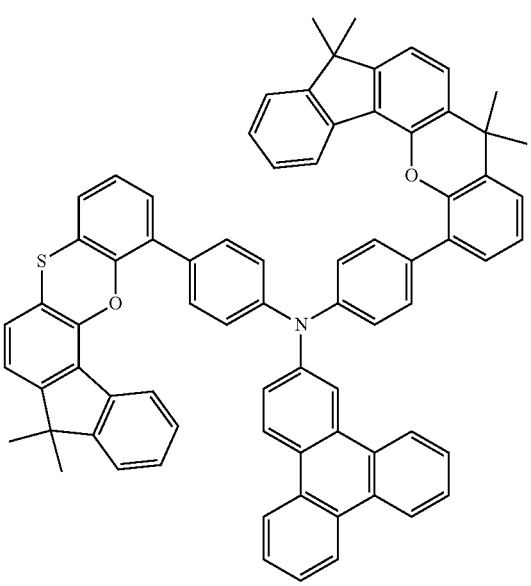

[D-47]
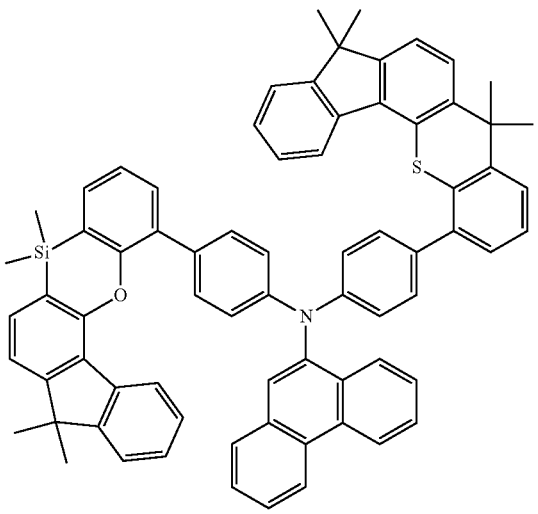
[D-48]
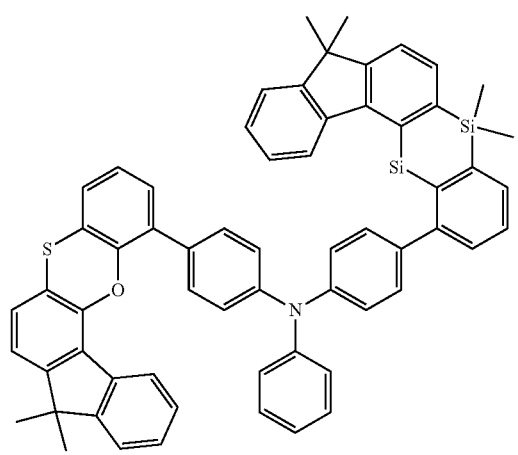
[D-49]
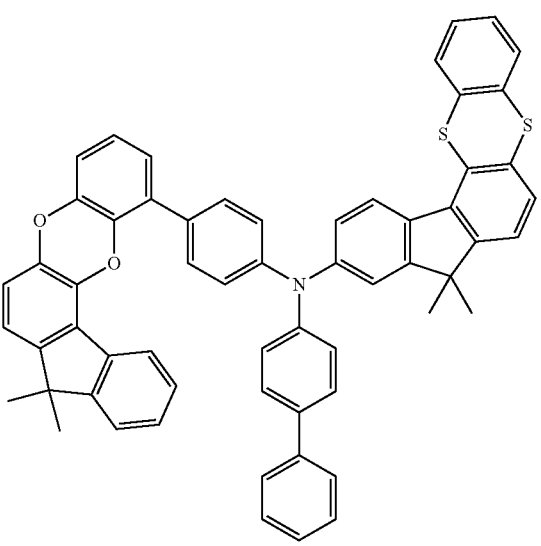
[D-50]
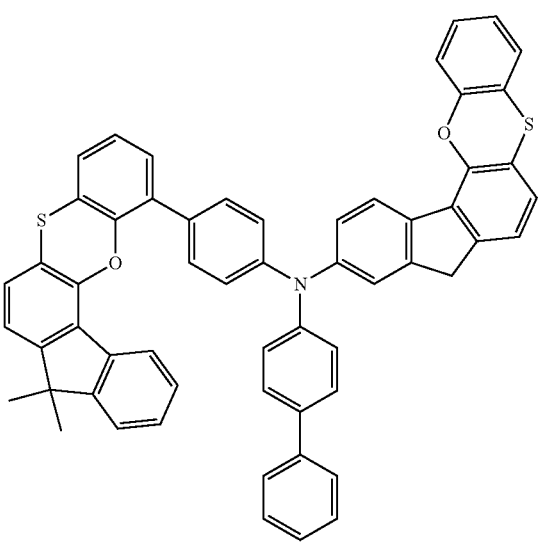
[D-51]
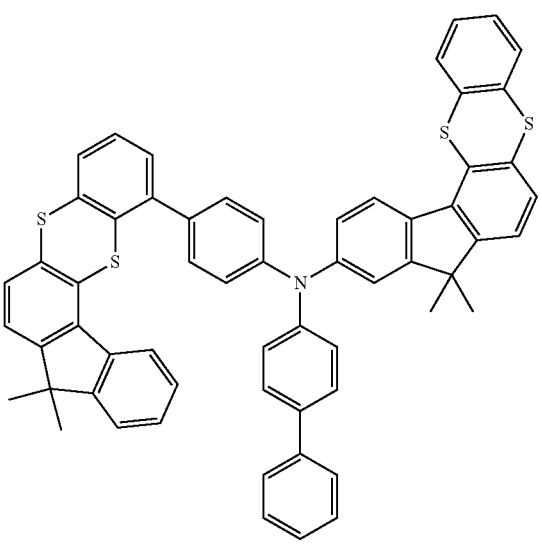
[D-52]
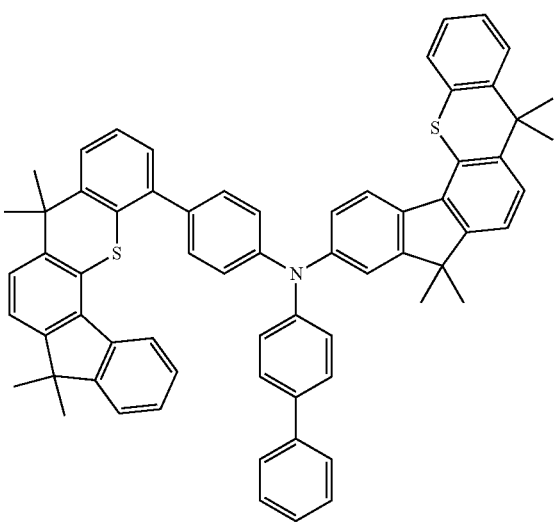

-continued
[D-53]
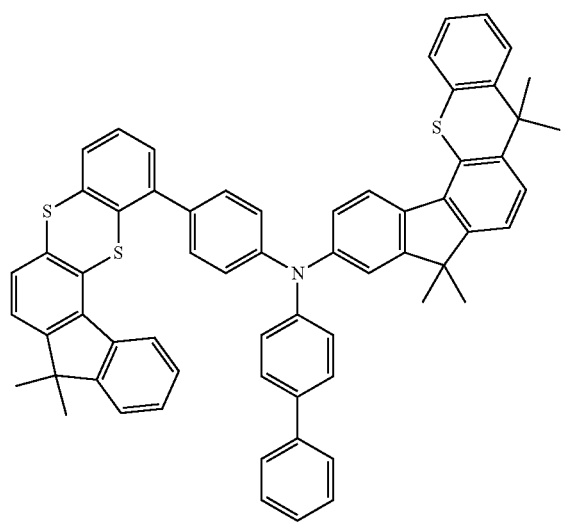
[D-54]
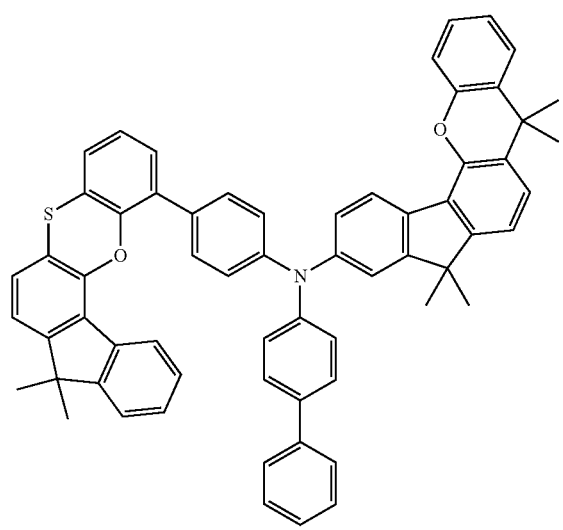
[D-55]
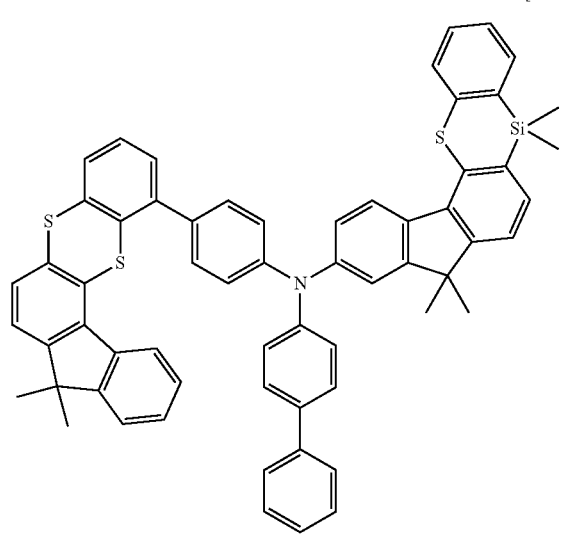
-continued
[D-56]
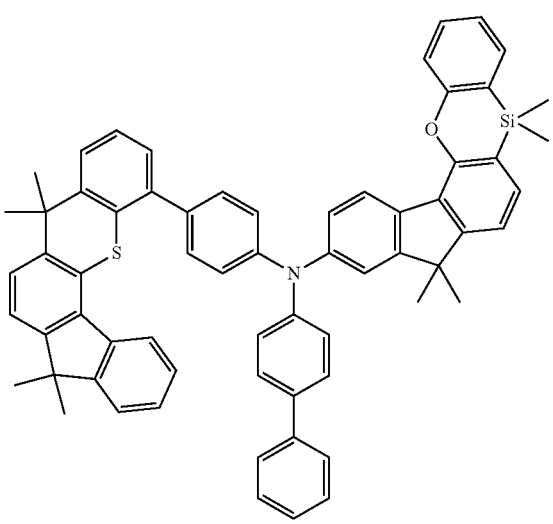
[D-57]
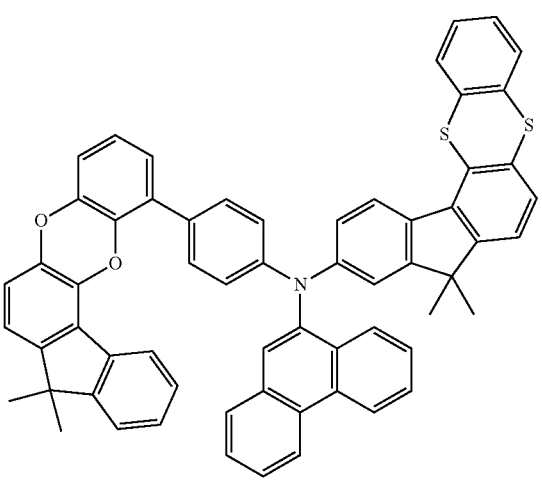
[D-58]
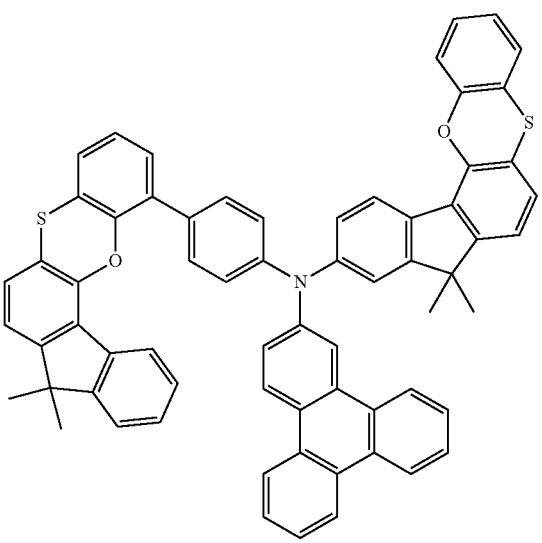

[D-59]
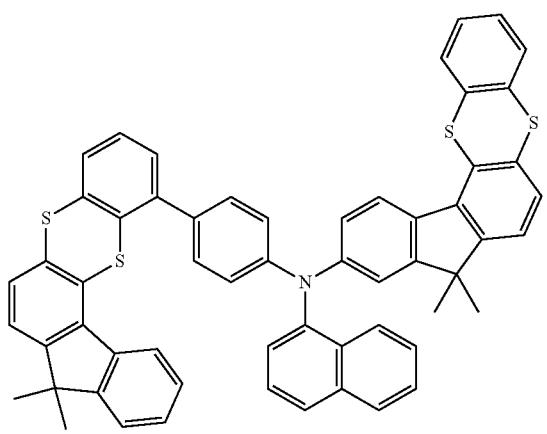
[D-60]
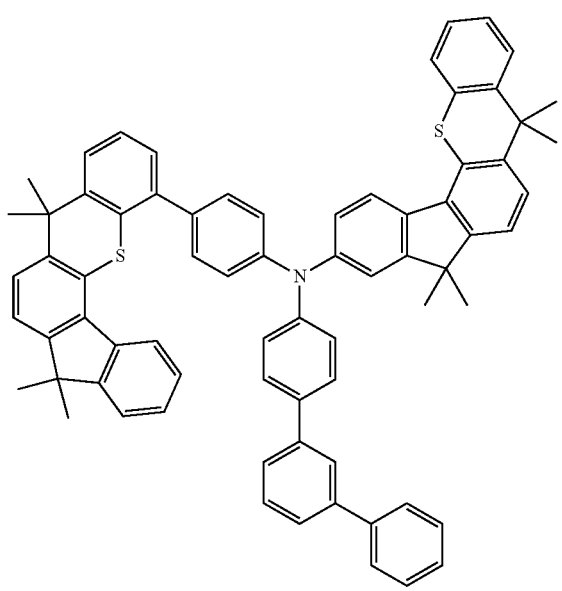
[D-61]
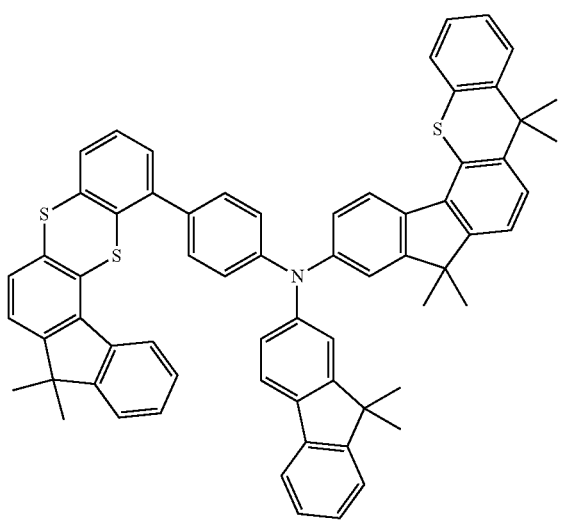
[D-62]
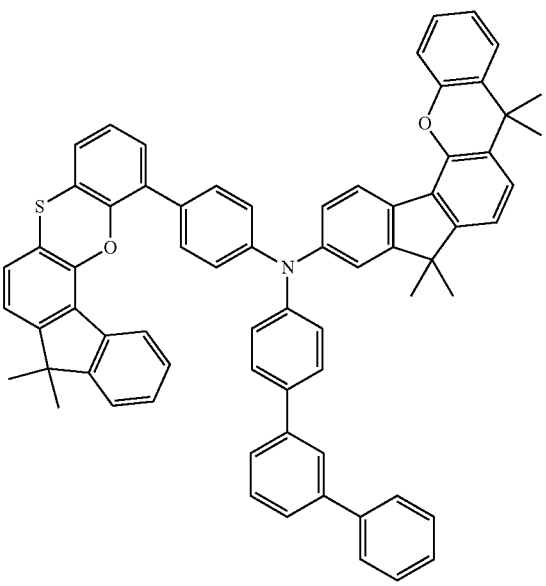
[D-63]
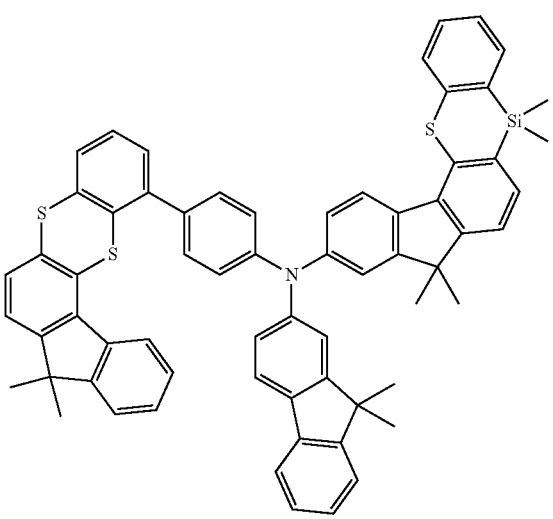
[D-64]
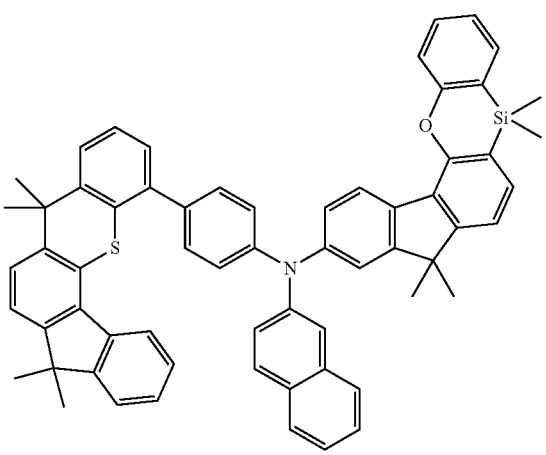

More specifically, the compound for an organic optoelectronic device may be represented by one of the following Chemical Formulae E-1 to E-192, but is not limited thereto.
[E-1]
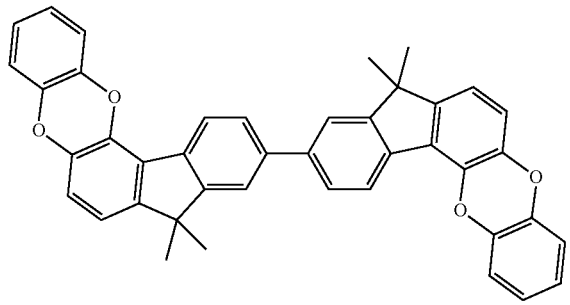
[E-2]
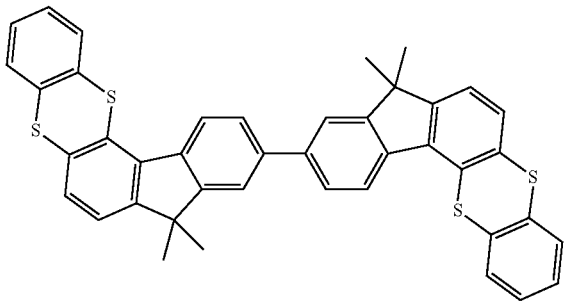
[E-3]
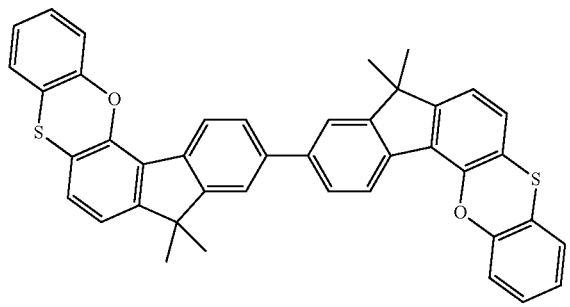
[E-4]
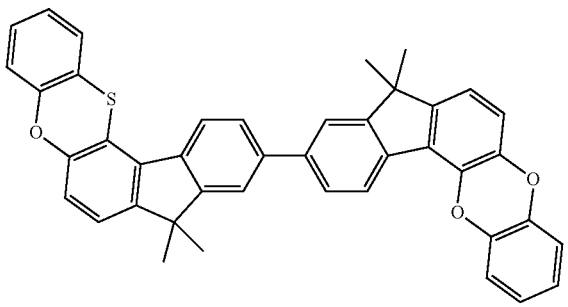
[E-5]
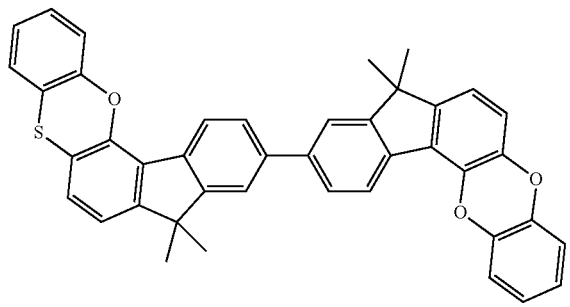
[E-6]
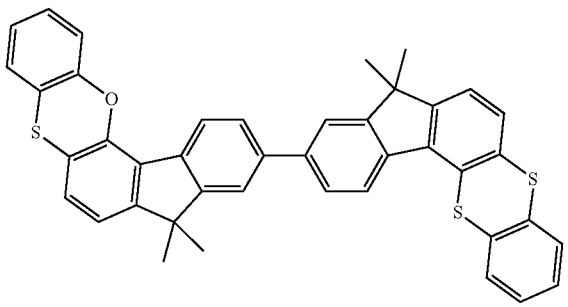
[E-7]
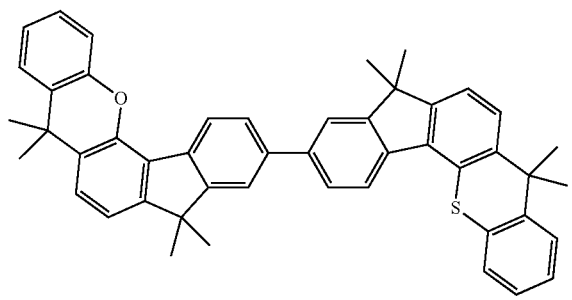
[E-8]
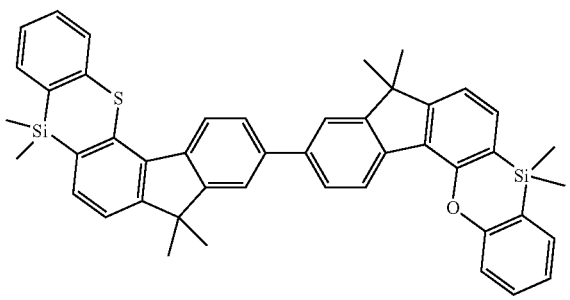

-continued
[E-9]
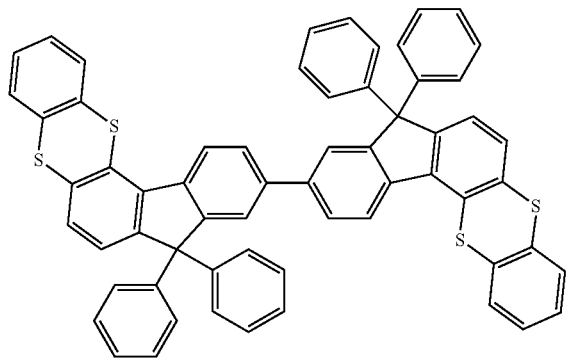
[E-10]
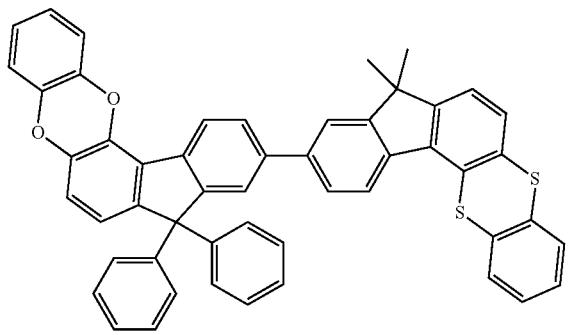
[E-11]
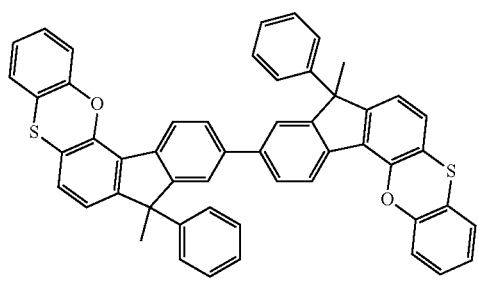
[E-12]
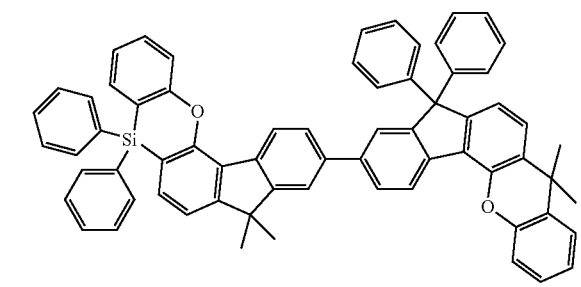
[E-13]
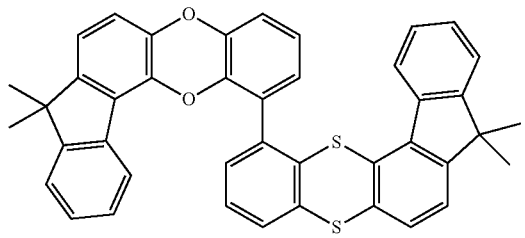
[E-14]
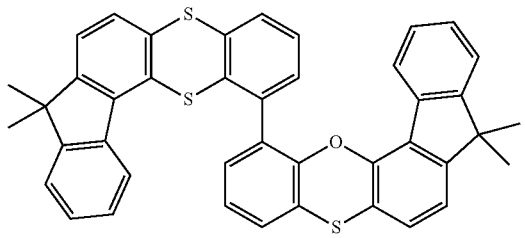
[E-15]
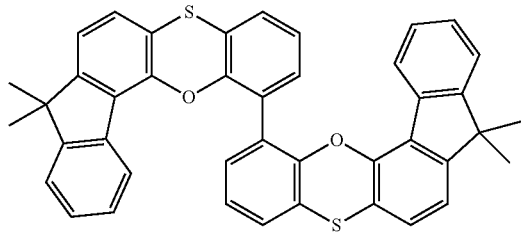
[E-16]
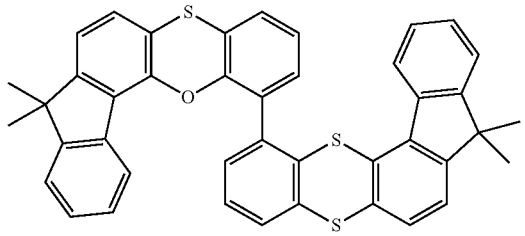
[E-17]
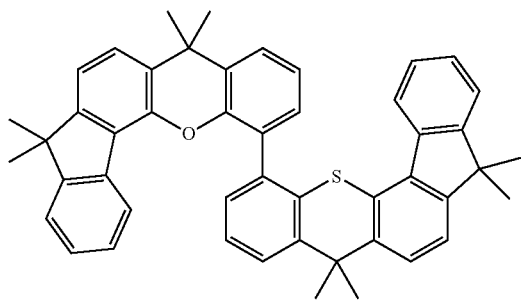
[E-18]
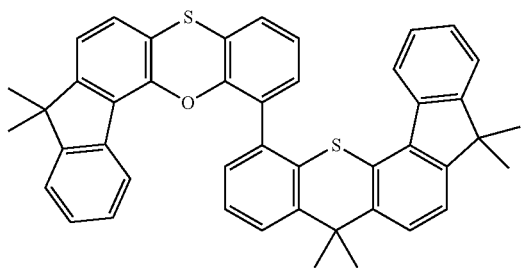

-continued
[E-19]
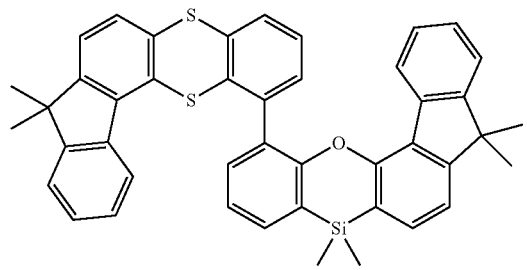
[E-20]
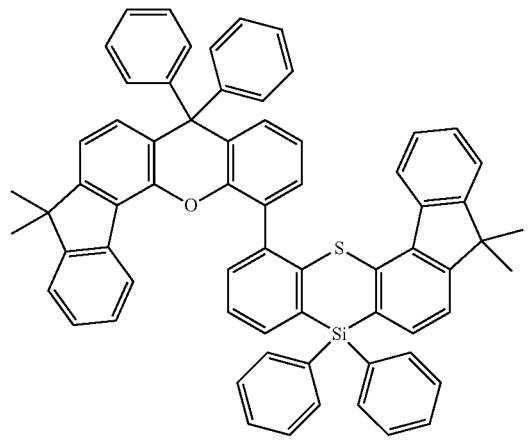
[E-21]
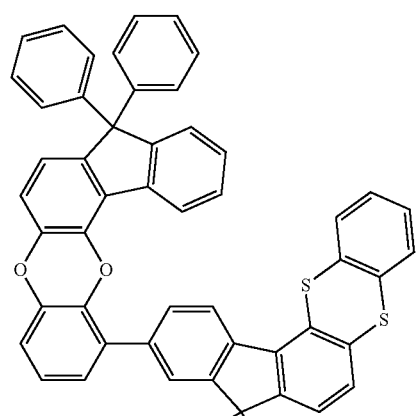
[E-22]
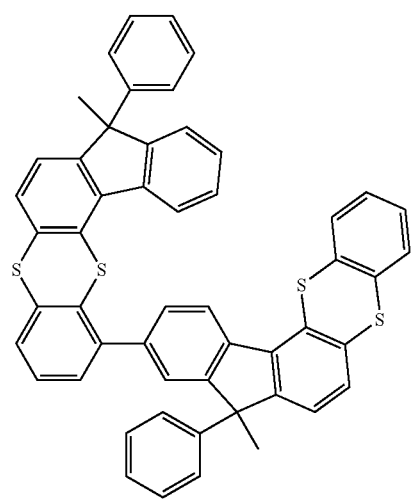
[E-23]
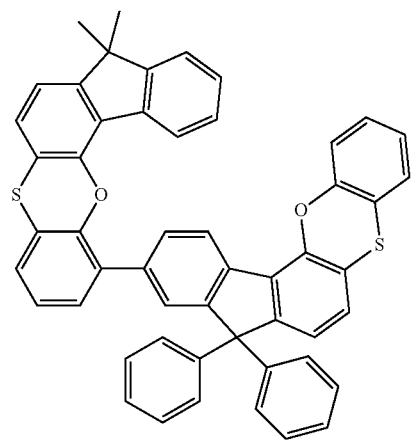
[E-24]
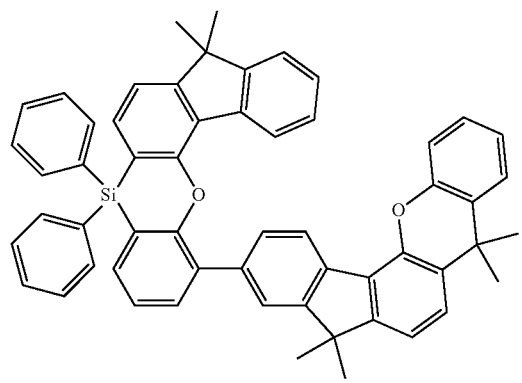

-continued
[E-25]
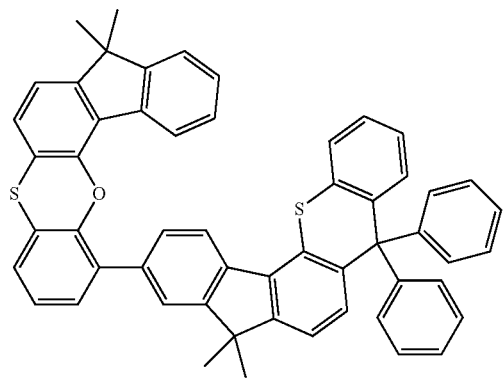
[E-26]
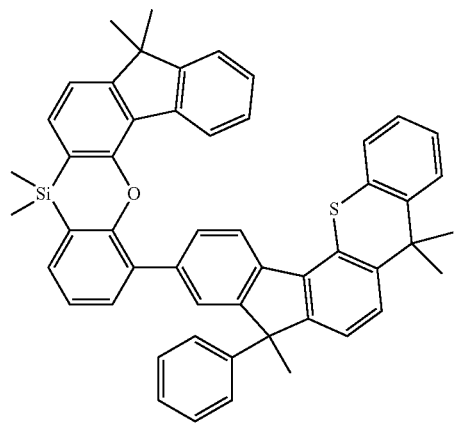
[E-27]
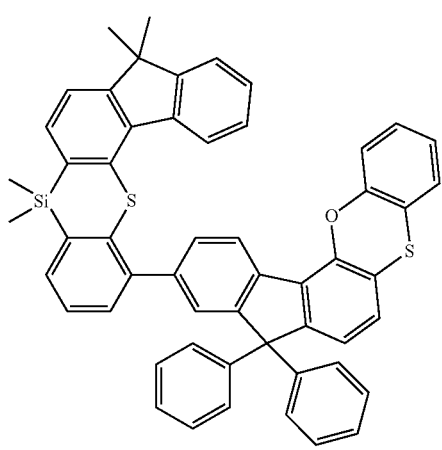
[E-28]
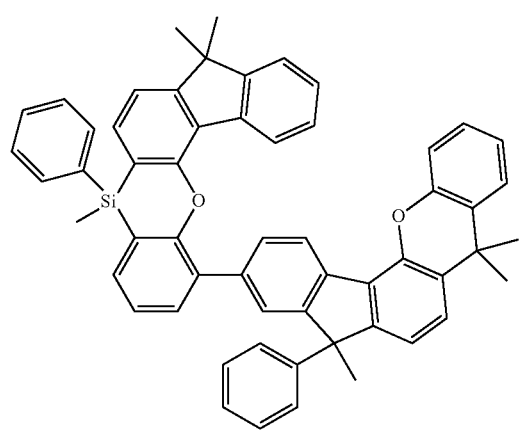
[E-29]
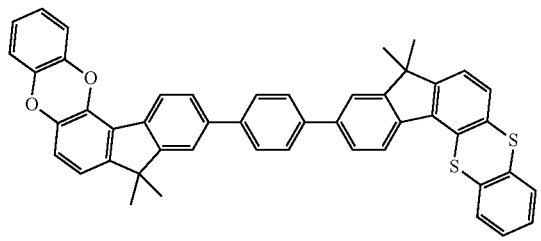
[E-30]
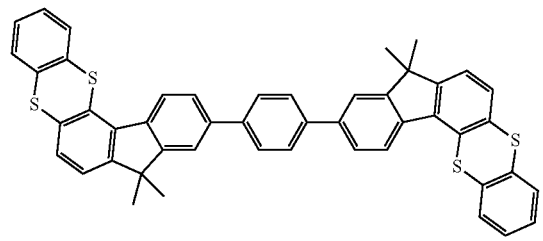
[E-31]
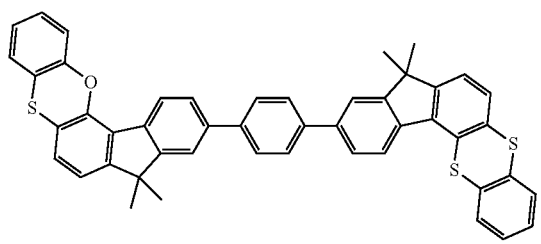
[E-32]
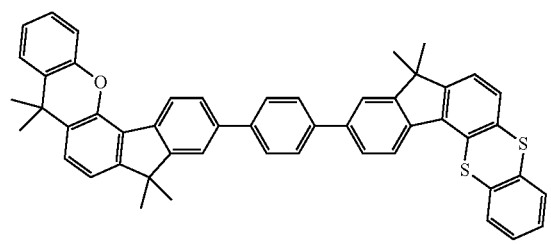

-continued
[E-33]
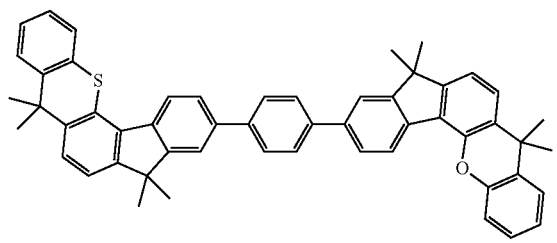
[E-34]
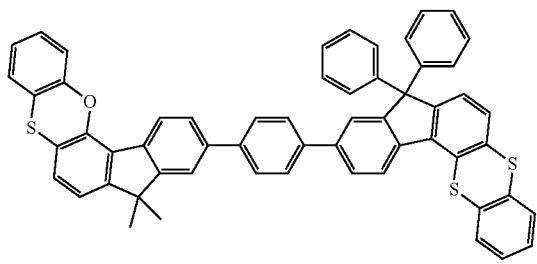
[E-35]
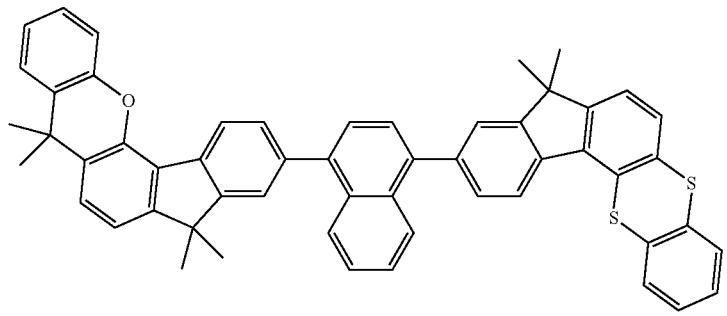
[E-36]
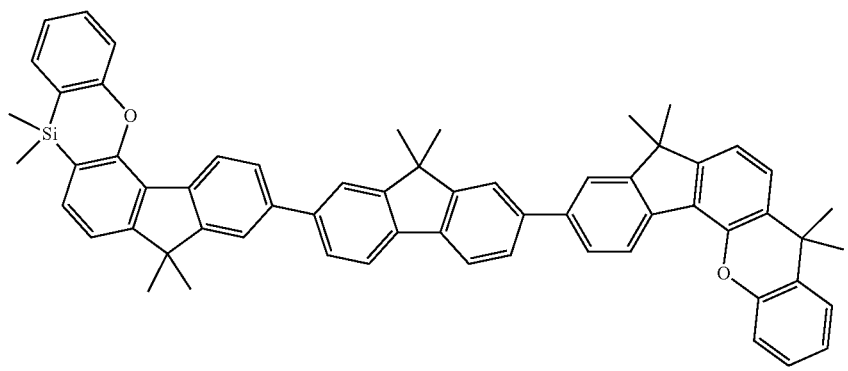
[E-37]
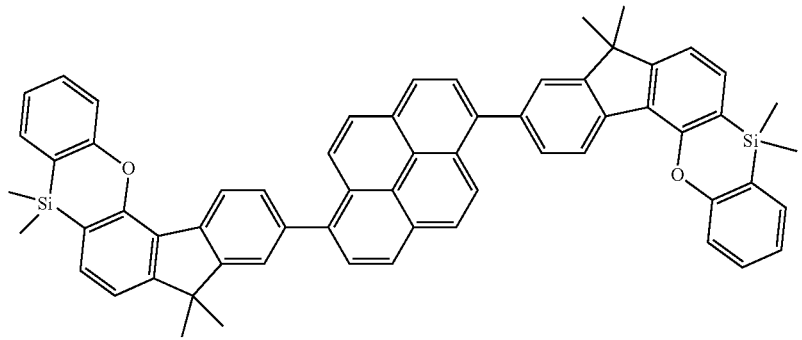
[E-38]
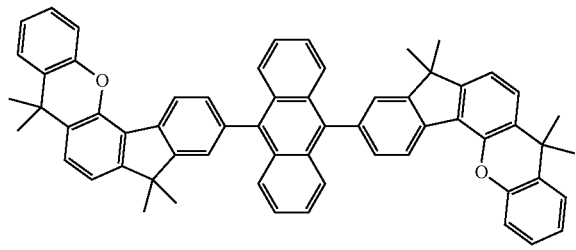
[E-39]
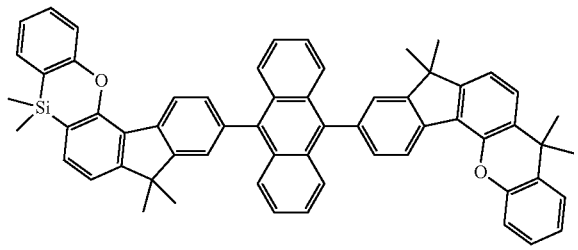

-continued
[E-40]
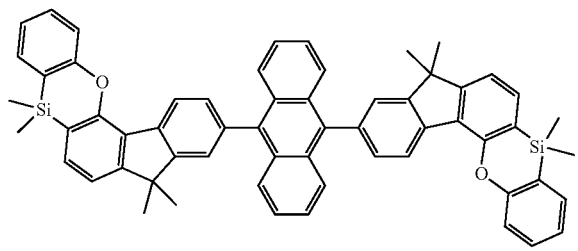
[E-41]
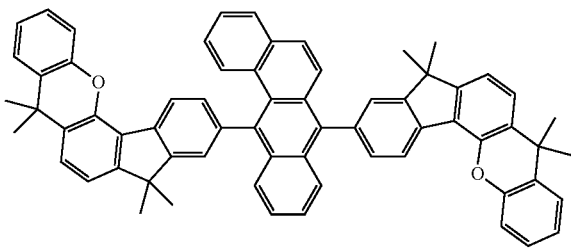
[E-42]
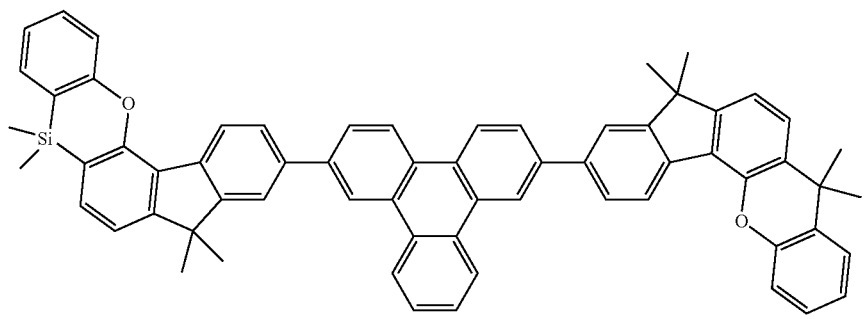
[E-43]
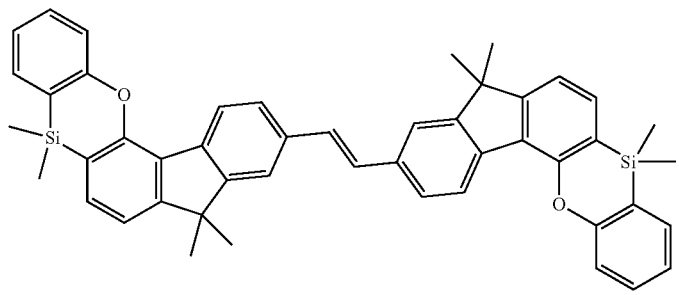
[E-44]
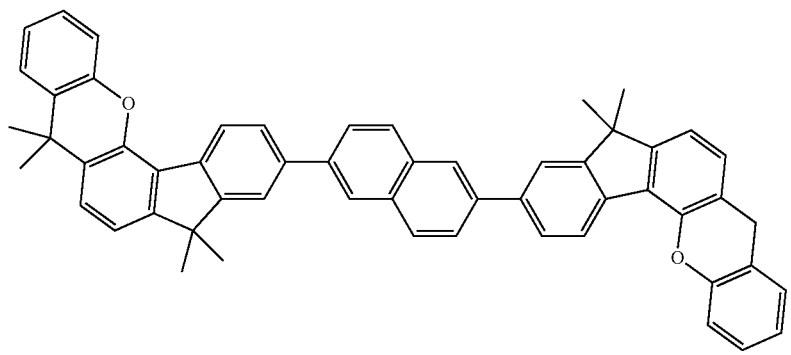
[E-45]
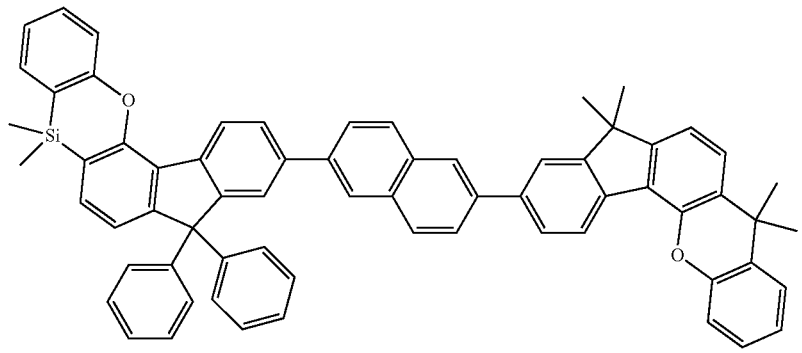

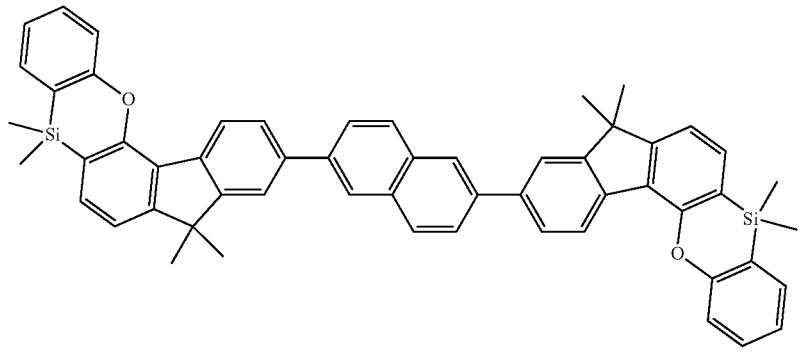
[E-46]
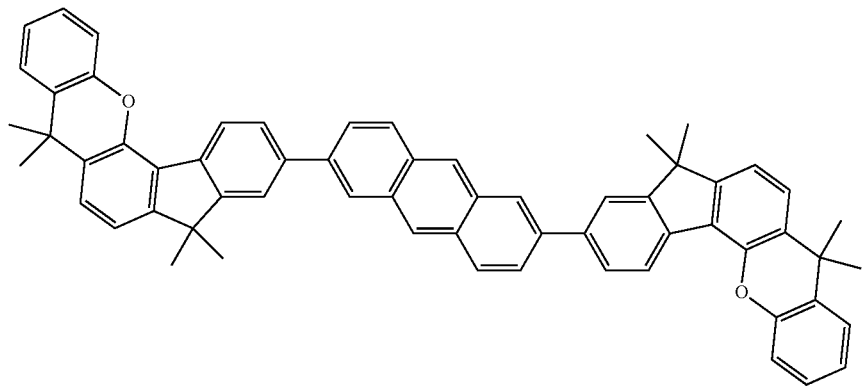
[E-47]
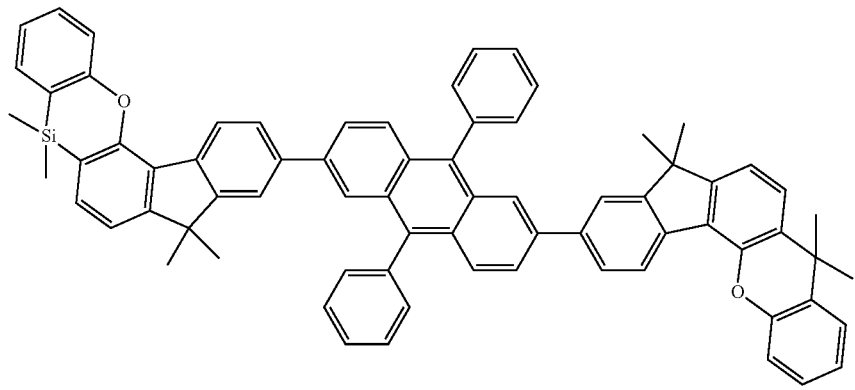
[E-48]
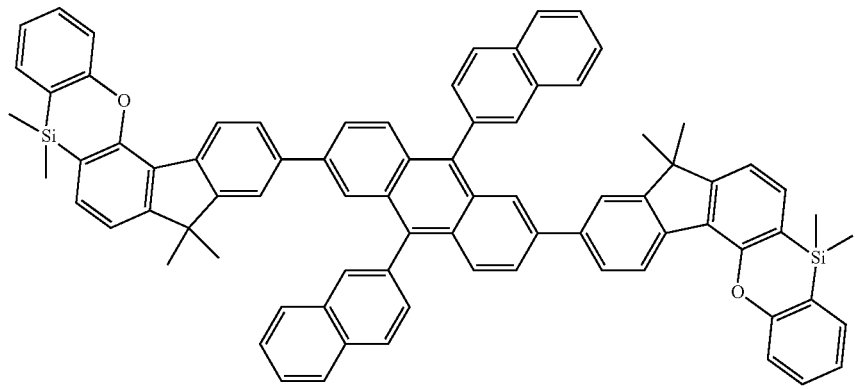
[E-49]

-continued
[E-50]
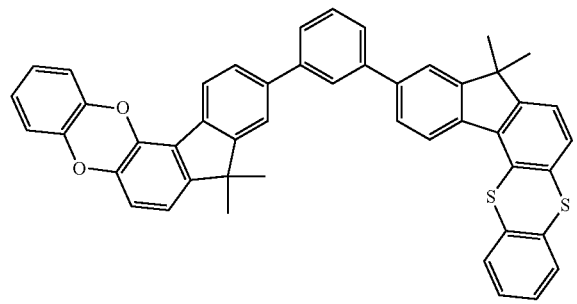
[E-51]
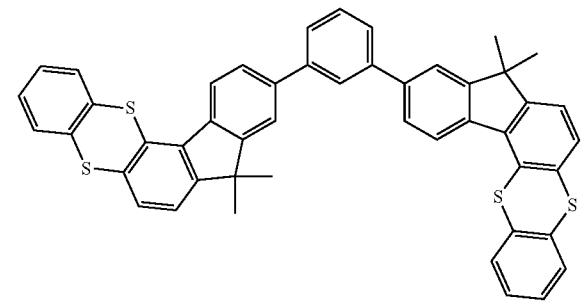
[E-52]
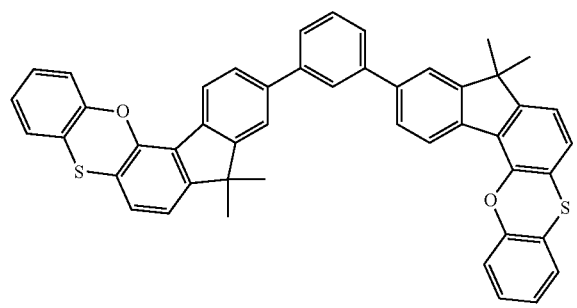
[E-53]
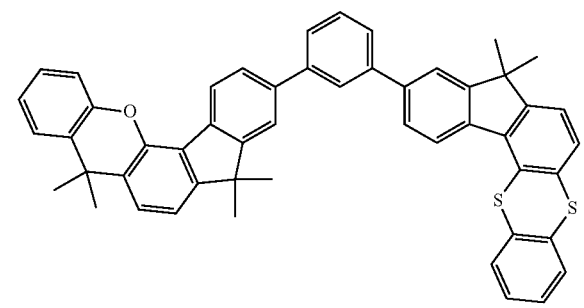
[E-54]
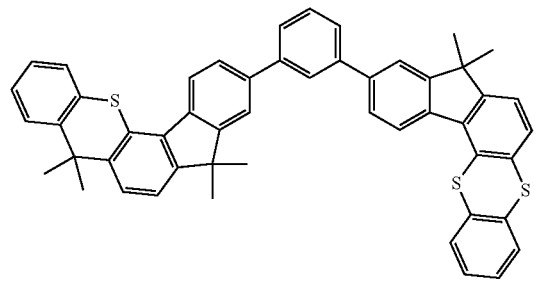
[E-55]
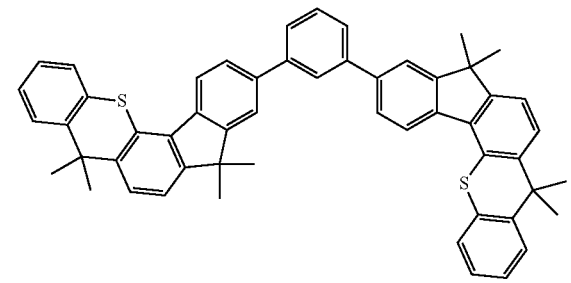
[E-56]
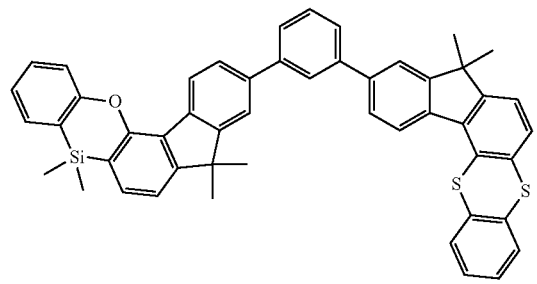
[E-57]
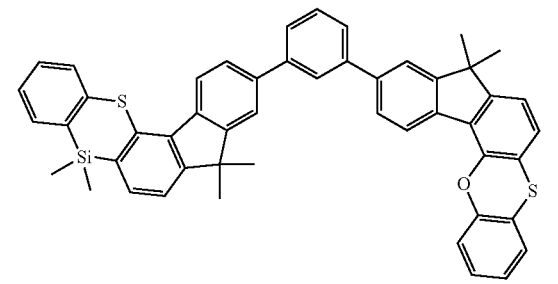
[E-58]
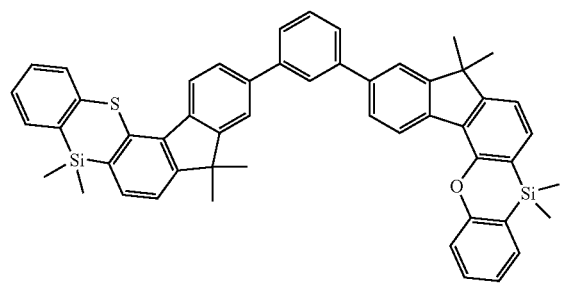
[E-59]
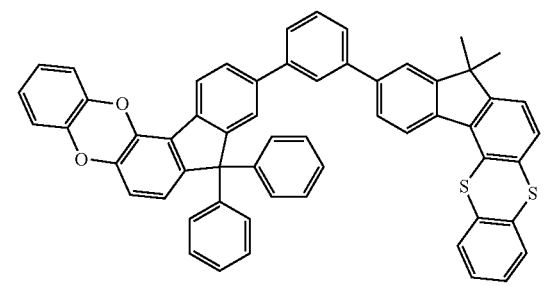

-continued
[E-60]
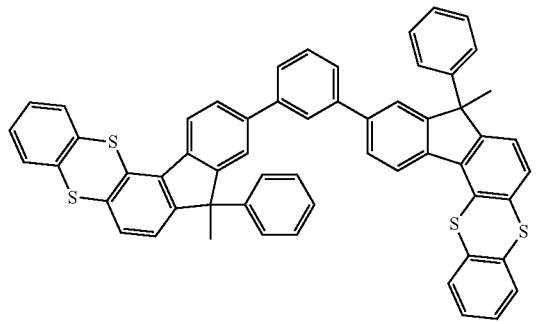
[E-61]
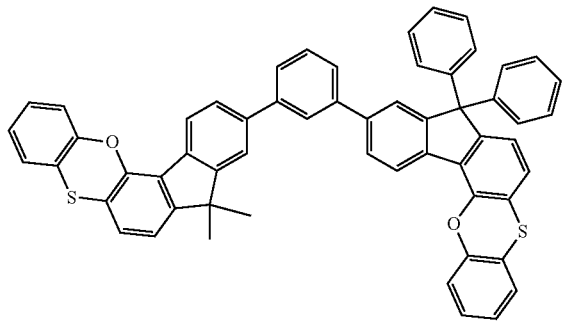
[E-62]
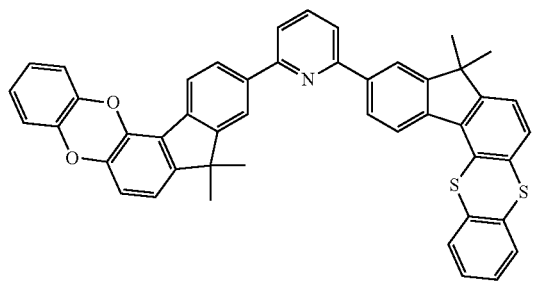
[E-63]
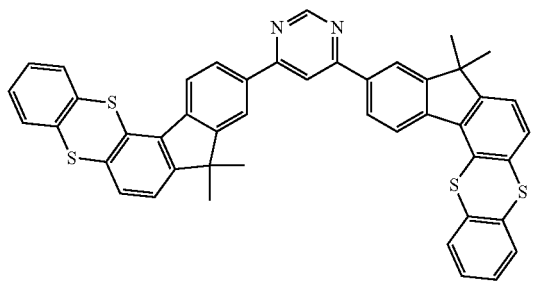
[E-64]
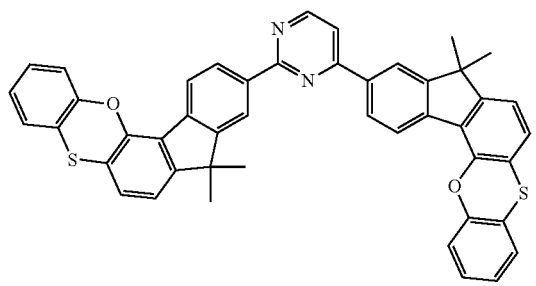
[E-65]
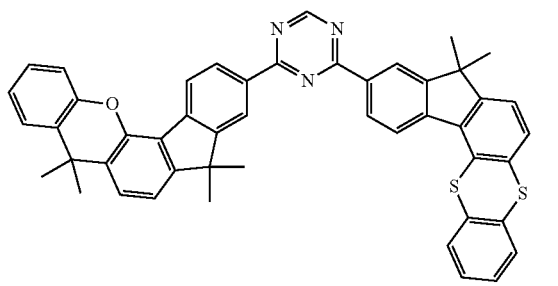
[E-66]
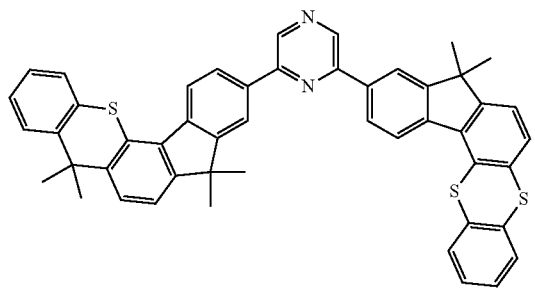
[E-67]
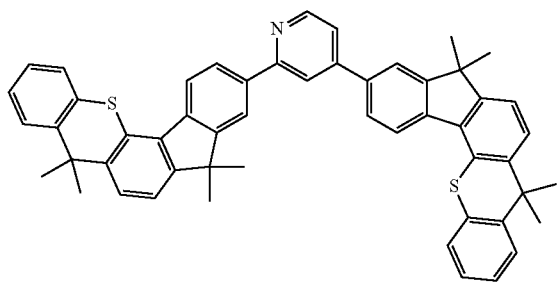

-continued
[E-68]
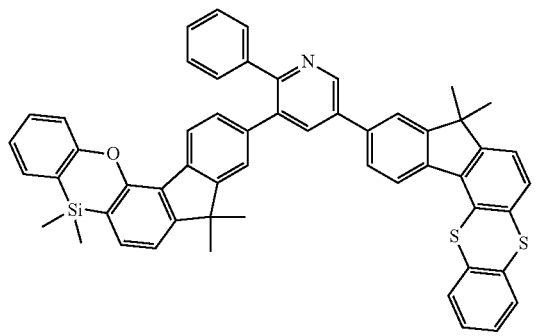
[E-69]
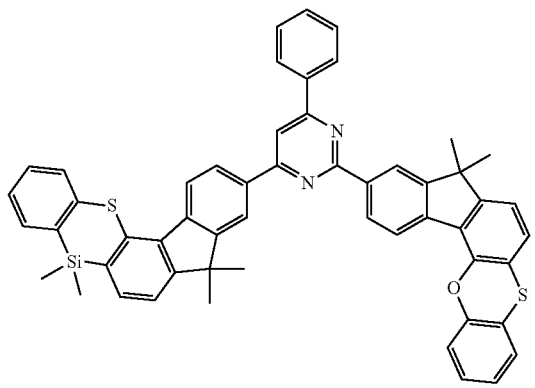
[E-70]
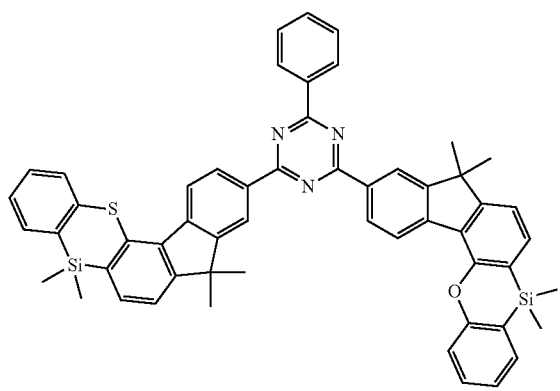
[E-71]
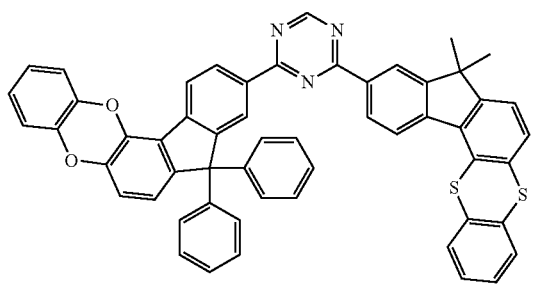
[E-72]
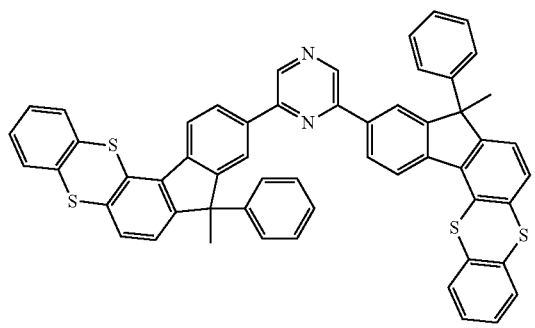
[E-73]
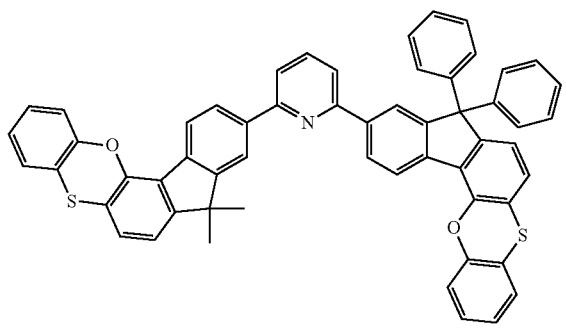
[E-74]
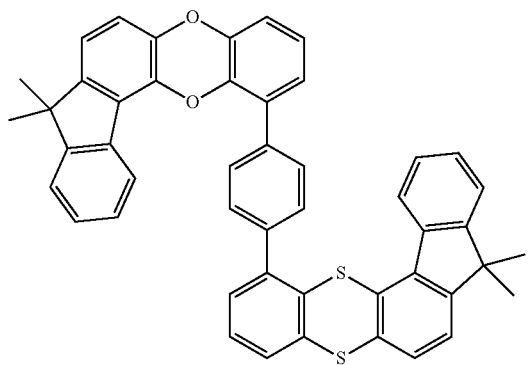
[E-75]
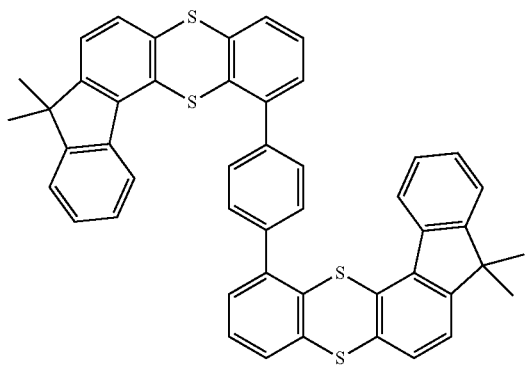

-continued
[E-76]
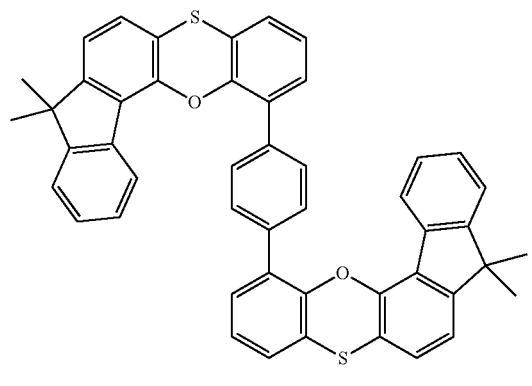
[E-77]
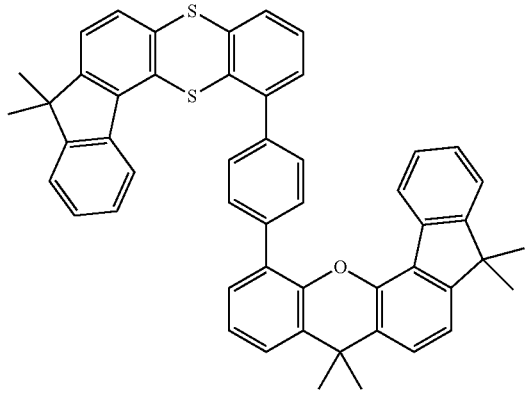
[E-78]
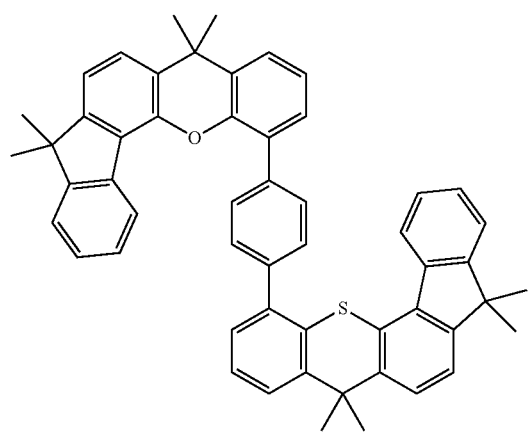
[E-79]
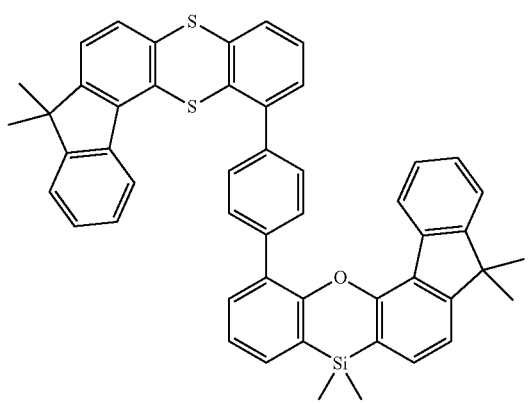
[E-80]
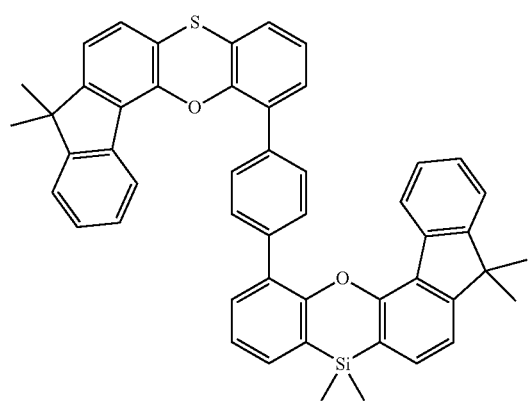
[E-81]
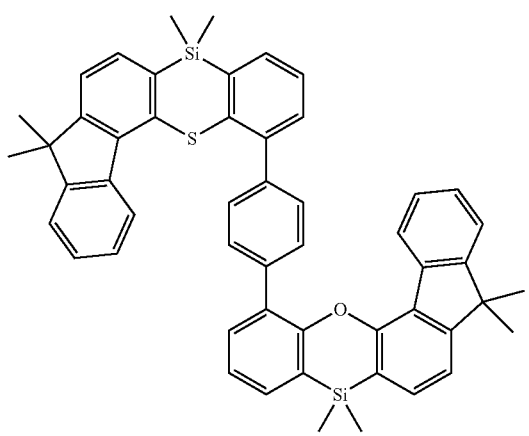

-continued
[E-82]
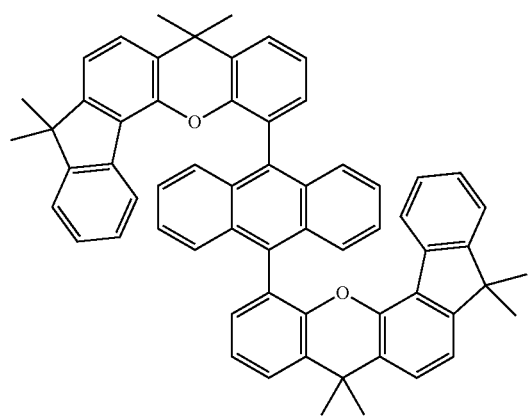
[E-83]
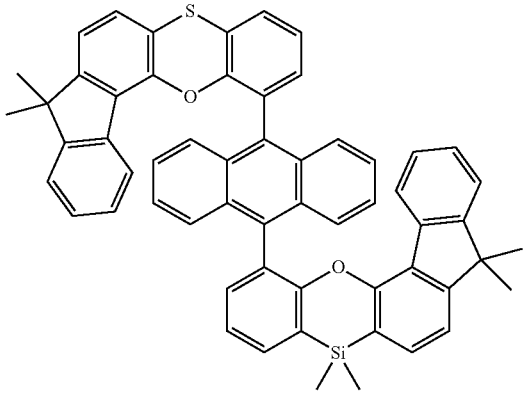
[E-84]
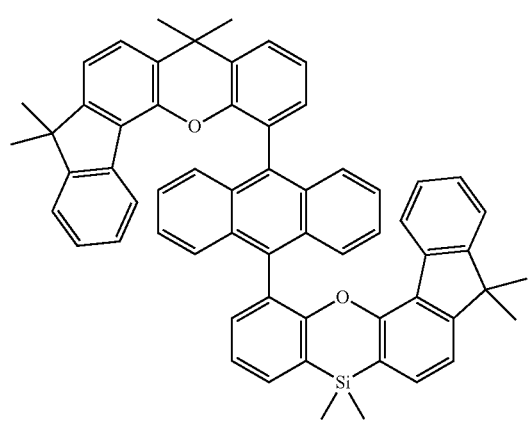
[E-85]
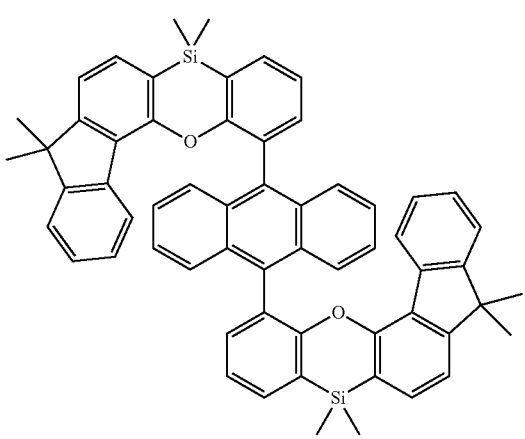
[E-86]
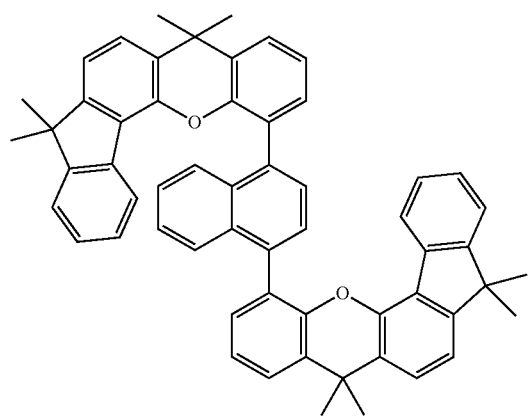
[E-87]
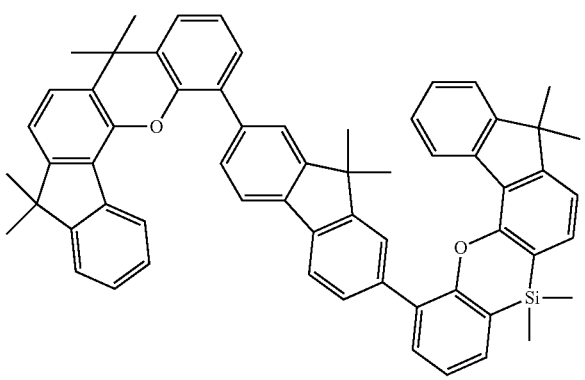

-continued
[E-88]
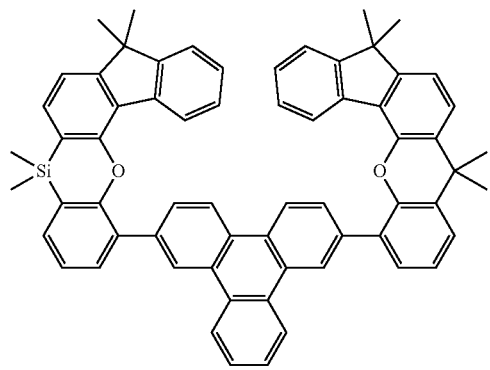
[E-89]
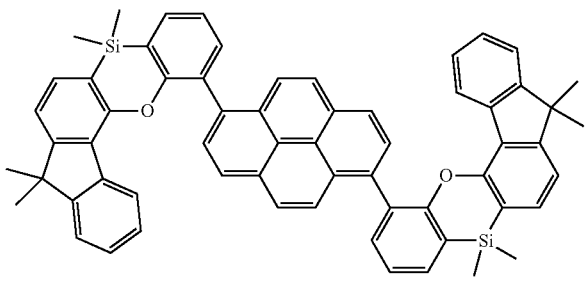
[E-90]
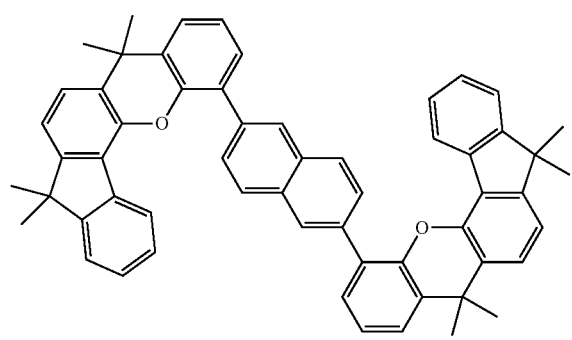
[E-91]
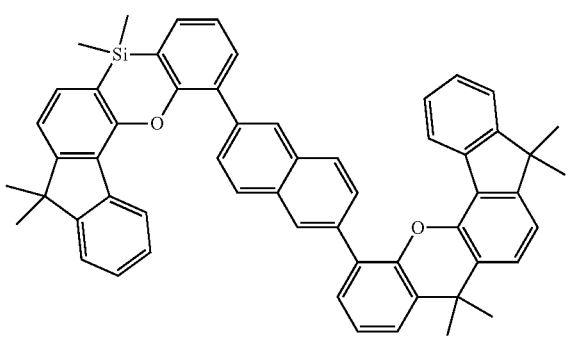
[E-92]
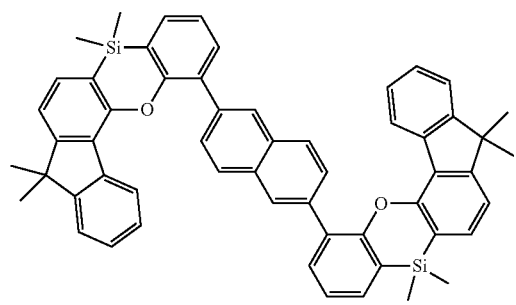
[E-93]
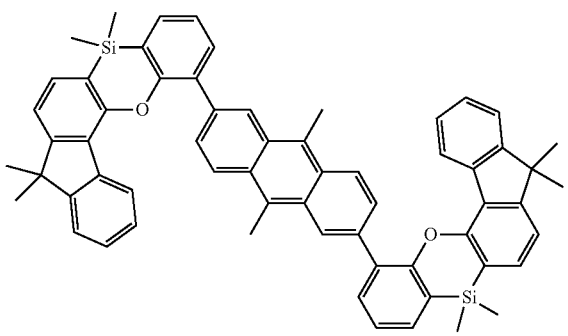
[E-94]
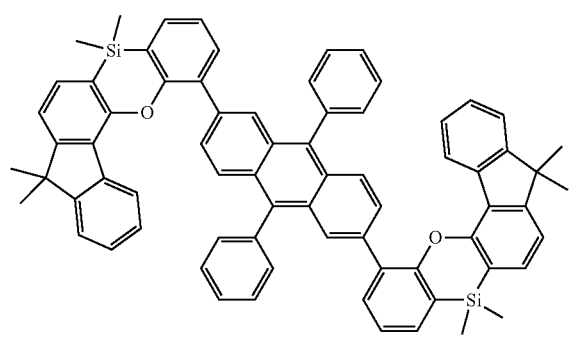
[E-95]
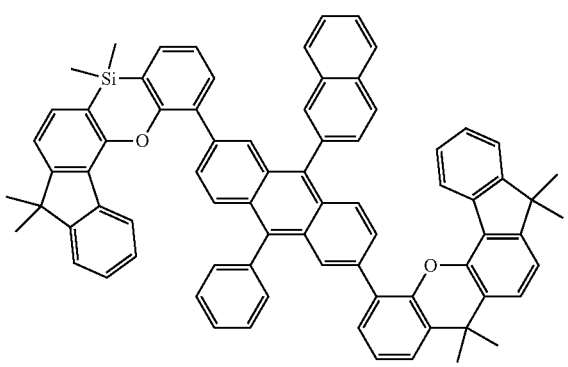

-continued
[E-96]
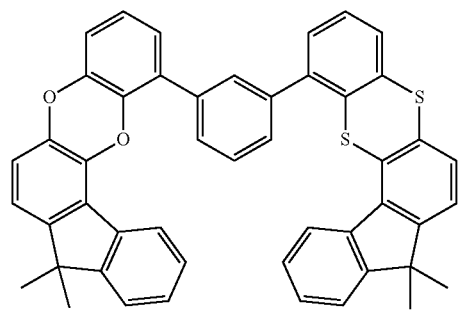
[E-97]
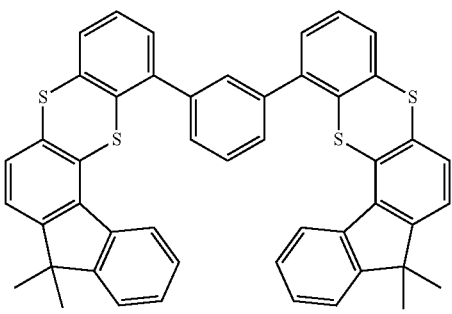
[E-98]
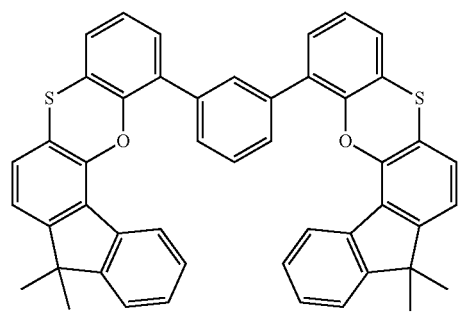
[E-99]
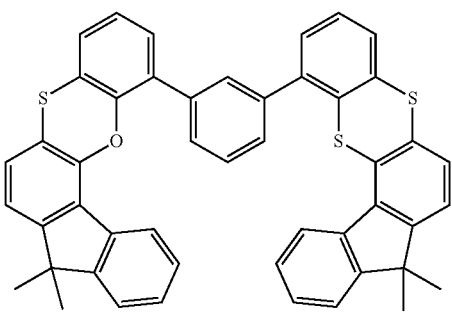
[E-100]
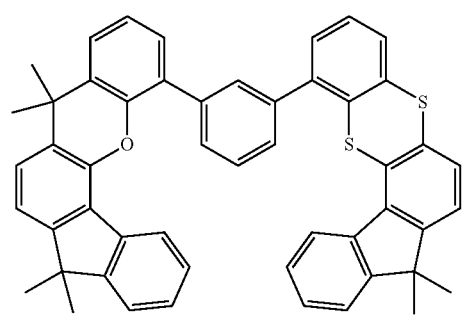
[E-101]
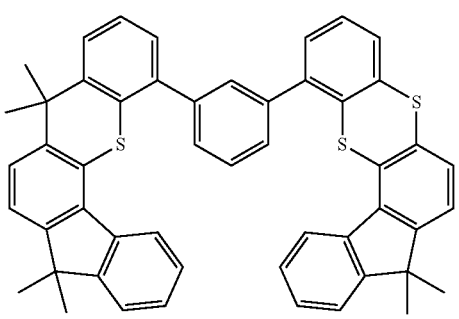
[E-102]
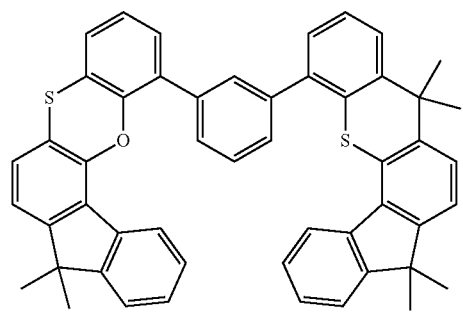
[E-103]
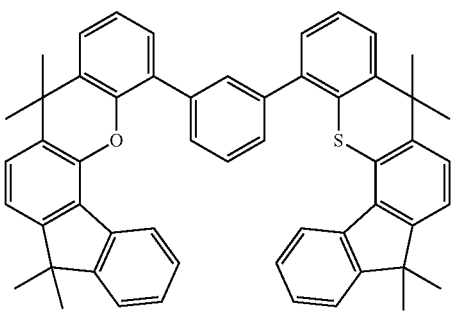
[E-104]
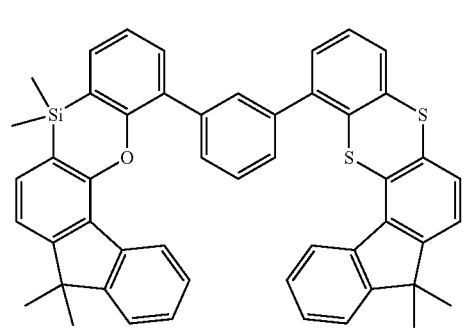
[E-105]
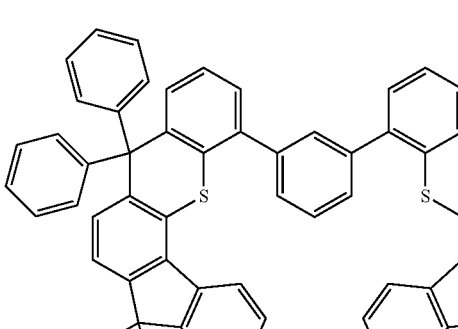

-continued
[E-106]
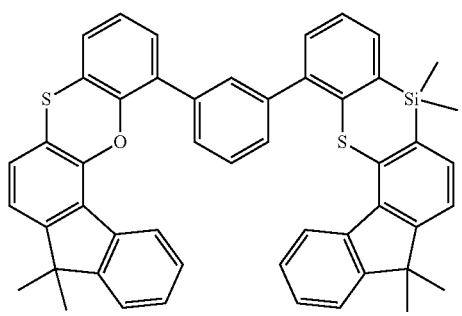
[E-107]
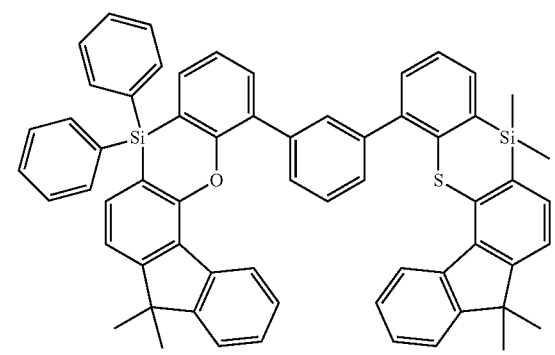
[E-108]
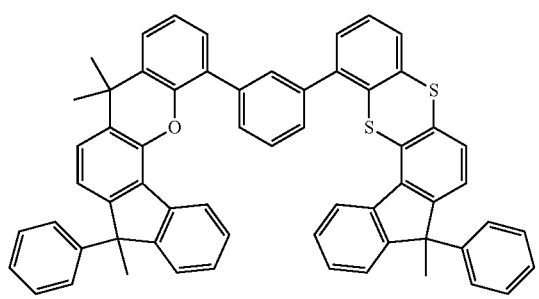
[E-109]
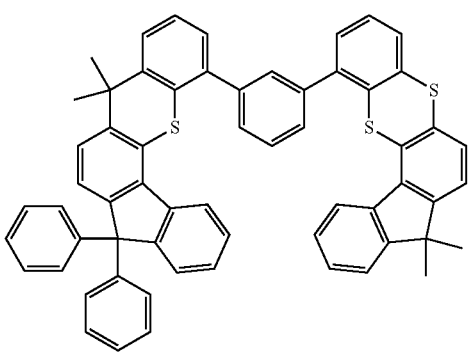
[E-110]
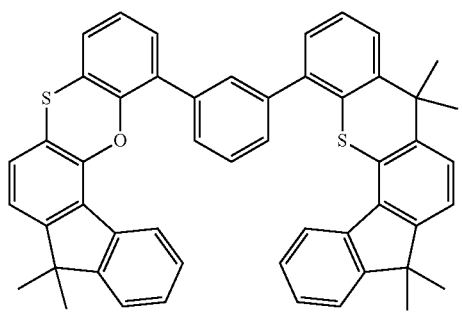
[E-111]
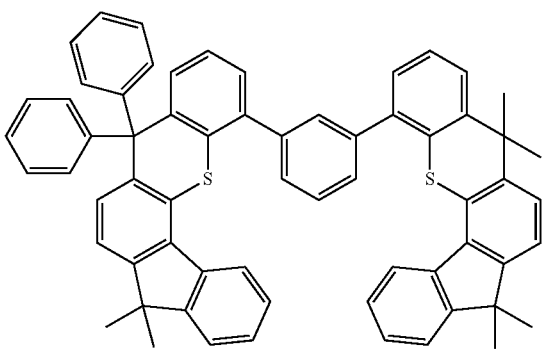
[E-112]
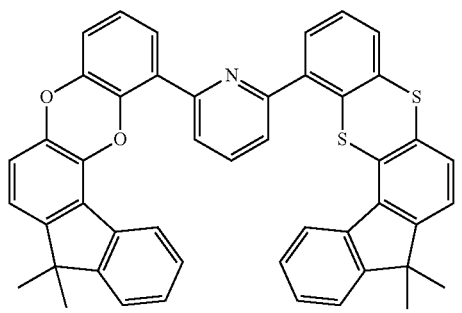
[E-113]
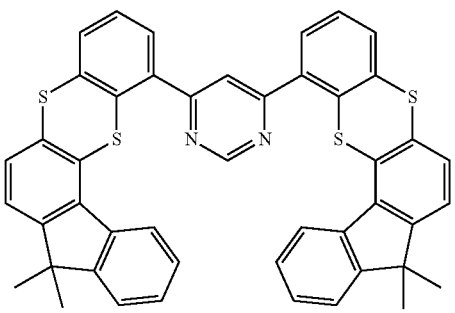

[E-114]
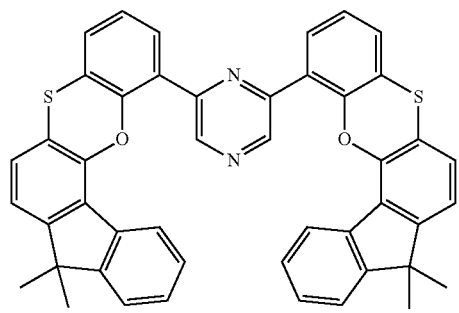
[E-115]
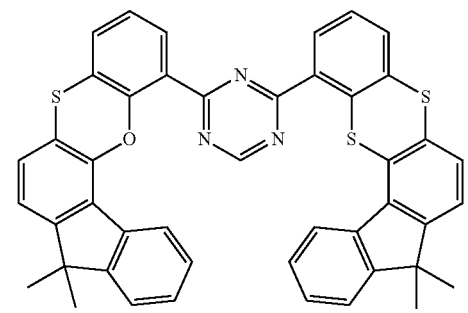
[E-116]
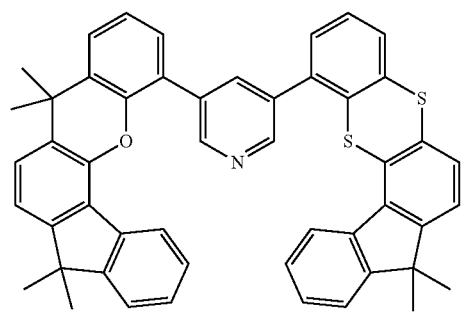
[E-117]
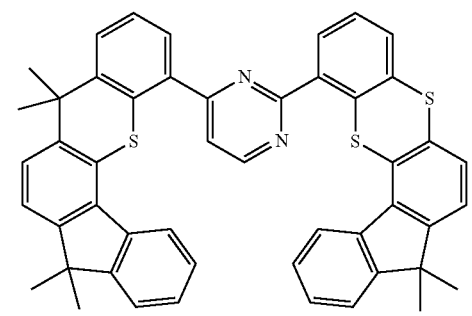
[E-118]
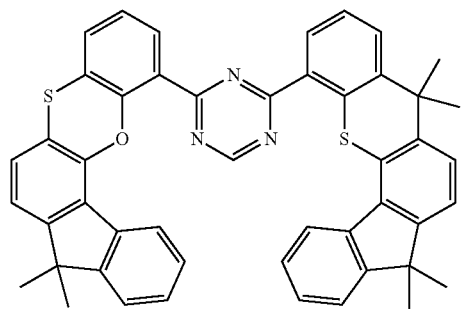
[E-119]
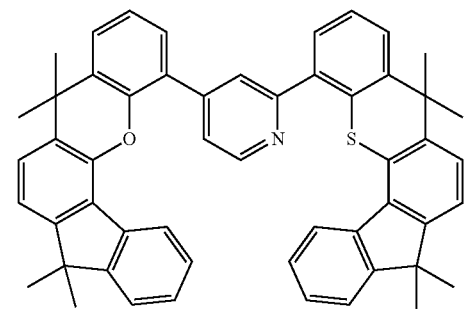
[E-120]
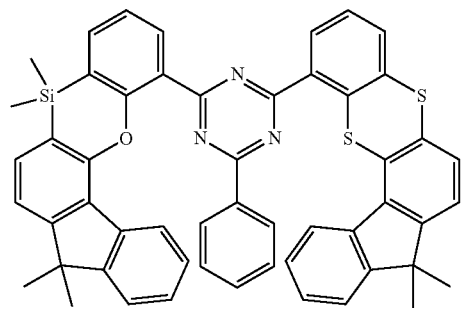
[E-121]
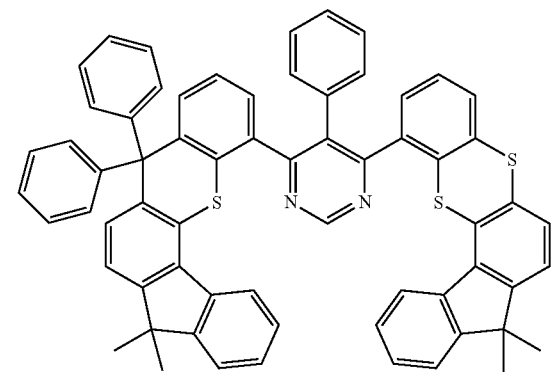

-continued
[E-122]
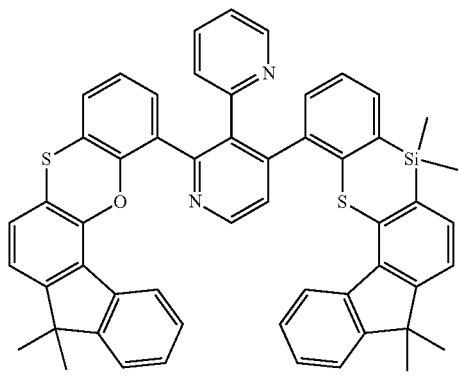
[E-123]
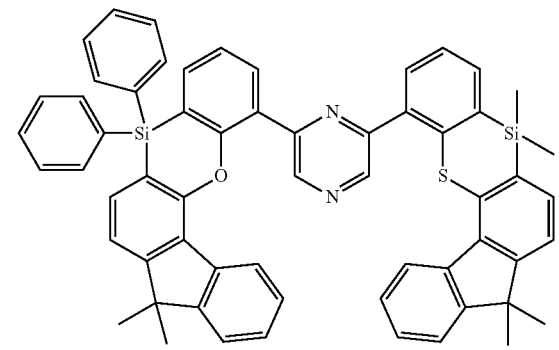
[E-124]
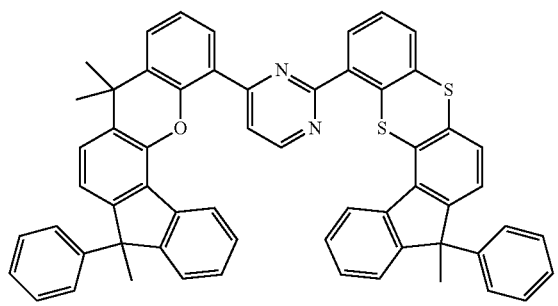
[E-125]
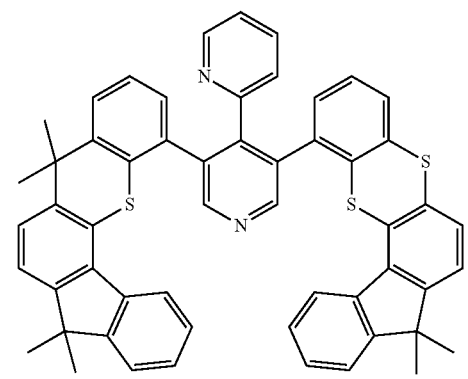
[E-126]
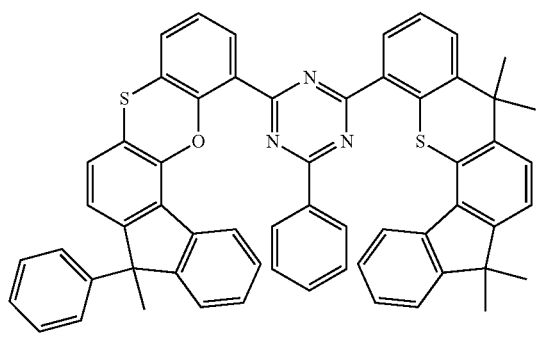
[E-127]
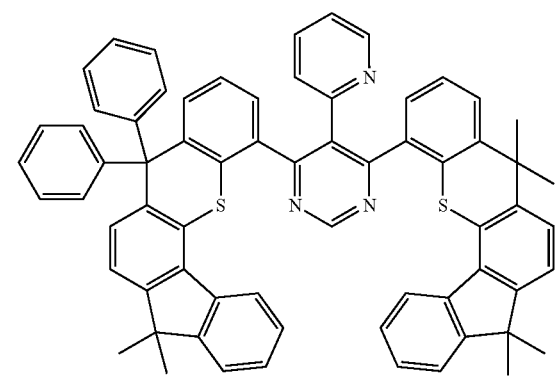
[E-128]
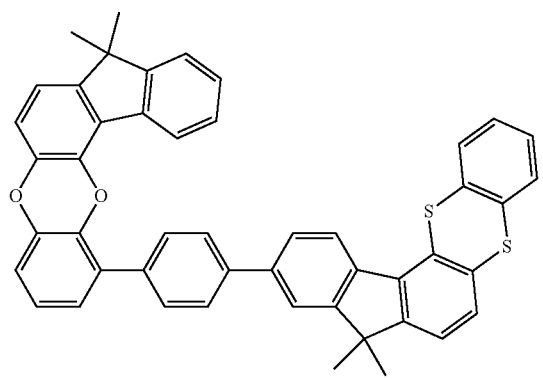
[E-129]
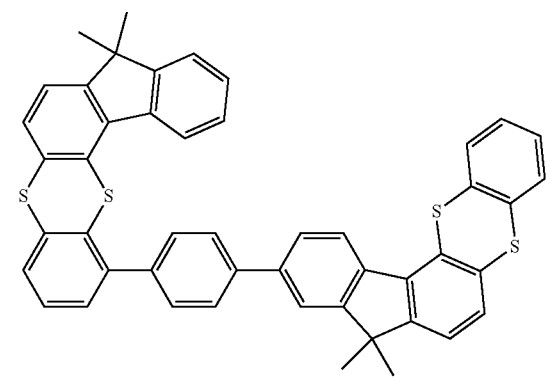

-continued
[E-130]
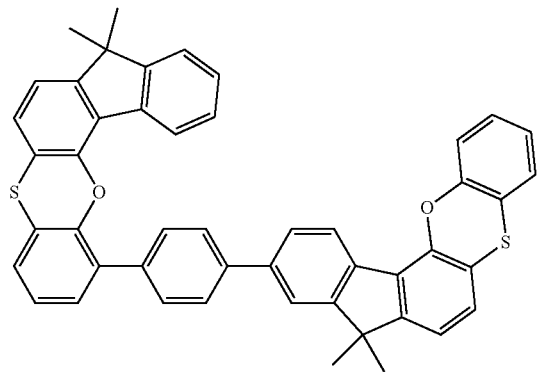
[E-131]
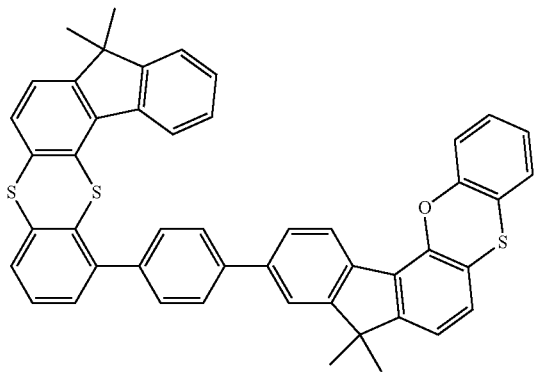
[E-132]
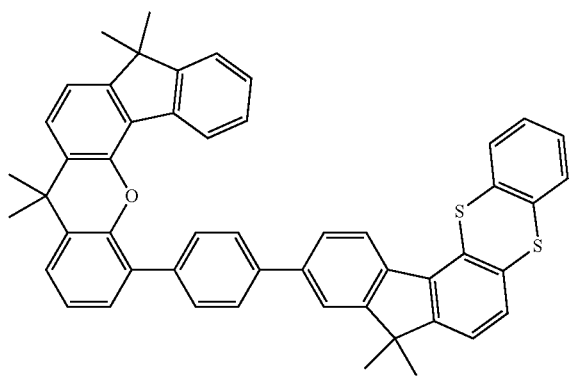
[E-133]
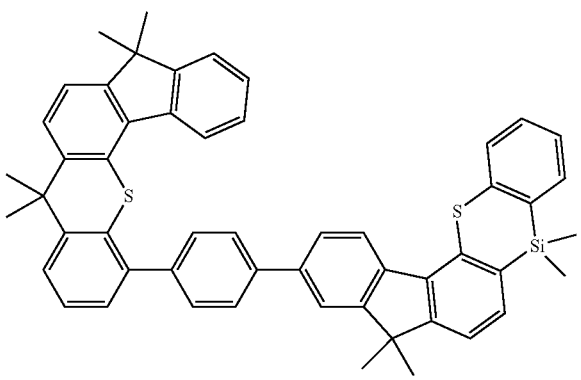
[E-134]
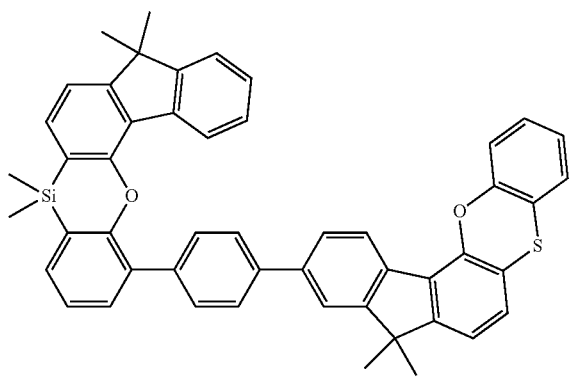
[E135]
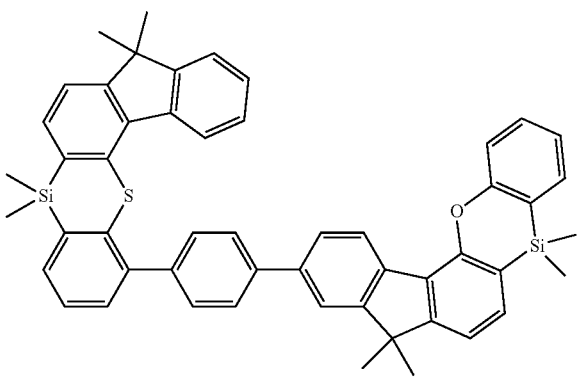
[E-136]
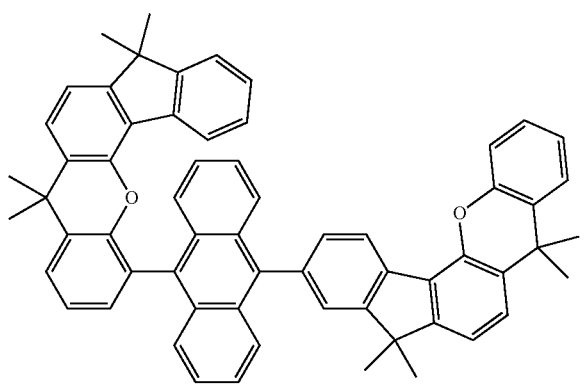
[E-137]
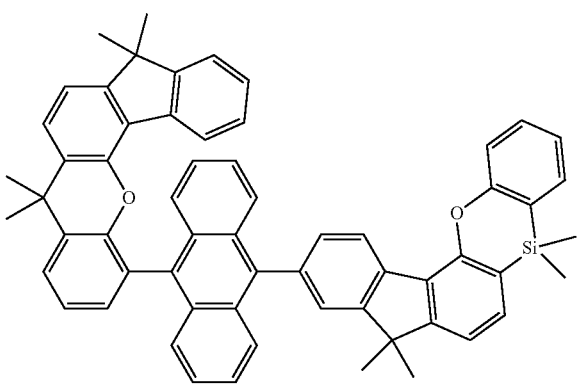

-continued
[E-138]
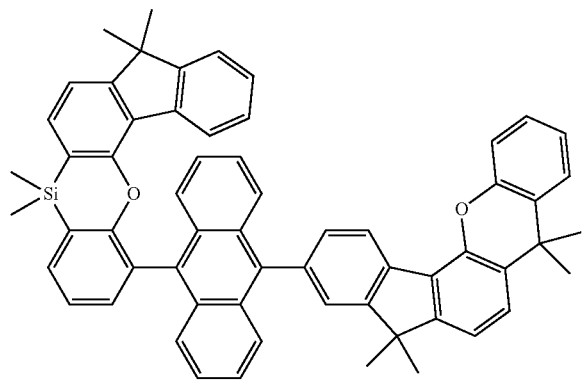
[E-139]
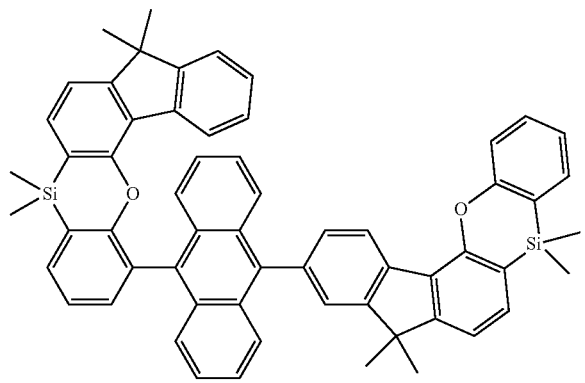
[E-140]
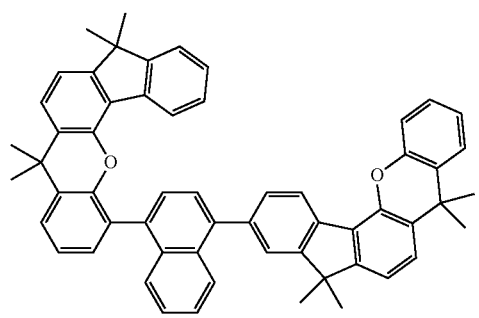
[E-141]
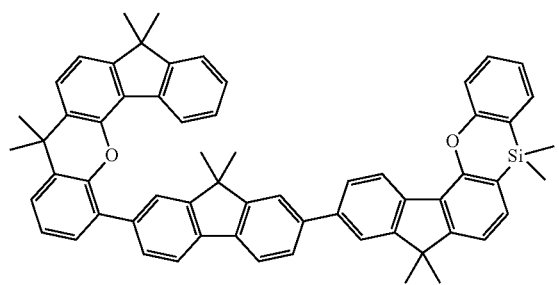
[E-142]
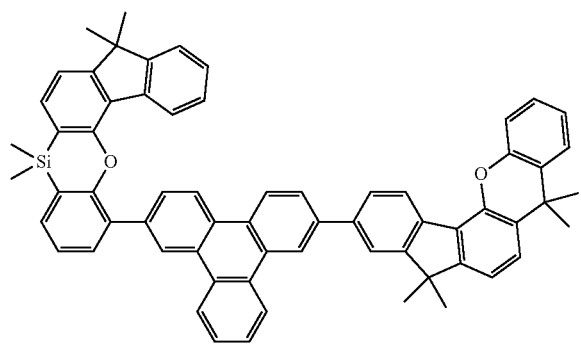
[E-143]
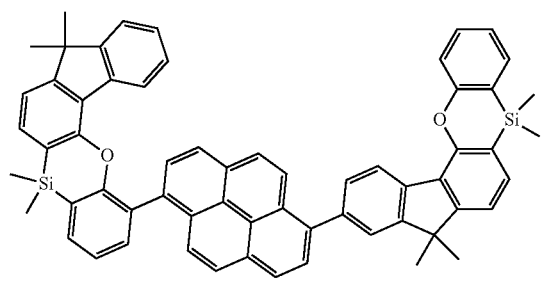
[E-144]
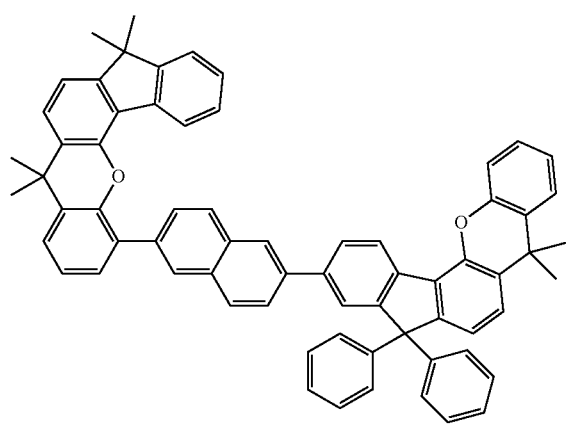
[E-145]
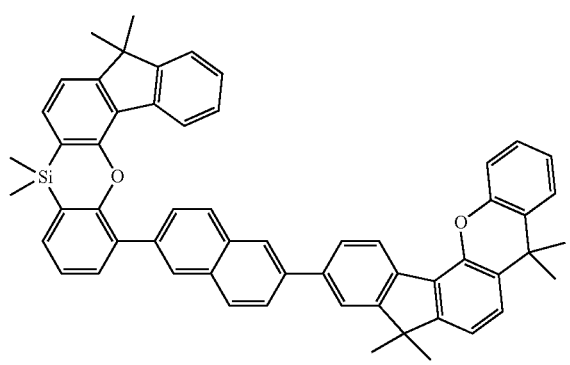

-continued
[E-146]
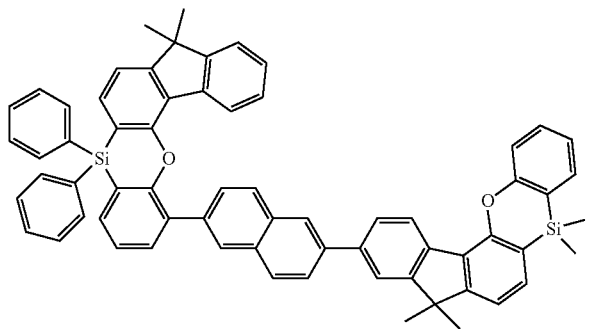
[E-147]
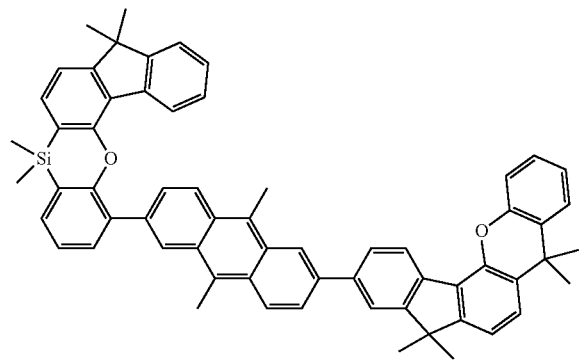
[E-148]
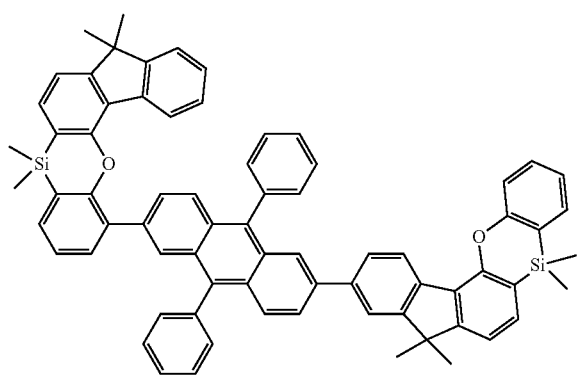
[E-149]
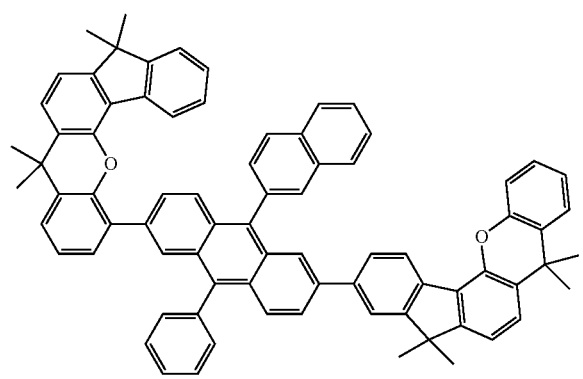
[E-150]
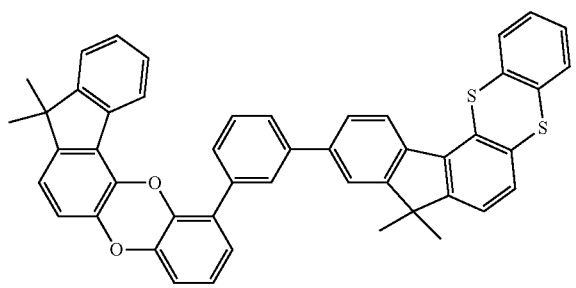
[E-151]
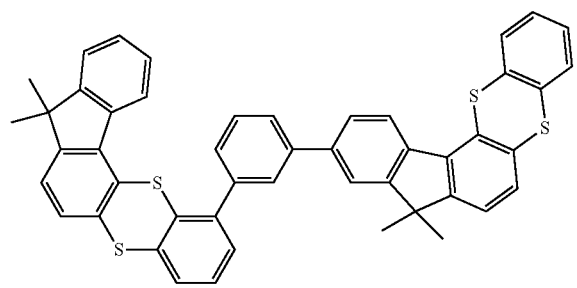
[E-152]
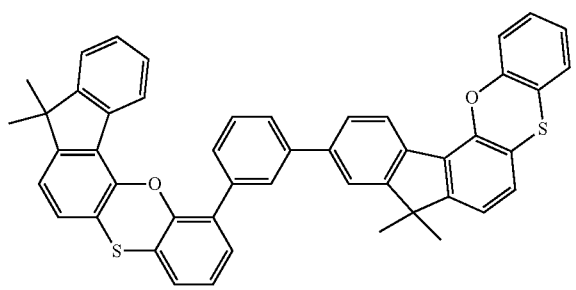
[E-153]
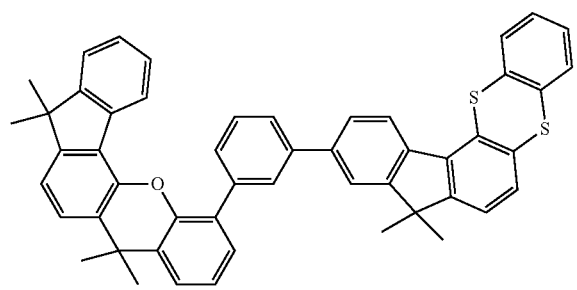

-continued
[E-154]
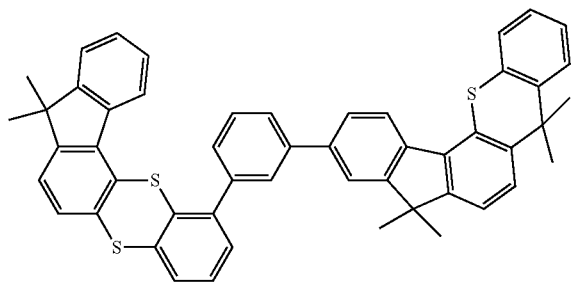
[E-155]
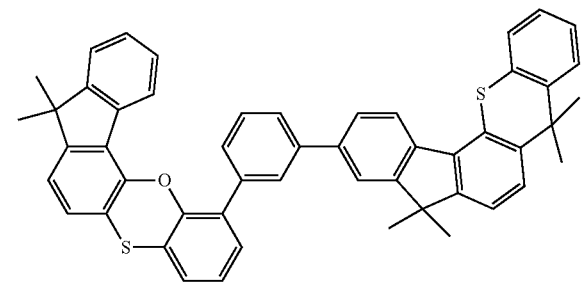
[E-156]
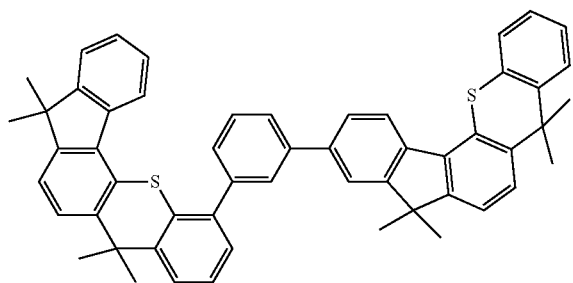
[E-157]
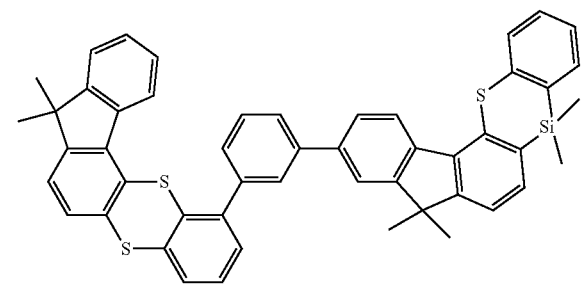
[E-158]
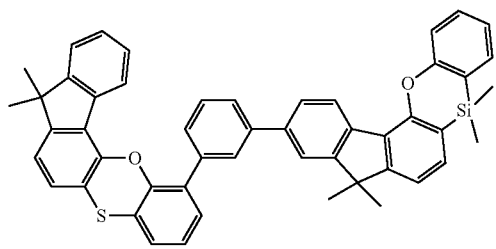
[E-159]
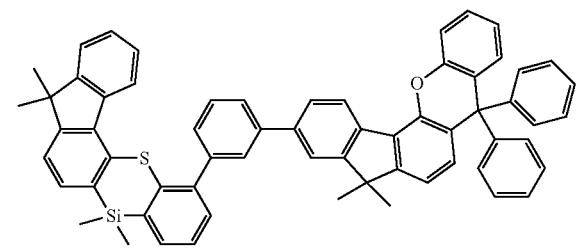
[E-160]
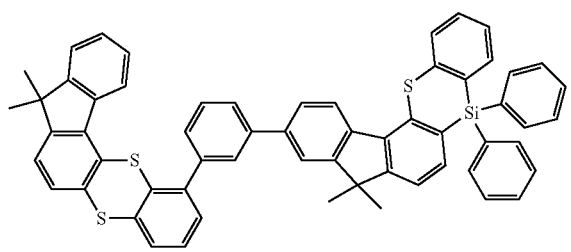
[E-161]
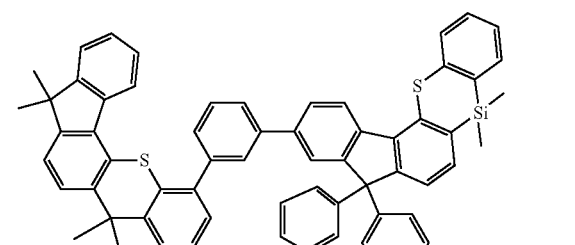
[E-162]
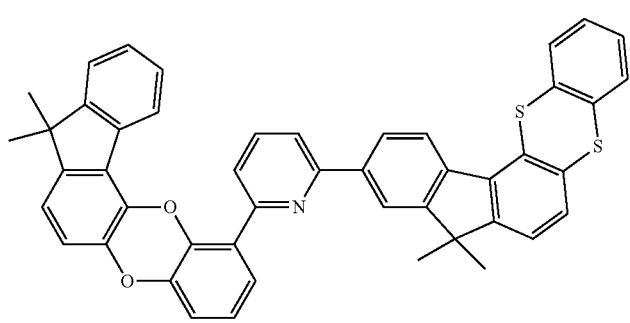

-continued
[E-163]
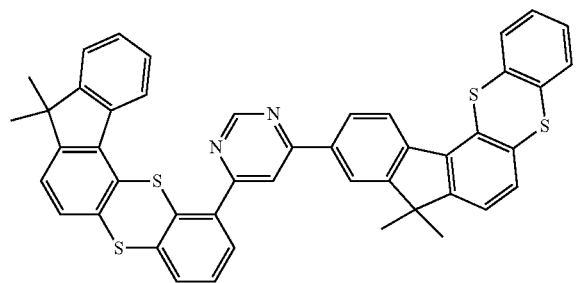
[E-164]
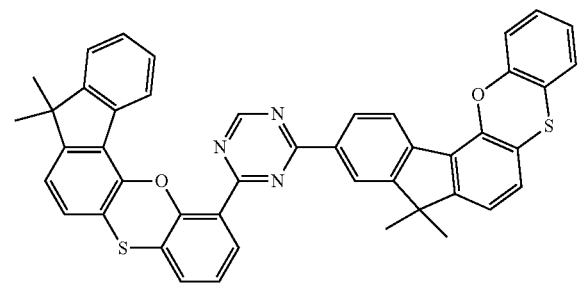
[E-165]
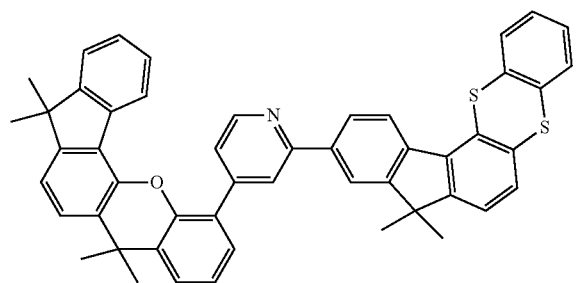
[E-166]
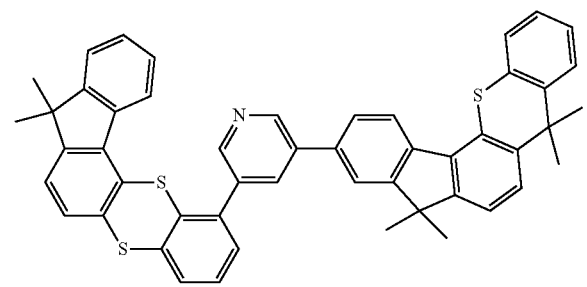
[E-167]
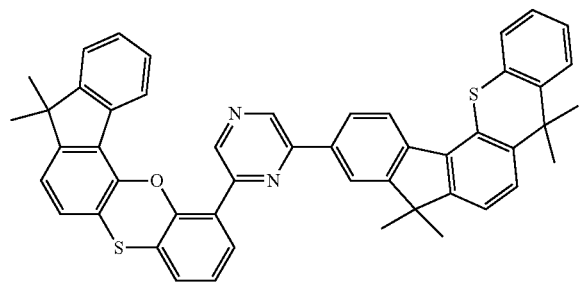
[E-168]
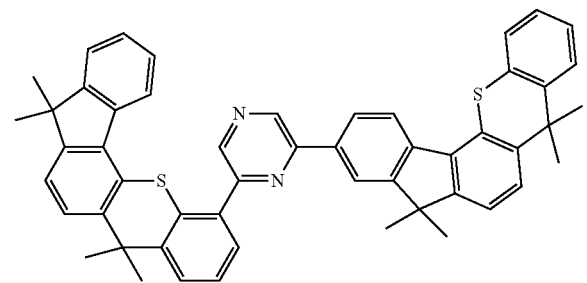
[E-169]
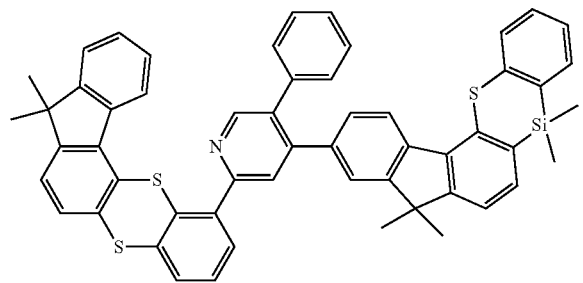
[E-170]
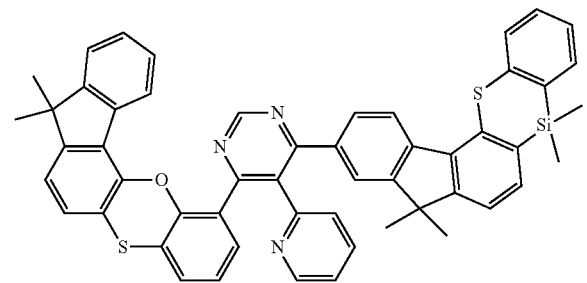
[E-171]
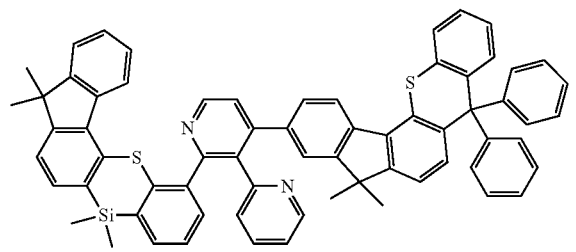
[E-172]
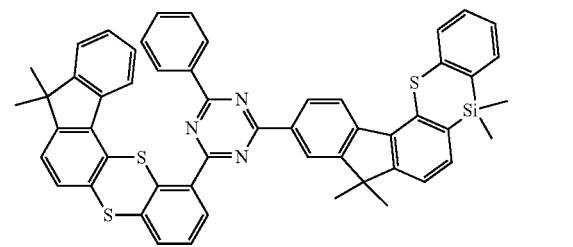

-continued
[E-173]
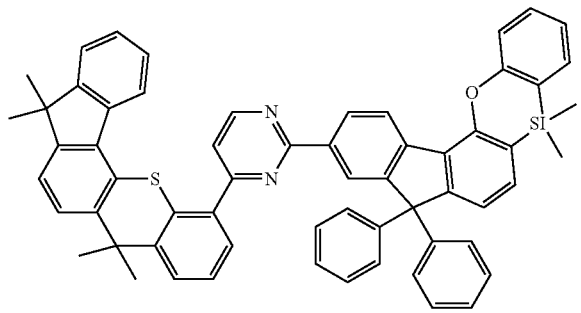
[E-174]
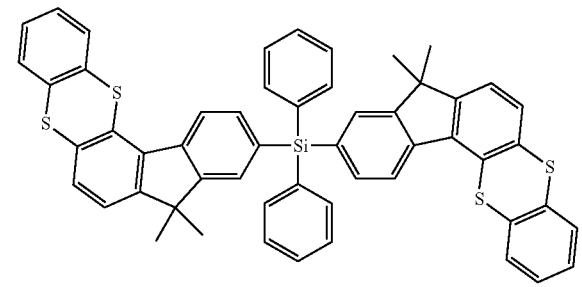
[E-175]
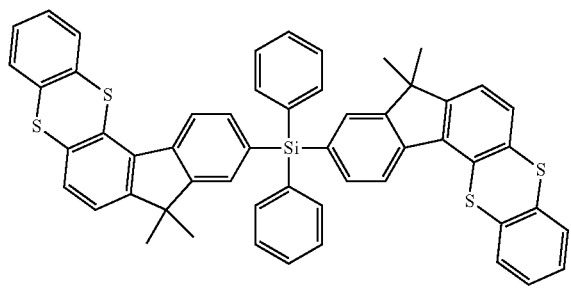
[E-176]
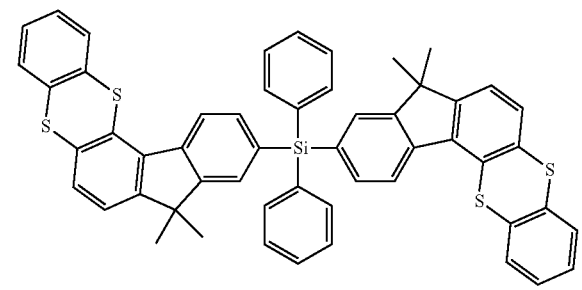
[E-177]
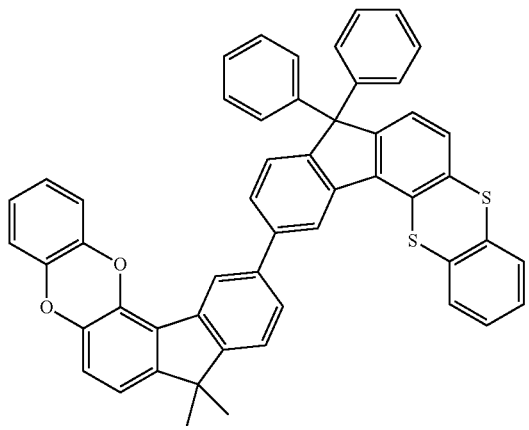
[E-178]
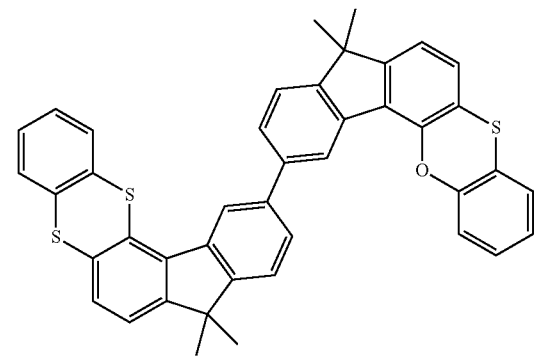
[E-179]
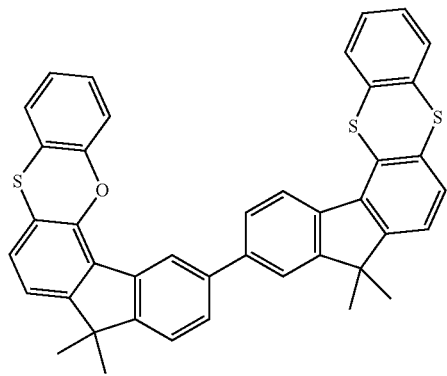
[E-180]
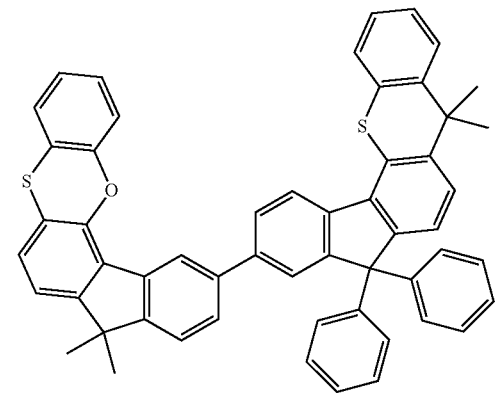

-continued
[E-181]
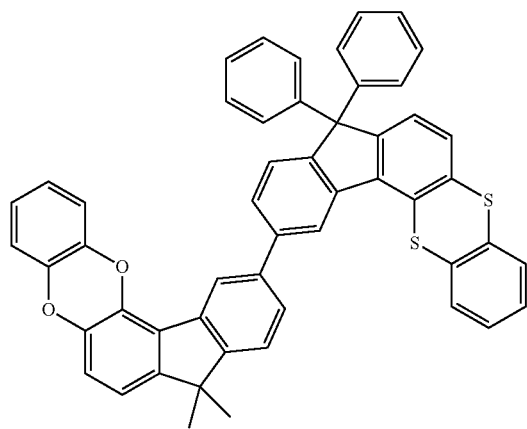
[E-182]
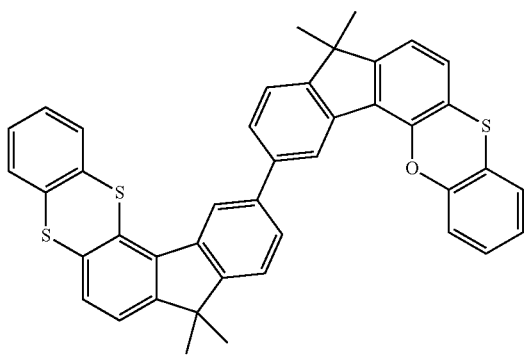
[E-183]
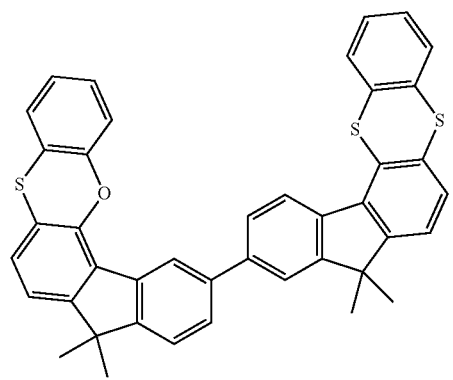
[E-184]
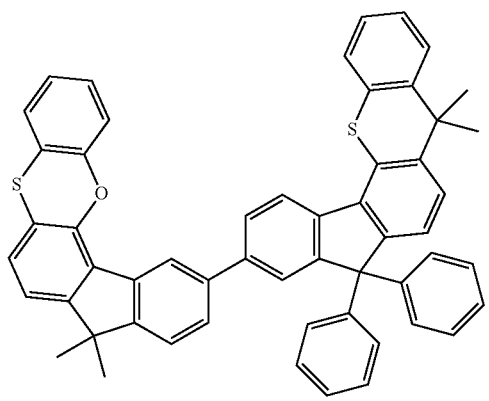
[E-185]
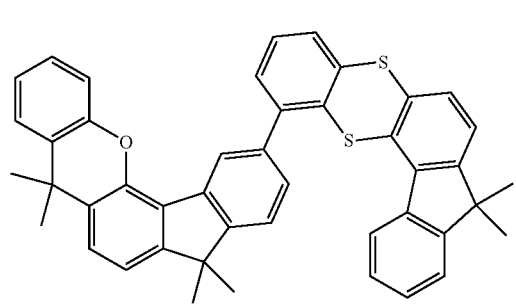
[E-186]
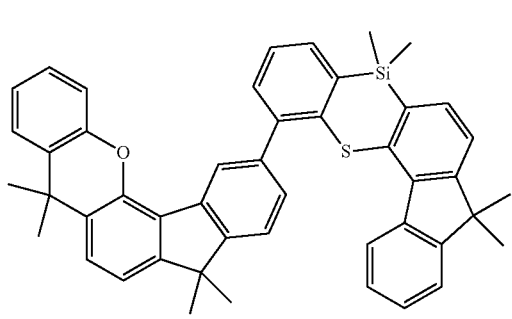
[E-187]
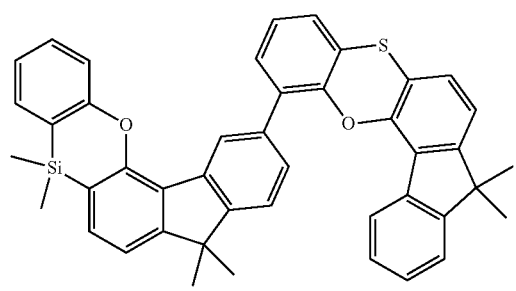
[E-188]
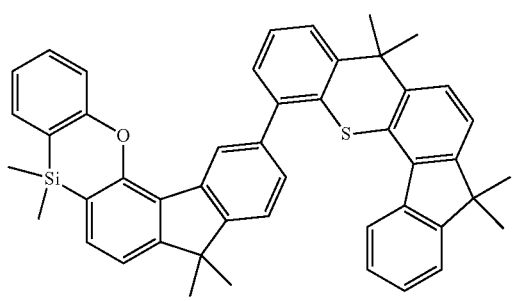

-continued

[E-189]
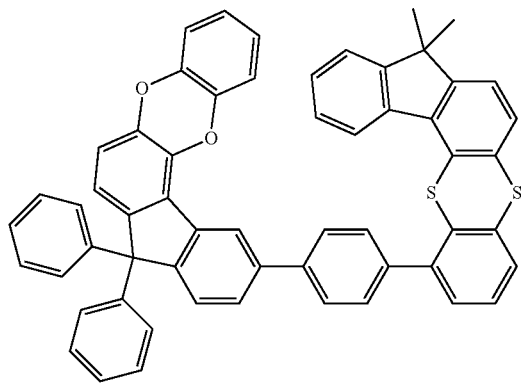

[E-190]
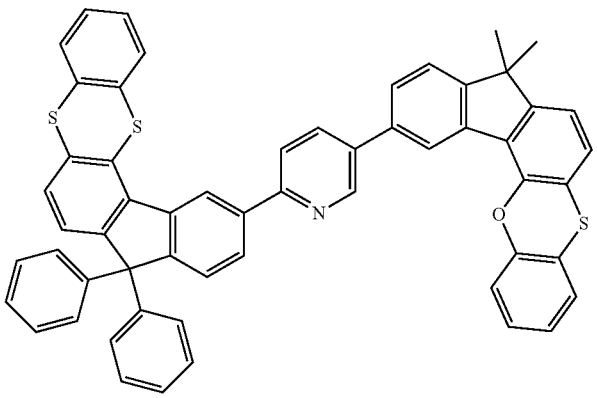

[E-191]
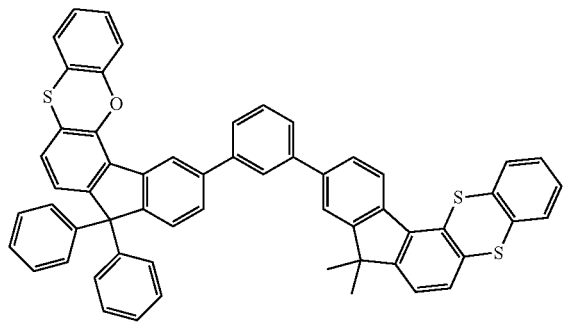

[E-192]
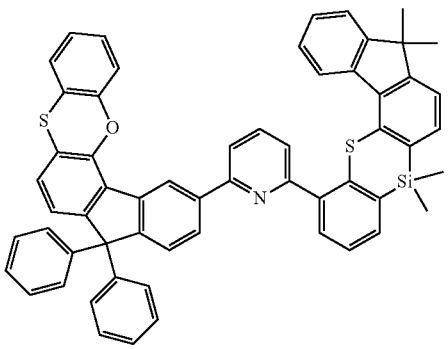

According to the embodiment of the present invention, the compound includes a functional group having the electron characteristics when both electron and hole characteristics are required, and thus may effectively improve the life-span of an organic light-emitting device and decrease a driving voltage thereof.

The compound for an organic optoelectronic device has a maximum light emitting wavelength in a range of about 320 to about 520 am and a triplet excited energy (T1) ranging from greater than or equal to about 2.0 eV, and specifically, from about 2.0 to about 4.0 eV, and thus may well transport a host charge having high triplet excited energy to a dopant and increase luminous efficiency of the dopant, and is also freely adjusted regarding HOMO and LUMO energy levels and decreases a driving voltage, and accordingly may be usefully applied as a host material or a charge transport material.

In addition, the compound for an organic optoelectronic device has photoactive and electrical activities, and thus may be usefully applied for a nonlinear optic material, an electrode material, a discolored material, a light switch, a sensor, a module, a wave guide, an organic transistor, a laser, a light absorbent, a dielectric material, a separating membrane, and the like.

The compound for an organic optoelectronic device including the compounds has a glass transition temperature of greater than or equal to 90° C. and a thermal decomposition temperature of greater than or equal to 400° C., indicating improved thermal stability. Thereby, it is possible to produce an organic photoelectric device having high efficiency.

The compound for an organic optoelectronic device including the compounds may play a role of emitting light or injecting and/or transporting electrons, and may also act as a light emitting host with an appropriate dopant In other words, the compound for an organic optoelectronic device may be used as a phosphorescent or fluorescent host material, a blue light emitting dopant material, or an electron transport material.

Since the compound for an organic optoelectronic device according to one embodiment is used for an organic thin layer, and it may improve the life-span characteristic, efficiency characteristic, electrochemical stability, and thermal stability of an organic optoelectronic device, and decrease the driving voltage.

Further, according to another embodiment, an organic optoelectronic device that includes the compound for an organic optoelectronic device is provided. The organic optoelectronic device may include an organic photoelectric device, an organic light-emitting device, an organic solar cell, an organic transistor, an organic photoconductor drum, an organic memory device, and the like. Particularly, the compound for an organic optoelectronic device according to one embodiment may be included in an electrode or an electrode buffer layer in an organic solar cell to improve the quantum efficiency, and it may be used as an electrode material for a gate, a source-drain electrode, or the like in the organic transistor.

Hereinafter, an organic light-emitting device is described.

According to another embodiment of the present invention, an organic light-emitting device includes an anode, a cathode, and at least one organic thin layer between the anode and the cathode, and at least one organic thin layer may include the compound for an organic optoelectronic device according to one embodiment of the present invention.

The organic thin layer that may include the compound for an organic optoelectronic device may include a layer selected from the group consisting of an emission layer, a hole transport layer (HTL), a hole injection layer (HIL), an electron transport layer (ETL), an electron injection layer (EIL), a hole blocking layer, and a combination thereof. The at least one layer includes the compound for an organic optoelectronic device according to one embodiment Particularly, the compound for an organic optoelectronic device according to one embodiment may be included in a hole transport layer (HTL) or a hole injection layer (HIL). In addition, when the compound for an organic optoelectronic device is included in the emission layer, the compound for an organic optoelectronic device may be included as a phosphorescent or fluorescent host, and particularly, as a fluorescent blue dopant material.

FIGS. 1 to 5 are cross-sectional views showing organic light-emitting devices including the compound for an organic optoelectronic device according to one embodiment of the present invention.

Referring to FIGS. 1 to 5, organic light-emitting devices 100, 200, 300, 400, and 500 according to one embodiment include at least one organic thin layer 105 interposed between an anode 120 and a cathode 110.

The anode 120 includes an anode material laving a large work function to help hole injection into an organic thin layer. The anode material includes: a metal such as nickel, platinum, vanadium, chromium, copper, zinc, and gold, or alloys thereof a metal oxide such as zinc oxide, indium oxide, indium tin oxide (ITO), and indium zinc oxide (IZO); a combination of a metal and an oxide such as ZnO:Al and $SnO_2$:Sb; or a conductive polymer such as poly(3-methylthiophene), poly[3,4-(ethylene-1,2-dioxy)thiophene] (PEDT), polypyrrole, and polyaniline, but is not limited thereto. It is preferable to include a transparent electrode including indium tin oxide (ITO) as an anode.

The cathode 110 includes a cathode material having a small work function to help electron injection into an organic thin layer. The cathode material includes: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, $LiO_2$/Al, LiF/Ca, LiF/Al, and $BaF_2$/Ca, but is not limited thereto. It is preferable to include a metal electrode including aluminum as a cathode.

First, referring to FIG. 1, the organic light-emitting device 100 includes an organic thin layer 105 including only an emission layer 130.

Figure 2:
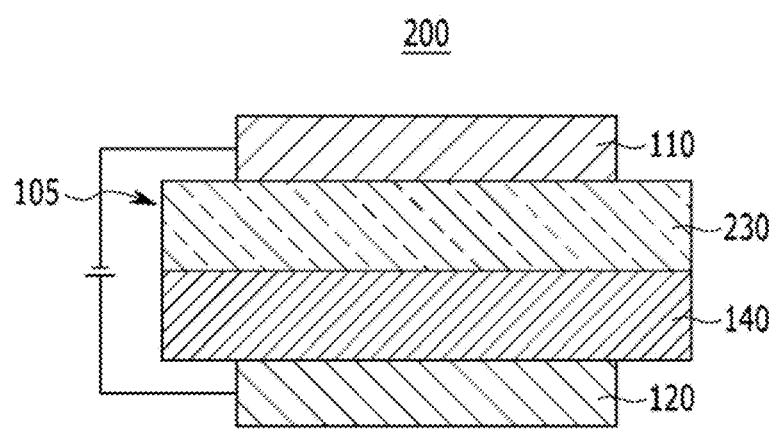

Referring to FIG. 2, a double-layered organic light-emitting device 200 includes an organic thin layer 105 including an emission layer 230 including an electron transport layer (ETL), and a hole transport layer (HTL) 140. As shown in FIG. 2, the organic thin layer 105 includes a double layer of the emission layer 230 and the hole transport layer (IL) 140. The emission layer 230 also functions as an electron transport layer (ETL), and the hole transport layer (HTL) 140 layer has an improved binding property with a transparent electrode such as ITO or an improved hole transport capability.

Figure 3:
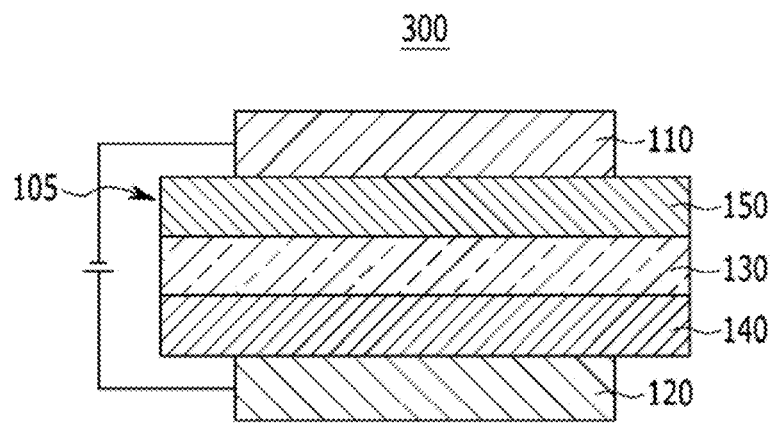

Referring to FIG. 3, a three-layered organic light-emitting device 300 includes an organic thin layer 105 including an electron transport layer (ETL) 150, an emission layer 130, and a hole transport layer (HTL) 140. The emission layer 130 is independently installed, and layers having an improved electron transport capability or an improved hole transport capability are separately stacked.

Figure 4:
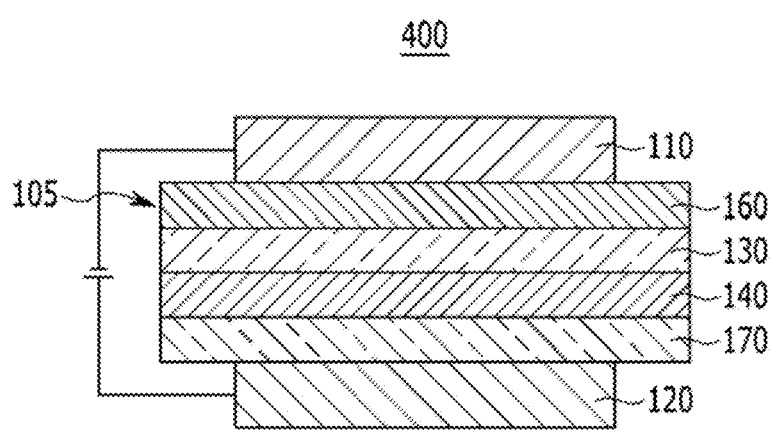

Referring to FIG. 4, a four-layered organic light-emitting device 400 includes an organic thin layer 105 including an electron injection layer (EIL) 160, an emission layer 130, a hole transport layer (HTL) 140, and a hole injection layer (HIL) 170 for adherence with the cathode made of ITO.

Figure 5:
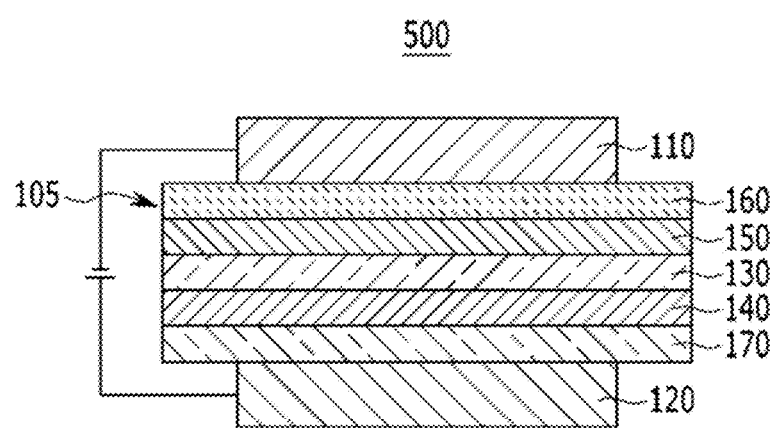

Referring to FIG. 5, a five-layered organic light-emitting device 500 includes an organic thin layer 105 including an electron transport layer (ETL) 150, an emission layer 130, a hole transport layer (HTL) 140, and a hole injection layer (HIL) 170, and father includes an electron injection layer (EIL) 160 to achieve a low voltage.

In FIGS. 1 to 5, the organic thin layer 105 including at least one selected from the group consisting of an electron transport layer (ETL) 150, an electron injection layer (EIL) 160, emission layers 130 and 230, a hole transport layer (HTL) 140, a hole injection layer (HIL) 170, and combinations thereof includes a compound for an organic optoelectronic device. The compound for an organic optoelectronic device may be used for an electron transport layer (ETL) 150 including the electron transport layer (ETL) 150 or electron injection layer (EIL) 160. When it is used for the electron transport layer (ETL), it is possible to provide an organic light-emitting device having a more simple structure because it does not require an additional hole blocking layer (not shown).

Furthermore, when the compound for an organic optoelectronic device is included in the emission layers 130 and 230, the compound for the organic optoelectronic device may be included as a phosphorescent or fluorescent host or a fluorescent blue dopant.

The organic light-emitting device may be fabricated by: forming an anode on a substrate; forming an organic thin layer in accordance with a dry coating method such as evaporation, sputtering, plasma plating, and ion plating, or a wet costing method such as spin costing, dipping, and flow coating; and providing a cathode thereon.

Another embodiment of the present invention provides a display device including the organic light-emitting device according to the embodiment.

Hereinafter, the embodiments are illustrated in more detail with reference to examples. These examples, however, are not in any sense to be interpreted as limiting the scope of the invention.

(Preparation of Compound for Organic Optoelectronic Device)

SYNTHESIS OF INTERMEDIATE

Synthesis of Intermediate M-1

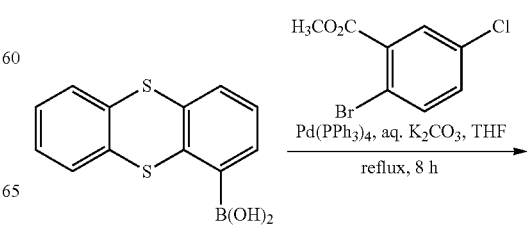

[Reaction Scheme 1]

-continued

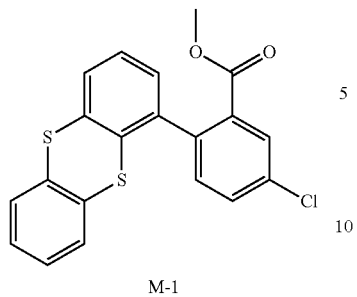

M-1

20 g (76.88 mmol) of thianthrene-1-boronic acid, 21.1 g (84.57 mmol) of methyl-2-bromo-5-chlorobenzoate and 0.89 g (0.769 mmol) of tetrakistriphenylphosphinepalladium were put in a flask and dissolved in 257 mL of tetrahydrofuran under a nitrogen atmosphere, 128 ml of an aqueous solution obtained by dissolving 17 g (115.3 mmol) of potassium carbonate was added thereto, and the mixture was refluxed and agitated for 8 hours at 70° C. When the reaction was complete, the resultant was extracted with ethylacetate, and the extraction solution was dried with magnesium sulfate and filtered and then, concentrated under a reduced pressure. Then, a product therefrom was purified with n-hexane/ethylacetate (9:1 of a volume ratio) through silica gel column chromatography, obtaining 26.9 g of a target compound of an intermediate M-1 (a yield of 91%).

LC-Mass (calcd.: 384.00 g/mol, measured.: M+1=385.11 g/mol)

Synthesis of Intermediate M-2

[Reaction Scheme 2]

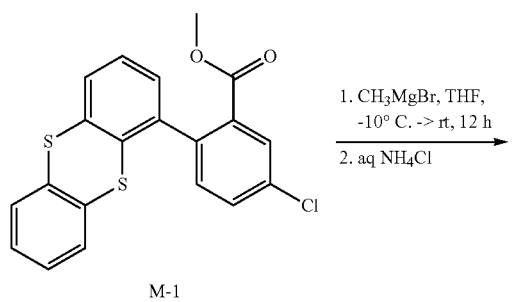

-continued

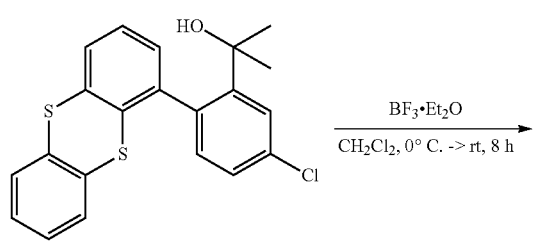

M-2

25 g (64.95 mmol) of the intermediate M-1 was put in a three-necked round-bottomed flask heated under vacuum and dissolved in 325 mL of anhydrous tetrahydrofuran under a nitrogen atmosphere, and the solution was cooled down to 10° C. and agitated.

Then, 54 mL of 3.0 M methyl magnesium bromide (162.4 mmol in diethylether) was slowly added thereto for 30 minutes. The reaction solution was heated up to room temperature and agitated under a nitrogen atmosphere for 12 hours. The reaction solution was cooled down to 0° C., and an aqueous solution obtained by dissolving 10.4 g (194.85 mmol) of ammonium chloride in 100 mL of distilled water was slowly added thereto. The reaction solution was extracted with distilled water and diethylether, and an organic layer solution obtained therefrom was dried with magnesium sulfate and filtered and then, concentrated under a reduced pressure. The dried residue was put in a 3-necked round-bottomed flask and dissolved in 325 mL of anhydrous dichloromethane under a nitrogen atmosphere, and the solution was cooled down to 0° C. and agitated. Herein, 4 mL (32.5 mmol) of borontrifluoride diethyl etherate was slowly added thereto for 10 minutes, and the mixture was heated up to mom temperature and agitated for 12 hours. When the reaction was complete, a sodium bicarbonate aqueous solution was slowly added thereto at 0° C., and the mixture was agitated for 30 minutes. The reaction solution was extracted with dichloromethane/distilled water, and the extraction solution was dried with magnesium sulfate and filtered and then, concentrated under a reduced pressure. Then, a product therefrom was purified with n-hexane/dichloromethane (9:1 of a volume ratio) through silica gel column chromatography, obtaining 15.5 g of a target compound of an intermediate M-2 (a yield: 65%).

LC-Mass (calcd.: 366.03 g/mol, measured.: M+1=367.14 g/mol)

Synthesis of Intermediate M-3

[Reaction Scheme 3]

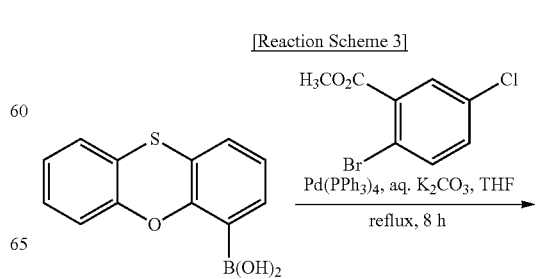

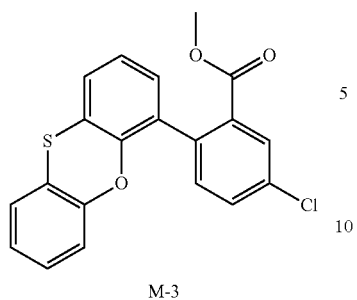

M-3

18.8 g (76.88 mmol) of 4-phenoxathiinylboronic acid, 21.1 g (84.57 mmol) of methyl-2-bromo-5-chlorobenzoate and 0.89 g (0.769 mmol) of tetrakistriphenylphosphinepalladium were put in a flask and dissolved in 257 mL of tetrahydrofuran under a nitrogen atmosphere, 128 ml of an aqueous solution obtained by dissolving 17 g (115.3 mmol) of potassium carbonate was added thereto, and the mixture was refluxed and agitated at 70° C. for 8 hours. When the reaction was complete, the resultant was extracted with ethylacetate, and the extraction solution was dried with magnesium sulfate and filtered and then, concentrated under a reduced pressure. A product therefrom was purified with n-hexane/ethylacetate (9:1 of a volume ratio) through silica gel column chromatography, obtaining 26.1 g of a target compound of an intermediate M-3 (a yield of 92%).

LC-Mass (calcd.: 368.03 g/mol, measured.: M+1=369.21 g/mol)

Synthesis of Intermediate M-4

[Reaction Scheme 4]

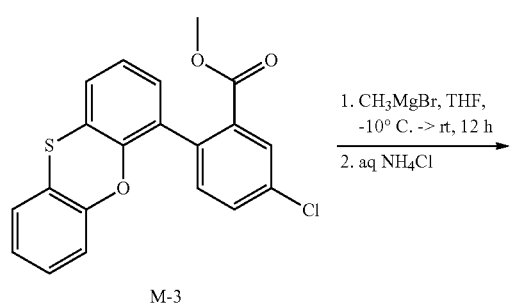

M-3

24 g (64.95 mmol) of the intermediate M-3 was put in a 3-necked round-bottomed flask heated and dried under vacuum and dissolved in 325 mL of anhydrous tetrahydrofuran under a nitrogen atmosphere, and the solution was cooled down to −10° C. and agitated.

Herein, 54 mL of 3.0 M methyl magnesium bromide (162.4 mmol in diethylether) was slowly added thereto for 30 minutes. The reaction solution was heated up to room temperature and then, agitated under a nitrogen atmosphere for 12 hours. The reaction solution was cooled down to 0° C., and an aqueous solution obtained by dissolving 10.4 g (194.85 mmol) of ammonium chloride in 100 mL of distilled water was slowly added thereto. The reaction solution was extracted with distilled water and diethylether, and an organic layer solution obtained therefrom was dried with magnesium sulfate and filtered and then, concentrated under a reduced pressure. The dried residue was put in a 3-necked round-bottomed flask and dissolved in 325 mL of anhydrous dichloroethane under a nitrogen atmosphere, and the solution was cooled down to 0° C. and agitated. Then, 4 mL (32.5 mmol) of borontrifluoride diethyl etherate was slowly added thereto for 10 minutes, and the mixture was heated up to room temperature and then, agitated for 12 hours. When the reaction was complete, a sodium bicarbonate aqueous solution was slowly added thereto at 0° C., and the mixture was slowly agitated for 30 minutes. The reaction solution was extracted with dichloromethane/distilled water, and the extraction solution was dried with magnesium sulfate and filtered and then, concentrated under a reduced pressure. A product therefrom was purified with n-hexane/dichloromethane (9:1 of a volume ratio) through silica gel column chromatography, obtaining 15.5 g of a target compound of an intermediate M-2 (a yield of 68%).

LC-Mass (calcd.: 350.05 g/mol, measured.: M+1=351.18 g/mol)

Synthesis of Intermediate M-5

[Reaction Scheme 5]

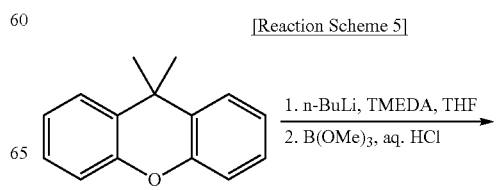

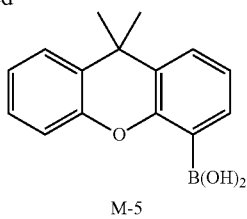

M-5

30 g (142.7 mmol) of 9,9-dimethyl xanthene was put in a 2-necked round-bottomed flask heated and dried under vacuum and dissolved in 476 mL of anhydrous tetrahydrofuranm under a nitrogen atmosphere, and then, the solution was cooled down to −40° C. and agitated.

Herein, 57 mL (142.7 mmol in hexane) of 2.5 M n-butyllithium was slowly added thereto, and then, 16.5 g (142.7 mmol) of N,N,N'N'-tetramethylethylenediamine was added thereto. The reaction solution was heated up to room temperature and agitated under a nitrogen atmosphere for 8 hours. The reaction solution was cooled down to −78° C., 10.9 g (157 mmol) of trimethylborate dissolved in 10 mL of anhydrous tetrahydrofuran was slowly added thereto, and the mixture was agitated at room temperature for 8 hours. The reaction solution was cooled down to 0° C., 234 mL of a 2N HCl aqueous solution was added thereto, and the mixture was agitated at room temperature for one hour. When the reaction was complete, the resultant was extracted with distilled water and diethylether, and an organic layer solution obtained therefrom was dried with magnesium sulfate and filtered and then, concentrated under a reduced pressure. The obtained reaction solution was dissolved in acetone, and the solution was recrystallized with n-hexane, obtaining 23.6 g of a target compound of a white solid intermediate M-5 (a yield of 65%).

GC-Mass (calcd.: 254.11 g/mol, measured.: M+1=255.42 g/mol)

Synthesis of Intermediate M-6

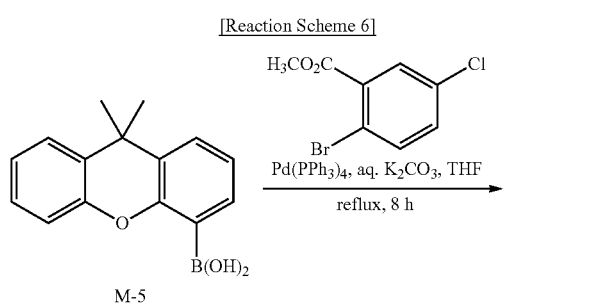

[Reaction Scheme 6]

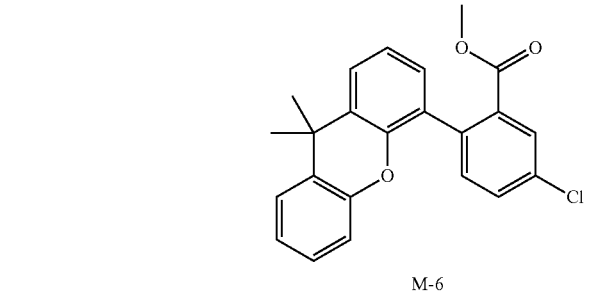

M-6

19.5 g (76.88 mmol) of the intermediate M-5, 21.1 g (84.57 mmol) of methyl-2-bromo-5-chlorobenzoate and 0.89 g (0.769 mmol) of tetrakistriphenylphosphinepalladium were put in a flask, 128 ml of an aqueous solution obtained by dissolving 17 g (115.3 mmol) of potassium carbonate in 257 mL of tetrahydrofuran was added thereto under a nitrogen atmosphere, and the mixture was refluxed and agitated at 70° C. for 8 hours. When the reaction was complete, the resultant was extracted with ethylacetate, and an extraction solution obtained therefrom was dried with magnesium sulfate and filtered and then, concentrated under a reduced pressure. A product therefrom was purified with n-hexane/ethylacetate (9:1 of a volume ratio) through silica gel column chromatography, obtaining 26.2 g of a target compound of an intermediate M-6 (a yield of 90%).

LC-Mass (calcd.: 378.10 g/mol, measured.: M+1=379.31 g/mol)

Synthesis of Intermediate M-7

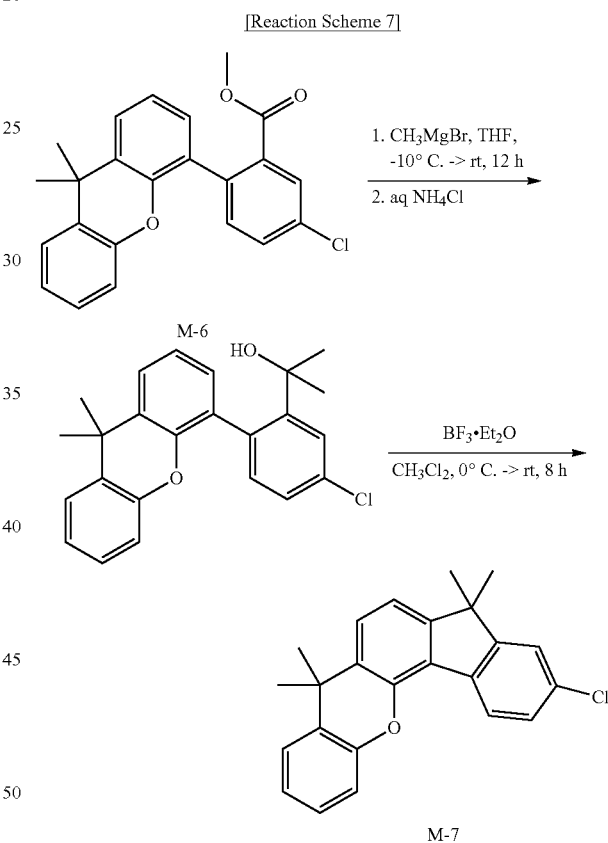

[Reaction Scheme 7]

M-7

24.6 g (64.95 mmol) of the intermediate M-6 was put in a 3-necked round-bottomed flask heated and dried under vacuum and dissolved in 325 mL of anhydrous tetrahydrofuran under a nitrogen atmosphere, and the solution was cooled down to −10° C. and agitated.

Then, 54 mL (162.4 mmol in diethylether) of 3.0 M methyl magnesium bromide was slowly added thereto for 30 minutes. The mixture was heated to room temperature and agitated under a nitrogen atmosphere for 12 hours. The reaction solution was cooled down to 0° C., and an aqueous solution obtained by dissolving 10.4 g (194.85 mmol) of ammonium chloride in 100 mL of distilled water was slowly added thereto. The reaction solution was extracted with distilled water and diethylether, and an organic layer solution obtained therefrom was dried with magnesium sulfate and filtered and then, concentrated under a reduced pressure. The dried residue was put in a 3-necked round-bottomed flask and dissolved in 325 mL of anhydrous dichloromethane under a nitrogen atmosphere, and the solution was cooled down to 0° C. and agitated. Then, 4 mL (32.5 mmol) of borontrifluoride diethyl etherate was slowly added thereto for 10 minutes, and the mixture was heated up to room temperature and then, agitated for 12 hours. When the reaction was complete, a sodium bicarbonate aqueous solution was slowly added thereto at 0° C., and the mixture was agitated for 30 minutes. The reaction solution was extracted with dichloromethane/distilled water, and an extraction solution obtained therefrom was dried with magnesium sulfate and filtered and then, concentrated under a reduced pressure. A product obtained therefrom was purified with n-hexane/dichloromethane (9:1 of a volume ratio) through silica gel column chromatography, obtaining 15.7 g of a target compound of an intermediate M-7 (a yield of 67%).

LC-Mass (calcd.: 360.13 g/mol, measured.: M+1=361.26 g/mol)

Synthesis of Intermediate M-4

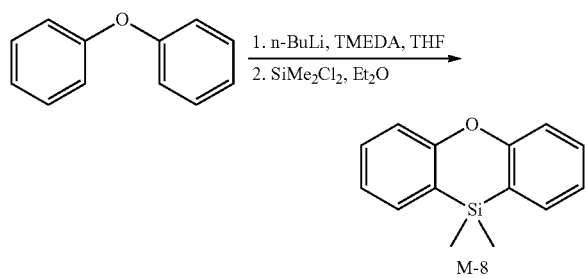

60 g (352.6 mmol) of diphenylether was put in a 2-necked round-bottomed flask heated and dried under vacuum and dissolved in 352 mL of anhydrous tetrahydrofuran under a nitrogen atmosphere, and the solution was cooled down to 0° C. and then, agitated.

Then, 310 mL of 2.5 M n-butyllithium (776 mmol in hexane) was slowly added thereto, and 90.2 g (776 mmol) of N,N,N',N'-tetramethylethylenediamine was added thereto. The reaction solution was heated up to room temperature and then, agitated under a nitrogen atmosphere for 16 hours. The reaction solution was cooled down to 0° C., and 45.6 g (352.6 mmol) of a solution obtained by dissolving dimethyldichlorosilane in 60 mL of anhydrous diethylether was slowly added thereto, and the mixture was agitated at room temperature for 16 hours. The reaction solution was cooled down to 0° C., 240 mL of distilled water was added thereto, and the mixture was agitated at room temperature for 30 minutes. When the reaction was complete, the resultant was extracted with distilled water and diethylether, an organic layer solution obtained therefrom was dried with magnesium sulfate and filtered and then, concentrated under a reduced pressure. A product therefrom was recrystallized with methanol, obtaining 35.2 g of a target compound of a white solid intermediate M-8 (a yield of 44%).

GC-Mass (calcd.: 226.08 g/mol, measured.: M+1=227.27 g/mol)

Synthesis of Intermediate M-9

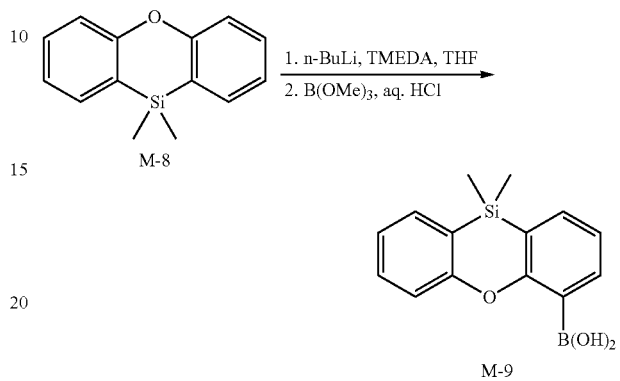

32.3 g (142.7 mmol) of the intermediate M-8 was put in a 2-necked round-bottomed flask heated and dried under vacuum and dissolved in 476 mL of anhydrous tetrahydrofuran under a nitrogen atmosphere, and the solution was cooled down to −40° C. and agitated.

Then, 57 mL of 2.5 M n-butyllithium (142.7 mmol in hexane) was slowly added thereto, and 16.5 g (142.7 mmol) of N,N,N',N'-tetramethylethylenediamine was added thereto. The mixture was heated up to room temperature and then, agitated under a nitrogen atmosphere for 8 hours. The reaction solution was cooled down to −78° C., a solution obtained by dissolving 10.9 g (157 mmol) of trimethylborate in 10 mL of anhydrous tetrahydrofuran was slowly added thereto, and the mixture was agitated at room temperature for 8 hours. The reaction solution was cooled down to 0° C., 234 mL of a 2N HCl aqueous solution was added thereto, and the mixture was agitated at room temperature for one hour. When the reaction was complete, the resultant was extracted with distilled water and diethylether, and an organic layer solution obtained therefrom was dried with magnesium sulfate and filtered and then, concentrated under a reduced pressure. The obtained reaction solution was dissolved in acetone, and the solution was recrystallized with n-hexane, obtaining 22.7 g of a target compound of a white solid intermediate M-9 (a yield of 59%).

GC-Mass (calcd.: 270.09 g/mol, measured.: M+1=27135 g/mol)

Synthesis of Intermediate M-10

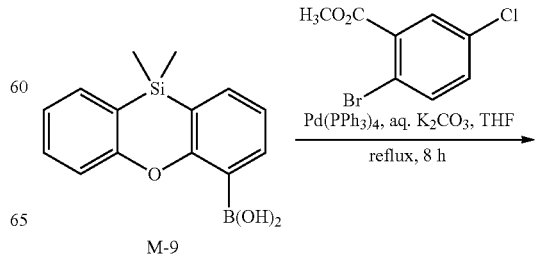

-continued

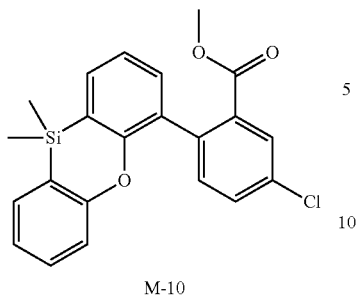

M-10

20.8 g (76.88 mmol) of the intermediate M-9, 21.1 g (84.57 mmol) of methyl-2-bromo-5-chlorobenzoate and 0.89 g (0.769 mmol) of tetrakistriphenylphosphinepalladium were put in a flask, 128 ml of an aqueous solution obtained by dissolving 17 g (115.3 mmol) of potassium carbonate in 257 mL of tetrahydrofuran was added thereto under a nitrogen atmosphere, and the mixture was refluxed and agitated at 70° C. for 8 hours. When the reaction was complete, the resultant was extracted with ethylacetate, and the extraction solution was dried with magnesium sulfate and filtered and then, concentrated under a reduced pressure. A product therefrom was purified with n-hexane/ethylacetate (9:1 of a volume ratio) through silica gel column chromatography, obtaining 27 g of a target compound of an intermediate M-10 (a yield of 89%).

LC-Mass (calcd.: 394.08 g/mol, measured.: M+1=395.29 g/mol)

Synthesis of Intermediate M-11

[Reaction Scheme 11]

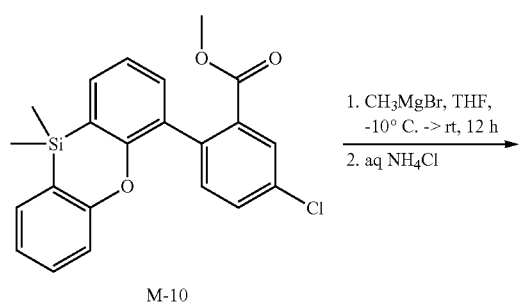

-continued

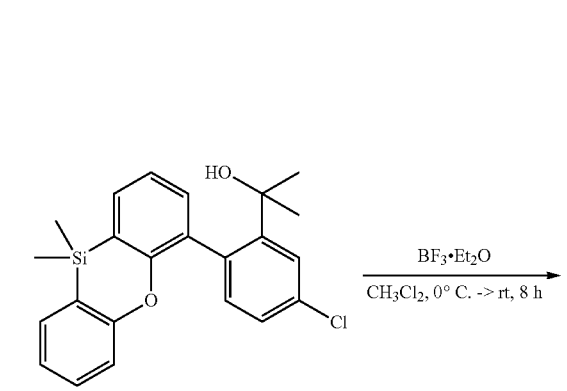

M-11

25.7 g (64.95 mmol) of the intermediate M-10 was put in a 3-necked round-bottomed flask heated and dried under vacuum and dissolved in 325 mL of anhydrous tetrahydrofuran under a nitrogen atmosphere, and the solution was cooled down to −10° C. and agitated.

Then, 54 mL of 3.0 M methyl magnesium bromide (162.4 mmol in diethylether) was slowly added thereto for 30 minutes. The mixture was heated up to room temperature and agitated under a nitrogen atmosphere for 12 hours. The reaction solution was cooled down to 0° C., and an aqueous solution obtained by dissolving 10.4 g (194.85 mmol) of ammonium chloride in 100 mL of distilled water was slowly added thereto. The reaction solution was extracted with distilled water and diethylether, and an organic layer solution obtained therefrom was dried with magnesium sulfate and filtered and then, concentrated under a reduced pressure. The dried residue was put in a 3-necked round-bottomed flask and dissolved in 325 mL of anhydrous dichloromethane under a nitrogen atmosphere, and the solution was cooled down to 0° C. and agitated. Then, 4 mL (32.5 mmol) of borontrifluoride diethyl etherate was slowly added thereto for 10 minutes, and the mixture was heated up to room temperature and agitated for 12 hours. When the reaction was complete, a sodium bicarbonate aqueous solution was slowly added thereto at 0° C., and the mixture was agitated for 30 minutes. The reaction solution was extracted with dichloromethane/distilled water, and the extraction solution was dried with magnesium sulfate and filtered and then, concentrated under a reduced pressure. Then, a product therefrom was purified with n-hexane/dichloromethane (9:1 of a volume ratio) through silica gel column chromatography, obtaining 15.9 g of a target compound of an intermediate M-11 (a yield of 65%).

LC-Mass (calcd.: 376.11 g/mol, measured.: M+1=377.25 g/mol)

Synthesis of Intermediate M-12

[Reaction Scheme 12]

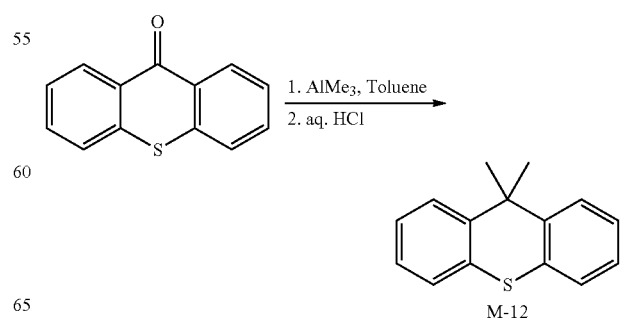

M-12

40 g (188.4 mmol) of tioxanthene-9-one was put in a 2-necked round-bottomed flask heated and dried under vacuum, 377 mL of anhydrous toluene was added thereto under a nitrogen atmosphere, and the mixture was cooled down to 0° C. and agitated.

Then, 188 mL of 2.0 M trimethylaluminum (377 mmol in toluene) was slowly added thereto, and the mixture was heated up to room temperature and agitated under a nitrogen atmosphere for 12 hours.

The reaction solution was slowly added to slurry obtained by mixing 188 mL of a 6N HCl aqueous solution and 181 g of ice, and the mixture was agitated at room temperature for 30 minutes. When the reaction was complete, the resultant was extracted with distilled water and toluene, and an organic layer solution obtained therefrom was dried with magnesium sulfate and filtered and then, concentrated under a reduced pressure. Then, a product therefrom was purified with n-hexane through silica gel column chromatography, obtaining 34.1 g of a target compound of an intermediate M-12 (a yield of 80%).

LC-Mass (calcd.: 226.08 g/mol, measured.: M+1=227.35 g/mol)

Synthesis of Intermediate M-13

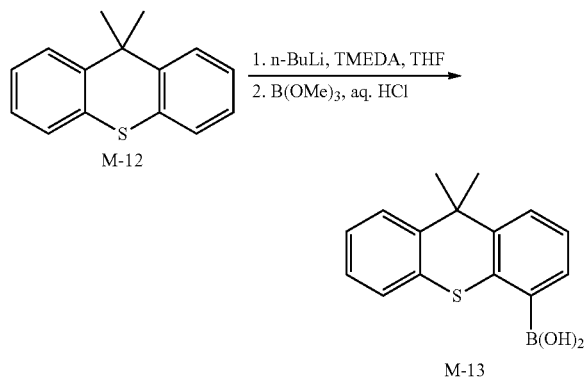

32.3 g (142.7 mmol) of the intermediate M-12 was put in a 2-necked round-bottomed flask heated and dried under vacuum, 476 mL of anhydrous tetrahydrofuran was added thereto under a nitrogen atmosphere, and the mixture was cooled down to −40° C. and agitated.

Then, 57 mL of 2.5 M n-butyllithium (142.7 mmol in hexane) was slowly added thereto, and 16.5 g (142.7 mmol) of N,N,N',N'-tetramethylethylenediamine was added thereto. The reaction solution was heated up to room temperature and agitated under a nitrogen atmosphere for 8 hours. The reaction solution was cooled down to −78° C., 10.9 g (157 mmol) of trimethylborate dissolved in 10 mL of anhydrous tetrahydrofuran was slowly added thereto, and the mixture was agitated at room temperature for 8 hours. The reaction solution was cooled down to 0° C., 234 mL of a 2N HCl aqueous solution was added thereto, and the mixture was agitated at room temperature for 1 hour. When the reaction was complete, the resultant was extracted with distilled water and diethylether, and an organic layer solution obtained therefrom was dried with magnesium sulfate and filtered and then, concentrated under a reduced pressure. The reaction solution was dissolved in acetone and recrystallized with n-hexane obtaining 23.5 g of a target compound of a white solid intermediate M-13 (a yield of 61%).

GC-Mass (calcd.: 270.09 g/mol, measured.: M+1=271.27 g/mol)

Synthesis of Intermediate M-14

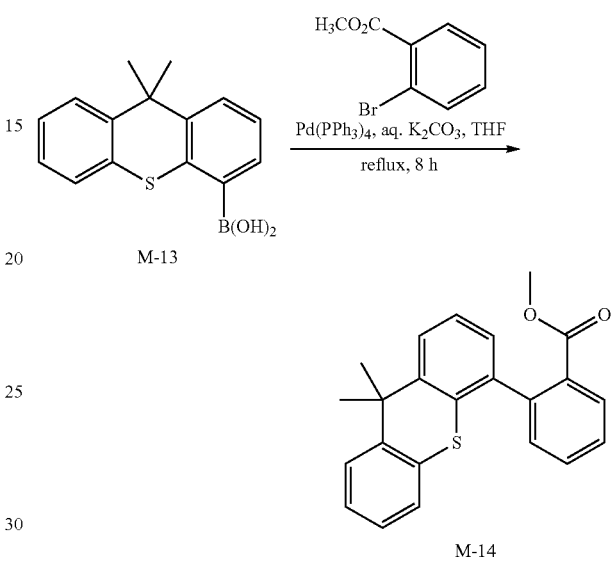

20.8 g (76.88 mmol) of the intermediate M-13, 18.2 g (84.57 mmol) of methyl-2-bromobenzoate and 0.89 g (0.769 mmol) of tetrakistriphenylphosphinepalladium were put in a flask, and dissolved in 257 mL of tetrahydrofuran under a nitrogen atmosphere, and then 128 ml of an aqueous solution obtained by dissolving 17 g (115.3 mmol) of potassium carbonate was added thereto, and the mixture was refluxed and agitated for 8 hours at 70° C. When the reaction was complete, the resultant was extracted with ethylacetate, and the extraction solution was dried with magnesium sulfate and filtered and then, concentrated under a reduced pressure. Then, a product therefrom was purified with n-hexane/ethylacetate (9:1 of a volume ratio) through silica gel column chromatography, obtaining 25.5 g of a target compound of an intermediate M-14 (a yield of 92%).

LC-Mass (calcd.: 360.12 g/mol, measured.: M+1=361.25 g/mol)

Synthesis of Intermediate M-15

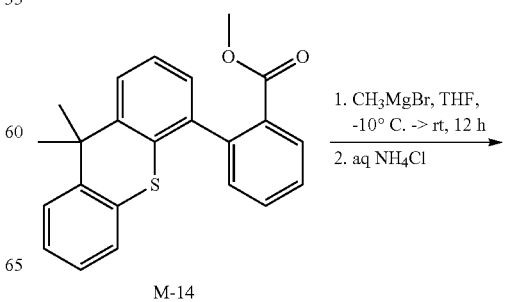

-continued

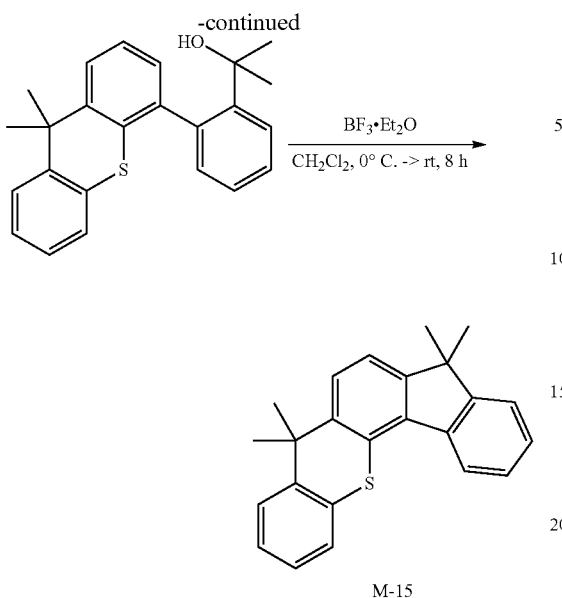

Synthesis of Intermediate M-16

[Reaction Scheme 16]

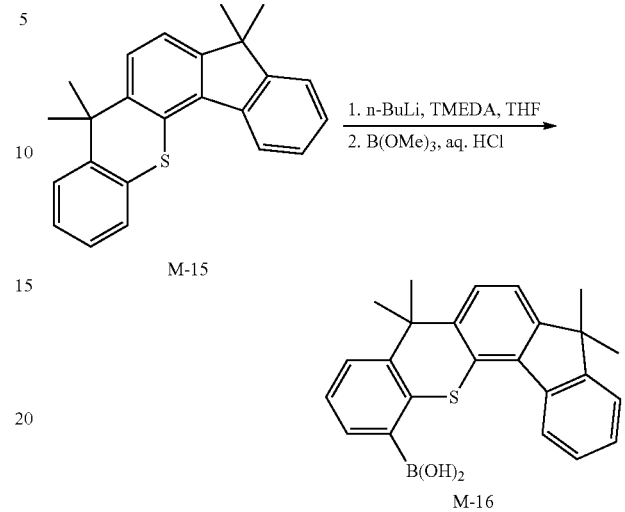

23.4 g (64.95 mmol) of the intermediate M-14 was put in a 3-necked round-bottomed flask heated and dried under vacuum and dissolved in 325 mL of anhydrous tetrahydrofuran under a nitrogen atmosphere, and the solution was cooled down to −10° C. and agitated.

Then, 54 mL of 3.0 M methyl magnesium bromide (162.4 mmol in diethylether) was slowly added thereto for 30 minutes. The mixture was heated up to room temperature and agitated under a nitrogen atmosphere for 12 hours. The reaction solution was cooled down to 0° C., and an aqueous solution obtained by dissolving 10.4 g (194.85 mmol) of ammonium chloride in 100 mL of distilled water was slowly added thereto. The reaction solution was extracted with distilled water and diethylether, and an organic layer solution obtained therefrom was dried with magnesium sulfate and filtered and then, concentrated under a reduced pressure. The dried residue was put in a 3-necked round-bottomed flask and dissolved in 325 mL of anhydrous dichloromethane under a nitrogen atmosphere, and the solution was cooled down to 0° C. and agitated. Then, 4 mL (32.5 mmol) of borontrifluoride diethyl etherate was slowly added thereto for 10 minutes, and the mixture was heated to room temperature and agitated for 12 hours. When the reaction was complete, a sodium bicarbonate aqueous solution was slowly added thereto at 0° C., and the mixture was agitated for 30 minutes. The reaction solution was extracted with dichloromethane/distilled water, and the extraction solution was dried with magnesium sulfate and filtered and then, concentrated under a reduced pressure. Then, a product therefrom was purified with n-hexane/dichloromethane (9:1 of a volume ratio) through silica gel column chromatography, obtaining 14.7 g of a target compound of an intermediate M-15 (a yield of 66%).

LC-Mass (calcd.: 342.14 g/mol, measured.: M+1=343.19 g/mol)

24.5 g (71.4 mmol) of the intermediate M-19 was put in a 2-necked round-bottomed flask heated and dried under vacuum and dissolved in 238 mL of anhydrous tetrahydrofuran under a nitrogen atmosphere, and the solution was cooled down to −40° C. and agitated.

Then, 28.6 mL of 2.5 M n-butyllithium (71.4 mmol in hexane) was slowly added thereto, and 8.3 g (71.4 mmol) of N,N,N',N'-tetramethylethylenediamine was added thereto. The mixture was heated up to room temperature and agitated under a nitrogen atmosphere for 8 hours. The reaction solution was cooled down to −78° C., 8.9 g (85.7 mmol) of trimethylborate dissolved in 10 mL of anhydrous tetahydrofurrmn was slowly added thereto, and the mixture was agitated at room temperature for 8 hours. The reaction solution was cooled down to 0° C., 117 mL of a 2N HCl aqueous solution was added thereto, and the mixture was agitated at room temperature for one hour. When the reaction was complete, the resultant was extracted with distilled water and diethylether, and an organic layer solution was dried with magnesium sulfate and filtered and then, concentrated under a reduced pressure. The reaction solution was dissolved in acetone and recrystallized with n-hexane, obtaining 17.9 g of a target compound of a white solid intermediate M-16 (a yield of 65%).

GC-Mass (calcd.: 386.1 g/mol, measured.: M+1=387.19 g/mol)

Synthesis of Intermediate M-17

[Reaction Scheme 17]

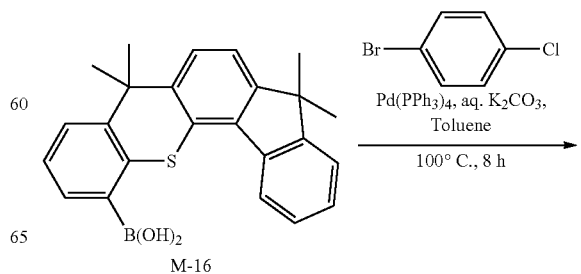

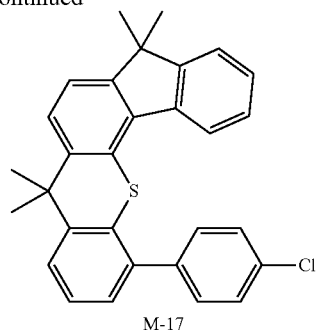

M-17

18 g (46.6 mmol) of the intermediate M-16, 8.9 g (46.6 mmol) of 1-bromo-4-chlorobenzene and 0.54 g (0.466 mmol) of tetrakistriphenylphosphinepalladium were put in a flask and dissolved in 233 mL of toluene under a nitrogen atmosphere, and 80 ml of an aqueous solution obtained by dissolving 10.3 g (69.9 mmol) of potassium carbonate was added thereto, and the mixture was refluxed and agitated at 100° C. for 8 hours. When the reaction was complete, the resultant was extracted with ethylacetate, and an extraction solution obtained therefrom was dried with magnesium sulfate and filtered and then, concentrated under a reduced pressure. Then, a product therefrom was purified with n-hexane/dichloromethane (9:1 of a volume ratio) through silica gel column chromatography, obtaining 19.2 g of a target compound of an intermediate M-17 (a yield of 91%).

LC-Mass (calcd.: 452.14 g/mol, measured.: M+1=453.23 g/mol)

Synthesis of Intermediate M-18

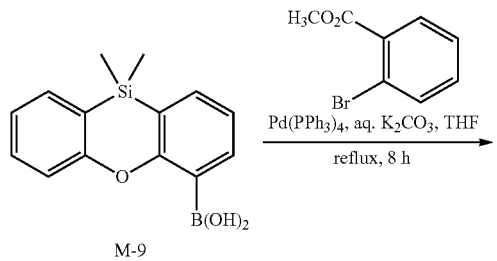

M-18

20.8 g (76.88 mmol) of the intermediate M-9, 18.2 g (84.57 mmol) of methyl-2-bromobenzoate and 0.89 g (0.769 mmol) of tetrakistriphenylphosphinepalladium were put in a flask and 257 mL of tetrahydrofuran under a nitrogen atmosphere, 128 ml of an aqueous solution obtained by dissolving 17 g (115.3 mmol) of potassium carbonate was added thereto, and the mixture was refluxed and agitated at 70° C. for 8 hours. When the reaction was complete, the resultant was extracted with ethylacetate, and an extraction solution obtained therefrom was dried with magnesium sulfate and filtered and then, concentrated under a reduced pressure. Then, a product was purified with n-hexane/ethylacetate (9:1 of a volume ratio) through silica gel column chromatography, obtaining 24.9 g of a target compound of an intermediate M-18 (a yield of 90%).

LC-Mass (calcd.: 360.12 g/mol, measured.: M+1=361.33 g/mol)

Synthesis of Intermediate M-19

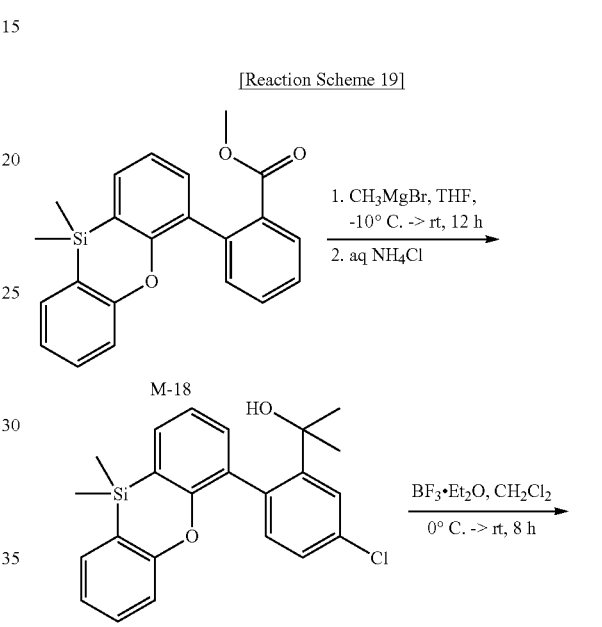

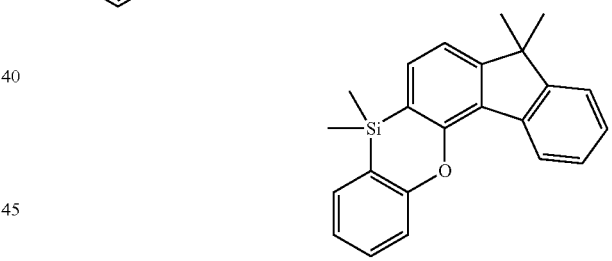

M-19

23.4 g (64.95 mmol) of the intermediate M-18 was put in a 3-neckd round-bottomed flask heated and dried under vacuum and dissolved in 325 mL of anhydrous tetrahydrofuran under a nitrogen atmosphere, and the solution was cooled down to −10° C. and agitated.

Then, 54 mL of 3.0 M methyl magnesium bromide (162.4 mmol in diethylether) was slowly added thereto for 30 minutes. The mixture was heated up to room temperature and agitated under a nitrogen atmosphere for 12 hours. The reaction solution was cooled down to 0° C., and an aqueous solution obtained by dissolving 10.4 g (194.85 mmol) of ammonium chloride in 100 mL of distilled water was slowly added thereto. The reaction solution was extracted with distilled water and diethylether, and an organic layer solution obtained therefrom was dried with magnesium sulfate and filtered and then, concentrated under a reduced pressure. The dried residue was put in a 3-necked round-bottomed flask and dissolved in 325 mL of anhydrous dichloromethane under a nitrogen atmosphere, and the solution was cooled down to 0° C. and agitated. Then, 4 mL (32.5 mmol) of borontrifluoride diethyl etherate was slowly added thereto for 10 minutes, and the mixture was heated up to room temperature and agitated for 12 hours. When the reaction was complete, a sodium bicarbonate aqueous solution was slowly added thereto at 0° C., and the mixture was agitated for 30 minutes. The resultant was extracted with dichloromethane/distilled water, an extraction solution obtained therefrom was dried with magnesium sulfate and filtered and then, concentrated under a reduced pressure. Then, a product therefrom was purified with n-hexane/dichloromethane (9:1 of a volume ratio) through silica gel column chromatography, obtaining 15.1 g of a target compound of an intermediate M-19 (a yield of 68%).

LC-Mass (calcd.: 342.14 g/mol, measured.: M+1=343.22 g/mol)

Synthesis of Intermediate M-20

[Reaction Scheme 20]

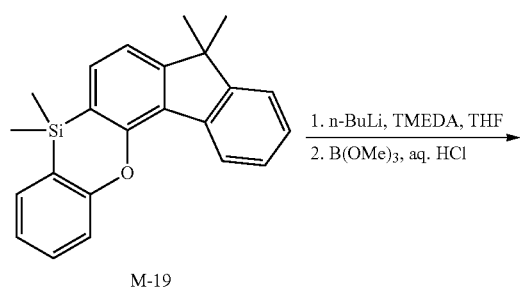

M-19

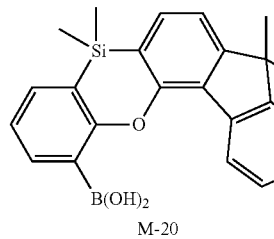

M-20

24.5 g (71.4 mmol) of the intermediate M-19 was put in a 2-necked round-bottomed flask heated and dried under vacuum and dissolved in 238 mL of anhydrous tetrahydrofuran under a nitrogen atmosphere, and the solution was cooled down to −40° C. and agitated.

Then, 28.6 mL of 2.5 M n-butyllithium (71.4 mmol in hexane) was slowly added thereto, and 8.3 g (71.4 mmol) of N,N,N',N'-tetramethylethylenediamine was added thereto. The mixture was heated up to room temperature and agitated under a nitrogen atmosphere for 8 hours. The reaction solution was cooled down to −78° C., 8.9 g (85.7 mmol) of trimethylborate dissolved in 10 mL of anhydrous tetrahydrofuran was slowly added thereto, and the mixture was agitated at room temperature for 8 hours. The reaction solution was cooled down to 0° C., 117 mL of a 2N HCl aqueous solution was added thereto, and the mixture was agitated at room temperature for one hour. When the reaction was complete, the resultant was extracted with distilled water and diethylether, and an organic layer solution obtained therefrom was dried with magnesium sulfate and filtered and then, concentrated under a reduced pressure. The reaction solution was dissolved in acetone and recrystallized with n-hexane, obtaining 18.5 g of a target compound of a white solid intermediate M-20 (a yield of 67%).

C-Mass (calcd.: 386.15 g/mol, measured.: M+1=387.24 g/mol)

Synthesis of Intermediate M-21

[Reaction Scheme 21]

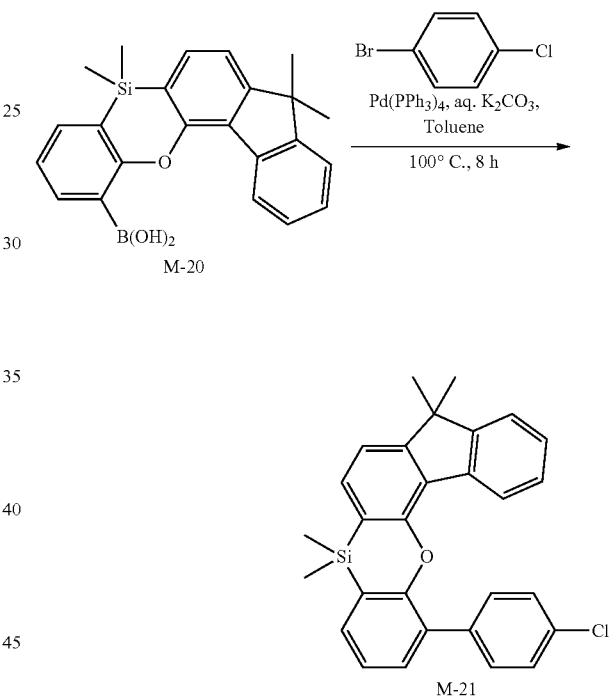

18 g (46.6 mmol) of the intermediate M-20, 8.9 g (46.6 mmol) of 1-bromo-4-chlorobenzene and 0.54 g (0.466 mmol) of tetrakistriphenylphosphinepalladium were put in a flask and dissolved in 233 mL of toluene under a nitrogen atmosphere, 80 ml of an aqueous solution obtained by dissolving 10.3 g (69.9 mmol) of potassium carbonate was added thereto, and the mixture was refluxed and agitated at 100° C. for 8 hours. When the reaction was complete, the resultant was extracted with ethylacetate and an extraction solution was dried with magnesium sulfate and filtered and then, concentrated under a reduced pressure. Then, a product therefrom was purified with n-hexane/dichloromethane (9:1 of a volume ratio) through silica gel column chromatography, obtaining 19.6 g of a target compound of an intermediate M-21 (a yield of 93%).

LC-Mass (calcd.: 452.14 g/mol, measured.: M+1=453.28 g/mol)

Synthesis of Intermediate M-22

[Reaction Scheme 22]

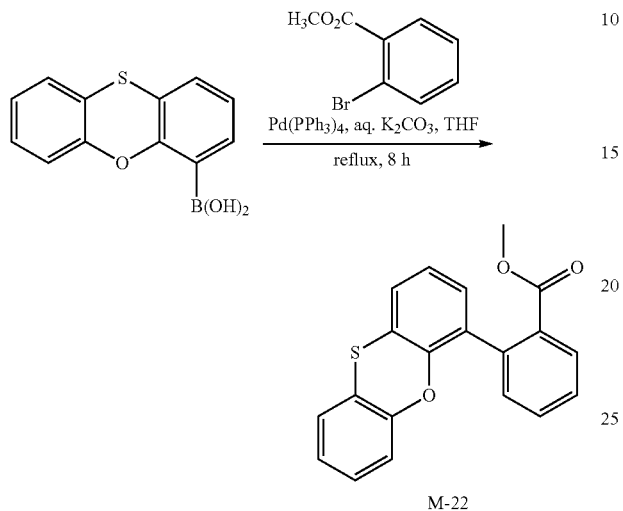

18.8 g (76.88 mmol) of 4-phenoxathiinylboronic acid, 18.2 g (84.57 mmol) of methyl-2-bromobenzoate and 0.89 g (0.769 mmol) of tetrakistriphenylphosphine palladium were put in a flask and dissolved in 257 mL of tetrahydrofuran under a nitrogen atmosphere, 128 ml of an aqueous solution obtained by dissolving 17 g (115.3 mmol) of potassium carbonate was added thereto, and the mixture was refluxed and agitated at 70° C. for 8 hours. When the reaction was complete, the resultant was extracted with ethylacetate, and an extraction solution obtained therefrom was dried with magnesium sulfate and filtered and then, concentrated under a reduced pressure. Then, a product therefrom was purified with n-hexane/ethylacetate (9:1 of a volume ratio) through silica gel column chromatography, obtaining 23.4 g of a target compound of an intermediate M-22 (a yield of 91%).

LC-Mass (calcd.: 334.39 g/mol, measured.: M+1=335.28 g/mol)

Synthesis of Intermediate M-23

[Reaction Scheme 23]

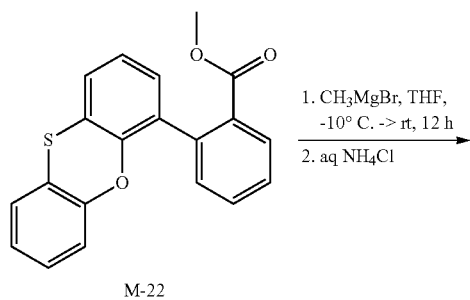

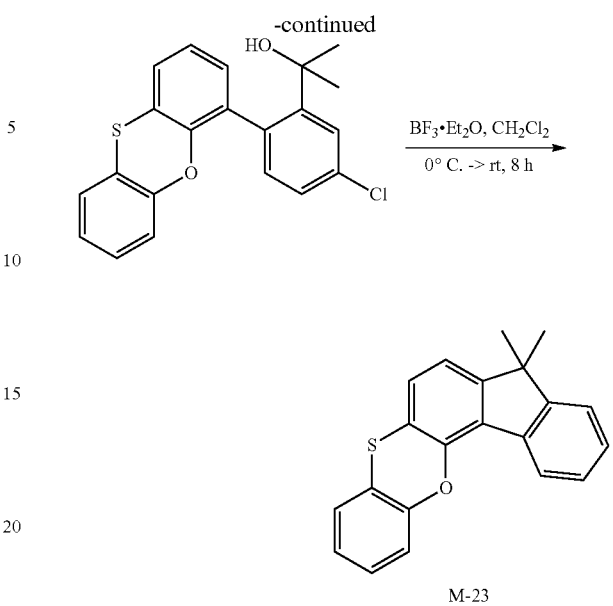

21.7 g (64.95 mmol) of the intermediate M-22 was put in a 3-necked round-bottomed flask heated and dried under vacuum and dissolved in 325 mL of anhydrous tetrahydrofuran under a nitrogen atmosphere, and the solution was cooled down to −10° C. and agitated.

Then, 54 mL of 3.0 M methyl magnesium bromide (162.4 mmol in diethylether) was slowly added thereto for 30 minutes. The mixture was heated up to room temperature and agitated for 12 hours under a nitrogen atmosphere. The reaction solution was cooled down to 0° C., and an aqueous solution obtained by dissolving 10.4 g (194.85 mmol) of ammonium chloride in 100 mL of distilled water was slowly added thereto. The reaction solution was extracted with distilled water and diethylether, and an organic layer solution was dried with magnesium sulfate and filtered and then, concentrated under a reduced pressure. The dried residue was put in a 3-necked round-bottomed flask and dissolved in 325 mL of anhydrous dichlormethane under a nitrogen atmosphere, and the solution was cooled down to 0° C. and agitated. Then, 4 mL (32.5 mmol) of borontrifluoride diethyl etherate was slowly added thereto for 10 minutes, and the mixture was heated up to room temperature and agitated for 12 hours. When the reaction was complete, a sodium bicarbonate aqueous solution was slowly added thereto at 0° C., and the mixture was agitated for 30 minutes. The reaction solution was extracted with dichloromethane/distilled water, and the extraction solution was dried with magnesium sulfate and filtered and then, concentrated under a reduced pressure. Then, a product therefrom was purified with n-hexane/dichloromethane (9:1 of a volume ratio) through silica gel column chromatography, obtaining 13.2 g of a target compound of an intermediate M-23 (a yield of 64%).

LC-Mass (calcd.: 316.42 g/mol, measured.: M+1=317.55 g/mol)

Synthesis of Intermediate M-24

[Reaction Scheme 24]

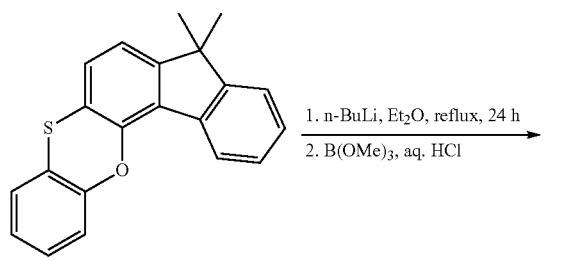

13 g (41.08 mmol) of the intermediate M-23 was put in a 2-necked round-bottomed flask heated and dried under vacuum and dissolved in 410 mL of anhydrous diethylether under a nitrogen atmosphere, and the solution was cooled down to 0° C. and agitated.

Then, 16.4 mL of 2.5 M n-butyllithium (41.08 mmol in hexane) was added thereto, and the mixture was heated and then, refluxed and agitated under a nitrogen atmosphere for 24 hours. The reaction solution was cooled down to −40° C., a solution obtained by dissolving 4.7 g (45.2 mmol) of trimethylborate in 10 mL of anhydrous diethylether was slowly added thereto, and the mixture was agitated at room temperature for 12 hours. The reaction solution was cooled down to 0° C., 68 mL of a 2N HCl aqueous solution was added thereto, and the mixture was agitated at room temperature for one hour. When the reaction was complete, the resultant was extracted with distilled water and diethylether, and an organic layer solution was dried with magnesium sulfate and filtered and then, concentrated under a reduced pressure. The reaction solution was dissolved in acetone, and the solution was recrystallized with n-hexane, obtaining 7.7 g of a target compound of a white solid intermediate M-24 (a yield of 52%).

GC-Mass (calcd.: 360.10 g/mol, measured.: M+1=361.28 g/mol)

Synthesis of Intermediate M-25

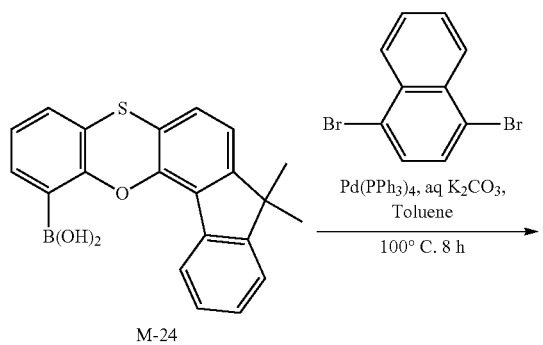

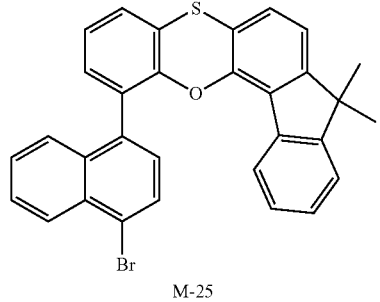

7 g (19.43 mmol) of the intermediate M-24, 8.3 g (29.15 mmol) of 1,4-dibromonaphthalene and 0.23 g (0.194 mmol) of tetrakistriphenylphosphinepalladium were put in a flask and dissolved in 190 mL of toluene under a nitrogen atmosphere, 60 ml of an aqueous solution obtained by dissolving 4.3 g (29.14 mmol) of potassium carbonate was added thereto, and the mixture was refluxed and agitated at 100° C. for 8 hours. When the reaction was complete, the resultant was extracted with ethylacetate, and the extraction solution was dried with magnesium sulfate and filtered and then, concentrated under a reduced pressure. Then, a product therefrom was purified with n-hexane/dichloromethane (9:1 of a volume ratio) through silica gel column chromatography, obtaining 7.9 g of a target compound of an intermediate M-25 (a yield of 78%).

LC-Mass (calcd.: 520.05 g/mol, measured.: M+1=521.16 g/mol)

Synthesis of Intermediate M-26

[Reaction Scheme 26]

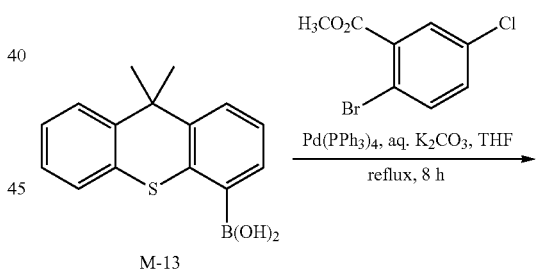

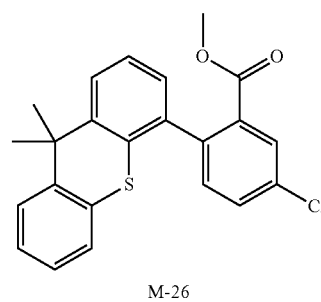

20.8 g (76.88 mmol) of the intermediate M-13, 21.1 g (84.57 mmol) of methyl-2-bromo-5-chlorobenzoate and 0.89 g (0.769 mmol) of tetrakistriphenylphosphinepalladium were put in a flask and dissolved in 257 mL of tetrahydrofuran under a nitrogen atmosphere, 128 ml of an aqueous solution obtained by dissolving 17 g (1153 mmol) of potassium carbonate was added thereto, and the mixture was refluxed and agitated at 70° C. for 8 hours. When the reaction was complete, the resultant was extracted with ethylacetate, and the extraction solution was dried with magnesium sulfate and filtered and then, concentrated under a reduced pressure. Then, a product therefrom was purified with n-hexan/ethylacetate (9:1 of a volume ratio) through silica gel column chromatography, obtaining 27.3 g of a target compound of an intermediate M-26 (a yield of 90%).

LC-Mass (calcd.: 394.08 g/mol, measured.: M+1=395.16 g/mol)

Synthesis of Intermediate M-27

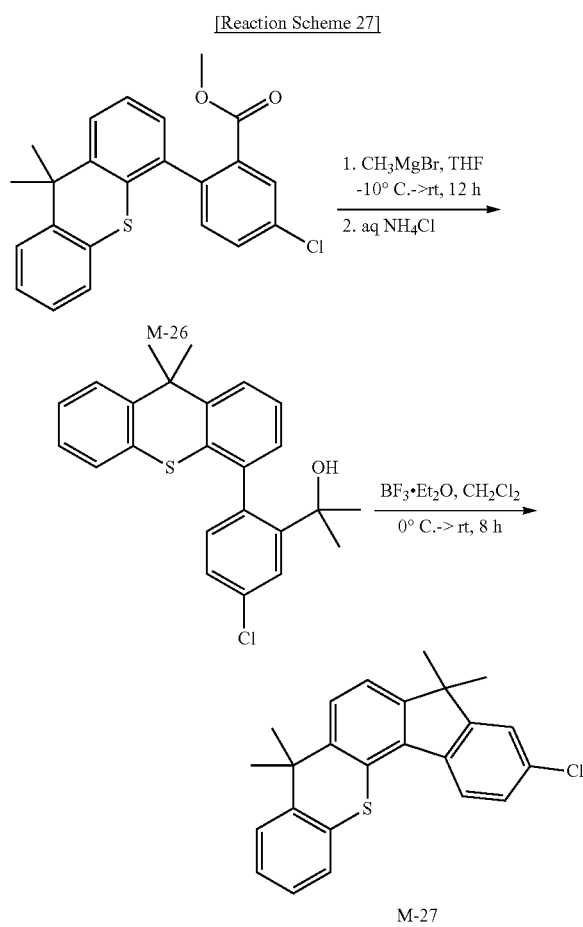

M-27

25.6 g (64.95 mmol) of the intermediate M-26 was put in a 3-necked round-bottomed flask heated and dried under vacuum and dissolved in 325 mL of anhydrous tetrahydrofuran under a nitrogen atmosphere, and the solution was cooled down to −10° C. and agitated.

Then, 54 mL of 3.0 M methyl magnesium bromide (162.4 mmol in diethylether) was slowly added thereto for 30 minutes. The mixture was agitated at room temperature under a nitrogen atmosphere for 12 hours. The reaction solution was cooled down to 0° C., and an aqueous solution obtained by dissolving 10.4 g (194.85 mmol) of ammonium chloride in 100 mL of distilled water was slowly added thereto. The obtained mixture was extracted with distilled water and diethylether, and an organic layer solution obtained therefrom was dried with magnesium sulfate and filtered and then, concentrated under a reduced pressure. The dried residue was put in a 3-neckedd round-bottomed flask and dissolved in 325 mL of anhydrous dichloromethane under a nitrogen atmosphere, and the solution was cooled down to 0° C. and agitated. Then, 4 mL (32.5 mmol) of borontrifluoride diethyl etherate was slowly added thereto for 10 minutes, and the mixture was heated up to room temperature and agitated for 12 hours. When the reaction was complete, a sodium bicarbonate aqueous solution was slowly added thereto, and the mixture was agitated at 0° C. for 30 minutes. The reaction solution was extracted with dichloromethane/distilled water, and the extraction solution was dried with magnesium sulfate and filtered and then, concentrated under a reduced pressure. Then, a product was purified with n-hexane/dichloromethane (9:1 of a volume ratio) through silica gel column chromatography, obtaining 15.4 g of a target compound of an intermediate M-27 (a yield of 63%).

LC-Mass (calcd.: 376.11 g/mol, measured.: M+1=377.23 g/mol)

Synthesis of Intermediate M-28

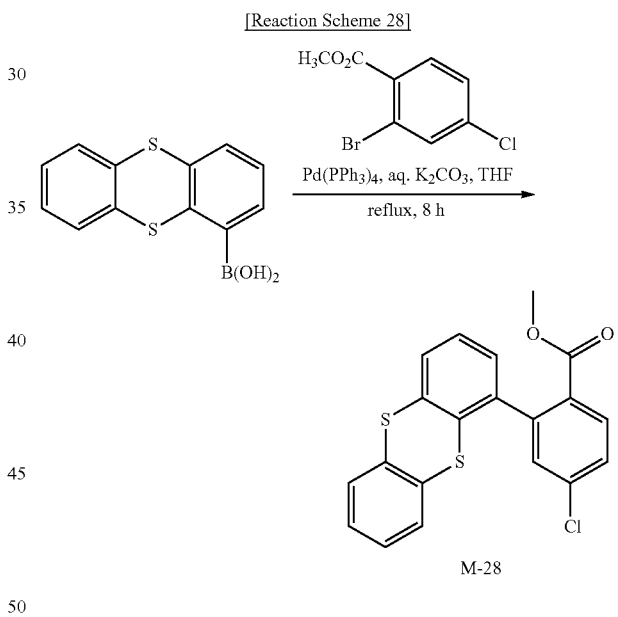

M-28

20 g (76.88 mmol) of thianthrene-1-boronic acid, 21.1 g (84.57 mmol) of methyl-2-bromo-4-chlorobenzoate and 0.89 g (0.769 mmol) of tetrakistriphenylphosphinepalladium were put in a flask and dissolved in 257 mL of tetrahydrofuran under a nitrogen atmosphere, 128 ml of an aqueous solution obtained by dissolving 17 g (115.3 mmol) of potassium carbonate was added thereto, and the mixture was refluxed and agitated at 70° C. for 8 hours. When the reaction was complete, the resultant was extracted with ethylacetate, and the extraction solution was dried with magnesium sulfate and filtered and then, concentrated under a reduced pressure. Then, a product therefrom was purified with n-hexane/ethylacetate (9:1 of a volume ratio) through silica gel column chromatography, obtaining 27.2 g of a target compound of an intermediate M-28 (a yield of 92%).

LC-Mass (calcd.: 384.00 g/mol, measured.: M+1=385.21 g/mol)

Synthesis of Intermediate M-29

[Reaction Scheme 29]

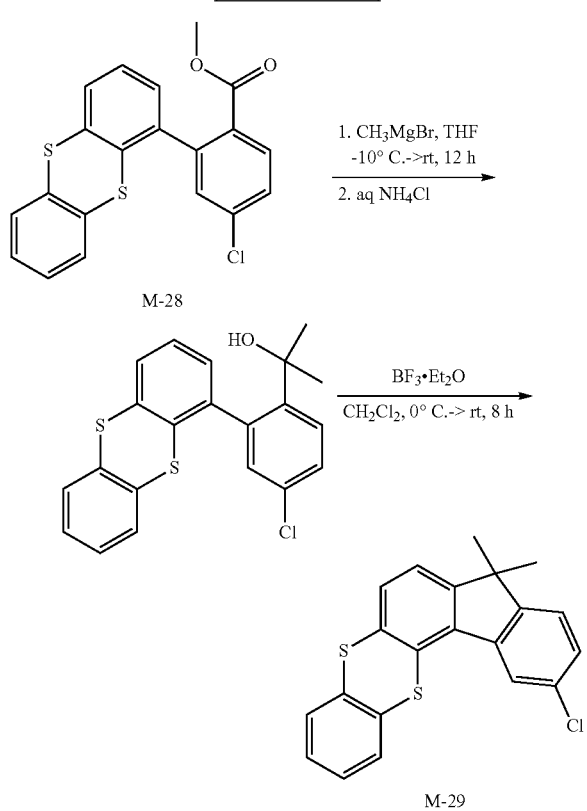

25 g (64.95 mmol) of the intermediate M-28 was put in a 3-necked round-bottomed flask heated and dried under vacuum and dissolved in 325 mL of anhydrous tetrahydrofuran under a nitrogen atmosphere, and the solution was cooled down to −10° C. and agitated.

Then, 54 mL of 3.0 M methyl magnesium bromide (162.4 mmol in diethylether) was slowly added thereto for 30 minutes. The mixture was heated up to room temperature and agitated under a nitrogen atmosphere for 12 hours. The reaction solution was cooled down to 0° C., and 100 mL of an aqueous solution obtained by dissolving 10.4 g (194.85 mmol) of ammonium chloride in distilled water was slowly added thereto. The reaction solution was extracted with distilled water and diethylether, and an organic layer solution obtained therefrom was dried with magnesium sulfate and filtered and then, concentrated under a reduced pressure. The dried residue was put in a 3-necked round-bottomed flask and dissolved in 325 mL of anhydrous dichloromethane under a nitrogen atmosphere, and the solution was cooled down to 0° C. and agitated. Then, 4 mL (32.5 mmol) of borontrifluoride diethyl etherate was slowly added thereto for 10 minutes, and the mixture was heated up to room temperature and agitated for 12 hours. When the reaction was complete, a sodium bicarbonate aqueous solution was slowly added thereto at 0° C., and the mixture was agitated for 30 minutes. The reaction solution was extracted with dichloromethane/distilled water, and the extraction solution was dried with magnesium sulfate and filtered and then, concentrated under a reduced pressure. Then, a product therefrom was purified with n-hexane/dichloromethane (9:1 of a volume ratio) through silica gel column chromatography, obtaining 16.7 g of a target compound of an intermediate M-29 (a yield of 70%).

LC-Mass (calcd.: 366.03 g/mol, measured.: M+1=367.14 g/mol)

EXAMPLE 1

Preparation of Compound Represented by Chemical Formula A-2

[Reaction Scheme 28]

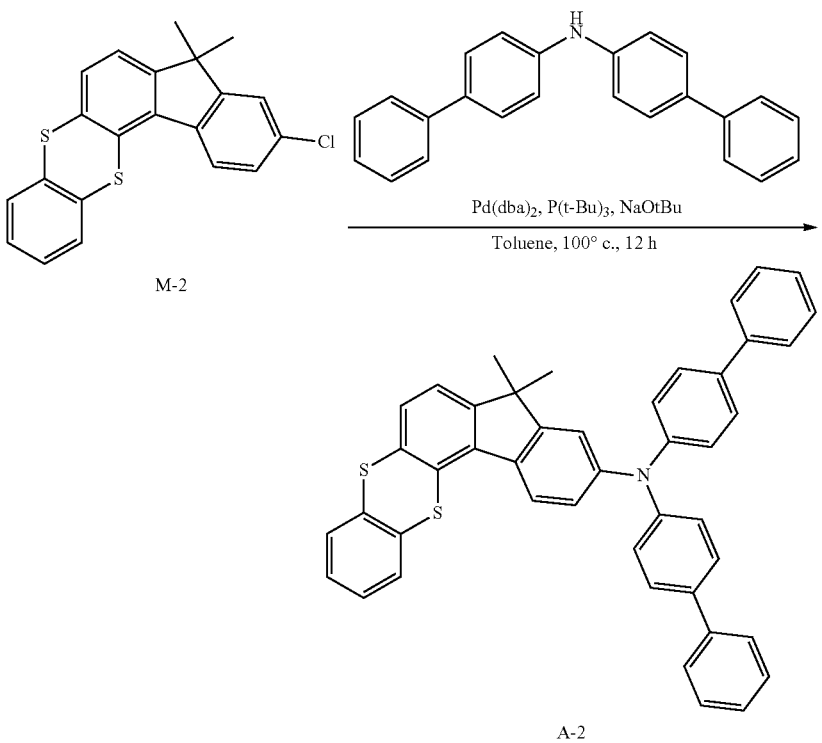

11.2 g (30.59 mmol) of the intermediate M-2, 9.8 g (30.59 mmol) of bis-biphenyl-4-yl-mine, and 3.8 g (39.8 mmol) of sodium t-butoxide were put in a round-bottomed flask, 200 mL of toluene was added thereto, and 0.19 g (0.92 mmol) of tri-tert-butylphosphine and 20.18 g (0.31 mmol) of Pd(dba)$_2$ were added thereto, and the mixture was agitated under a nitrogen atmosphere for 12 hours at 100° C. When the reaction was complete, the resultant was extracted with toluene and distilled water, and an organic layer obtained therefrom was dried with magnesium sulfate and filtered and then, concentrated under a reduced pressure. Then, a product therefrom was purified with n-hexane/dichloromethane (7:3 of a volume ratio) through silica gel column chromatography, obtaining 18.1 g of a target compound A-2 (a yield of 91%).

LC-Mass (calcd.: 651.21 g/mol, measured.: M+1=652.32 g/mol)

EXAMPLE 2

Preparation of Compound Represented by Chemical Formula A-3

10.7 g (30.59 mmol) of the intermediate M-4, 9.8 g (30.59 mmol) of bis-biphenyl-4-yl-amine, and 3.8 g (39.8 mmol) of sodium t-butoxide were put in a round-bottomed flask, 200 mL of toluene was added thereto, 0.19 g (0.92 mmol) of tri-tert-butylphosphine and 20.18 g (0.31 mmol) of Pd(dba)$_2$ were added thereto, and the mixture was agitated under a nitrogen atmosphere for 12 hours at 100° C. When the reaction was complete, the resultant was extracted with toluene and distilled water, and an organic layer obtained therefrom was dried with magnesium sulfate and filtered and then, concentrated under a reduced pressure. Then, a product therefrom was purified with n-hexane/dichloromethane (7:3 of a volume ratio) through silica gel column chromatography, obtaining 18.1 g of a target compound A-3 (a yield of 93%).

LC-Mass (calcd.: 635.23 g/mol, measured.: M+1=636.51 g/mol)

[Reaction Scheme 29]

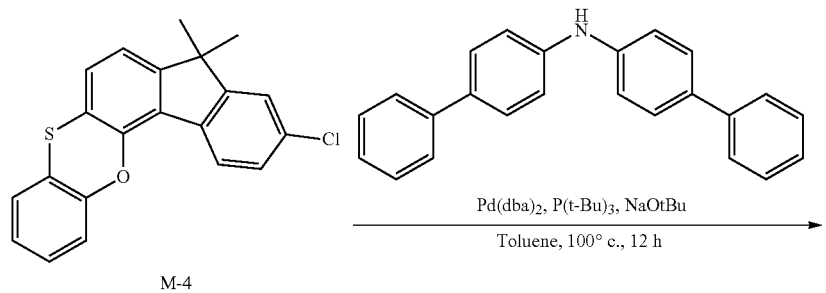

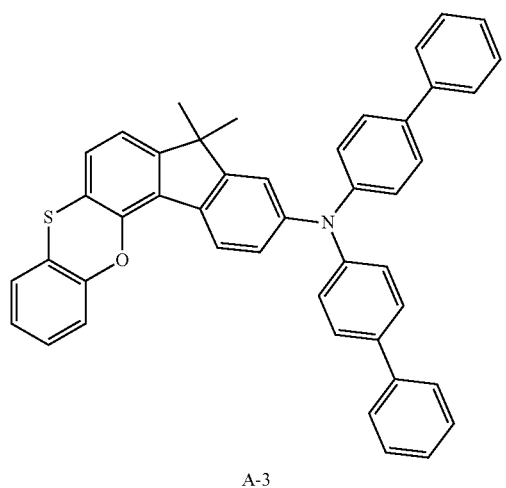

A-3

EXAMPLE 3

Preparation of Compound Represented by Chemical Formula A-37

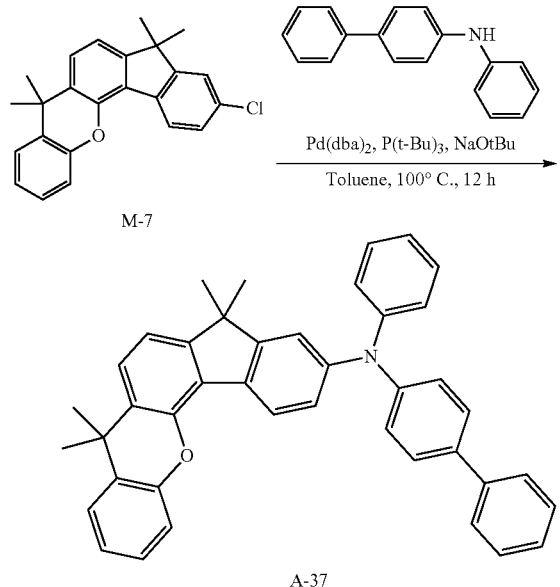

11.04 g (30.59 mmol) of the intermediate M-7, 7.5 g (30.59 mmol) of biphenyl-4-yl-phenyl-amine, and 3.8 g (39.8 mmol) of sodium t-butoxide were put in a round-bottomed flask, 200 mL of toluene was added thereto, 0.19 g (0.92 mmol) of tri-tert-butylphosphine and 20.18 g (0.31 mmol) of Pd(dba)$_2$ were added thereto, and the mixture was agitated under a nitrogen atmosphere for 12 hours at 100° C. When the reaction was complete, the resultant was extracted with toluene and distilled water, and an organic layer obtained therefrom was dried with magnesium sulfate and filtered and then, concentrated under a reduced pressure. Then, a product therefrom was purified with n-hexane/dichloromethane (7:3 of a volume ratio) through silica gel column chromatography, obtaining 15.7 g of a target compound A-37 (a yield of 90%).

LC-Mass (calcd.: 569.278/mol, measured.: M+1=570.36 g/mol)

EXAMPLE 4

Preparation of Compound Represented by Chemical Formula A-39

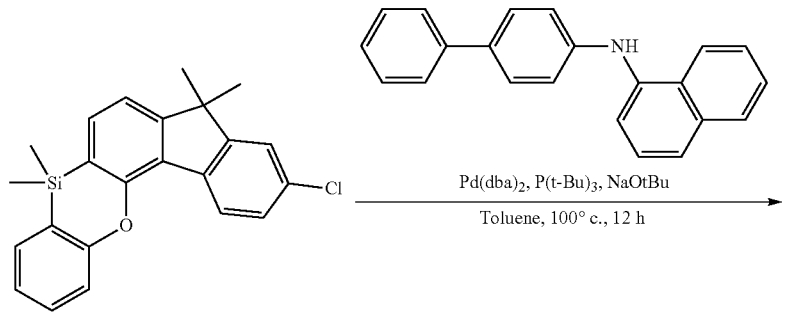

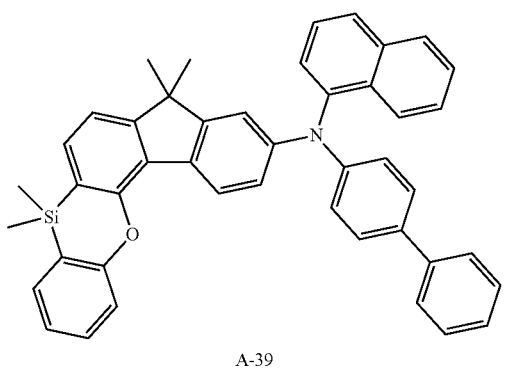

11.5 g (30.59 mmol) of the intermediate M-11, 9.0 g (30.59 mmol) of biphenyl-4-yl-naphthalen-1-yl-amine, and 3.8 g (39.8 mmol) of sodium t-butoxide were put in a round-bottomed flask, 200 mL of toluene, 0.19 g (0.92 mmol) of tri-tert-butylphosphine and 20.18 g (0.31 mmol) of Pd(dba)$_2$ were added thereto, and the mixture was agitated under a nitrogen atmosphere for 12 hours at 100° C. When the reaction was complete, the resultant was extracted with toluene and distilled water, and an organic layer was dried with magnesium sulfate and filtered and then, concentrated under a reduced pressure. Then, a product therefrom was purified with n-hexane/dichloromethane (7:3 of a volume ratio) through silica gel column chromatography, obtaining 17.9 g of a target compound A-39 (a yield of 92%).

LC-Mass (calcd.: 635.26 g/mol, measured.: M+1=636.31 g/mol)

EXAMPLE 5

Preparation of Compound Represented by Chemical Formula B-10

13.9 g (30.59 mmol) of the intermediate M-17, 9.0 g (30.59 mmol) of biphenyl-4-yl-naphthalen-1-yl-amine, and 3.8 g (39.8 mmol) of sodium t-butoxide were put in a round-bottomed flask, 200 mL of toluene was added thereto, and 0.19 g (0.92 mmol) of tri-tert-butylphosphine and 20.18 g (0.31 mmol) of Pd(dba)$_2$ were added thereto, and then, the mixture was agitated under a nitrogen atmosphere for 12 hours at 100° C. When the reaction was complete, the resultant was extracted with toluene and distilled water, and an organic layer obtained therefrom was dried with magnesium sulfate and filtered and then, concentrated under a reduced pressure. Then, a product was purified with n-hexane/dichloromethane (7:3 of a volume ratio) through silica gel column chromatography, obtaining 19.4 g of a target compound B-10 (a yield of 89%).

LC-Mass (calcd.: 711.30 g/mol, measured.: M+1=712.28 g/mol)

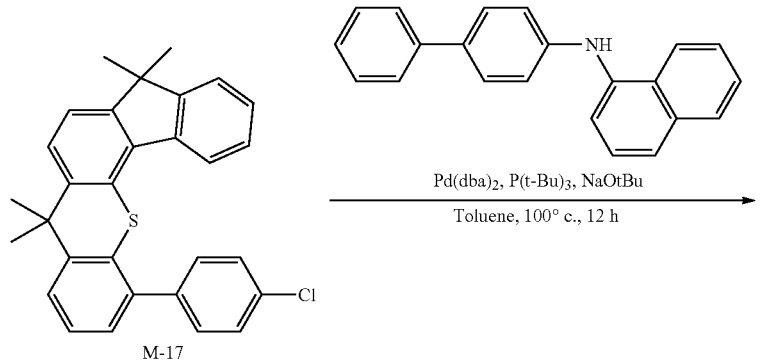

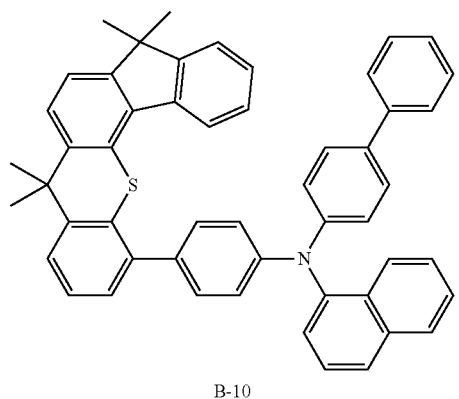

EXAMPLE 6

Preparation of Compound Represented by Chemical Formula B-11

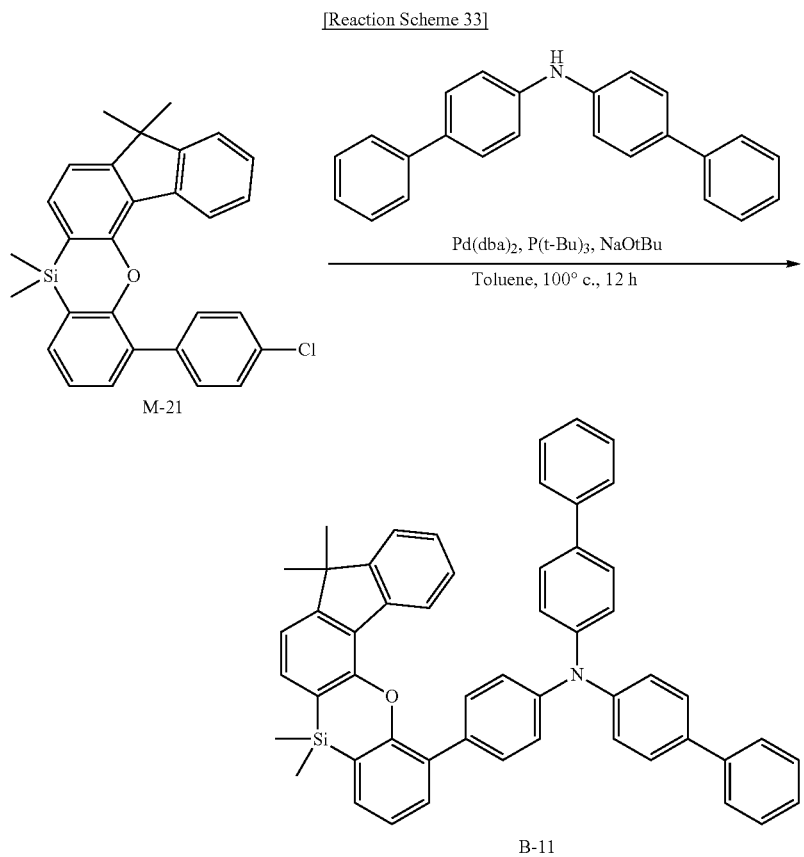

13.9 g (30.59 mmol) of the intermediate M-21, 9.8 g (30.59 mmol) of bis-biphenyl-4-yl-amine, and 3.8 g (39.8 mmol) of sodium t-butoxide were put in a round-bottomed flask, 200 mL of toluene was added thereto, and 0.19 g (0.92 mmol) of tri-tert-butylphosphine and 20.18 g (0.31 mmol) of Pd(dba)$_2$ were added thereto, and then, the mixture was agitated under a nitrogen atmosphere for 12 hours at 100° C. When the reaction was complete, the resultant was extracted with toluene and distilled water, and an organic layer obtained therefrom was dried with magnesium sulfate and filtered and then, concentrated under a reduced pressure. Then, a product therefrom was purified with n-hexane/dichloromethane (7:3 of a volume ratio) through silica gel column chromatography, obtaining 20.3 g of a target compound B-11 (a yield of 90%).

LC-Mass (calcd.: 737.31 g/mol, measured.: M+1=738.28 g/mol)

EXAMPLE 7

Preparation of Compound Represented by Chemical Formula B-19

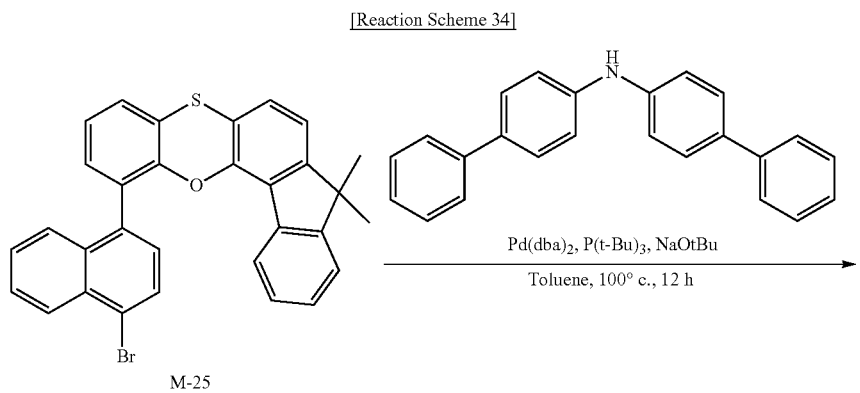

-continued

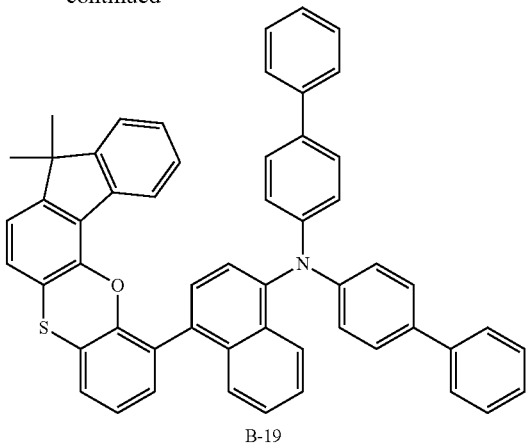

B-19

16 g (30.59 mmol) of the intermediate M-25, 9.8 g (30.59 mmol) of bis-biphenyl-4-yl-amine, and 3.8 g (39.8 mmol) of sodium t-butoxide were put in a round-bottomed flask, 200 mL of toluene was added thereto, and 0.19 g (0.92 mmol) of tri-tert-butylphosphine and 20.18 g (0.31 mmol) of Pd(dba)$_2$ were added thereto, and then, the mixture was agitated under a nitrogen atmosphere for 12 hours at 100° C. When the reaction was complete, the resultant was extracted with toluene and distilled water, and an organic layer obtained therefrom was dried with magnesium sulfate and filtered and then, concentrated under a reduced pressure. Then, a product therefrom was purified with n-hexane/dichloromethane (7:3 of a volume ratio) through silica gel column chromatography, obtaining 20.5 g of a target compound B-19 (a yield of 88%)

LC-Mass (calcd.: 761.28 g/mol, measured.: M+1=762.31 g/mol)

EXAMPLE 8

Preparation of Compound Represented by Chemical Formula D-5

[Reaction Scheme 35]

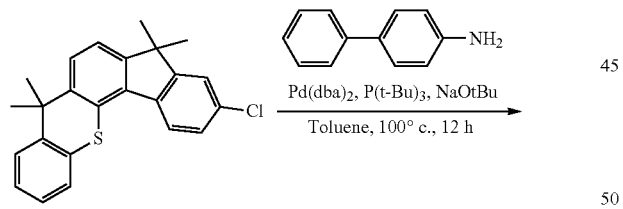

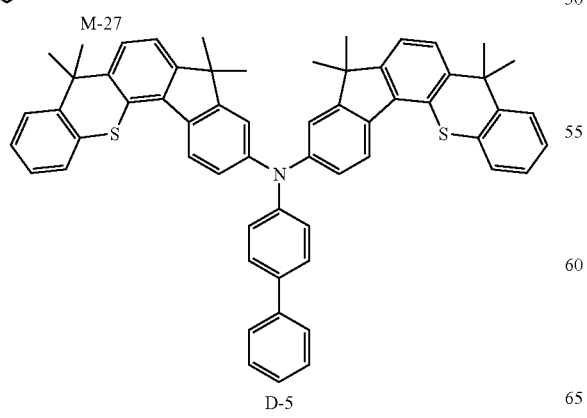

D-5

11.5 g (30.59 mmol) of the intermediate M-27, 2.6 g (15.3 mmol) of 4-aminobiphenyl, and 3.8 g (39.8 mmol) of sodium t-butoxide were put in a round-bottomed flask, 200 mL of toluene, and 0.19 g (0.92 mmol) of tri-tert-butylphosphine and 20.18 g (0.31 mmol) of Pd(dba)$_2$ were added thereto, and then, the mixture was agitated under a nitrogen atmosphere for 12 hours at 100° C. When the reaction was complete, the resultant was extracted with toluene and distilled water, and an organic layer was dried with magnesium sulfate and filtered and then, concentrated under a reduced pressure. Then, a product therefrom was purified with n-hexane/dichloromethane (7:3 of a volume ratio) through silica gel column chromatography, obtaining 11.2 g of a target compound D-5 (a yield of 86%).

LC-Mass (calcd.: 849.35 g/mol, measured.: M+1=850.16 g/mol)

EXAMPLE 9

Preparation of Compound Represented by Chemical Formula D-20

[Reaction Scheme 36]

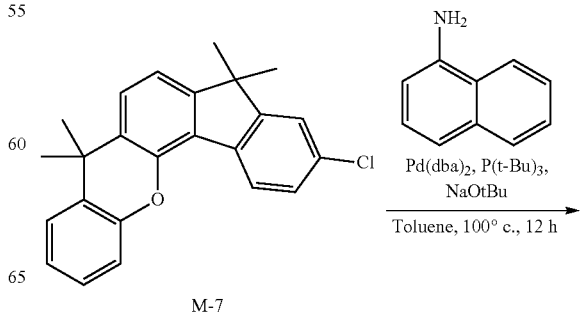

M-7

-continued

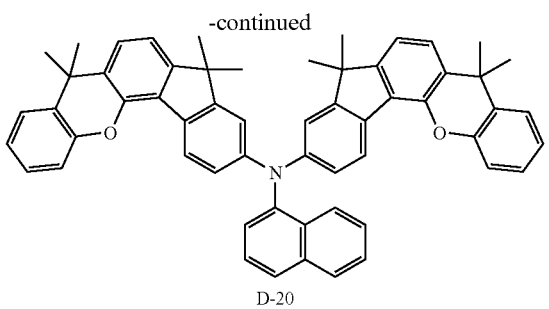

D-20

11.04 g (30.59 mmol) of the intermediate M-7, 2.2 g (15.3 mmol) of 1-aminonaphthalene, and 3.8 g (39.8 mmol) of sodium t-butoxide were put in a round-bottomed flask, 200 mL of toluene was added thereto, and 0.19 g (0.92 mmol) of tri-tert-butylphosphine and 20.18 g (0.31 mmol) of Pd(dba)$_2$ were added thereto, and then, the mixture was agitated under a nitrogen atmosphere for 12 hours at 100° C. When the reaction was complete, the resultant was extracted with toluene and distilled water, and an organic layer was dried with magnesium sulfate and filtered and then, concentrated under a reduced pressure. Then, a product therefrom was purified with n-hexane/dichloromethane (7:3 of a volume ratio) through silica gel column chromatography obtaining 11 g of a target compound D-20 (a yield of 90%).

LC-Mass (calcd.: 791.38 g/mol, measured.: M+1=792.42 g/mol)

EXAMPLE 10

Preparation of Compound Represented by Chemical Formula A-165

[Reaction Scheme 37]

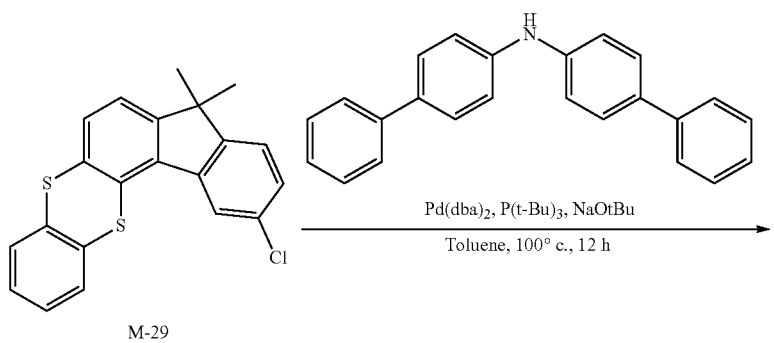

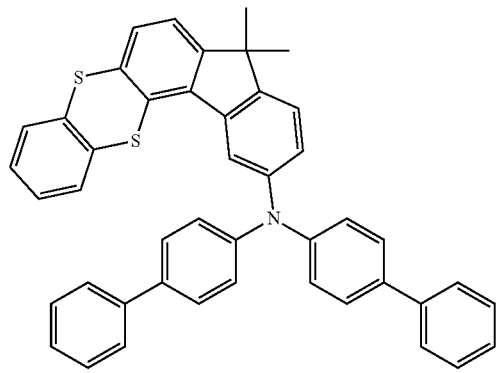

A-165

11.2 g (30.59 mmol) of the intermediate M-29, 9.8 g (30.59 mmol) of bis-biphenyl-4-ylamine, and 3.8 g (39.8 mmol) of sodium t-butoxide were put in a round-bottomed flask, 200 mL of toluene was added thereto, and 0.19 g (0.92 mmol) of tri-tert-butylphosphine and 20.18 g (0.31 mmol) of $Pd(dba)_2$ were added thereto, and then, the mixture was agitated under a nitrogen atmosphere for 12 hours at 100° C. When the reaction was complete, the resultant was extracted with toluene and distilled water, and an organic layer obtained therefrom was dried with magnesium sulfate and filtered, and then, concentrated under a reduced pressure. Then, a product therefrom was purified with n-hexane/dichloromethane (7:3 of a volume ratio) through silica gel column chromatography, obtaining 18.5 g of a target compound of A-165 (a yield of 93%).

LC-Mass (calcd.: 651.21 g/mol, measured.: M+1=652.32 g/mol)

(Manufacture of Organic Light-Emitting Device)

EXAMPLE 11

A glass substrate was coated with ITO (indium tin oxide) to be 1500 Å thick and then, ultrasonic wave-washed with a distilled water. After washing with distilled water, the glass substrate was ultrasonic wave-washed with a solvent such as isopropylalcohol, acetone, methanol and the like, dried, moved to a plasma-cleaner, and then, cleaned with oxygen plasma for 5 minutes and moved to a vacuum depositor. The obtained ITO transparent electrode was used as an anode, and a 600 Å-thick hole injection layer (HIL) was formed on the ITO substrate by vacuum-depositing 4,4'-bis[N-[4-{N,N-bis(3-methylphenyl)amino}-phenyl]-N-phenylamino]biphenyl (DNTPD). Subsequently, a 300 Å-thick hole transport layer (HTL) was formed thereon by vacuum-depositing the compound of Example 1. On the hole transport layer (HTL), a 250 Å-thick emission layer was formed by vacuum-depositing 9,10-di-(2-naphthyl)anthracene (ADN) as a host and 2,5,8,11-tetra(tert-butyl)perylene (TBPe) as a dopant in an amount of 3 wt %.

Then, on the emission layer, a 250 Å-thick electron transport layer (ETL) was formed by vacuum-depositing Alq3. On the electron transport layer (ETL), 10 Å-thick LiF and 1000 Å-thick Al were sequentially vacuum-deposited to form a cathode, manufacturing an organic light-emitting device.

The organic light-emitting device had a structure of having five organic thin layers, specifically A structure of Al 1000 Å/LiF 10 Å/Alq 3250 Å/EML [ADN:TBPe=97:3] 250 Å/HTL 300 Å/DNTPD 600 Å/ITO 1500 Å.

EXAMPLE 12

An organic light-emitting device was manufactured according to the same method as Example 10 except for using the compound of Example 2 instead of the compound of Example 1.

EXAMPLE 13

An organic light-emitting device was manufactured according to the same method as Example 10 except for using the compound of Example 3 instead of the compound of Example 1.

EXAMPLE 14

An organic light-emitting device was manufactured according to the same method as Example 10 except for using the compound of Example 4 instead of the compound of Example 1.

EXAMPLE 15

An organic light-emitting device was manufactured according to the same method as Example 10 except for using the compound of Example 5 instead of the compound of Example 1.

EXAMPLE 16

An organic light-emitting device was manufactured according to the same method as Example 10 except for using the compound of Example 6 instead of the compound of Example 1.

EXAMPLE 17

An organic light-emitting device was manufactured according to the same method as Example 10 except for using the compound of Example 7 instead of the compound of Example 1.

EXAMPLE 18

An organic light-emitting device was manufactured according to the same method as Example 10 except for using the compound of Example 8 instead of the compound of Example 1.

EXAMPLE 19

An organic light-emitting device was manufactured according to the same method as Example 10 except for using the compound of Example 9 instead of the compound of Example 1.

COMPARATIVE EXAMPLE 1

An organic light-emitting device was manufactured according to the same method as Example 11 except for using NPB instead of the compound of Example 1. The structure of the NPB is provided in the following.

The DNTPD, ADN, TBPe, NPB, Alq3 used to manufacture the organic light-emitting devices had a structure as follows.

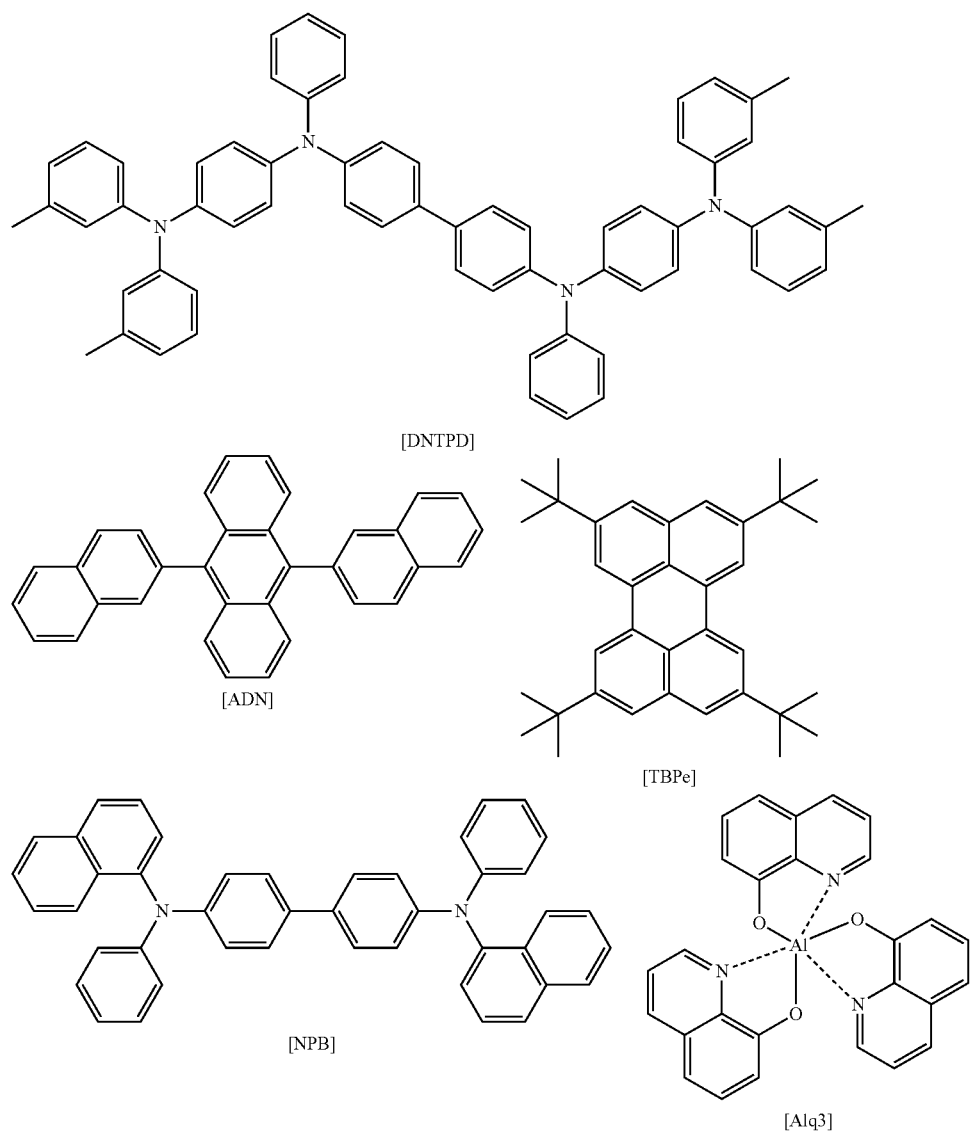

(Performance Measurement of Organic Light-Emitting Device)

Current density change, luminance change, and luminous efficiency of each organic light-emitting device according to the Examples 11 to 19 and Comparative Example 1 depending on a voltage were measured. Specific measurement methods are as follows, and the remits are shown in the following Table 1.

(1) Measurement of Current Density Change Depending on Voltage Change

The obtained organic light-emitting devices were measured for current value flowing in the unit device while increasing the voltage from 0 V to 10 V using a current-voltage meter (Keithley 2400), the measured current value was divided by area to provide the results.

(2) Measurement of Luminance Change Depending on Voltage Change

Luminance was measured by using a luminance meter (Minolta Cs-1000A), while the voltage of the organic light-emitting devices was increased from 0 V to 10 V.

(3) Measurement of Luminous Efficiency

The luminance, current density, and voltage obtained from the (1) and (2) were used to calculate current efficiency (cd/A) at the same current density (10 mA/cm$^2$).

TABLE 1

| Devices | Compound in hole transport layer (HTL) | Voltage (V) | Color (EL color) | Efficiency (cd/A) | Half life-span (h) at 1000 cd/m$^2$ |
|---|---|---|---|---|---|
| Example 11 | A-2 | 6.3 | Blue | 6.3 | 1,610 |
| Example 12 | A-3 | 6.2 | Blue | 6.5 | 1,720 |
| Example 13 | A-37 | 6.7 | Blue | 6.3 | 1,590 |
| Example 14 | A-39 | 6.5 | Blue | 6.4 | 1,690 |
| Example 15 | B-10 | 6.8 | Blue | 5.9 | 1,390 |
| Example 16 | B-11 | 6.8 | Blue | 6.1 | 1,460 |
| Example 17 | B-19 | 6.7 | Blue | 6.1 | 1,430 |
| Example 18 | D-5 | 6.7 | Blue | 6.2 | 1,280 |

TABLE 1-continued

| Devices | Compound in hole transport layer (HTL) | Voltage (V) | Color (EL color) | Efficiency (cd/A) | Half life-span (h) at 1000 cd/m² |
|---|---|---|---|---|---|
| Example 19 | D-20 | 6.6 | Blue | 6.4 | 1,310 |
| Comparative Example 1 | NPB | 7.1 | Blue | 4.9 | 1,250 | current density: 10 mA/cm²

Referring to the Table 2, when hole transport layers for an organic light-emitting device according to the Example 11 to 19 were used, a driving voltage organic of a light emitting diode may be lowered, and luminance and efficiency may be improved.

In addition, half-life life-span of the Example 11 to Example 19 are remarkably improved compared with the Comparative Example 1, and particularly the half-life life-span of the Example 12 is 1,720 hours (h) which is about 37% or more improved compared with Comparative Example 1.

The device results of Examples me considered to be sufficient for device commercialization because a life-span of a device is a requirement for actual device commercialization.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic optoelectronic device, the compound being represented by a combination of the following Chemical Formulae 1 and 2:

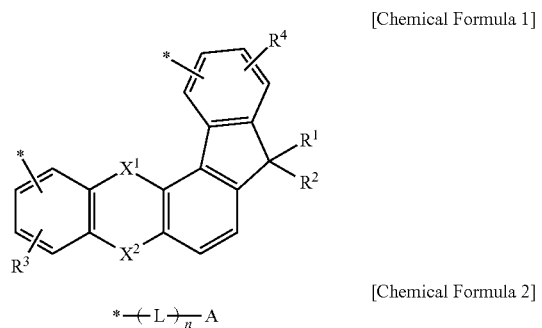

[Chemical Formula 1]

[Chemical Formula 2]

wherein, in Chemical Formulae 1 and 2,
X¹ and X² are each independently —O—, —S—, —C$R^aR^b$—, or —Si$R^aR^b$—, in which $R^a$ and $R^b$ are each independently a substituted or unsubstituted C1 to C10 alkyl group, or a substituted or unsubstituted C6 to C30 aryl group, R¹ to R⁴ are each independently hydrogen, deuterium, a substituted or unsubstituted C1 to C10 alkyl group, a substituted or unsubstituted C6 to C30 aryl group or a substituted or unsubstituted C2 to C30 heteroaryl group, A is a substituted or unsubstituted C6 to C30 aryl group, a substituted or unsubstituted C2 to C30 heteroaryl group, or —N(L¹$_m$R')(L²$_o$R"), in which R' and R" of —N(L¹$_m$R')(L²$_o$R") are each independently hydrogen, deuterium, a substituted or unsubstituted C1 to C10 alkyl group, a substituted or unsubstituted C6 to C30 aryl group or a substituted or unsubstituted C2 to C30 heteroaryl group, L is —SiR'R"—, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, in which R' and R" of —SiR'R"— are each independently hydrogen, deuterium, a substituted or unsubstituted C1 to C10 alkyl group, a substituted or unsubstituted C6 to C30 aryl group or a substituted or unsubstituted C2 to C30 heteroaryl group, L¹ and L² are each independently a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group, n, m, and o are each independently integers of 0 to 3, and

* of Chemical Formula 2 indicates a binding position with one * of Chemical Formula 1, and the other * of Chemical Formula 1 is hydrogen.

2. The compound for an organic optoelectronic device as claimed in claim 1, wherein R¹ to R⁴ are each independently hydrogen, deuterium, a substituted or unsubstituted C1 to C10 alkyl group, or a substituted or unsubstituted C6 to C30 aryl group.

3. The compound for an organic optoelectronic device as claimed in claim 1, wherein A is a substituted or unsubstituted C6 to C30 aryl group or a substituted or unsubstituted C2 to C30 heteroaryl group.

4. The compound for an organic optoelectronic device as claimed in claim 1, wherein the compound is represented by one of the following Chemical Formulae A-2, A-3, A-37, A-39, and A-169:

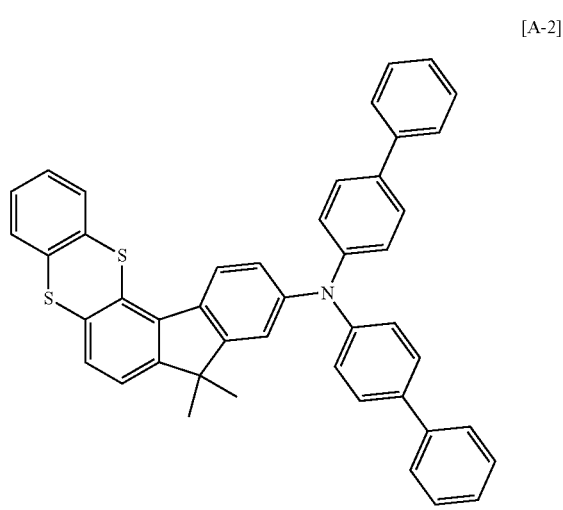

[A-2]

[A-3]
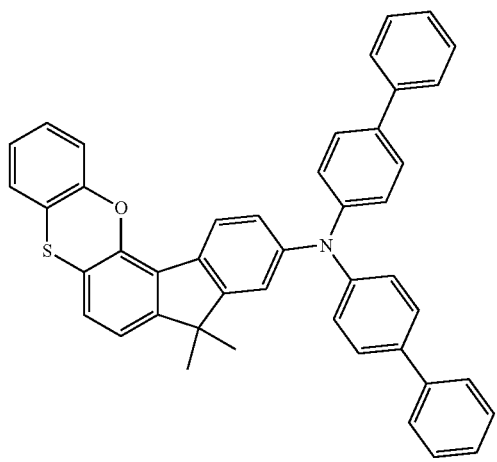
[A-169]
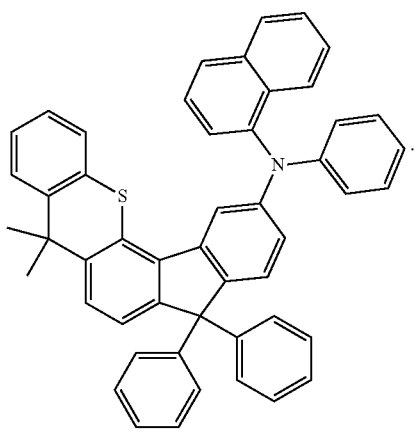
5. The compound for an organic optoelectronic device as claimed in claim 1, wherein the compound is represented by one of the following Chemical Formulae B-10, B-11, and B-19:
[A-37]
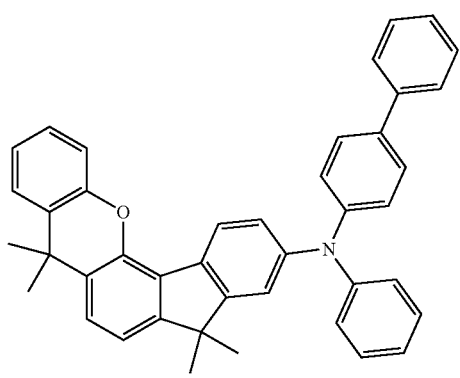
[B-10]
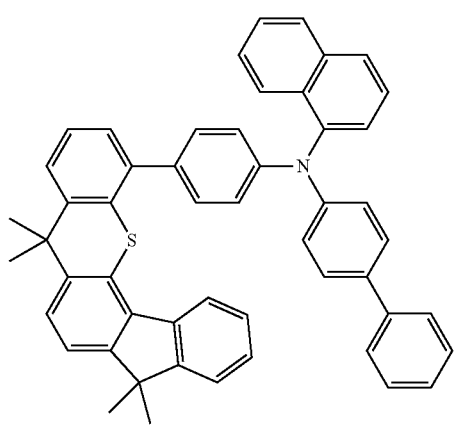
[A-39]
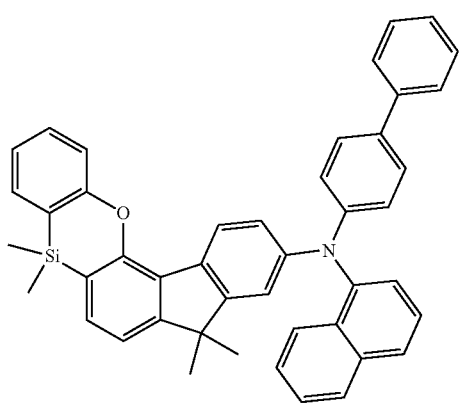
[B-11]
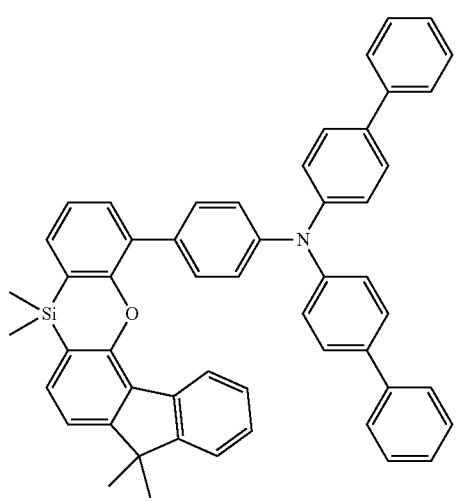

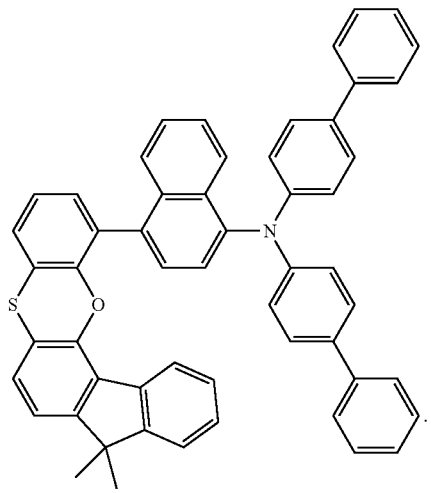

[B-19]

6. The compound for an organic optoelectronic device as claimed in claim 1, wherein the compound is represented by the following Chemical Formula D-5 or Chemical Formula D-20:

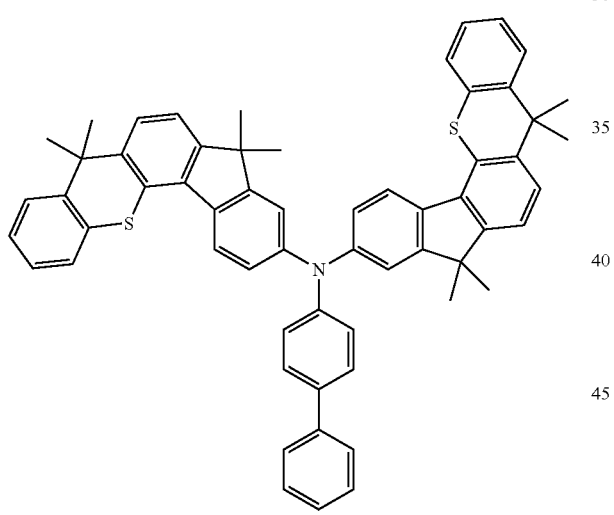

[D-5]

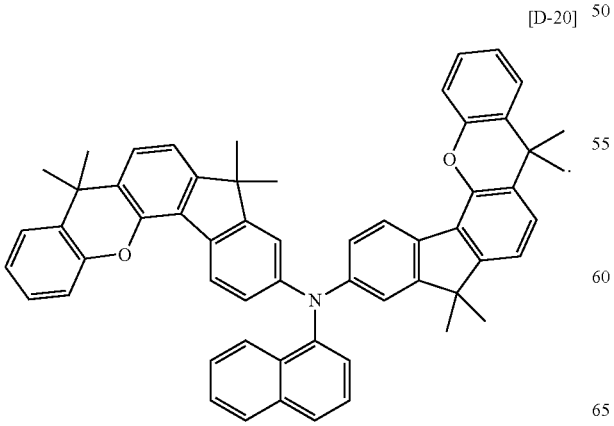

[D-20]

7. The compound for an organic optoelectronic device as claimed in claim 1, wherein the compound has a triplet exciton energy (T1) of 2.0 eV or greater.

8. The compound for an organic optoelectronic device as claimed in claim 1, wherein the organic optoelectronic device is an organic photoelectric device, an organic light emitting device, an organic solar cell, an organic transistor, an organic photo conductor drum, or an organic memory device.

9. The compound for an organic optoelectronic device as claimed in claim 1, wherein A is $-N(L^1_m R')(L^2_o R'')$.

10. The compound for an organic optoelectronic device as claimed in claim 1, wherein:
A is $-N(L^1_m R')(L^2_o R'')$, and
one of R' or R'' of $-N(L^1_m R')(L^2_o R'')$ is a group represented by the following Chemical Formula 3:

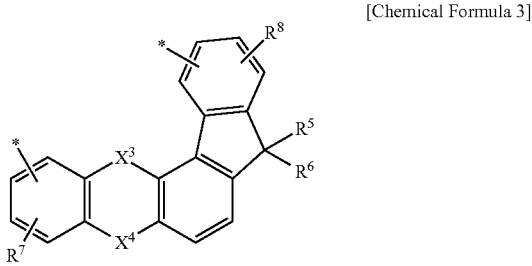

[Chemical Formula 3]

wherein, in Chemical Formula 3,
$X^3$ and $X^4$ are each independently $-O-$, $-S-$, $-CR^a R^b-$, or $-SiR^a R^b-$, in which $R^a$ and $R^b$ are each independently a substituted or unsubstituted C1 to C10 alkyl group, or a substituted or unsubstituted C6 to C30 aryl group, $R^5$ to $R^8$ are each independently hydrogen, deuterium, a substituted or unsubstituted C1 to C10 alkyl group, a substituted or unsubstituted C6 to C30 aryl group or a substituted or unsubstituted C2 to C30 heteroaryl group, and one * of Chemical Formula 3 indicates a bond with $L^1$ or $L^2$ of $-N(L^1_m R')(L^2_o R'')$ and the other * of Chemical Formula 3 is hydrogen.

11. The compound for an organic optoelectronic device as claimed in claim 10, wherein:
A is $-N(L^1_m R')(L^2_o R'')$, and
R' of $-N(L^1_m R')(L^2_o R'')$ is a group represented by the Chemical Formula 3, and R'' of $-N(L^1_m R')(L^2_o R'')$ is a group represented by the Chemical Formula 4:

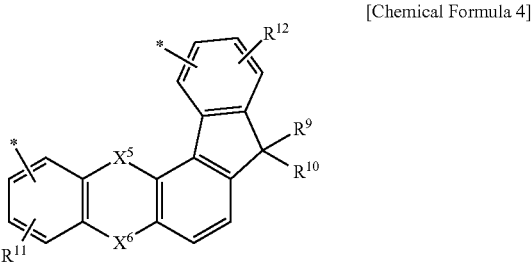

[Chemical Formula 4]

wherein, in Chemical Formula 4,
$X^5$ and $X^6$ are each independently $-O-$, $-S-$, $CR^a R^b-$, or $-SiR^a R^b-$, in which $R^a$ and $R^b$ are each independently a substituted or unsubstituted C1 to C10 alkyl group, or a substituted or unsubstituted C6 to C30 aryl group, $R^9$ to $R^{12}$ are each independently hydrogen, deuterium, a substituted or unsubstituted C1 to C10 alkyl group, a substituted or unsubstituted C6 to C30 aryl group or a substituted or unsubstituted C2 to C30 heteroaryl group, and one * of the Chemical Formula 4 indicates a bond with $L^1$ or $L^2$ of $-N(L^1{}_mR')(L^2{}_oR'')$ and the other * of Chemical Formula 4 is hydrogen.

12. An organic light-emitting device, comprising:
an anode;
a cathode; and
at least one organic thin layer between the anode and the cathode,
wherein the at least one organic thin layer includes the compound for an organic optoelectronic device as claimed in claim 1.

13. The organic light-emitting device as claimed in claim 12, wherein the at least one organic thin layer includes an emission layer, a hole transport layer (HTL), a hole injection layer (HIL), an electron transport layer (ETL), an electron injection layer (EIL), a hole blocking layer, or a combination thereof.

14. The organic light-emitting device as claimed in claim 12, wherein:
the at least one organic thin layer includes a hole transport layer (HTL) or a hole injection layer (HIL), and
the compound is included in the hole transport layer (HTL) or the hole injection layer (HIL).

15. The organic light-emitting device as claimed in claim 12, wherein:
the at least one organic thin layer includes an emission layer, and
the compound is included in the emission layer.

16. The organic light-emitting device as claimed in claim 12, wherein:
the at least one organic thin layer includes an emission layer, and
the compound is a phosphorescent or fluorescent host material in the emission layer.

17. A display device comprising the organic light-emitting device as claimed in claim 12.

* * * * *